US011730790B2

(12) United States Patent
Barasch et al.

(10) Patent No.: US 11,730,790 B2
(45) Date of Patent: *Aug. 22, 2023

(54) MUTANT NGAL PROTEINS AND USES THEREOF

(71) Applicant: The Trustees of Columbia University in the City of New York, New York, NY (US)

(72) Inventors: Jonathan Barasch, New York, NY (US); Andong Qiu, Bronx, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 163 days.

This patent is subject to a terminal disclaimer.

(21) Appl. No.: 16/819,891

(22) Filed: Mar. 16, 2020

(65) Prior Publication Data
US 2021/0038686 A1 Feb. 11, 2021

Related U.S. Application Data

(60) Continuation of application No. 15/376,327, filed on Dec. 12, 2016, now Pat. No. 10,588,937, which is a division of application No. 13/684,060, filed on Nov. 21, 2012, now Pat. No. 9,534,027, which is a continuation-in-part of application No. PCT/US2011/037774, filed on May 24, 2011.

(60) Provisional application No. 61/354,973, filed on Jun. 15, 2010, provisional application No. 61/347,587, filed on May 24, 2010.

(51) Int. Cl.
*A61K 38/17* (2006.01)
*C07K 14/47* (2006.01)
*A61K 31/357* (2006.01)

(52) U.S. Cl.
CPC .......... *A61K 38/1709* (2013.01); *C07K 14/47* (2013.01); *A61K 31/357* (2013.01)

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | |
| 4,640,909 A | 2/1987 | Ramsden et al. | |
| 5,627,034 A | 5/1997 | Gould et al. | |
| 6,071,880 A | 6/2000 | Acott et al. | |
| 6,114,123 A | 9/2000 | Murry et al. | |
| 6,136,526 A | 10/2000 | Venge | |
| 6,447,989 B1 | 9/2002 | Comper | |
| 6,492,325 B1 | 12/2002 | Cosgrove | |
| 6,664,385 B1 | 12/2003 | Sanicola-Nadel et al. | |
| 6,710,028 B2 | 3/2004 | Lehmann et al. | |
| 6,825,037 B1 | 11/2004 | Funk et al. | |
| 6,861,404 B1 | 3/2005 | Cohen et al. | |
| 7,141,382 B1 | 11/2006 | Parikh et al. | |
| 7,153,660 B2 | 12/2006 | Moses et al. | |
| 7,776,824 B2 | 8/2010 | Barasch et al. | |
| 8,247,376 B2 | 8/2012 | Barasch et al. | |
| 9,578,541 B2 | 2/2017 | Seenappa et al. | |
| 9,624,281 B2 | 4/2017 | Barasch et al. | |
| 10,588,937 B2 | 3/2020 | Barasch et al. | |
| 2002/0128194 A1 | 9/2002 | Green et al. | |
| 2003/0109420 A1 | 6/2003 | Valkirs et al. | |
| 2004/0102383 A1 | 5/2004 | Cincotta et al. | |
| 2004/0132984 A1 | 7/2004 | Dieckmann et al. | |
| 2004/0219603 A1 | 11/2004 | Devarajan et al. | |
| 2005/0201981 A1 | 9/2005 | Liu et al. | |
| 2005/0214219 A1 | 9/2005 | Green et al. | |
| 2005/0261191 A1 | 11/2005 | Barasch et al. | |
| 2005/0272101 A1 | 12/2005 | Devarajan et al. | |
| 2007/0037232 A1 | 2/2007 | Barasch et al. | |
| 2007/0092911 A1 | 4/2007 | Buechler et al. | |
| 2007/0105166 A1 | 5/2007 | Moses et al. | |
| 2007/0154897 A1 | 7/2007 | Yen et al. | |
| 2007/0161125 A1 | 7/2007 | Rosenfeld et al. | |
| 2007/0172906 A1 | 7/2007 | Valkirs et al. | |
| 2007/0196876 A1 | 8/2007 | Moses et al. | |

(Continued)

FOREIGN PATENT DOCUMENTS

WO     WO-02/24866 A2     3/2002
WO     WO-03/029462 A1     4/2003

(Continued)

OTHER PUBLICATIONS

NCBI NP_00555.2 downloaded from https://www.ncbi.nlm.nih.gov/protein/NP_005555.2?report=genbank&log$=protalign&blast_rank=10&RID=D44AY149013 on Jul. 15, 2022 (Year: 2022).*

Abergel et al., "Anthrax pathogen evades the mammalian immune system through stealth siderophore production," PNAS, vol. 103, No. 49, pp. 18499-18503 (2006).

Abergel et al., "Microbial Evasion of the Immune System: Structural Modifications of Enterobactin Impair Siderocalin Recognition," Author Manuscript, 9 pages, Published in final edited form as: J. Am. Chem. Soc., vol. 128, pp. 10998-10999 (2006).

(Continued)

*Primary Examiner* — Brian Gangle
*Assistant Examiner* — Andrea K McCollum
(74) *Attorney, Agent, or Firm* — Wilmer Cutler Pickering, Hale and Dorr LLP

(57) ABSTRACT

In one aspect the present invention is directed to mutant Neutrophil gelatinase-associated lipocalin (NGAL) proteins that have the ability to bind to siderophores, such as enterochelin, and to chelate and transport iron, and that are excreted in the urine. Such NGAL mutants, and complexes thereof with siderophores, can be used to clear excess iron from the body, for example in the treatment of iron overload. The NGAL mutants of the invention also have antibacterial activity and can be used in the treatment of bacterial infections, such as those of the urinary tract.

11 Claims, 38 Drawing Sheets

Specification includes a Sequence Listing.

(56) References Cited

U.S. PATENT DOCUMENTS

| | | |
|---|---|---|
| 2007/0254370 A1 | 11/2007 | Devarajan et al. |
| 2008/0014604 A1 | 1/2008 | Devarajan et al. |
| 2008/0014644 A1 | 1/2008 | Barasch et al. |
| 2008/0050832 A1 | 2/2008 | Buechler et al. |
| 2008/0057590 A1 | 3/2008 | Urdea et al. |
| 2008/0090304 A1 | 4/2008 | Barasch et al. |
| 2008/0095782 A1 | 4/2008 | Xu et al. |
| 2008/0254485 A1 | 10/2008 | Valkirs et al. |
| 2009/0019551 A1 | 1/2009 | Haga et al. |
| 2009/0055099 A1 | 2/2009 | Rosenfeld et al. |
| 2009/0082443 A1 | 3/2009 | Otto et al. |
| 2009/0123941 A1 | 5/2009 | Devarajan et al. |
| 2009/0123970 A1 | 5/2009 | Tu et al. |
| 2009/0124572 A1 | 5/2009 | Nelson |
| 2009/0142774 A1 | 6/2009 | Devarajan et al. |
| 2009/0170143 A1 | 7/2009 | Uttenthal et al. |
| 2009/0181407 A1 | 7/2009 | Devarajan et al. |
| 2009/0191551 A1 | 7/2009 | Morrow et al. |
| 2009/0215094 A1 | 8/2009 | Barasch et al. |
| 2009/0269777 A1 | 10/2009 | Birkenmeyer et al. |
| 2009/0298073 A1 | 12/2009 | Gerhold et al. |
| 2009/0305963 A1 * | 12/2009 | Sukhatme ............ A61P 35/00 435/6.14 |
| 2009/0311213 A1 | 12/2009 | Thiboutot et al. |
| 2010/0015648 A1 | 1/2010 | Barasch et al. |
| 2010/0028919 A1 | 2/2010 | Devarajan et al. |
| 2010/0047837 A1 | 2/2010 | Devarajan et al. |
| 2010/0093812 A1 | 4/2010 | Bergeron, Jr. |
| 2010/0105150 A1 | 4/2010 | Adamczyk et al. |
| 2010/0122355 A1 | 5/2010 | Paragas et al. |
| 2010/0184089 A1 | 7/2010 | Barasch et al. |
| 2010/0189643 A1 | 7/2010 | Chilkoti et al. |
| 2010/0227418 A1 | 9/2010 | Devarajan et al. |
| 2010/0233728 A1 | 9/2010 | Devarajan et al. |
| 2010/0233739 A1 | 9/2010 | Barasch et al. |
| 2010/0233740 A1 | 9/2010 | Barasch et al. |
| 2010/0234765 A1 | 9/2010 | Barasch et al. |
| 2010/0254970 A1 | 10/2010 | Barasch et al. |
| 2011/0091912 A1 | 4/2011 | Barasch et al. |
| 2011/0262353 A1 | 10/2011 | Skerra et al. |
| 2011/0268818 A1 | 11/2011 | Barasch et al. |
| 2012/0083421 A1 | 4/2012 | Barasch et al. |
| 2012/0214177 A1 | 8/2012 | Barasch et al. |
| 2013/0072580 A1 | 3/2013 | Barasch et al. |
| 2013/0149725 A1 | 6/2013 | Barasch et al. |
| 2013/0157932 A1 | 6/2013 | Barasch et al. |
| 2017/0016923 A1 | 1/2017 | Nielsen |
| 2018/0153889 A1 | 6/2018 | Henry et al. |
| 2019/0211341 A1 | 7/2019 | Butler et al. |

FOREIGN PATENT DOCUMENTS

| | | |
|---|---|---|
| WO | WO-2004/005544 A2 | 1/2004 |
| WO | WO-04/088276 A2 | 10/2004 |
| WO | WO-2005/107793 | 11/2005 |
| WO | WO-2005/107993 | 11/2005 |
| WO | WO-05/121788 A2 | 12/2005 |
| WO | WO-2006/066587 | 6/2006 |
| WO | WO-06/078717 A2 | 7/2006 |
| WO | WO-2006078717 A2 * | 7/2006 ........... A61K 38/164 |
| WO | WO-06/091035 A1 | 8/2006 |
| WO | WO-2007013919 A2 | 2/2007 |
| WO | WO-07/047458 A2 | 4/2007 |
| WO | WO-2007/044994 | 4/2007 |
| WO | WO-2008116867 A1 | 10/2008 |
| WO | WO-2009/114699 | 9/2009 |
| WO | WO-2010/033847 | 3/2010 |
| WO | WO-2010/045585 | 4/2010 |
| WO | WO-2010057184 A2 | 5/2010 |
| WO | WO-2010/148216 | 12/2010 |
| WO | WO-2011/053832 | 5/2011 |
| WO | WO-2011062469 A2 | 5/2011 |
| WO | WO-2011/140554 | 11/2011 |
| WO | WO-2011/149962 | 12/2011 |
| WO | WO-2012/022742 A1 | 2/2012 |
| WO | WO-2012/042061 A1 | 4/2012 |
| WO | WO-2012/068545 A1 | 5/2012 |
| WO | WO-2014/081980 A2 | 5/2014 |

OTHER PUBLICATIONS

Abergel et al., "The Siderocalin/Enterobactin Interaction: A Link between Mammalian Immunity and Bacterial Iron Transport," Author Manuscript, 28 pages, Published in final edited form as: J. Am. Chem. Soc., vol. 130, pp. 11524-11534 (2008).

Allen, K.J., et al., "Iron-Overload-Related Disease in HFE Hereditary Hemochromatosis," N. Engl. J. Med., vol. 358, pp. 221-230 (2008).

Alteri et al., "Mucosal Immunization with Iron Receptor Antigens Protects against Urinary Tract Infection," PLoS Pathogens, vol. 5, Issue 9, e1000586, pp. 1-12 (Sep. 2009).

American Hemochromatosis Society, "FAQ's About Hemochromatosis/Iron Overload", pp. 1-14 (2019).

Andrews, "Disorders of Iron Metabolism," N. Engl. J. Med., vol. 341, pp. 1986-1995 (1999).

Andrews, "Iron homeostasis: insights from genetics and animal models," Nature Reviews, vol. 1, pp. 208-217 (Dec. 2000).

Andrews, "Iron Metabolism: Iron Deficiency and Iron Overload," Annual Review of Genomics and Human Genetics, vol. 1, pp. 75-98 (2000).

Argyropoulou et al., "Liver, bone marrow, pancreas and pituitary gland iron overload in young and adult thalassemic patients: A T2 relaxometry study," Eur. Radiol., vol. 17, 3025-3030 (2007).

Argyropoulou et al., "MRI evaluation of tissue iron burden in patients with β-thalassaemia major," Pediatr. Radiol., vol. 37, pp. 1191-1200 (2007).

Avdeef et al. "Coordination Chemistry of Microbial Iron Transport Compounds. 9. Stability Constants for Catechol Models of Enterobactin," J. Am. Chem. Soc., vol. 100, No. 17, pp. 5362-5370 (Aug. 16, 1978).

Axelsson et al., "Studies of the release and turnover of a human neutrophil lipocalin," Scand. J. Clin. Lab Invest., vol. 55, No. 7, pp. 577-588 (Nov. 1995).

Bachman et al., "Interaction of Lipocalin 2, Transferrin, and Siderophores Determines the Replicative Niche of Klebsiella pneumoniae during Pneumonia," mBio, vol. 3, No. 6, pp. 1-8 (2012).

Bahram et al., "Experimental hemochromatosis due to MHC class I HFE deficiency: Immune status and iron metabolism," Proc. Natl. Acad. Sci. USA., 96, No. 23, pp. 13312-13317 (1999).

Baliga et al., "Evidence for cytochrome P-450 as a source of catalytic iron in myoglobinuric acute renal failure," Kidney Int., vol. 49, pp. 362-369 (1996).

Baliga et al., "In vitro and in vivo evidence suggesting a role for iron in cisplatin-induced nephrotoxicity," Kidney Int., vol. 53, pp. 394-401 (1998).

Baliga et al., "Increase in bleomycin-detectable iron in ischaemia/reperfusion injury to rat kidneys," Biochem. J., vol. 291, pp. 901-905 (1993).

Bander et al., "Long-term effects of 24-hour unilateral ureteral obstruction on renal function in the rat," Kidney Int., vol. 28, pp. 614-620 (1985).

Bao et al. "Iron Traffics in Circulation Bound to a Siderocalin (Ngal)-Catechol Complex," Author Manuscript, 20 pages, Published in final edited form as: Nat. Chem. Biol., vol. 6, No. 8, pp. 602-609 (2010).

Barasch and Mori, "Cell Biology: Iron Thievery," Nature, vol. 432, pp. 811-813 (2004).

Barasch et al., "A ureteric bud cell line induces nephrogenesis in two steps by two distinct signals," American Journal of Physiology, Renal Physiology, vol. 271, No. 1, pp. F50-F61 (Jul. 1, 1996).

Baron et al., "Renal Preservation after Warm Ischemia Using Oxygen Free Radical Scavengers to Prevent Reperfusion Injury," Journal of Surgical Research, vol. 51, pp. 60-65 (1991).

Barr et al., "Urinary Creatinine Concentrations in the U.S. Population: Implications for Urinary Biologic Monitoring Measurements," Environmental Health Perspectives, vol. 113, pp. 192-200 (2005).

(56) References Cited

OTHER PUBLICATIONS

Bennett et al., "Urine NGAL predicts severity of acute injury after cardiac surgery: A prospective Study," Clin. J. Am. Soc. Nephrol., 3(3), pp. 665-673 (May 2008).
Berdoukas et al., "Liver iron concentration and fibrosis in a cohort of transfusion-dependent patients on long-term desferrioxamine therapy," The Hematology Journal, vol. 5, pp. 572-578 (2005).
Berger et al., "Lipocalin 2-deficient mice exhibit increased sensitivity to *Escherichia coli* infection but not to ischemia-reperfusion injury," Proc. Nat. Acad. Sci. USA, vol. 103, No. 6, pp. 1834-1839 (2006).
Bernhardt, "Coordination chemistry and biology of chelators for the treatment of iron overload disorders," Dalton Trans., pp. 3214-3220 (2007).
BioPorto Diagnostice A/S, "NGal Rapid ELISA Kit (Kit 037)," Revision: NR2007-12-EN, Dec. 2007 (84 pages), Retrieved from internet <www.piercenet.com/files/kit037.PDF>.
BioPorto Diagnostics A/S, "Human NGAL Rapid ELISA Kit (Kit 037)," Revision: Sep. 2010, Sep. 2010 (4 pages), Retrieved from internet <www.bioporto.com/products/bioporto_diagnostics/ngal_elisa_kits/ngal_rapid_elisa_kit_ce_ivd>.
Blaser et al., "A sandwich enzyme immunoassay for the determination of neutrophil lipocalin in body fluids," Clin. Chim. Acta vol. 235, pp. 137-145 (1995).
Boelaert and Locht, "Side-effects of desferrioxamine in dialysis patients," Nephrol. Dial. Transplant., Suppl. 1, pp. 43-46 (1993).
Bohle et al., "Significance of Tubulointerstitial Changes in the Renal Cortex for the Excretory Function and Concentration Ability of the Kidney: A Morphometric Contribution," Am. J. Nephrol., vol. 7, pp. 421-433 (1987).
Bolignano et al., "Neutrophil Gelatinase Associated Lipocalin Reflects the Severity of Renal Impairment in Subjects Affected by Chronic Kidney Disease," Kidney Blood Press. Res., vol. 31, pp. 255-258 (2008).
Bolignano et al., "Neutrophil Gelatinase-Associated Lipocalin in Patients with Autosomal-Dominant Polycystic Kidney Disease," Am. J. Nephrol., vol. 27, pp. 373-378 (2007).
Bolignano et al., "Urinary Neutrophil Gelatinase Associated Lipocalin (Ngal) is Associated with Severity of Renal Disease in Proteinuric Patients," Nephrol. Dial. Transplant., vol. 23, pp. 414-416 (2008).
Bork, "Powers and Pitfalls in Sequence Analysis: The 70% Hurdle," Genome Res., vol. 10, pp. 398-400 (2000).
Borregaard et al., "Neutrophil gelatinase-associated lipocalin, a siderophore-binding eukaryotic protein," BioMetals, vol. 19, pp. 211-215 (2006).
Borwein et al., "Diagnostic efficacy of screening tests for hereditary hemochromatosis," Can. Med. Assoc. J., vol. 131, pp. 895-901 (1984).
Bosque et al., "Assessment of the developmental toxicity of deferoxamine in mice," Arch. Toxicol., 69, pp. 467-471 (1995).
Bowie et al., "Deciphering the Message in Protein Sequences: Tolerance to Amino Acid Substitutions," Science, vol. 247, pp. 1306-1310 (1990).
Brenner et al., "Effects of losartan on renal and cardiovascular outcomes in patients with type 2 diabetes and nephropathy," N. Engl. J. Med., vol. 345, No. 12, pp. 861-869 (Sep. 20, 2001).
Breuer et al., "The assessment of serum nontransferrin-bound iron in chelation therapy and iron supplementation," Blood, vol. 95, No. 9, pp. 2975-2982 (2000).
Bundgaard et al., "Molecular Cloning and Expression of a cDNA Encoding NGAL: A Lipocalin Expressed in Human Neutrophils," Biochem. Biophys. Res. Commun., vol. 202, pp. 1468-1475 (1994).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., vol. 111, pp. 2129-2138 (1990).
Burrus, et al., "Identification of a Cysteine-Rich Receptor for Fibroblast Growth Factors", Mol. Cell Biol. 12(12): 5600-5609, Dec. 1992 (10 pages).

Carmella et al., "Quantitative analysis of catechol and 4-methylcatechol in human urine," Food Chem. Toxic., vol. 20, pp. 587-590 (1982).
Christensen and Birn, "Megalin and cubilin: multifunction endocytic receptors," Nature Reviews Molecular Cell Biology, vol. 3, pp. 258-268 (Apr. 2002).
Chu et al., "Siderophore uptake in bacteria and the battle for iron with the host; a bird's eye view," Biometals, vol. 23, pp. 601-611 (2010).
Chua et al., "Nontransferrin-bound iron uptake by hepatocytes is increased in the Hfe knockout mouse model of hereditary hemochromatosis," Blood, vol. 104, pp. 1519-1525 (2004).
Cohen, "New Advances in Iron Chelation Therapy," Hematology-American Hematology Society Hematology Education Program, pp. 42-47 (2006).
Cooper et al., "Urinary Iron Speciation in Nephrotic Syndrome," Am. J. Kidney Dis., vol. 25, pp. 314-319 (1995).
Cowland et al., "Neutrophil Gelatinase-Associated Lipocalin Is Up-Regulated in Human Epithelial Cells by IL-1$\beta$, but not by TNF-$\alpha$," J. Immunol., vol. 171, pp. 6630-6639 (2003).
Crisponi and Remelli "Iron chelating agents for the treatment of iron overload" Coordination Chemistry Reviews, vol. 252, pp. 1225-1240 (2008).
Cunningham et al., "Complications of $\beta$-thalassemia major in North America," Blood, vol. 104, No. 1, 34-39 (2004).
D'Amico et al., "Tubulointerstitial Damage in Glomerular Diseases: Its Role in the Progression of Renal Damage," Am. J. Kidney Dis., vol. 26, pp. 124-132 (1995).
Damman et al., "Urinary neutrophil gelatinase associated lipocalin (NGAL), a marker of tubular damage, is increased in patients with chronic heart failure," European Journal of Heart Failure, vol. 10, pp. 997-1000 (2008).
Darbari, D.S., et al., "Circumstances of Death in Adult Sickle Cell Disease Patients," Am. J. Hematol., 81, pp. 858-863 (2006).
de Vries et al., "Exogenous alpha-1-acid glycoprotein protects against renal ischemia-reper-fusion injury by inhibition of inflammation and apoptosis," Transplantation 78(8), pp. 1116-1124 (Oct. 27, 2004).
de Vries et al., "Reduction of circulating redox-active iron by apotransferrin protects against renal ischemia-reperfusion injury," Transplantation, vol. 77, No. 5, pp. 669-675 (Mar. 15, 2004).
de Zeeuw, D. et al., "Renal risk and renoprotection among ethnic groups with type 2 diabetic nephropathy: a post hoc analysis of RENAAL," Kidney International, vol. 69, pp. 1675-1682 (2006).
Åkerstrom et al., "Lipocalins: unity in diversity," Biochim. Biophys. Acta., vol. 1482, pp. 1-8 (2000).
Dent et al., "Plasma neutrophil gelatinase-associated lipocalin predicts acute kidney injury, morbidity and mortality after pediatric cardiac surgery: a prospective uncontrolled cohort study," Critical Care, vol. 11, No. 6, 8 pages (2007).
Devarajan et al., "Gene expression in early ischemic renal injury: clues toward pathogenesis, biomarker discovery, and novel therapeutics," Molecular Genetics and Metabolism, vol. 80, pp. 365-376 (2003).
Devarajan, "Neutrophil gelatinase-associated lipocalin: new paths for an old shuttle," Author Manuscript, 12 pages, Published in final edited form as: Cancer Therapy, vol. 5(B), pp. 463-470 (2007).
Devarajan, "Novel biomarkers for the early prediction of acute kidney injury," Cancer Therapy, vol. 3, pp. 477-488 (2005).
Devireddy et al., "A Cell-Surface Receptor for Lipocalin 24p3 Selectively Mediates Apoptosis and Iron Uptake," Cell, vol. 123, pp. 1293-1305 (2005).
Ding et al., "Urinary neutrophil gelatinase-associated lipocalin (NGAL) is an early biomarker for renal tubulointerstitial injury in IgA nephropathy," Clin. Immunol., vol. 123, pp. 227-234 (2007).
Doneanu et al., "Characterization of a Noncovalent Lipocalin Complex by Liquid Chromatography/Electrospray Ionization Mass Spectrometry," J. Biomol. Tech., vol. 15, pp. 208-212 (2004).
Eddy et al., "A Relationship Between Proteinuria and Acute Tubulointerstitial Disease in Rats with Experimental Nephrotic Syndrome," Am. J. Pathol., vol. 138, No. 5, pp. 1111-1123, 1991.
Eddy, "Progression in Chronic Kidney Disease," Adv. Chronic Kidney Dis., vol. 12, No. 4, 353-365 (2005).

(56) References Cited

OTHER PUBLICATIONS

Eddy, "Proteinuria and interstitial injury," Nephrol. Dial. Transplant., vol. 19, 277-281 (2004).
Eichler et al., "Human neutrophil lipocalin, a highly specific marker for acute exacerbation in cystic fibrosis," Eur. Respir. J., vol. 14, pp. 1145-1149 (1999).
Emery, Thomas, "Exchange of Iron by Gallium in Siderophores," Biochemistry, vol. 25, pp. 4629-4633 (1986).
Esbach and Adamson, "Iron overload in renal failure patients: Changes since the introduction of erythropoietin therapy," Kidney International, vol. 55, pp. S35-S43 (1999).
Esson et al., "Diagnosis and Treatment of Acute Tubular Necrosis," Ann. Intern. Med. vol. 137, pp. 744-753 (2002).
Evans et al., "Nature of non-transferrin-bound iron: studies on iron citrate complexes and thalassemic sera," Journal of Biological Inorganic Chemistry, vol. 13, pp. 57-74 (2008).
Extended European Search Report issued by the European Patent Office for Application No. 11787264.8 dated Oct. 7, 2014 (5 pages).
Extended European Search Report dated Oct. 30, 2013, for European Patent Application No. 09815299.4 (7 pages).
Fernández et al., "The Matrix Metalloproteinase-9/Neutrophil Gelatinase-Associated Lipocalin Complex Plays a Role in Breast Tumor Growth and Is Present in the Urine of Breast Cancer Patients," Clin. Cancer Res., vol. 11, No. 15, pp. 5390-5395 (Aug. 1, 2005).
Fischbach et al., "The pathogen-associated iroA gene cluster mediates bacterial evasion of lipocalin 2," Proc. Natl. Acad. Sci. USA, vol. 103, pp. 16502-16507 (2006).
Fjaertoft et al., "Human Neutrophil Lipocalin (HNL) as a Diagnostic Tool in Children with Acute Infections: A Study of the Kinetics," Acta Paediatrica, vol. 94, pp. 661-666 (2005).
Flo et al., "Lipocalin 2 mediates an innate immune response to bacterial infection by sequestrating iron," Nature, vol. 432, pp. 917-921 (2004).
Fluckinger et al., "Human Tear Lipocalin Exhibits Antimicrobial Activity by Scavenging Microbial Siderophores," Antimicrob. Agents Chemother., vol. 48, No. 9, pp. 3367-3372 (2004).
Fung et al., "Increased prevalence of iron-overload associated endocrinopathy in thalassaemia versus sickle-cell disease," Br. J. Haematol., vol. 135, pp. 574-582 (2006).
Garcia et al., "Redundancy and Specificity of *Escherichia coli* Iron Acquisition Systems during Urinary Tract Infection," Infection and Immunity, vol. 79, No. 3, pp. 1225-1235 (Mar. 2011).
Garcia-Tsao et al., "Acute Kidney Injury in Cirrhosis," Hepatology, vol. 48, No. 6, pp. 2064-2077 (2008).
Gaspari et al., "Plasma Clearance of Nonradioactive Iohexol as a Measure of Glomerular Filtration Rate," J. Am. Soc. Nephrol., vol. 6, pp. 257-263 (1995).
Goetz et al., "Ligand Preference Inferred from the Structure of Neutrophil Gelatinase Associated Lipocalin," Biochemistry, vol. 39, pp. 1935-1941 (2000).
Goetz et al., "The Neutrophil Lipocalin NGAL Is a Bacteriostatic Agent that Interferes with Siderophore-Mediated Iron Acquisition," Mol. Cell, vol. 10, pp. 1033-1043 (2002).
Gonzalez-Michaca et al., "Heme: a determinant of life and death in renal tubular epithelial cells," Am. J. Physiol. Renal. Physiol., vol. 286, pp. F370-F377 (2004).
Guterman et al., "Feasability of enterochelin as an iron-chelating drug: studies with human serum and a mouse model system," Gen. Pharmacol., vol. 9, pp. 123-127 (1978).
Gwira et al., "Expression of Neutrophil Gelatinase-Associated Lipocalin Regulates Epithelial Morphogenesis in Vitro," J. Biol. Chem., vol. 280, pp. 7875-7882 (2005).
Hall et al., "IL-18 and Urinary NGAL Predict Dialysis and Graft Recovery After Kidney Transplantation," J. Am. Soc. Nephrol., vol. 21, pp. 189-197 (2010).
Han et al., "Kidney Injury Molecule-1 (KIM-1): A novel biomarker for human renal proximal tubule injury," Kidney Int. vol. 62, pp. 237-244 (2002).

Han et al., "Urinary Biomarkers in the Early Diagnosis of Acute Kidney Injury," Author Manuscript, 17 pages, Published in final edited form as: Kidney Int., vol. 73, No. 7, pp. 863-869 (2008).
Harris et al., "Lysosomal iron accumulation and tubular damage in rat puromycin nephrosis and ageing," Clin. Exp. Pharmacol. Physiol., vol. 21, pp. 73-81 (1994).
Herget-Rosenthal et al., "Early detection of acute renal failure by serum cystatin C," Kidney Int. vol. 66, pp. 1115-1122 (2004).
Herget-Rosenthal et al., "Prognostic Value of Tubular Proteinuria and Enzymuria in Nonoliguric Acute Tubular Necrosis," Clin. Chem., vol. 50, No. 3, pp. 552-558 (2004).
Hershko and Peto, "Non-transferrin Plasma Iron," British Journal of Haematology, vol. 66, pp. 149-151 (Jun. 1987).
Hill et al., "A new morphologic index for the evaluation of renal biopsies in lupus nephritis," Kidney Int., vol. 58, pp. 1160-1173 (2000).
Hod et al., "Transfusion of red blood cells after prolonged storage produces harmful effects that are mediated by iron and inflammation," Blood, vol. 115, pp. 4284-4292 (2010).
Hoette et al., "The Role of Electrostatics in Siderophore Recognition by the Immunoprotein Siderocalin," Author Manuscript, 20 pages, Published in final edited form as: J. Am. Chem. Soc., vol. 130, No. 51, pp. 17584-17592 (Dec. 24, 2008).
Hoffbrand et al., "Role of deferiprone in chelation therapy for transfusional iron overload," Blood, vol. 102, pp. 17-24 (2003).
Holmes et al., "Siderocalin (Lcn 2) Also Binds Carboxymycobactins, Potentially Defending against Mycobacterial Infections through Iron Sequestration," Structure, vol. 13, pp. 29-41 (2005).
Zou et al., "Receiver-Operating Characteristic Analysis for Evaluating Diagnostic Tests and Predictive Models," Circulation, vol. 115, pp. 654-657 (2007).
Horowitz et al., "Lipophilic siderophores of *Mycobacterium tuberculosis* prevent cardiac reperfusion injury," Proc. Natl. Acad. Sci. USA, vol. 95, pp. 5263-5268 (Apr. 1998).
Howard et al., "Urinary albumin, transferrin and iron excretion in diabetic patients," Kidney Int., vol. 40, pp. 923-926 (1991).
Hunsicker et al., "Predictors of the progression of renal disease in the Modification of Diet in Renal Disease Study," Kidney Int., vol. 51, pp. 1908-1919 (1997).
Huynh et al., "Reference Values of Urinary Neutrophil Gelatinase-Associated Lipocalin in Very Low Birth Weight Infants," Author Manuscript, 5 pages, Published in final edited form as: Pediatr. Res. vol. 66, pp. 528-532 (2009).
Hvidberg et al., "The endocytic receptor megalin binds the iron transporting neutrophil-gelatinase-associated lipocalin with high affinity and mediates its cellular uptake," FEBS Letters, vol. 579, pp. 773-777 (2005).
Iannetti et al., "The neutrophil gelatinase-associated lipocalin (NGAL), a NF-κB-regulated gene, is a survival factor for thyroid neoplastic cells," Proc. Natl. Acad. Sci. USA, vol. 105, No. 37, pp. 14058-14063 (2008).
Ichimura et al., "Kidney Injury Molecule-1 (KIM-1), a Putative Epithelial Cell Adhesion Molecule Containing a Novel Immunoglobulin Domain, Is Up-regulated in Renal Cells after Injury," J. Biol. Chem., vol. 273, pp. 4135-4142 (1998).
International Search Report and Written Opinion for Application No. PCT/US2010/054811 dated Dec. 23, 2010 (10 pages).
International Search Report and Written Opinion for International Application No. PCT/US09/61050 dated May 25, 2010 (8 pages).
International Search Report and Written Opinion for International Application No. PCT/US10/39018 dated Aug. 17, 2010 (8 pages).
International Search Report and Written Opinion for International Application No. PCT/US2005/015799 dated Nov. 17, 2005 (7 pages).
International Search Report and Written Opinion for International Application No. PCT/US2011/035757 dated Jul. 27, 2011 (10 pages).
International Search Report and Written Opinion for International Application No. PCT/US2011/037774 dated Sep. 8, 2011 (7 pages).
International Search Report and Written Opinion for International Application No. PCT/US2013/071344 dated May 12, 2014 (14 pages).

(56) References Cited

OTHER PUBLICATIONS

International Search Report and Written Opinion for International Patent Application No. PCT/US09/36972 dated Feb. 24, 2010 (10 pages).
Jewett et al., "Novel Method to Examine the Formation of Unstable 2:1 and 3:1 Complexes of Catecholamines and Iron(III)," Journal of Inorganic Biochemistry, vol. 66, pp. 165-173 (1997).
Johnson et al., "Parenteral iron formulations differentially affect MCP-1, HO-1, and NGAL gene expression and renal responses to injury," Am. J. Physiol. Renal Physiol., vol. 299, pp. F426-F435 (2010).
Jones et al., "Low Molecular Weight Iron-Binding Factor from Mammalian Tissue That Potentiates Bacterial Growth," J. Exp. Med., vol. 151, pp. 418-428 (1980).
Kaiser et al., "Interactions between NKG2x Immunoreceptors and HLA-E Ligands Display Overlapping Affinities and Thermodynamics," J. Immunol., vol. 174, pp. 2878-2884 (2005).
Kalinowski and Richardson, "The Evolution of Iron Chelators for the Treatment of Iron Overload Disease and Cancer," Pharmacol. Rev., vol. 57, No. 4, pp. 547-583 (2005.
Kamijo et al., "Urinary liver-type fatty acid binding protein as a useful biomarker in chronic kidney disease," Molecular and Cellular Biochemistry, vol. 284, pp. 175-182 (2006).
Karpishin, R. B., et al., "Spectroscopic Studies of the Electronic Structure of Iron(III) Tris(catecholates)," J. Am. Chem. Soc., vol. 113, pp. 2977-2984 (1991).
Keberle, "The Biochemistry of Desferrioxamine and Its Relation to Iron Metabolism," Annals of the New York Academy of Sciences, vol. 119, Issue 2, pp. 758-768 (1964).
Kjeldsen et al., "Characterization of two ELISAs for NGAL, a newly described lipocalin in human neutrophils," Journal of Immunological Methods, vol. 198, 155-164 (1996).
Kjeldsen et al., "Human neutrophil gelatinase-associated lipocalin and homologous proteins in rat and mouse," Biochim. Biophys. Acta, vol. 1482, pp. 272-283 (2000).
Kjeldsen et al., "Isolation and Primary Structure of NGAL, a Novel Protein Associated with Human Neutrophil Gelatinase," J. Biol. Chem. 268, No. 14, pp. 10425-10432 (1993).
Klotman, "Pathogenesis and Treatment of HIV-Associated Nephropathy," Topics in HIV Medicine, vol. 9, Issue 2, pp. 27-29 (Jun. 2001).
Kok et al., "Renal Drug Delivery With Low-Molecular-Weight Proteins: The Effect of Charge Modifications on the Body Distribution of Drug-Lysozyme Conjugates," Drug Delivery 6, pp. 1-8 (1999).
Kowdley and Kaplan, "Iron-chelation therapy with oral deferiprone—toxicity or lack of efficacy," New England Journal of Medicine, vol. 339, No. 7, pp. 468-469 (Aug. 13, 1998).
Kozyraki and Gofflot, "Multiligand Endocytosis and Congenital Defects: Roles of Cubilin, Megalin and Amnionless," Current Pharmaceutical Design, vol. 13, pp. 3038-3046 (2007).
Kribben et al., "Pathophysiology of Acute Renal Failure," J. Nephrol., vol. 12 (suppl 2), pp. S142-S151 (1999).
Kubes et al., "Therapeutic Potential of Inhibiting Leukocyte Rolling in Ischemia/Reperfusion," J. Clin. Invest., vol. 95, pp. 2510-2519 (Jun. 1995).
Kuzmič, "Program DYNAFIT for the Analysis of Enzyme Kinetic Data: Application to HIV Proteinase," Anal. Biochem., vol. 237, pp. 260-273 (1996).
Lang et al., "Development of a Stable Isotope Dilution Analysis with Liquid Chromatography-Tandem Mass Spectrometry Detection for the Quantitative Analysis of Di- and Trihydroxybenzenes in Foods and Model Systems," J. Agric. Food Chem., vol. 54, pp. 5755-5762 (2006).
Lasko et al., "The use of receiver operating characteristic curves in biomedical informatics," Journal of Biomedical Informatics, vol. 38, pp. 404-415 (2005).
Laskowski et al., "PROCHECK: a program to check the stereochemical quality of protein structures," J. Appl. Cryst., vol. 26, pp. 283-291 (1993).
Lazar et al., "Transforming Growth Factor □: Mutation of Aspartic Acid 47 and Leucine 48 Results in Different Biological Activities," Mol. Cell. Biol., vol. 8, No. 3, pp. 1247-1252 (1988).
Leheste et al., "Hypocalcemia and osteopathy in mice with kidney-specific megalin gene defect," FASEB J., vol. 17, pp. 247-249 (2003).
Leheste et al., "Megalin Knockout Mice as an Animal Model of Low Molecular Weight Proteinuria," Am. J. Pathol., vol. 155, No. 4, pp. 1361-1370 (1999).
Lerma et al., "Current Diagnosis & Treatment Nephrology & Hypertension," McGraw Hill Education, Chapter 36, pp. 313-319, (2009).
Levey et al., "A More Accurate Method to Estimate Glomerular Filtration Rate from Serum Creatinine: A New Prediction Equation," Ann. Intern. Med. vol. 130, No. 6, pp. 461-470 (1999).
Lewis et al., "Renoprotective effect of the angiotensin receptor antagonist irbesartan in patients with nephropathy due to type 2 diabetes," N. Engl. J. Med., vol. 345, No. 12, pp. 851-860 (Sep. 20, 2001).
Li et al., "Crystal Structures of RAE-1β and Its Complex with the Activating Immunoreceptor NKG2D," Immunity, vol. 16, pp. 77-86 (Jan. 2002).
Li et al., "Detection of intracellular iron by its regulatory effect," Am. J. Physiol. Cell Physiol., vol. 287, pp. C1547-C1559 (2004).
Li et al., "Scara5 Is a Ferritin Receptor Mediating Non-Transferrin Iron Delivery," Author Manuscript, 22 pages, Published in final edited form as: Dev. Cell, vol. 16, pp. 35-46 (2009).
Liang et al., "WebFEATURE: An interactive web tool for identifying and visualizing functional sites on macromolecular structures," Nucleic Acids Res. vol. 31, No. 13, pp. 3324-3327 (2003).
Liangos et al., "Urinary N-Acetyl-β-(D)-Glucosaminidase Activity and Kidney Injury Molecule-1 Level are Associated with Adverse Outcomes in Acute Renal Failure," J. Am. Soc. Nephrol., vol. 18, pp. 904-912 (2007).
Loomis and Raymond, "Solution Equilibria of Enterobactin and Metal-Enterobactin Complexes," Inorganic Chemistry, vol. 30, pp. 906-911 (1991).
Lorenz et al., "Iron overload in kidney transplants: Prospective analysis of biochemical and genetic markers," Kidney Int, vol. 67, pp. 691-697 (2005).
Mackensen-Haen et al., "The consequences for renal function of widening of the interstitium and changes in the tubular epithelium of the renal cortex and outer medulla in various renal diseases," Clin. Nephrol., vol. 37, No. 2, pp. 70-77 (1992).
Magil, A.B., "Tubulointerstitial Lesions in Human Membranous Glomerulonephritis: Relationship to Proteinuria," Am. J. Kidney Dis., vol. 25, No. 3, pp. 375-379 (Mar. 1995).
Makris et al., "Urinary neutrophil gelatinase-associated lipocalin (NGAL) as an early marker of acute kidney injury in critically ill multiple trauma patients," Clin. Chem. Lab. Med., vol. 47, No. 1, pp. 79-82 (2009).
Mandalunis et al., "Experimental Renal Failure and Iron Overload: A Histomorphometric Study in Rat Tibia," Toxicol. Pathol., vol. 33, pp. 398-403 (2005).
Matsuo et al., "Crucial roles of binding sites for NF-κB and C/EBPs in IκB-ζ-mediated transcriptional activation," Biochem. J., vol. 405, pp. 605-615, 2007.
Matthaeus et al., "Acute Ischemic Renal Failure Induces Expression of Neutrophil Gelatinase-Associated Lipocalin and Matrix Metalloproteinase-9 in Damaged Tubuli," Kidney Blood Press. Res., vol. 24, Congress of Nephrology, p. 342 (2001).
Matthaeus et al., "Co-Regulation of Neutrophil Gelatinase-Associated Lipocalin and Matrix Metalloproteinase-9 in the Postischemic Rat Kidney," J. Am. Soc. Nephrol., vol. 12, p. 787A (2001).
Mayo Clinic, "Hemochromatosis", www.mayoclinic.org/diseases-conditions/hemochromatosis/diagnosis-treatment/drc-20351448, 2019 (9 pages).
McBeth et al., "A New Twist in TCR Diversity Revealed by a Forbidden αβ TCR," J. Mol. Biol., vol. 375, No. 5, pp. 1306-1319 (2008).
McFarland et al., "Thermodynamic Analysis of Degenerate Recognition by the NKG2D Immunoreceptor: Not Induced Fit but Rigid Adaptation," Immunity, vol. 19, pp. 803-812 (2003).

(56) References Cited

OTHER PUBLICATIONS

Meneghini, "Iron Homeostasis, Oxidative Stress, and DNA Damage," Free Radical Biology & Medicine, vol. 23, No. 5, pp. 783-792 (1997).
Metcalfe "How does early chronic kidney disease progress? A Background Paper prepared for the UK Consensus Conference on Early Chronic Kidney Disease," Nephrol. Dial. Transplant., 22 (Suppl. 9), ix26ix-30 (2007).
Mishra et al., "Amelioration of Ischemic Acute Renal Injury by Neutrophil Gelatinase-Associated Lipocalin," J. Am. Soc. Nephrol., vol. 15, pp. 3073-3082 (2004).
Mishra et al., "Identification of Neutrophil Gelatinase-Associated Lipocalin as a Novel Early Urinary Biomarker for Ischemic Renal Injury," J. Am. Soc. Nephrol., vol. 14, pp. 2534-2543 (2003).
Mishra et al., "Neutrophil gelatinase-associated lipocalin (NGAL) as a biomarker for acute renal injury after cardiac surgery," Lancet, vol. 365, pp. 1231-1238 (2005).
Mishra et al., "Neutrophil Gelatinase-Associated Lipocalin: A Novel Early Urinary Biomarker for Cisplatin Nephrotoxicity," Am. J. Nephrol., vol. 24, pp. 307-315 (2004).
Mishra J. et al., "Kidney NGAL is a Novel Early Marker of Acute Injury Following Transplantation," Pediatr. Nephrol., vol. 21, pp. 856-863 (2006).
Mitsnefes MM et al., "Serum neutrophil gelatinase-associated lipocalin as a marker of renal function in children with chronic kidney disease," Pediatr. Nephrol., vol. 22, pp. 101-108 (2006).
Moestrup and Verroust, "Megalin- and Cubilin-Mediated Endocytosis of Protein-Bound Vitamins, Lipids, and Hormones in Polarized Epithelia," Annual Review of Nutrition, vol. 21, pp. 407-428 (2001).
Moestrup et al., "Analysis of Ligand Recognition by the Purified α2-Macroglobulin Receptor (low Density Lipoprotein Receptor-related Protein). Evidence that high affinity of α2-macroglobulin-proteinase complex is achieved by binding to adjacent receptors," J. Biol. Chem., vol. 266, pp. 14011-14017 (1991).
Monier et al., "Gelatinase isoforms in urine from bladder cancer patients," Clinica Chimica Acta, vol. 299, pp. 11-23 (2000).
Mori and Nakao, "Neutrophil gelatinase associated lipocalin as the real time indicator of active kidney damage," Kidney Int., vol. 71, pp. 967-970 (2007).
Mori et al., "Endocytic delivery of lipocalin-siderophore-iron complex rescues the kidney from ischemia-reperfusion injury," J. Clin. Invest., vol. 115, No. 3, pp. 610-621 (Mar. 2005).
Murshudov et al., "Refinement of Macromolecular Structures by the Maximum-Likelihood Method," Acta Cryst., vol. D53, Part 3, pp. 240-255 (1997).
Nankivell et al., "Iron Accumulation in Human Chronic Renal Disease," Am. J. Kidney Dis., vol. 20, pp. 580-584 (1992).
National Kidney Foundation, "K/DOQI clinical practice guidelines for chronic kidney disease: evaluation, classification, and stratification," Am. J. Kidney Dis., vol. 39 (suppl 1), pp. SI-S266 (2002).
Nelson et al., "Bacterial colonization of nasal mucosa induces expression of siderocalin, an iron-sequestering component of innate immunity," Cell Microbiol., vol. 7, pp. 1404-1417 (2005).
Zweig and Campbell, "Receiver-Operating Characteristic (ROC) Plots: A Fundamental Evaluation Tool in Clinical Medicine," Clin. Chem., vol. 39, No. 4, pp. 561-577 (1993).
Nguyen et al., "Novel Early Biomarkers of Acute Kidney Injury," [Abstract] J. Am. Soc. Nephrol., vol. 17, p. 49A (2006).
Nickolas et al., "Diagnostic and Prognostic Stratification in the Emergency Department Using Urinary Biomarkers of Nephron Damage," Journal of the American College of Cardiology, vol. 59, No. 3, pp. 246-255 (2012).
Nickolas, T. L., et al., "Monomeric neutrophil gelatinase associated lipocalin is associated with tubulointerstitial damage in chronic kidney disease," Author Manuscript, 10 pages, Published in final edited form as: Kidney International, vol. 82, No. 6, pp. 718-722 (Sep. 2012).
Nickolas, T.L., et al., "Sensitivity and specificity of a single emergency department measurement of urinary neutrophil gelatinase-associated lipocalin for diagnosing acute kidney injury," Ann. Intern. Med., vol. 148, pp. 810-819 (2008).
Olivieri et al., "Visual and Auditory Neurotoxicity in Patients Receiving Subcutaneous Deferoxamine Infusions," N. Engl. J. Med., vol. 314, No. 14, pp. 869-873 (1986).
Otwinowski, "Processing of X-ray Diffraction Data Collected in Oscillation Mode," Methods in Enzymology, vol. 276: Macromolecular Crystallography, part A, C.W. Carter, Jr. & R. M. Sweet, Eds. (Academic Press New York), pp. 307-326, 62 pages total (1997).
Paller and Hedlund, "Extracellular iron chelators protect kidney cells from hypoxia/reoxygenation," Free Radical Biology and Medicine, vol. 17, No. 6, pp. 597-603 (1994).
Paller and Hedlund, "Role of iron in postischemic renal injury in the rat," Kidney Int., vol. 34, pp. 474-480 (1988).
Paller and Jacob, "Cytochrome P-450 mediates tissue-damaging hydroxyl radical formation during reoxygenation of the kidney," Proc. Natl. Acad. Sci. USA., vol. 91, pp. 7002-7006 (Jul. 1994).
Paragas et al., "NGAL-Siderocalin in Kidney Disease," Author Manuscript, 20 pages, Published in final edited form as: Biochimica et Biophysica Acta, vol. 1823, No. 9, pp. 1451-1458 (2012).
Paragas et al., "The Ngal Reporter Mouse Detects the Response of the Kidney to Injury in Real Time," Author Manuscript, 18 pages, Published in final edited form as: Nat. Med., vol. 17, No. 2, pp. 216-222 (Feb. 2011).
Paragas et al., "Urinary NGAL Marks Cystic Disease in HIV-Associated Nephropathy," J. Am. Soc. Nephrol., vol. 20(8), pp. 1687-1692 (Aug. 2009).
Parikh et al., "Urinary IL-18 is an early predictive biomarker of acute kidney injury after cardiac surgery," Kidney Int., vol. 70, pp. 199-203 (2006).
Parikh et al., "Urinary Interleukin-18 is a Marker of Human Acute Tubular Necrosis," Am. J. Kidney Dis., vol. 43, No. 3, pp. 405-414 (Mar. 2004).
Parikh et al., "Urine IL-18 Is an Early Diagnostic Marker for Acute Kidney Injury and Predicts Mortality in the Intensive Care Unit," J. Am. Soc. Nephrol., vol. 16, pp. 3046-3052 (2005).
Parikh et al., "Urine NGAL and IL-18 are Predictive Biomarkers for Delayed Graft Function Following Kidney Transplantation," Am. J. Transplant, vol. 6, pp. 1639-1645 (2006).
Parravicini et al., "Reference Range of Urinary Neutrophil Gelatinase-Associated Lipocalin in Very Low-Birth-Weight Infants: Preliminary Data," Am. J. Perinatol., vol. 26, No. 6, pp. 437-440 (2009).
Perron et al., "Predicting How Polyphenol Antioxidants Prevent DNA Damage by Binding to Iron," Inorganic Chemistry, vol. 47, No. 14, pp. 6153-6161 (2008).
Perrone et al., "Serum Creatinine as an Index of Renal Function: New Insights into Old Concepts," Clin. Chem., vol. 38, No. 10, pp. 1933-1953 (1992).
Playford et al., "Effects of Mouse and Human Lipocalin Homologues 24p3/Lcn2 and Neutrophil Gelatinase-Associated Lipocalin on Gastrointestinal Mucosal Integrity and Repair," Gastroenterology, vol. 131, pp. 809-817 (2006).
Prinsen et al., "Transferrin Synthesis Is Increased in Nephrotic Patients Insufficiently to Replace Urinary Losses," J. Am. Soc. Nephrol., vol. 12, pp. 1017-1025 (2001).
Remuzzi et al., "Understanding the Nature of Renal Disease Progression," Kidney Int., vol. 51, pp. 2-15 (1997).
Rennickand Quebbemann, "Site of excretion of catechol and catecholamines: renal metabolism of catechol," Am. J. Physiol., vol. 218, No. 5, pp. 1307-1312 (1970).
Rubinstein et al., "The novel role of neutrophil gelatinase-b associated lipocalin (NGAL)/Lipocalin-2 as a biomarker for lupus nephritis," Autoimmunity Reviews, vol. 7, pp. 229-234 (2008).
Russo et al., "IroN Functions as a Siderophore Receptor and Is a Urovirulence Factor in an Extraintestinal Pathogenic Isolate of *Escherichia coli*," Infection and Immunity, vol. 70, No. 12, pp. 7156-7160 (Dec. 2002).
Russo et al., "The Siderophore Receptor IroN of Extraintestinal Pathogenic *Escherichia coli* Is a Potential Vaccine Candidate," Infection and Immunity, vol. 71, No. 12, pp. 7164-7169 (Dec. 2003).

(56) References Cited

OTHER PUBLICATIONS

Saad et al., "The preventive role of deferoxamine against acute doxorubicin-induced cardiac, renal and hepatic toxicity in rats," Pharmacological Research, vol. 43, No. 3, pp. 211-218 (2001).
Sawahata et al., "Biotransformation of Phenol to Hydroquinone and Catechol by Rat Liver Microsomes," Mol. Pharmacol., vol. 23, No. 2, pp. 453-460 (Mar. 1983).
Saweirs and Goddard, "What are the best treatments for early chronic kidney disease? A Background Paper prepared for the UK Consensus Conference on Early Chronic Kidney Disease," Nephrol. Dial. Transplant., vol. 22 (Suppl. 9), pp. ix31-ix38 (2007).
Schmidt-Ott et al., "Dual Action of Neutrophil Gelatinase-Associated Lipocalin," J. Am. Soc. Nephrol., vol. 18, pp. 407-413 (2007).
Schmidt-Ott et al., "Neutrophil gelatinase-associated lipocalin-mediated iron traffic in kidney epithelia," Curr. Opin. Nephrol. Hypertens., vol. 15, pp. 442-449 (2006).
Schmitt et al., "Tubulo Interstitial Alterations in Type I Membranoproliferative Glomerulonephritis, An Investigation of 259 Cases," Path. Res. Pract., vol. 182, pp. 6-10 (1987).
Schwartz et al., "Earliest cardiac toxicity induced by iron overload selectively inhibits electrical conduction," J. Appl. Physiol., vol. 93, pp. 746-751 (2002).
Singbartl et al., "Blocking P-selectin protects from ischemia/reperfusion-induced acute renal failure," FASEB J., vol. 14, pp. 48-54 (Jan. 2000).
Sise et al., "Urine neutrophil gelatinase-associated lipocalin identifies unilateral and bilateral urinary tract obstruction," Nephrol. Dial. Transplant., vol. 26, pp. 4132-4135 (2011).
Smith and Martell et al., "Critical Stability Constants, vol. 4: Inorganic Complexes," Plenum Press, New York, Table of Contents, 3 pages (1976).
Smith, "Origin of urinary pyrocatechol," Nature, vol. 190, pp. 167 (1961).
Soler-García et al., "Iron-Related Proteins: Candidate Urine Biomarkers in Childhood HIV-Associated Renal Diseases" Clin. J. Am. Soc. Nephrol., vol. 4, pp. 763-771 (2009).
Stone et al., "PJ34, a poly-ADP-ribose polymerase inhibitor, modulates renal injury after thoracic aortic ischemia/reperfusion," Surgery, vol. 138, pp. 368-374 (2005).
Strong et al., "Expression, purification, crystallization and crystallographic characterization of dimeric and monomeric human neutrophil gelatinase associated lipocalin (NGAL)," Acta Crystallographica, vol. D54, pp. 93-95 (1998).
Supplemental European Search Report dated Sep. 6, 2016 for European Patent Application No. 13856275.6 (8 pages).
Supplementary European Search Report dated Oct. 4, 2011 for European Application No. EP 09720017.4 (6 pages).
Supplementary European Search Report dated Oct. 7, 2014 for European Application No. EP 11787264.8 (5 pages).
Sanchez et al., "Catechol releases iron(III) from ferritin by direct chelation without iron(II) production," Dalton Trans., No. 4, pp. 811-813 (Feb. 21, 2005).
Trinder et al., "Molecular pathogenesis of iron overload," Gut, vol. 51, pp. 290-295 (2002).
Vaidya et al., "Biomarkers of Acute Kidney Injury," Author Manuscript, 29 pages, Published in final edited form as: Ann. Rev. Pharmacol. Toxicol., vol. 48, pp. 463-493 (2008).
Vera et al., "Protective Effect of Carbon Monoxide-Releasing Compounds in Ischemia-Induced Acute Renal Failure," J. Am. Soc. Nephrol., vol. 16, pp. 950-958 (2005).
Vigdorovich et al., "Expression and Characterization of a Soluble, Active Form of the Jaagsiekte Sheep Retrovirus Receptor Hyal2," J. Virol., vol. 79, No. 1, pp. 79-86 (2005).
Volpe et al., "NGAL Controls the Metastatic Potential of Anaplastic Thyroid Carcinoma Cells," The Journal of Clinical Endocrinology & Metabolism, vol. 98, No. 1, pp. 228-235 (Jan. 2013).
Wagener et al., "Association between Increases in Urinary Neutrophil Gelatinase-associated Lipocalin and Acute Renal Dysfunction After Adult Cardiac Surgery," Anesthesiology, vol. 105, pp. 485-491 (2006).
Wagener et al., "Increased Incidence of Acute Kidney Injury with Aprotinin Use during Cardiac Surgery Detected with Urinary NGAL," Am. J. Nephrol., vol. 28, pp. 576-582 (2008).
Walker and Shah, "Evidence Suggesting a Role for Hydroxyl Radical in Gentamicin-induced Acute Renal Failure in Rats," J. Clin. Invest., vol. 81, pp. 334-341 (1988).
Wang et al., "Iron Deposition in Renal Biopsy Specimens from Patients With Kidney Diseases," Am. J. Kidney Dis., vol. 38, No. 5, pp. 1038-1044 (Nov. 2001).
Ward et al., "An Iron-Based Molecular Redox Switch as a Model for Iron Release from Enterobactin via the Salicylate Binding Mode," Inorg. Chem., vol. 38, pp. 5007-5017 (1999).
Wehrmann, et al., "Long-term prognosis of focal sclerosing glomerulonephritis. An analysis of 250 cases with particular regard to tubulointerstitial changes," Clin, Nephrol., vol. 33, pp. 115-122 (1990).
Wei et al., "Neutrophil gelatinase-associated lipocalin suppresses cyst growth by Pkd1 null cells in vitro and in vivo," Author Manuscript, 16 pages, Published in final edited form as: Kidney Int., vol. 74, pp. 1310-1318 (2008).
Windus et al., "Fatal Rhizopus Infections in Hemodialysis Patients Receiving Deferoxamine," Annals of Internal Medicine, vol. 107, pp. 678-680 (1987).
Wu and Paller, "Iron Loading Enhances Susceptibility to Renal Ischemia in Rats," Ren. Fail., vol. 16, No. 4, pp. 471-480 (1994).
Wyatt and Klotman, "HIV-1 and HIV-Associated Nephropathy 25 Years Later," Clin. J. Am. Soc. Nephrol., vol. 2, pp. S20-S24 (2007).
Wyatt et al., "Acute renal failure in hospitalized patients with HIV: risk factors and impact on in-hospital mortality," AIDS, vol. 20, pp. 561-565 (2006).
Xu et al., "Interactions between Lipids and Human Anti-HIV Antibody 4E10 Can Be Reduced without Ablating Neutralizing Activity," J. Virol., vol. 84, No. 2, pp. 1076-1088 (Jan. 2010).
Xu et al., "Serum measurements of human neutrophil lipocalin (HNL) discriminate between acute bacterial and viral infections," Scand. J. Clin. Lab Invest., vol. 55, pp. 125-131 (1995).
Yan et al., "The High Molecular Weight Urinary Matrix Metalloproteinase (MMP) Activity is a complex of Gelatinase B/MMP-9 and Neutrophil Gelatinase-associated Lipocalin (NGAL): Modulation of MMP-9Activity by NGAL," The Journal of Biological Chemistry, vol. 276, pp. 37258-37265 (2001).
Yang et al., "An Iron Delivery Pathway Mediated by a Lipocalin," Mol. Cell, vol. 10, pp. 1045-1056 (Nov. 2002).
Yang et al., "Iron, Lipocalin, and Kidney Epithelia," Am. J. Physiol. Renal Physiol., vol. 285, pp. F9-F18. Review (2003).
Zager, "Combined Mannitol and Deferoxamine Therapy for Myohemoglobinuric Renal Injury and Oxidant Tubular Stress, Mechanistic and Therapeutic Implications," J. Clin. Invest., vol. 90, pp. 711-719 (1992).
Zappitelli et al., "Urine neutrophil gelatinase-associated lipocalin is an early marker of acute kidney injury in critically ill children: a prospective cohort study," Crit. Care vol. 11:R84, 11 pages (2007).
Zhao et al., "Structural characterization of glycoprotein NGAL, an early predictive biomarker for acute kidney injury," Carbohydr. Res., vol. 345, pp. 2252-2261 (2010).

\* cited by examiner

Figure 2:
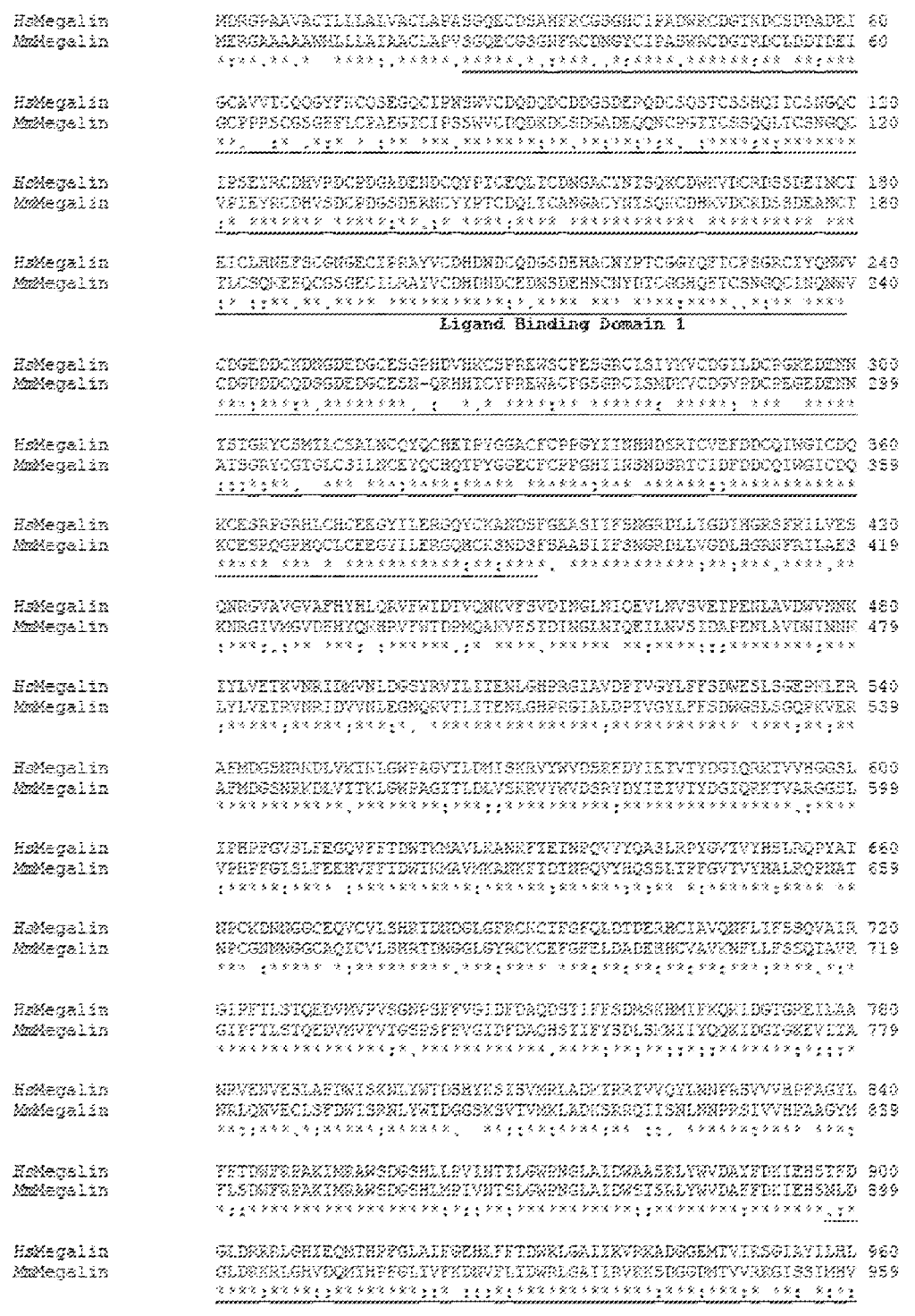

| | | |
|---|---|---|
| HsMegalin | MDRGPAAVACTLLIAIVRCLAFASGQECDSAHFRCGSGHCIPADWRCDGIKDCSDDADEI | 60 |
| MmMegalin | MRRGAAAAWLLLAIAACLAPVSGQECGSSNFRCDNGYCIPASWRCDGTRICLEDTDEI | 60 |

*(The remainder of Figure 2 is a multi-panel protein sequence alignment between HsMegalin and MmMegalin, with conservation symbols below each pair of aligned rows. A region labeled "Ligand Binding Domain 1" is underlined beneath one block of the alignment. Residue counts at the right margin progress through 120, 180, 240, 300, 360, 420, 480, 540, 600, 660, 720, 780, 840, 900, and 960 for HsMegalin, and 120, 180, 240, 299, 359, 419, 479, 539, 599, 659, 719, 779, 839, 899, 959 for MmMegalin. The sequence text is rendered at low resolution and is not clearly legible in detail.)*

```
HsMegalin    EHLECVTLDIEEQKLYWRVDERGVIERGNVDGIDPMILVHQLSRPNGIAVHGSFLYYTDE 1978
MmMegalin    EHLEVVTLDIQEQKLYWAVTSPGVIEPGNVDGTERMILVHRLAHFWGLVVHGSFLYYSDE 1979

HsMegalin    QYEVIERVDKATGANKIVLKDNVPNLAGLQVYPRNAAESSNGCSRNKWACQQICLPVPG 2038
MmMegalin    QYEVIERVDNSSGGNKVVFRDNIPYLPGLAPYHRPNRADSSNGCSHNFNACQQICLPVPS 2039

HsMegalin    GLPSCRCATGFKLNPDNRSCSPYNSFIVVSRLSAIPGFSLELSDHSETFVPVAGQGRNAL 2098
MmMegalin    GKFSCACASGFRLSPDGRSCSPYRSFIVVSMLPAVRGFSLELSDHSERNVPVAGQGRFVL 2099

HsMegalin    HVPNDVSSGPITWCDFSGSVASDNAIARIKPDGSSLMNIVTEGCIGENGVRGIAVDMVAGN 2158
MmMegalin    HADVDVANGSIYNCDFSSSVRSSRGIRRIKFPNGSNFTNIVTIGIGANSIPFVAVDMVAGN 2159

HsMegalin    LYFTNRAFVSETLIEVLRISTTYRPVLLKVTVDMPRHIVVDFYNPYLFWADYGQRPKIERS 2218
MmMegalin    LYSTNAFVIETLIEVIPISTTYRRVLLNVSVDMPPHIVVDFKHRYLFWADYGQKPKIERS 2219

HsMegalin    FLDCTHRTVLVSEGIVIPRGLAVDRSDGYVTWVDDSLDIIASIPIRGENSEVTRYGSRYP 2278
MmMegalin    FLDCTNRIVLVSEGIVIPRGLAVDRSDTGSYIYNVDDSLDIIAKIHRDGGESQVVRTGSSRYP 2279

HsMegalin    IFYGITVFENGILWVDRNLRKIFQASNEPERTEPSTVIRDNISWLRDVIIFDRQVQPRGE 2338
MmMegalin    TPYGITVFGESTIRNVDRNLPKVFQASKQPGNTDPFTVIRDSINLLRDVTIFDEHVQFLSP 2339

HsMegalin    AEVNNKPCLENNGGCSHLCFALSGLRIPKCDCAPGTLQSDGKNCAISTENFLIPALSNSL 2398
MmMegalin    RELNNNPCLQSNGGCSHFCFALPELPTPYCGCAFGILEDIGKNCATSREDFLIYSLNHSL 2399

HsMegalin    RSLHLDPENESPFFQTINVEKIVMSLDYDSVSIRIYFTQNLASGVEGQISYATLSSGIETP 2458
MmMegalin    PSLEFDPQLENLPFQAISVEGNAIALDYDRPNSPIFSTQKLNPIRGQISYVNLYSGASSP 2459

HsMegalin    TVIASGIGTRDGIAFDWITPRIYTSBYLNQMINSMAEDGSNKIVTARVSRPRKIVLDPCQ 2518
MmMegalin    IILLSRIGVTDGIASDWINRRKIYISDFSRQTIKGNAEDGSNPAVIAPVSNFPDAIVLDPCR 2519

HsMegalin    GYLTWADNDTHAMTERATLGSNFKVFTYNSSLVNPSGLTLDTEEDLAYWPDASLQRIERS 2578
MmMegalin    GYMYWILDWGTRASIEPATLGSNFPVPIVRTSLVNSRGLAILDLETDLLYWADASLQKIERS 2579

HsMegalin    FLTGVDPEVIVRAAVHAFGLTLYGQTIYWIDLYTQRIYRANKYDGSGQIANTINLLSQFR 2638
MmMegalin    ILTGSNPREVVISTAFRSFGLTVYGQTIYWTDFYTKRIYRANKYDESDLIANTTRLSIQPS 2639

HsMegalin    GINTVVKNQKQQCNHPCEQFNGGCSHICAPGPNRAECQCPHEGFWYLANSPNHCIVERGE 2698
MmMegalin    GISTVVKTQQGQCSNPCIQFWGGCSHICAPGPNGAECQCPHEGSWYLANENKYCVVDIGR 2699

HsMegalin    RCGASSFTCSNGPCISEEWKCDHDRDCGDGSDEHESVCALHTCSPEAFTCRNGRCVQYSY 2758
MmMegalin    RCHQFQFTCLNGACISQISWCDKNDCGDSSDELPTVCAEHTCKSTASTCANSKCVPYHY 2759

HsMegalin    RCDYYRDCGDGSDEAGCLFRDCKATTEFMCRNRSCIPREFICNGVDNCRESNTSDEKNCP 2818
MmMegalin    RCDFYRDCGDNSDEAGCLFRSCNSITESTCSNGRCIPLSYVCNGINHCHDNDTSDEKNCP 2819

HsMegalin    DRTCQSSFTKCHESNICIPRVYLCDGDNDCGDRSDENFTYCTTHTCSSSEFQCAS-SKCI 2877
MmMegalin    PITCQSDFAKCQETRICVSFAPLCDGDNDCGDSEDENPIYCASHTCRSNEFQCVSRHRCT 2879
```

Fig. 2 (cont.)

```
HsMegalin    PQHWYCDQETDCFDASDEPASCGHSERECLADEFRCDGQDCIPSEWICDGDNDCGDNSDE  2937
MmMegalin    PSTHYCDSEARCVDSSEEPRTCGRSLNSCSANQFRCDNGRCISSSNVCDSDNDCGDNSDE  2939

HsMegalin    DERHQCDQNQNCSDSEFLCVRDESPDRACIPQSWVCDGDVDCTDGTDENQNCTRRICSENE  2997
MmMegalin    DQRHNCELQSCSSTEFTCINSRFRNRACIPQHRVCRGDADCADALNELQNCTMRACSTGE  2999
                         Ligand Binding Domain 3

HsMegalin    PTCGYSLCIPKIFRCDPHNDCGDYSDERSCLYQFCQDNQFTCQNGRCISKTFVCDEDNDC  3057
MmMegalin    FSCANGRCIRQSFPCDKPNDCGDYSSERGCSYPFCRDEQFTCQNSQCITKLYVCDEDNDC  3059

HsMegalin    GSGSDEIHLCHIPEFTCPPHEFKCDNGRCIEMNRLCNHLDDCLDNSDERGCGINECHDF  3117
MmMegalin    GSGSDEQHLCHIPEFTCPPHQFRCINGRCIENSTVCNHVDGCSDNSDERGCGINECQDS  3119

HsMegalin    SISRCRNCTDTLTSFYCSCRPGYHLNSDRKTCVDIRECIENPFVCSQKCENVIGSYICR  3177
MmMegalin    SISRCRNCTDTITSFYCSCLPGYKLNSDRKTCVDIPECKETPQLCSQHCENVIGSYICR  3179

HsMegalin    CAPGYLREPDGKTCRQNSNIEPYLIPSNPYYLSNLIIDSYFYSLILEGLSNPVVALDFDPV  3237
MmMegalin    CAPGYIREPDGKSCRQNSNIEPYLVPSNRYYIERNLIIDPSYSLILQGLSNPVVALDFDPV  3239

HsMegalin    EKRLYNIDTQRQVIERMFLNKINKEIINHRLEKAESLAVEKVSRHLYWLDRRLDGLFVS  3297
MmMegalin    EERLYWISREKQIIERMPLNKTNQEIIISHKLRPAESLAVENVSRFLYWLDAILDCLFVS  3299

HsMegalin    DLNGGHKPNLAQHCVDANNIPCFDNPRGLALRPQYGYLYWADWGHPAYIGRVGMDGTNKS  3357
MmMegalin    DLEGPQRNLAQHCVDAKNTFCFENPRGIVLHPQRGTVIWADWGDHAYIARIGMDGTNKT  3359

HsMegalin    VIISTKLENPRGITIDYTNELLYNADAHLGYIEYSDLEGHHRHTVYDGALPHPFAITIFE  3417
MmMegalin    VIISTKIENPRAITIDYTNELLYNADAHLGYIEFSDLEGHHPHTVYDGTLPHPFRLIIFE  3419

HsMegalin    DIIYWIDWNIKIVERGRKYDGSNRQILVNTIHRPFDIRVYHPYPQPIVSNPCGIKNGGCS  3477
MmMegalin    DIVFNIDWNIKIVEKGNKYDGSGRVVLYNITHKPFDIHVLRPYPQPIMSNPCKINGGCS  3479

HsMegalin    HLCLIKPGGKGFTCECPDDFKILQLSGSTYCNPNCSSTQFLCRNNENCIPINWKCDGQRD  3537
MmMegalin    HLCLIKAGGRGFTCECPDUFQIVQLADKILCNPHCSSTQFLCGNNENCIPINWKCDGQRD  3539

HsMegalin    CSDGSDELALCPQPFCRLGQFQCSDRNCISPQTILCNRHQNCPDGSDEDRLLCENHHCDSN  3597
MmMegalin    CSDGSDESDLCHRPCRLGQFQCRDGNCTSPQALCNARQDCRIGSDEDRVLCEHHPCEAN  3599

HsMegalin    EWQCANKRCIPESWQCDTFRDCEDNSDEDSSHCASRICRPGQFKCANGRCIPQANKCDVD  3657
MmMegalin    EWQCANKRCIPEYWQCDSVDDCLDNSDEDPSHCASRTCRPGQFYCINGRCIPQSWKCDVD  3659

HsMegalin    NDCGDHSDEPIEECMSSAHLCDNSTEFSCKTNYRCIPKHAVCNGVDDCRDNSDEQGCEER  3717
MmMegalin    NDCGDYSDEPIHECMTAYNCDNHIEFSCKTNYRCIPQNAVCNGFDSCRDNSDEQGCESV  3719
                                     Ligand Binding Domain 4

HsMegalin    TCHPVGDFRCKNHHCIPLRWQCDGQNDCGDNSDEERCARECTESEFSCVRQQCIPSRWI  3777
MmMegalin    PCHPSSDFRCGNHHCIPLNWKCDGEDDCGDNSDEESCVEPECTESEFRCADQQCIPSRNV  3779
```

Fig. 2 (cont.)

```
HsMegalin  CRYNDCGDNSDERDCEMRTCRRFYFQCTSGRCVHSELKCDGSADCLDASDEADCPTRFF  3837
MmMegalin  CRQENDCGDNSDERDCEMSTCRFEHFQCTSGRCVEKALACDGRADCLDASDESACPTRFF  3839

HsMegalin  DRAYCQATEFECKHHVCIPFTWKCDGEDDCGDGSDEELHLCLDVPCNSPNRFPCDNSRCI  3897
MmMegalin  NGTYCFAANFECKHHVCIQSFNICDGEMDCVDGSDEETHLCFNVPCESPQRFPCDNSPCI  3899

HsMegalin  YGHEVCNGVDDCGDGTDETEERCRKPTPKPCTEYEYRCGNGHCIPHDNYCDDADDCGDNS  3957
MmMegalin  YGNQLCNGVDDCGDGSDESEERCRKPTSKPCTETEYRCSNGNCVSQHYVCDNVDDCGDLS  3959

HsMegalin  DELQCRHGHERICRENICEQNCTQLNEGGFICSCTAGFEINVFDRTSCLDINECEQFGTC  4017
MmMegalin  DETQCHLCENRICAENICEQNCTQLSNGGFICSCPGFFNPSTLDRNSCQDINECEEFGIC  4019

HsMegalin  PQHCRNTKGSYECVCADGFTEMSDRPGERCAAEGSSPLLLLPDNVRIRKYNLSSERFSEY  4077
MmMegalin  PQSCRNSKGSYECFCVDGFRSMSTHYGERCAADGSPPLLLLPENVRIRKYNISSERFSEY  4079

HsMegalin  LQDEEYIQAVDYDWDFKDIGLSVYYYPVRGRGSNFGAIKRAYIDFFESGRNNLVQEVDLK  4137
MmMegalin  LEEEERIQAIDYDWDFEGIGLSVYYYPVLSQGSQFGAIKRAYLDFTSGSNNFVREVDLG  4139

HsMegalin  LFYVNQPDGIAVNWVGRHIYWSDVFNKRIEVAKLDGTPKWLISTDLQPRAIAVNPKLG  4197
MmMegalin  LFYLNQPDGLAVNWVGRHIYWSDANSQRIEVATLDGTPKWLITTQLQPRAIAVNPKLG  4199

HsMegalin  IMFWTDNGKEPKIESAMMNGEDRKILVFEDLGWPTGLSIDTLENDKIYWSDFKEDVIETI  4257
MmMegalin  IMFWTDQGKQPKIESAMMNGERKSVLASANLGWPNGLSIDYLNGDKIYWSDSKEDVIESI  4259

HsMegalin  KYDGTDRRVIAMEAMNPYSLDIFEDQLYNISHENGEVWKQNHFGQGKKERILVVNPWLTQ  4317
MmMegalin  KYDGTDRRLIINPAMNPYSLDIFEDQLYNVAKENGEVWKQNHFGKGNKERLIVVNPWLTQ  4319

HsMegalin  VRIFRQLRYNKSVFNLCKQICSHLCLLRPGGYSCACPQGSSSFIEGSTTECDAAIELPIDL  4377
MmMegalin  VRIFRQLRYHQSVSNFCKQVCSHLCLLRPGGYSCACPQGSDFVIGSTVECDAASELPITM  4379

HsMegalin  PSPCRCMHGGNCYEDETDLPWCKCPSGYTGKTCEMAFSKGISPGTIAVAVLATILLIVVI  4437
MmMegalin  PSPCRCMHGGSCYFDEMDLPWCKCSSGYSGEYCEIGLERGIPPG-TTMALLLTFAMVIIV  4438

HsMegalin  GALAIAGFSHYPRTGSLLPALPKLPSLSSLVEPSERGNEYTFRSGADLDMDIGVSGFGPE  4497
MmMegalin  GALVLVGFSHYPKTGSLLPSLPKLPSLSSLAKPSERGREVTFRSGADVEMDIGVSPFGPE  4498

HsMegalin  TAIDRSHERKSEDFVMEMGNQPIIFENPMISARDSAVKVVQPIQ--------VIVSENVDHK  4550
MmMegalin  TIIDRSHRMNEQFVMEVGSQFVISENPMYAAKISTSRVGLAVQGSFSVSSQVIVFESNVENQ  4558

HsMegalin  NYGSFINPSEIVFETNPTSFAASGTQVIKNNLFKPASEQITNFENFIYAQMENFQKESVA  4610
MmMegalin  NYGRSIDPSEIVFEPSPASPGASEIQGFIKNNIFKPASEQITNFENFIYAEMDTEQKESVA  4618

HsMegalin  ATPPPSPSLPRKFKPSSRRDPTPTYSAIEDTFKDTAHLVKEDSEV  4655
MmMegalin  VAPPPSPSLPAK---ASRRSSTPGYTATEDTFKDTAHLVKEDSDV  4660
```

Fig. 2 (cont.)

>K3 Ngal mutant (SEQ ID NO: 2)
QDSTSDLIPAPPLSSVPLQQNPQDNQFQGKWYVVGLAGNA
ILREDEDPQKMYATIYELKEDKSYNVTSVLFRDDGCDYWI
RTFVPGCQPGEFTLGNIQSYPGLTSYLVRVVSTNYNQFAM
VFFKKVSQNQEYFKITLYGRTKELTSELQENPIRFSKSLG
LPENNIVFPVPIDQCIDG >Wild-type Ngal protein (SEQ ID NO: 1)
QDSTSDLIPAPPLSKVPLQQNFQDNQFQGKWYVVGLAGNA
ILREDKDPQKMYATIYELKEDKSYNVTSVLFRKKKCDYWI
RTFVPGCQPGEFTLGNIKSYPGLTSYLVRVVSTNYNQHAM
VFFKKVSQNREYFKITLYGRTKELTSELKENPIRFSKSLG
LPENHIVFPVPIDQCIDG

| | |
|---|---|
| K3 60 | QDSTSDLIPAPPLSSVPLQQNPQDNQFQGKWYVVGLAGNAILREDEDPQKMYATIYELKE |
| Wild-type 60 | QDSTSDLIPAPPLSKVPLQQNFQDNQFQGKWYVVGLAGNAILREDKDPQKMYATIYELKE |
| | ************ ,**************************,********** |
| K3 120 | DKSYNVTSVLFRDDGCDYWIRTFVPGCQPGEFTLGNIQSYPGLTSYLVRVVSTNYNQFAM |
| Wild-type 120 | DKSYNVTSVLFRKKKCDYWIRTFVPGCQPGEFTLGNIKSYPGLTSYLVRVVSTNYNQHAM |
| | ********** ,, ***********************,************** , |
| K3 178 | VFFKKVSQNQEYFKITLYGRTKELTSELQENPIRFSKSLGLPENNIVFPVPIDQCIDG |
| Wild-type 178 | VFFKKVSQNREYFKITLYGRTKELTSELKENPIRFSKSLGLPENHIVFPVPIDQCIDG |
| | *******,***************,*******,*********** |

Fig. 19

- K3 Ngal + second C mutated to S

QDSTSDLIPAPPLSSVPLQQNFQDNQFQGKWYVVGLAGNA
ILREDEDPQKMYATIYELKEDKSYNVTSVLFRDDGCDYWI
RTFVPGSQPGEFTLGNIQSYPGLTSYLVRVVSTNYNQFAM
VFFKKVSQNQEYFKITLYGRTKELTSELQENFIRFSKSLG
LPENNIVFPVPIDQCIDG

Fig. 21

MUTANT 1=K3
MUTANT 2=K3CYS

MUTANT NGAL PROTEINS AND USES THEREOF

This application is a continuation application to U.S. patent application Ser. No. 15/376,327 filed Dec. 12, 2016 which is a divisional application of U.S. patent application Ser. No. 13/684,060 filed Nov. 21, 2012 which is a continuation-in-part of International Application No. PCT/US2011/037774, filed on May 24, 2011, which claims the benefit of U.S. Provisional Patent Application No. 61/347,587, filed May 24, 2010, and U.S. Provisional Patent Application No. 61/354,973, filed Jun. 15, 2010, the contents of each of which are hereby incorporated by reference.

GOVERNMENT SUPPORT

This invention was made with government support under DK073462 awarded by the National Institutes of Health. The government has certain rights in the invention

SEQUENCE LISTING

The instant application contains a Sequence Listing which has been submitted in ASCII format via EFS-Web and is hereby incorporated by reference in its entirety.

All patents, patent applications and publications cited herein are hereby incorporated by reference in their entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

NGAL (Lipocalin 2) is a small protein with a molecular weight of about 22 kD. NGAL binds to iron-binding siderophores, such as enterochelin, with high affinity and thus chelates and traffics iron. Once produced in cells, NGAL is secreted into the extracellular space and transported to the kidney where it passes the filtration barrier of the glomerulus and enters the primary urine. However NGAL is then efficiently reabsorbed by megalin receptors localized on the apical side of the epithelia of the proximal tubules. Once NGAL is reabsorbed and endocytosed, it is trafficked to lysosomes and degraded. Once degraded, any iron which NGAL transported to the kidney is reabsorbed.

SUMMARY OF THE INVENTION

The present invention is based, in part, on the development of mutant versions of the NGAL protein that are not reabsorbed in the kidney and thus, unlike wild-type NGAL, are excreted in significant amounts in the urine. Like wild-type NGAL, these mutant forms of NGAL have the ability to bind to iron-binding siderophores, such as enterochelin. Thus, these NGAL mutants can be used to traffic iron out of the body by facilitating its excretion in the urine. As such, the mutant NGAL proteins of the invention can be used in the treatment of iron overload and diseases and disorders associated with iron overload. In addition, the mutant NGAL proteins of the invention have bacteriostatic activity and can be used to treat bacterial infections of the urinary tract.

These and other aspects of the present invention are described in more detail below, and in other sections of this application.

In one embodiment the present invention provides a mutant NGAL protein comprising an amino acid sequence that is at least 70% identical to the sequence of wild-type human NGAL (SEQ ID NO.1), or a fragment thereof, wherein one or more residues from among Lys 15, Lys 46, Lys 50, Lys 59, Lys 62, Lys 73, Lys 74, Lys 75, Lys 98, His 118, Arg 130, Lys 149, and His 165 is mutated by deletion or by substitution with a non-positively charged amino acid residue, and wherein one or more of, or preferably all of, residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the mutant NGAL protein is able to bind to a siderophore and/or to a siderophore-iron complex, and/or is excreted in the urine, and/or has bacteriostatic activity.

In preferred embodiments five, six, seven, eight, nine, ten, or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In some embodiments the % of the mutant NGAL protein that accumulates in the urine following systemic administration of the mutant NGAL protein to a subject is greater than the % of WT NGAL protein that accumulates in the urine following systemic administration of WT NGAL protein to a subject. In some embodiments the % of the mutant NGAL protein that accumulates in the urine following systemic administration of the mutant NGAL protein to a subject is greater than 10-fold or greater than 100-fold more than the % of WT NGAL protein that accumulates in the urine following systemic administration of WT NGAL protein to a subject. In one embodiment the % of the mutant NGAL protein that accumulates in the urine three hours after systemic administration of the mutant NGAL protein to a subject is 1% or more, or 2% or more, or 5% or more, or 10% or more, or 20% or more. This is significantly higher than the % of WT NGAL protein that accumulates in the urine—typically only about 0.1% of WT NGAL that is administered to a subject systemically accumulates in the urine over the same time period.

In some embodiments the present invention provides a nucleic acid sequence that encodes a mutant NGAL protein. In some embodiments the present invention provides an expression vector comprising such a nucleic acid sequence operatively linked to a promoter. The present invention also provides bacterial cells and mammalian cells that stably express such nucleic acids and that may be useful for the production of recombinant mutant NGAL proteins.

The present invention also provides pharmaceutical compositions comprising the mutant NGAL proteins of the invention and pharmaceutical compositions comprising complexes of such mutant NGAL proteins together with a siderophore, such as enterochelin, pyrogallol, carboxymycobactin, catechol, or variants thereof.

In one embodiment, the siderophore is pH insensitive. In another embodiment, the siderophore binds to the mutant NGAL protein and iron at urinary pH. In another embodiment, the siderophore binds to the mutant NGAL protein and iron in the urine.

In one embodiment, the siderophore binds to the mutant NGAL protein and iron at blood pH. In another embodiment, the siderophore binds to the mutant NGAL protein and iron in the blood. In one embodiment, the mutant NGAL protein and the siderophore are present in a 1:1 molar ratio. In one embodiment, the mutant NGAL protein and the siderophore are present in a 1:3 molar ratio.

The present invention also provides methods for treating iron overload in a subject in need thereof, comprising administering to the subject an effect amount of a pharmaceutical composition comprising a mutant NGAL protein.

The present invention also provides methods for treating iron overload in a subject in need thereof, comprising administering to the subject an effect amount of a pharmaceutical composition comprising a mutant NGAL protein and a siderophore.

The present invention also provides methods for treating bacterial urinary tract infections in a subject in need thereof, comprising administering to the subject an effect amount of a pharmaceutical composition comprising a mutant NGAL protein.

The present invention also provides methods for treating bacterial urinary tract infections in a subject in need thereof, comprising administering to the subject an effect amount of a pharmaceutical composition comprising a mutant NGAL protein and a siderophore.

The present invention provides for a polypeptide that encodes a K3 NGAL protein and comprises an amino acid sequence that is identical to SEQ ID NO. 2.

The present invention also provides for a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a nucleic acid encoding a polypeptide that encodes a K3 NGAL protein and comprises an amino acid sequence that is identical to SEQ ID NO. 2. The present invention also provides for a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a pharmaceutical composition comprising a polypeptide that encodes a K3 NGAL protein and comprises an amino acid sequence that is identical to SEQ ID NO. 2. The present invention also provides for a pharmaceutical composition comprising a polypeptide that comprises an amino acid sequence that is at least 99% identical to SEQ ID No. 2, at least 95% identical to SEQ ID No. 2, at least 90% identical to SEQ ID No. 2, at least 80% identical to SEQ ID No. 2, or at least 70% identical to SEQ ID No. 2.

The present invention provides for a K3 NGAL protein comprising an amino acid sequence that is identical to SEQ ID NO:2, or a fragment thereof, wherein the K3 NGAL protein (a) is able to bind to a siderophore, and (b) is excreted in the urine.

The present invention also provides for a polypeptide that encodes a K3Cys protein and comprises an amino acid sequence that is identical to SEQ ID NO. 252.

The present invention also provides for a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a nucleic acid encoding a polypeptide that encodes a K3Cys protein and comprises an amino acid sequence that is identical to SEQ ID NO. 252. The present invention also provides for a nucleic acid encoding a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a pharmaceutical composition comprising a polypeptide that encodes a K3Cys protein and comprises an amino acid sequence that is identical to SEQ ID NO. 252. The present invention also provides for a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

In another aspect, the present invention provides for a K3Cys protein comprising an amino acid sequence that is identical to SEQ ID NO:252, or a fragment thereof, wherein the K3Cys protein (a) is able to bind to a siderophore, and (b) is excreted in the urine.

In one embodiment, the K3Cys protein has bacteriostatic activity.

In one embodiment, the % of the K3Cys protein that accumulates in the urine at a certain time following systemic administration of the K3Cys protein to a subject is greater than the % of WT NGAL protein that accumulates in the urine following systemic administration of the WT NGAL protein to a subject over the same time period.

In another embodiment, the % of the K3Cys protein that accumulates in the urine at a certain time following systemic administration of the K3Cys protein to a subject is about 1-fold, 2-fold, 5-fold, 10-fold, 20-fold, 30-fold, 50-fold, 60-fold, 70-fold, 80-fold, 90-fold or more greater than the % of WT NGAL protein that accumulates in the urine following systemic administration of WT NGAL protein to a subject over the same time period.

In another embodiment, the % of the K3Cys protein that accumulates in the urine at a certain time following systemic administration of the K3Cys protein to a subject is 10-fold or more greater than the % of WT NGAL protein that accumulates in the urine following systemic administration of WT NGAL protein to a subject over the same time period.

In another embodiment, the % of the K3Cys protein that accumulates in the urine at a certain time following systemic administration of the K3Cys protein to a subject is 100-fold or more greater than the % of WT NGAL protein that accumulates in the urine following systemic administration of WT NGAL protein to a subject over the same time period.

In one embodiment, the % of K3Cys protein that accumulates in the urine three hours after systemic administration of the K3Cys protein to a subject is about 1%, 2%, 5% or more. In another embodiment, the % of K3Cys protein that accumulates in the urine three hours after systemic administration of the K3Cys protein to a subject is about 10%, 20%, 30%, 40%, 50%, 60%, 70%, 80%, 90% or more. In one embodiment, the % of K3Cys protein that accumulates in the urine three hours after systemic administration of the K3Cys protein to a subject is about 15%, 25%, 35%, 45%, 55%, 65%, 75%, 85%, 95% or more.

In one embodiment, the % of K3Cys protein that accumulates in the urine three hours after systemic administration of the K3Cys protein to a subject is about 50% or more. In another embodiment, the % of K3Cys protein that accumulates in the urine three hours after systemic administration of the K3Cys protein to a subject is about 70% or more. In another embodiment, the % of K3Cys protein that accumulates in the urine three hours after systemic administration of the K3Cys protein to a subject is about 85% or more.

In one embodiment, the % of the K3Cys protein that accumulates in the kidney at a certain time following systemic administration of the K3Cys protein to a subject is lower than the % of WT NGAL protein that accumulates in the kidney following systemic administration of the WT NGAL protein to a subject over the same time period.

In another embodiment, the % of the K3Cys protein that accumulates in the kidney at a certain time following systemic administration of the K3Cys protein to a subject is about 1-fold, 2-fold, 5-fold, 10-fold, 20-fold, 30-fold, 50-fold, 60-fold, 70-fold, 80-fold, 90-fold or more lower than the % of WT NGAL protein that accumulates in the kidney following systemic administration of the WT NGAL protein to a subject over the same time period.

In one embodiment, the % of the K3Cys protein that accumulates in the kidney at a certain time following systemic administration of the K3Cys protein to a subject is 10-fold or more lower than the % of WT NGAL protein that accumulates in the kidney following systemic administration of WT NGAL protein to a subject over the same time period.

In another embodiment, the % of the K3Cys protein that accumulates in the kidney at a certain time following systemic administration of the K3Cys protein to a subject is 100-fold or more lower than the % of WT NGAL protein that accumulates in the kidney following systemic administration of WT NGAL protein to a subject over the same time period.

In one embodiment, the % of K3Cys protein that accumulates in the kidney three hours after systemic administration of the K3Cys protein to a subject is about 1% or less. In another embodiment, the % of K3Cys protein that accumulates in the kidney three hours after systemic administration of the K3Cys protein to a subject is about 2% or less. In another embodiment, the % of K3Cys protein that accumulates in the kidney three hours after systemic administration of the K3Cys protein to a subject is about 3% or less. In another embodiment, the % of K3Cys protein that accumulates in the kidney three hours after systemic administration of the K3Cys protein to a subject is about 4% or less. In another embodiment, the % of K3Cys protein that accumulates in the kidney three hours after systemic administration of the K3Cys protein to a subject is about 5% or less.

In another embodiment, the % of K3Cys protein that accumulates in the kidney three hours after systemic administration of the K3Cys protein to a subject is about 10%, 20%, 30%, 40%, 50%, 60%, 70%, 80%, 90% or less. In one embodiment, the % of K3Cys protein that accumulates in the kidney three hours after systemic administration of the K3Cys protein to a subject is about 15%, 25%, 35%, 45%, 55%, 65%, 75%, 85%, 95% or less.

In another aspect, the present invention provides for a pharmaceutical composition comprising a K3Cys protein comprising an amino acid sequence that is identical to SEQ ID NO:252, or a fragment thereof, wherein the K3Cys protein (a) is able to bind to a siderophore, and (b) is excreted in the urine.

In another aspect, the present invention provides for a pharmaceutical composition comprising a complex of a K3Cys protein comprising an amino acid sequence that is identical to SEQ ID NO:252, or a fragment thereof, and a siderophore, wherein the K3Cys protein (a) is able to bind to a siderophore, and (b) is excreted in the urine.

In one embodiment, the siderophore is selected from the group consisting of enterochelin, pyrogallol, carboxymycobactin, catechol, and variants thereof. In another embodiment, the siderophore is pH insensitive. In one embodiment, the siderophore binds to the K3Cys protein and iron at urinary pH. In another embodiment, the siderophore binds to the K3Cys protein and iron in the urine. In one embodiment, the siderophore binds to the K3Cys protein and iron at blood pH. In another embodiment, the siderophore binds to the K3Cys protein and iron in the blood.

In one embodiment, the K3Cys protein and the siderophore are present in a 1:1 molar ratio. In another embodiment, the K3Cys protein and the siderophore are present in a 1:3 molar ratio.

The present invention provides for a method for treating iron overload in a subject in need thereof, the method comprising administering to the subject an effective amount of a pharmaceutical composition comprising a polypeptide that encodes a K3Cys protein and comprises an amino acid sequence that is identical to SEQ ID NO. 252.

The present invention provides for a method for treating iron overload in a subject in need thereof, the method comprising administering to the subject an effective amount of a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a method for treating iron overload in a subject in need thereof, the method comprising administering to the subject an effective amount of a pharmaceutical composition comprising a K3Cys protein comprising an amino acid sequence that is identical to SEQ ID NO:252, or a fragment thereof, wherein the K3Cys protein (a) is able to bind to a siderophore, and (b) is excreted in the urine.

The present invention provides for a method for treating iron overload in a subject in need thereof, the method comprising administering to the subject an effective amount of a pharmaceutical composition comprising a complex of a K3Cys protein comprising an amino acid sequence that is identical to SEQ ID NO:252, or a fragment thereof, and a siderophore, wherein the K3Cys protein (a) is able to bind to a siderophore, and (b) is excreted in the urine.

The present invention also provides for a method of treating a urinary tract infection in a subject in need thereof, the method comprising administering to the subject an effective amount of a pharmaceutical composition comprising a polypeptide that encodes a K3Cys protein and comprises an amino acid sequence that is identical to SEQ ID NO. 252.

The present invention provides for a method for treating a urinary tract infection in a subject in need thereof, the method comprising administering to the subject an effective amount of a pharmaceutical composition comprising a polypeptide that comprises an amino acid sequence that is at least 99% identical to SEQ ID No. 252, at least 95% identical to SEQ ID No. 252, at least 90% identical to SEQ ID No. 252, at least 80% identical to SEQ ID No. 252, or at least 70% identical to SEQ ID No. 252.

The present invention provides for a method for treating a urinary tract infection in a subject in need thereof, the method comprising administering to the subject an effective amount of a pharmaceutical composition comprising a K3Cys protein comprising an amino acid sequence that is identical to SEQ ID NO:252, or a fragment thereof, wherein the K3Cys protein (a) is able to bind to a siderophore, and (b) is excreted in the urine.

The present invention provides for a method for treating a urinary tract infection in a subject in need thereof, the method comprising administering to the subject an effective amount of a pharmaceutical composition comprising a complex of a K3Cys protein comprising an amino acid sequence that is identical to SEQ ID NO:252, or a fragment thereof, and a siderophore, wherein the K3Cys protein (a) is able to bind to a siderophore, and (b) is excreted in the urine.

In another aspect, the present invention provides for a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In one embodiment, six or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid. In another embodiment, seven or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, eight or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid. In another embodiment, nine or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, ten or more residues from among Lys 15, Lys 46, Lys 50, Lys 59, Lys 62, Lys 73, Lys 74, Lys 75, Lys 98, His 118, Arg 130, Lys 149, and His 165 are substituted with a non-positively charged amino acid.

In one embodiment, the K3Cys mutant protein has bacteriostatic activity.

In one embodiment, the % of the K3Cys mutant protein that accumulates in the urine at a certain time following systemic administration of the K3Cys mutant protein to a subject is greater than the % of K3Cys protein that accumulates in the urine following systemic administration of the K3Cys protein to a subject over the same time period.

In another embodiment, the % of the K3Cys mutant protein that accumulates in the urine at a certain time following systemic administration of the K3Cys mutant protein to a subject is about 1-fold, 2-fold, 5-fold, 10-fold, 20-fold, 30-fold, 50-fold, 60-fold, 70-fold, 80-fold, 90-fold or more greater than the % of K3Cys protein that accumulates in the urine following systemic administration of K3Cys protein to a subject over the same time period.

In another embodiment, the % of the K3Cys mutant protein that accumulates in the urine at a certain time following systemic administration of the K3Cys mutant protein to a subject is 10-fold or more greater than the % of K3Cys protein that accumulates in the urine following systemic administration of K3Cys protein to a subject over the same time period.

In another embodiment, the % of the K3Cys mutant protein that accumulates in the urine at a certain time following systemic administration of the K3Cys mutant protein to a subject is 100-fold or more greater than the % of K3Cys protein that accumulates in the urine following systemic administration of K3Cys protein to a subject over the same time period.

In one embodiment, the % of K3Cys mutant protein that accumulates in the urine three hours after systemic administration of the K3Cys mutant protein to a subject is about 1%, 2%, 5% or more. In another embodiment, the % of K3Cys mutant protein that accumulates in the urine three hours after systemic administration of the K3Cys mutant protein to a subject is about 10%, 20%, 30%, 40%, 50%, 60%, 70%, 80%, 90% or more. In one embodiment, the % of K3Cys mutant protein that accumulates in the urine three hours after systemic administration of the K3Cys mutant protein to a subject is about 15%, 25%, 35%, 45%, 55%, 65%, 75%, 85%, 95% or more.

In one embodiment, the % of the K3Cys mutant protein that accumulates in the kidney at a certain time following systemic administration of the K3Cys mutant protein to a subject is lower than the % of K3Cys protein that accumulates in the kidney following systemic administration of the K3Cys protein to a subject over the same time period.

In another embodiment, the % of the K3Cys mutant protein that accumulates in the kidney at a certain time following systemic administration of the K3Cys mutant protein to a subject is about 1-fold, 2-fold, 5-fold, 10-fold, 20-fold, 30-fold, 50-fold, 60-fold, 70-fold, 80-fold, 90-fold or more lower than the % of K3Cys protein that accumulates in the kidney following systemic administration of the K3Cys protein to a subject over the same time period.

In one embodiment, the % of the K3Cys mutant protein that accumulates in the kidney at a certain time following systemic administration of the K3Cys mutant protein to a subject is 10-fold or more lower than the % of K3Cys protein that accumulates in the kidney following systemic administration of K3Cys protein to a subject over the same time period.

In one embodiment, the % of the K3Cys mutant protein that accumulates in the kidney at a certain time following systemic administration of the K3Cys mutant protein to a subject is 100-fold or more lower than the % of K3Cys protein that accumulates in the kidney following systemic administration of K3Cys protein to a subject over the same time period.

In one embodiment, the % of K3Cys mutant protein that accumulates in the kidney three hours after systemic administration of the K3Cys mutant protein to a subject is about 1% or less. In another embodiment, the % of K3Cys mutant protein that accumulates in the kidney three hours after systemic administration of the K3Cys mutant protein to a subject is about 2% or less. In another embodiment, the % of K3Cys mutant protein that accumulates in the kidney three hours after systemic administration of the K3Cys mutant protein to a subject is about 3% or less. In another embodiment, the % of K3Cys mutant protein that accumulates in the kidney three hours after systemic administration of the K3Cys mutant protein to a subject is about 4% or less. In another embodiment, the % of K3Cys mutant protein that accumulates in the kidney three hours after systemic administration of the K3Cys mutant protein to a subject is about 5% or less.

In another embodiment, the % of K3Cys mutant protein that accumulates in the kidney three hours after systemic administration of the K3Cys mutant protein to a subject is about 10%, 20%, 30%, 40%, 50%, 60%, 70%, 80%, 90% or less. In one embodiment, the % of K3Cys mutant protein that accumulates in the kidney three hours after systemic administration of the K3Cys mutant protein to a subject is about 15%, 25%, 35%, 45%, 55%, 65%, 75%, 85%, 95% or less.

In another aspect, the present invention provides for a nucleic acid sequence that encodes a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for an expression vector comprising a nucleic acid sequence that encodes a K3Cys mutant protein comprising an amino acid sequence that is at least 70% identical to the sequence of the K3Cys protein of SEQ ID NO:252, or a fragment thereof, operatively linked to a promoter, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a bacterial cell that stably expresses a nucleic acid sequence that encodes a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a mammalian cell that stably expresses a nucleic acid sequence that encodes a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a pharmaceutical composition comprising a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a pharmaceutical composition comprising a complex of a K3Cys mutant protein comprising an amino acid sequence that is at least 70% identical to the sequence of the K3Cys protein of SEQ ID NO:252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In one embodiment, the siderophore is selected from the group consisting of enterochelin, pyrogallol, carboxymycobactin, catechol, and variants thereof. In another embodiment, the siderophore is pH insensitive. In one embodiment, the siderophore binds to the K3Cys mutant protein and iron at urinary pH. In another embodiment, the siderophore binds to the K3Cys mutant protein and iron in the urine. In one embodiment, the siderophore binds to the K3Cys mutant protein and iron at blood pH. In another embodiment, the siderophore binds to the K3Cys mutant protein and iron in the blood.

In one embodiment, the K3Cys mutant protein and the siderophore are present in a 1:1 molar ratio. In another embodiment, the K3Cys mutant protein and the siderophore are present in a 1:3 molar ratio.

In another aspect, the present invention provides for a method for treating iron overload in a subject in need thereof, the method comprising administering to the subject an effective amount of a pharmaceutical composition comprising a K3Cys mutant protein.

In another aspect, the present invention provides for a method for treating iron overload in a subject in need thereof, the method comprising administering to the subject an effective amount of a pharmaceutical composition comprising a complex of a K3Cys mutant protein and a siderophore.

In another aspect, the present invention provides for a method for treating a urinary tract infection in a subject in need thereof, the method comprising administering to the subject an effective amount of a pharmaceutical composition comprising a K3Cys mutant protein.

In another aspect, the present invention provides for a method for treating a urinary tract infection in a subject in need thereof, the method comprising administering to the subject an effective amount of a pharmaceutical composition comprising a complex of a K3Cys mutant protein and a siderophore.

In another aspect, the present invention provides for a method for treating iron overload in a subject in need thereof, the method comprising administering to the subject an effective amount of a pharmaceutical composition comprising a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating iron overload in a subject in need thereof, the method comprising administering to the subject an effective amount of a pharmaceutical composition comprising a complex of a K3Cys mutant protein comprising an amino acid sequence that is at least 70% identical to the sequence of the K3Cys protein of SEQ ID NO:252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating a urinary tract infection in a subject in need thereof, the method comprising administering to the subject an effective amount of a pharmaceutical composition comprising a K3Cys mutant protein comprising an amino acid sequence that is at least 70% identical to the sequence of the K3Cys protein of SEQ ID NO:252, or a fragment thereof, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

In another aspect, the present invention provides for a method for treating a urinary tract infection in a subject in need thereof, the method comprising administering to the subject an effective amount of a pharmaceutical composition comprising a complex of a K3Cys mutant protein comprising an amino acid sequence that is at least 70% identical to the sequence of the K3Cys protein of SEQ ID NO:252, or a fragment thereof, and a siderophore, wherein (a) residues Asn 39, Ala 40, Tyr 52, Ser 68, Trp 79, Arg 81, Tyr 100, Tyr 106, Phe 123, Lys 125, Tyr 132, Phe 133, and Lysine 134 are either not mutated or are conservatively substituted, and wherein the K3Cys mutant protein (b) is able to bind to a siderophore, and (c) is excreted in the urine.

These and other embodiments of the invention are further described in the following sections of the application, including the Detailed Description, Examples, Claims, and Drawings.

BRIEF DESCRIPTION OF THE FIGURES

The patent or application file contains at least one drawing executed in color. Copies of this patent or patent application publication with color drawing(s) will be provided by the United States Patent and Trademark Office upon request and payment of the necessary fee.

FIG. 2. Comparison of human (SEQ ID NO: 19) and mouse (SEQ ID NO: 20) megalin proteins. The sequences of the human and mouse megalin proteins were aligned by using ClustalW2 (www.ebi.ac.uk/Tools/clustalw2/), and were shown to share 76% identity and 87% similarity, respectively.

FIG. 3A. NGAL mutants bind to enterochelin (Ent) and $^{55}Fe^{3+}$ to form a complex. Apo NGAL mutant protein (4 nmol) was mixed with equal molar Ent and $^{55}Fe^{3+}$, and incubated at room temperature (RT) for 30 minutes. The mixture was then washed for 4×5 minutes in a filter column with a 10 K cutoff, and the NGAL-bound Ent-$^{55}Fe^+$ was calculated as percentage of the starting total $^{55}Fe^{3+}$. FIGS. 3A-3D. The prepared NGAL-Ent-$^{55}Fe^{3+}$ complex was intraperitoneally injected into mice (female, 4 weeks), and the urine, FIG. 3B, was collected for 3 hours in a metabolic cage. Liver, FIG. 3C, and kidneys, FIG. 3D, were dissected and solubilized in 1MNaOH and 2% SDS for examination of $^{55}Fe^{3+}$ accumulation, expressed as a percentage of total NGAL-Ent-$^{55}Fe^{3+}$ complex.

FIG. 4A. Crystal structure of wild-type NGAL protein (Accession number: 1ng1A.pdb) was used to predict the 3D structure of the K3 mutant protein by using Swissmodel (www.swissmodel.expasy.org). The organization of the Ent-iron binding pocket in the K3 protein is predicted to be very similar to that in wild-type NGAL. FIG. 4B. The K3 mutant protein has less positively charged residues (arginine, lysine or histidine) on its surface in comparison to wild-type NGAL according to the modeled 3D structure. Positive charged residues are shown as ball-and-stick molecules, and the yellow color indicates the solvent accessible surface of the NGAL protein.

FIG. 6A. Left Enterochelin:Fe. The essential siderophore of gram negative organisms. It is composed of three catechol groups bound together by a backbone. Iron (red) is bound with affinity 10-49M. FIG. 6B. Right Enterochelin:Fe bound within the calyx of the Ngal protein with an affinity of 0.4 nM.

FIG. 15A. Fluorescence quenching analysis of Ngal with siderophores ("L") FIG. 15B, or Ngal with FeIII-siderophores ("FeL3"). Note that FeIII dramatically enhanced the affinity of Ngal for different catechols. 2,3DHBA=Ent.

FIG. 19. Shows sequences and amino acid alignment of WT NGAL (SEQ ID NO: 1) and K3 NGAL (SEQ ID NO: 2).

FIG. 21. Amino acid sequence of K3Cys protein (Seq ID NO: 252).

FIG. 22A. Left: Western blot of different species of NGAL. Wild type NGAL forms protein dimers (46-50KDa) from monomers (at 23-25KDa). Similarly the Mutant1 (K3 NGAL) forms dimers from monomers. However, Mutant2 (K3Cys) only forms monomers. Right. NGAL proteins (Wt, Mut1 and Mut2) were injected into mice, and the NGAL proteins in the urine (uWt=urinary wild-type protein; uMut1=urinary Mut1 K3 and uMut2=urinary Mut2 K3Cys) were collected at two different time points, and analyzed by Western Blot. For each protein (uWt, uMut1 and uMut2), the 1st lane on the Western blot represents proteins that were collected in the urine 20 min. after the injection and the 2nd lane on the Western blot represents proteins that were collected from the mouse at 180 min. after the injection. Very low levels of uWt appear in urine, whereas higher levels of both uMut1 and uMut2 appear in urine. uMut1 forms both monomers and dimers, whereas uMut2 only forms monomers. FIG. 22B. Mice were injected with NGAL proteins (Wt, Mut1 and Mut2) that were labeled with the dye Alexa Fluor™ 568 (Molecular Probes—Invitrogen), which covalently attaches to the proteins. The urinary NGAL proteins (uWt, uMut1 and uMut2) were subsequently collected from the urine, and tested for by color at either 20 min or 180 min after collection (see tubes from left to right: 1st tube: uWt; at 20 min; 2nd tube: uWt at 180 min. 3rd tube: uMut1 at 20 min; 4th tube: uMut1 at 180 min; 5th tube: uMut2 at 20 min; 6th tube: uMut2 at 180 min tube). The darker the color, the higher the amount of protein present in the urine. These data demonstrate that both K3 and K3Cys can traffic to the urine but K3Cys appears more efficient.

FIG. 23 and FIG. 24 are different mice. Note that iron associated with wild type NGAL remains in the kidney, while iron associated with the K3Cys is found in the urine, rather than in the kidney.

FIG. 29A. The conversion of HPF to fluorescein is detected in the presence of catechol and iron. When Ngal species are added, the activity is suppressed. Similarly when conversion of ferric to ferrous iron is detected (due to the intrinsic reductase activity of catechol groups), Ngal species suppressed the activity. Mutant Ngal was as effective as wt NGAL. FIG. 29B. The conversion of HPF to Fluorescin is detected in the presence of Ent and iron. The Ngal species are added, the activity is suppressed. Mutant Ngal was as effective as wt NGAL.

FIG. 29C. The conversion of HPF to fluorescein is detected in the presence of catechol or Ent and iron. When Ngal species are added, the activity is suppressed. Similarly when conversion of ferric to ferrous iron is detected (due to the intrinsic reductase activity of catechol groups), Ngal species suppressed the activity. Nutant Ngal was as effective as wt NGAL.

DETAILED DESCRIPTION

Figure 1:
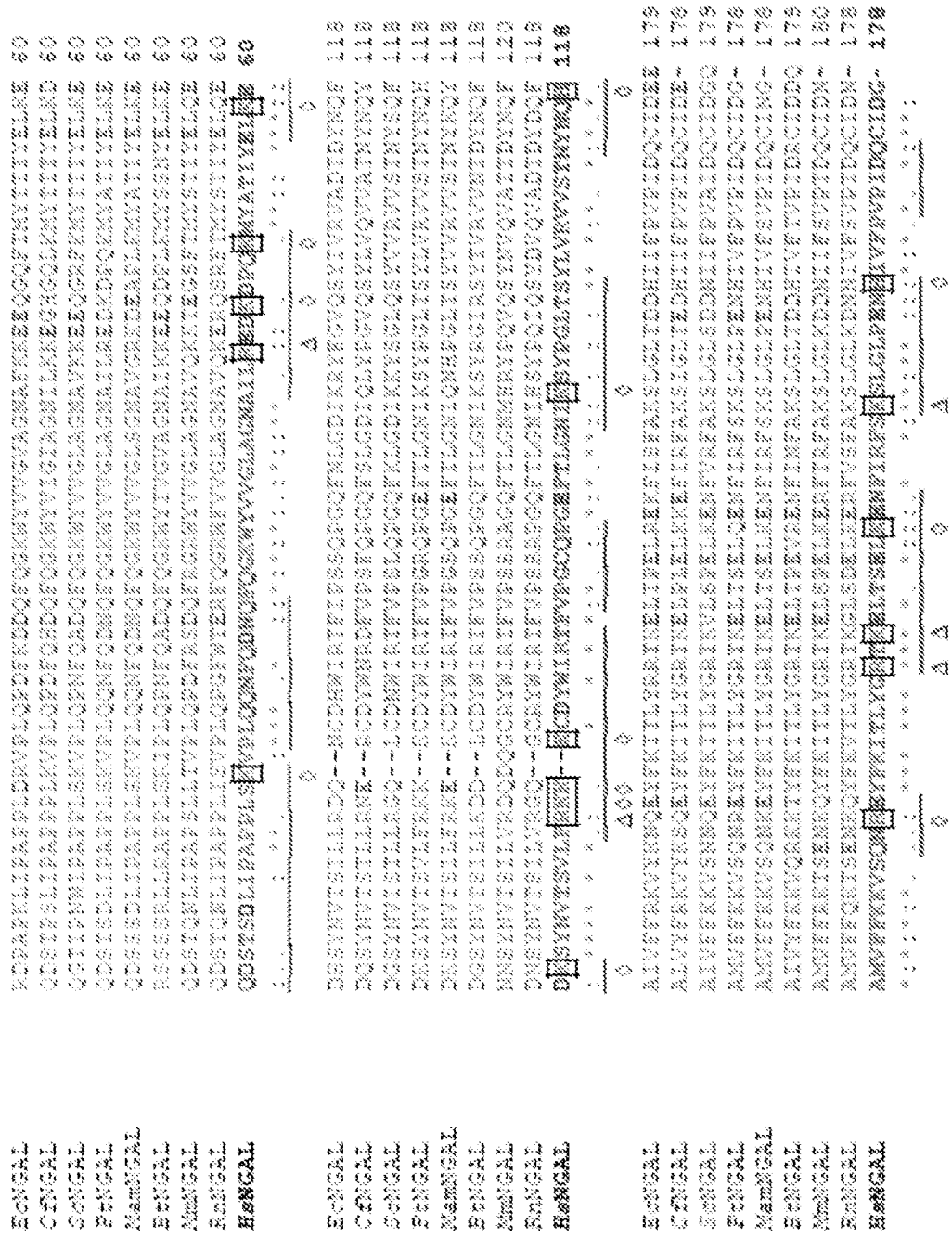
FIG. 1. Alignment of Ngal protein from human (HsNgal; NP_005555—WT Human NGAL—SEQ ID NO: 1), mouse (MmNgal; NP_032517, SEQ ID NO:17), rat (RnNgal; NP_570097, SEQ ID NO:18), Chimpanzee (PtNgal, XP_001153985, SEQ ID NO:14), bovine (BtNgal; XP_605012; SEQ ID NO:16), dog (CfNgal; SEQ ID NO:12), wild boar (SsNgal; SEQ ID NO:13), Rhesus Monkey (MamNgal, SEQ ID NO:15), and horse (*Equus caballus* (Ec) NGAL, SEQ ID NO:11). Human NGAL protein sequence is Bold, and the amino acid residues on the surface of NGAL proteins are underlined. Δ and ◊ indicate the conserved and the non-conserved positively charged residues (Arginine [R], Lysine [K] and Histidine [H]) on the surface of functional Ngal protein, respectively. Magenta: positive charged residues; Blue: negative charged residues; red: nonpolar and hydrophobic residues; Green: polar and hydrophilic residues.

The present invention is based, in part, on the development of mutant versions of the NGAL protein that are not reabsorbed in the kidney and thus, unlike wild-type NGAL, are excreted in the urine. These mutant forms of NGAL have the ability to bind to iron-binding siderophores, such as enterochelin, and can be used to traffic iron out of the body by excretion in the urine. As such, the mutant NGAL proteins of the invention can be used in the treatment of iron overload and diseases and disorders associated with iron overload. In addition, the mutant NGAL proteins of the invention have bacteriostatic activity and can be used to treat infections of the urinary tract. Thus, the present invention provides mutant NGAL proteins, pharmaceutical compositions comprising such mutant NGAL proteins, either alone or complexed with siderophores, and the use of such mutant NGAL proteins and compositions in the treatment of various disorders and diseases, such as in the treatment of disorders associated with iron overload and in the treatment of bacterial infections of the urinary tract. These and other aspects of the present invention are described more fully below, and also in other sections of this application.

As discussed herein, a series of defined mutations in the positive surface residues of Ngal were made and clones that traffic into the urine (i.e. bypassing megalin) were identified. A mutation in the unpaired cysteine was introduced to block the homodimerization of the NGAL mutant referred to as a "K3" NGAL. In the resultant new NGAL protein, called K3Cys, the cysteine residue at position 87 in K3 NGAL is substituted with a serine residue. This substitution resulted in the loss of dimerization of the K3Cys protein, which forms monomers. This K3Cys protein appeared earlier in the urine than K3 NGAL protein which was still capable of dimerization. This nearly complete loss of NGAL from the mouse by filtration and urinary excretion is most likely a result of the lower molecular weight of the monomeric—non dimerizable species.

ABBREVIATIONS AND DEFINITIONS

The abbreviation "NGAL" refers to Neutrophil Gelatinase Associated Lipocalin. NGAL is also referred to in the art as human neutrophil lipocalin, siderocalin, a-microp-globulin related protein, Scn-NGAL, lipocalin 2, 24p3, superinducible protein 24 (SIP24), uterocalin, and neu-related lipocalin. These alternative names for NGAL may be used interchangeably herein. Unless stated otherwise, the term "NGAL", as used herein, includes any NGAL protein, fragment, or mutant. In some embodiments the NGAL protein is wild-type human NGAL. In other embodiments the NGAL protein is a mutant NGAL protein.

The abbreviation hNGAL refers to human NGAL.

The abbreviation "WT" refers to wild-type, such as a wild-type nucleotide or amino acid sequence.

The abbreviation "K3Cys" refers to a mutant K3 NGAL protein (SEQ ID NO:2) that contains a cysteine residue at position 87. The amino acid sequence of K3Cys is represented by SEQ ID NO: 252. The designation "K3Cys" is used interchangeably with the designations "K3 Cys", "K3Cys protein", "K3 Cys NGAL" and "K3Cys NGAL".

The phrase "K3Cys mutant" refers to a K3Cys protein that contains one or more amino acid mutations, including, but not limited to, substitutions, deletions and insertions. The designation "K3Cys mutant" is used interchangeably with the designation "K3Cys mutant protein".

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

NGAL

NGAL is a small protein with a molecular weight of about 22 kD and is a siderophore binding protein. A siderophore is an organic molecule that binds to and chelates iron. Bacteria produce the siderophore enterochelin, and mammals endogenously express a similar type, but simpler molecule called catechol. Enterochelin has an extremely high affinity for iron, and wild type NGAL has a high affinity for the enterochelin-iron complex. The enterochelin-iron-NGAL complex is pH insensitive and the bound iron is redox inactive. Thus the iron bound by such NGAL complexes is not available to catalyze oxygen radical formation, making NGAL an ideal iron chelator for in vivo use.

NGAL, and once produced in cells, is secreted into extracellular space and quickly cleared by kidney with a half-life of 10 minutes. Serum and urine levels of the protein can become very high in a number of disease models. The NGAL protein is transported into the kidney of healthy humans and can pass the filtration barrier of the glomerulus (the cut-off size of filtration is about 70 kD) to enter the primary urine, but then NGAL is efficiently reabsorbed by megalin or megalin-cubilin-cubilin receptors localized on the apical side of the epithelia of the proximal tubules. Megalin is a universal receptor with broad substrate specificity and is expressed at the apical surface of the proximal tubules of the kidney where it is involved in protein reabsorption. The binding of megalin to its substrates is mediated by ionic interactions, and its negative charged substrate binding domains can efficiently bind to the positively charged surfaces of proteins in the urinary filtrate. Once absorbed and endocytosed, NGAL is trafficked to lysosomes, where it is degraded. Once degraded, the iron which NGAL transported to the kidney is reabsorbed.

K3 NGAL

The present invention provides mutant NGAL proteins, including, but not limited to those which have been mutated to remove positively charged residues that may be involved in the megalin interaction.

The terms "mutant NGAL protein" and "NGAL mutant" as used herein, refer to a protein or an amino acid sequence that differs by one or more amino acids from the amino acid sequence of WT human NGAL (SEQ ID NO.1, see sequence of HsNGAL in FIG. 1).

The invention provides for a mutant NGAL protein, K3 (or K3 NGAL, or K3 NGA1 protein), that has an amino acid sequence identical to SEQ ID NO: 2 (Table 2).

Like WT NGAL, K3 NGAL has high affinity for enterochelin-iron complexes but appear to have significantly reduced affinity for megalin. Thus, rather than being reabsorbed by a megalin receptor mediated mechanism in the kidney, K3 NGAL of the invention, and complexes of K3 NGAL with enterochelin and iron, are not efficiently reabsorbed in the kidney and are instead excreted in the urine. The K3 NGAL protein of the invention can thus be used to efficiently remove excessive iron from the body and traffic it into the urine in a safe redox inactive form. Furthermore, previous reports have shown that NGAL-enterochelin-iron has little or no chemical or cellular toxicity, suggesting that it could be safely used therapeutically, for example in the therapeutic treatment of diseases and disorders associated with iron overload, such as hemochromatosis.

K3Cys

The present invention provides a mutant K3 NGAL protein, "K3Cys", which comprises a K3 NGAL protein (SEQ ID NO:2) in which the cysteine residue at position 87 (Cysteine 87) was substituted with a serine residue. The amino acid sequence of K3Cys is identical to SEQ ID NO:252. Thus, rather than being reabsorbed by a megalin receptor mediated mechanism in the kidney, K3Cys, and complexes of this mutant with enterochelin and iron, are not efficiently reabsorbed in the kidney and are instead excreted in the urine. K3Cys can thus be used to efficiently remove excessive iron from the body and traffic it into the urine in a safe redox inactive form. Furthermore, previous reports have shown that NGAL-enterochelin-iron has little or no chemical or cellular toxicity, indicating that it could be safely used therapeutically, for example in the therapeutic treatment of diseases and disorders associated with iron overload, such as hemochromatosis.

In one aspect, the present invention provides a K3Cys protein that comprises, consists essentially of, or consists of an amino acid sequence that is identical to SEQ ID NO.252, and wherein the K3Cys protein: (a) is excreted in the urine or exhibits a greater level of excretion in the urine than the WT NGAL protein, and/or (b) is not reabsorbed in the proximal tubule of the kidney or exhibits a lower level of reabsorption in the proximal tubule of the kidney as compared to the WT NGAL protein, and/or (c) is not a substrate for reabsorption in the kidney by a megalin-cubilin-cubilin-receptor mediated mechanism, and/or (d) has reduced affinity for the megalin-cubilin-receptor as compared to the WT NGAL protein, and/or (e) has fewer positively charged residues on its solvent accessible surface as compared to the WT NGAL protein, and wherein the K3Cys protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity.

In another aspect, the present invention provides a K3Cys protein that comprises, consists essentially of, or consists of an amino acid sequence that is at least 70%, or at least 75%, or at least 80%, or at least 85%, or at least 90%, or at least 95%, or at least 98%, or at least 99% identical to SEQ ID NO.252, and wherein the K3Cys protein: (a) is excreted in the urine or exhibits a greater level of excretion in the urine than the WT NGAL protein, and/or (b) is not reabsorbed in the proximal tubule of the kidney or exhibits a lower level of reabsorption in the proximal tubule of the kidney as compared to the WT NGAL protein, and/or (c) is not a substrate for reabsorption in the kidney by a megalin-cubilin-cubilin-receptor mediated mechanism, and/or (d) has reduced affinity for the megalin-cubilin-receptor as compared to the WT NGAL protein, and/or (e) has fewer positively charged residues on its solvent accessible surface as compared to the WT NGAL protein, and wherein the K3Cys protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity.

K3Cys Mutants

The present invention also provides for K3Cys mutants, which comprise K3Cys proteins that contain one or more amino acid mutations, including, but not limited to, substitutions, deletions and insertions.

K3Cys mutants may have one or more "non conservative" changes, as compared to K3Cys, wherein a given amino acid is substituted with another amino acid that has different structural or chemical properties. In several embodiments of the invention basic/positively charged lysine, arginine, and/or histidine residues on the surface of K3Cys mutants, such as those that interact with megalin, are mutated by substituting these residues with non-basic/non-positively charged residues. These are non-conservative changes. For example, in several embodiments of the invention basic/positively charged lysine (Lys-K), arginine (Arg-R), and/or histidine (His-H), residues, such as those on the surface of K3Cys mutants that may be involved in the megalin interaction, are substituted with non-basic/non-positively charged residues such as alanine (Ala-A), asparagine (Asn-N), aspartic acid (Asp-D), cysteine (Cys-C), glutamine (Gln-Q), glutamic acid (glu-E), glycine (Gly-G), isoleucine (Ile-I), leucine (Leu-L), methionine (Met-M), phenylalanine (Phe-F), proline (Pro-P), serine (Ser-S), threonine (thr-T), tryptophan (Trp-W), tyrosine (Tyr-Y), and valine (Val-V). In some embodiments, basic/positively charged lysine, arginine, and/or histidine residues are substituted with negatively charged residues such as aspartic acid (Asp-D) and glutamic acid (Glu-E).

In some embodiments, the K3Cys mutant may have one or more "conservative" changes, as compared to K3Cys, wherein a given amino acid is substituted for another amino acid that has similar structural or chemical properties. For example, in some embodiments it is desirable to either leave the residues of the K3Cys mutant that are involved in the siderophore interaction intact or to only make conservative changes at those residues. Various other conservative amino acid substitutions may be made throughout the K3Cys mutant, such as conservative amino acid substitutions that do not destroy the ability of the K3Cys mutant to transport iron out of the body. One type of conservative amino acid substitution refers to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side chains is cysteine and methionine. Useful conservative amino acids substitution groups are: valine leucine isoleucine, phenylalanine tyrosine, lysine arginine, alanine valine, and asparagine glutamine.

The K3Cys mutant may contain various mutations (including additions, deletions, and substitutions), including, for example, additions to or deletions from the N- and/or C-termini of the K3Cys mutant. Any such mutations can be made to the extent that they do not adversely affect the ability of the K3Cys mutant to bind to a siderophore, to transport iron, and/or to be excreted in the urine.

In further embodiments, the K3Cys mutant may comprise one or more non-naturally occurring amino acids. Non-natural amino acids, such as those that contain unique side chain functional groups including halogens, unsaturated hydrocarbons, heterocycles, silicon, and organometallic units, can offer advantages in improving the stability of proteins. Many such non-naturally occurring amino acids are known. Such non-naturally occurring amino acids can be used in the K3Cys mutant.

In one embodiment the cysteine 87 residue of the K3Cys mutant is deleted. In another embodiment, the cysteine 87 residue of the K3Cys mutant is substituted with a non-positively charged amino acid (i.e. a non-conservative substitution). In another embodiment the cysteine 87 residue of the K3Cys mutant, is substituted with a negatively charged amino acid (i.e. a non-conservative substitution). In another embodiment, the cysteine 87 residue of the K3Cys mutant is substituted with an alanine residue. In another embodiment, the K3Cys mutant may comprise any combination of such mutations, i.e. any combination of deletions, substitutions for non-positively charged amino acids, or substitutions for negatively charged amino acids may be present at any one, two, three, four, five, six, seven, eight nine, ten, eleven, twelve, or all thirteen of the above listed amino acid residues. In preferred embodiments, the K3Cys mutant is not mutated (i.e. has the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one preferred embodiment the present invention provides a K3Cys mutant in which Lys (K) 15 is substituted with an uncharged amino acid, including, but not limited to, Ser (S). In one preferred embodiment the present invention provides a K3Cys mutant in which Lys (K) 46 is substituted with a negatively charged amino acid, including, but not limited to, Glu (E). In one preferred embodiment the present invention provides a K3Cys mutant in which Lys (K) 50 is substituted with an uncharged amino acid, including, but not limited to, Thr (T). In one preferred embodiment the present invention provides a K3Cys mutant in which Lys (K) 59 is substituted with an uncharged amino acid, including, but not limited to, Gln (Q). In one preferred embodiment the present invention provides a K3Cys mutant in which Lys (K) 62 is substituted with an uncharged amino acid, including, but not limited to, Gly (G). In one preferred embodiment the present invention provides a K3Cys mutant in which Lys (K) 73 is substituted with a negatively charged amino acid, including, but not limited to, Asp (D). In one preferred embodiment the present invention provides a K3Cys mutant in which Lys (K) 74 is substituted with a negatively charged amino acid, including, but not limited to, Asp (D). In one preferred embodiment the present invention provides a K3Cys mutant in which Lys (K) 75 is substituted with an aliphatic amino acid, including, but not limited to, Gly (G). In one preferred embodiment the present invention provides a K3Cys mutant in which Lys (K) 98 is substituted with an uncharged amino acid, including, but not limited to, Gln (Q). In one preferred embodiment the present invention provides a K3Cys mutant in which His (H) 118 is substituted with a non-polar amino acid, including, but not limited to, Phe (F). In one preferred embodiment the present invention provides a K3Cys mutant in which Arg (R) 130 is substituted with an uncharged amino acid, including, but not limited to, Gln (Q). In one preferred embodiment the present invention provides a K3Cys mutant in which Lys (K) 149 is substituted with an uncharged amino acid, including, but not limited to, Gln (Q). In one preferred embodiment the present invention provides a K3Cys mutant in which His (H) 165 is substituted with an uncharged amino acid, including, but not limited to, Asn (N).

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO.252), or a fragment thereof, wherein one, two, three, four, five, six, seven, eight, nine, ten, eleven, twelve, or all thirteen residues from among Lys 15, Lys 46, Lys 50, Lys 59, Lys 62, Lys 73, Lys 74, Lys 75, Lys 98, His 118, Arg 130, Lys 149, and His 165 is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the K3Cys mutant protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to the K3Cys protein. In some embodiments six or more of the thirteen listed amino acid positions are mutated as compared to the K3Cys protein. In some embodiments seven or more of the thirteen listed amino acid positions are mutated as compared to the K3Cys protein. In some embodiments eight or more of the thirteen listed amino acid positions are mutated as compared to the K3Cys protein. In some embodiments nine or more of the thirteen listed amino acid positions are mutated as compared to the K3Cys protein. In some embodiments ten or more of the thirteen listed amino acid positions are mutated as compared to the K3Cys protein. In preferred embodiments, such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In some embodiments, the K3Cys mutant has the amino acids specified in SEQ ID NO:252 (Table 2) at residues 15, 46, 59, 62, 73, 74, 75, 98, 118, 130, 149, and 165, but other amino acid residues can differ from the specified sequences provided that the K3Cys mutant protein is at least 70%, or at least 75%, or at least 80%, or at least 85%, or at least 90%, or at least 95%, or at least 98% identical to the sequence of the K3Cys protein (SEQ ID NO.:252), or a fragment thereof, and provided that the K3Cys mutant protein: (a) is excreted in the urine or exhibits a greater level of excretion in the urine than K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to K3Cys protein and/or WT NGAL, and/or (e) has fewer positively charged residues on its solvent accessible surface as compared to the K3Cys protein and/or WT NGAL, and also provided that the K3Cys mutant protein (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to the K3Cys protein. In some embodiments six or more of the thirteen listed amino acid positions are mutated as compared to the K3Cys protein. In some embodiments seven or more of the thirteen listed amino acid positions are mutated as compared to the K3Cys protein. In some embodiments eight or more of the thirteen listed amino acid positions are mutated as compared to the K3Cys protein. In some embodiments nine or more of the thirteen listed amino acid positions are mutated as compared to the K3Cys protein. In some embodiments ten or more of the thirteen listed amino acid positions are mutated as compared to the K3Cys protein. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments, a K3Cys mutant protein described above that has mutations in one or more of the thirteen non-conserved positive/basic surface residues, can also have mutations in one or more of the five conserved positive/based surface residues below, or one or more of the other mutations described in other following sections of this Detailed Description.

Five Conserved Positive/Basic Surface Residues in NGAL

The K3Cys protein contains five basic/positive surface amino acid residues that are conserved among human, rat, mouse, chimpanzee, cow, dog, wild boar and rhesus monkey species, namely residues Arg(R) 43, Arg(R) 72, Arg(R) 140, Lys(K) 142, and Lys(K) 157. In one embodiment, the present invention provides K3Cys mutant proteins having one, two, three, four, or all five of these amino acid positions mutated as compared to the K3Cys protein. In one embodiment the mutated amino acid residue or residues are deleted. In another embodiment the mutated amino acid residue or residues are substituted with a non-positively charged amino acid (i.e. a non-conservative change). In another embodiment the mutated amino acid residue or residues are substituted with a negatively charged amino acid (i.e. a non-conservative change). In another embodiment the K3Cys mutant protein may comprise any combination of such mutations, i.e. any combination of deletions, substitutions for non-positively charged amino acids, or substitutions for negatively charged amino acids may be provided at one, two, three, four, or five of the above listed amino acid residues.

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO.252), or a fragment thereof, wherein one, two, three, four, or all five residues from among (R) 43, Arg(R) 72, Arg(R) 140, Lys(K) 142, and Lys(K) 157 is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the K3Cys mutant protein also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments, the K3Cys mutant proteins described in this section that have mutations in one or more of the five conserved positive/basic surface residues, can also have mutations in one or more of the thirteen non-conserved positive/based surface residues described in the previous section of the Detailed Description, or one or more of the other mutations described in the following sections of this Detailed Description.

Additional Surface Residues in NGAL

The following amino acid residues are located on the surface of the K3Cys protein and can play a role in the interaction of the K3Cys protein with the megalin protein and/or in the reabsorption of the K3Cys protein in the kidney: amino acid residues 1-15, 17-26, 40-50, 57-62, 71-82, 84-89, 96-105, 114-118, 128-131, 134, 140-151, 157-165, and 170-174.

In one embodiment, the K3Cys mutant proteins of the invention comprise, consist of, or consist essentially of amino acid sequences that are based on the amino acid sequence of human K3Cys protein, or a fragment thereof, but that contain mutations at one or more of the individual amino acid residues located at residues 1-15, 17-26, 40-50, 57-62, 71-82, 84-89, 96-105, 114-118, 128-131, 134, 140-151, 157-165, and/or 170-174 of the K3Cys protein. In one embodiment one or more of the mutated amino acid residues can be deleted. In another embodiment one or more of the mutated amino acid residues can be substituted with a non-positively charged amino acid, including, but not limited to a negatively charged amino acid. In another embodiment the K3Cys mutant protein may comprise any combination of such mutations, i.e. any combination of deletions, substitutions for non-positively charged amino acids, and/or substitutions for negatively charged amino acids at any one or more of the above listed amino acid residues.

In some embodiments, K3Cys mutant proteins are mutated, at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134.

In other embodiments, K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides a K3Cys mutant protein that comprises, consists essentially of, or consists of an amino acid sequence that is at least 70%, or at least 75%, or at least 80%, or at least 85%, or at least 90%, or at least 95%, or at least 98% identical to the sequence of the K3Cys protein (SEQ ID NO.:252), or a fragment thereof, wherein one or more of the individual amino acid residues located at residues 1-15, 17-26, 40-50, 57-62, 71-82, 84-89, 96-105, 114-118, 128-131, 134, 140-151, 157-165, and/or 170-174 of the K3Cys mutant is deleted or substituted with a non-positively charged amino acid, such as a negatively charged amino acid, and wherein the K3Cys mutant protein: (a) is excreted in the urine or exhibits a greater level of excretion in the urine than the K3Cys protein and/or WT NGAL, and/or (b) is not reabsorbed in the proximal tubule of the kidney or exhibits a lower level of reabsorption in the proximal tubule of the kidney as compared to the K3Cys protein and/or WT NGAL, and/or (c) is not a substrate for reabsorption in the kidney by a megalin-cubilin-receptor mediated mechanism, and/or (d) has reduced affinity for the megalin-cubilin-receptor as compared to the K3Cys protein and/or WT NGAL, and/or (e) has fewer positively charged residues on its solvent accessible surface as compared to the K3Cys protein and/or WT NGAL, and wherein the the K3Cys protein (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such K3Cys mutant proteins are not mutated (i.e. have the same amino acid sequence as the K3Cys protein), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

NGAL Mutants

The present invention provides mutant NGAL proteins, including, but not limited to those which have been mutated to remove positively charged residues that may be involved in the megalin interaction. Like WT NGAL, the NGAL mutants of the invention have high affinity for enterochelin-iron complexes but appear to have significantly reduced affinity for megalin (Table 1). Thus, rather than being reabsorbed by a megalin receptor mediated mechanism in the kidney, the NGAL mutants of the invention, and complexes of these mutants with enterochelin and iron, are not efficiently reabsorbed in the kidney and are instead excreted in the urine. The mutant NGAL proteins of the invention can thus be used to efficiently remove excessive iron from the body and traffic it into the urine in a safe redox inactive form. Furthermore, previous reports have shown that NGAL-enterochelin-iron has little or no chemical or cellular toxicity, suggesting that it could be safely used therapeutically, for example in the therapeutic treatment of diseases and disorders associated with iron overload, such as hemochromatosis.

The terms "mutant NGAL protein" and "NGAL mutant" as used herein, refer to a protein or an amino acid sequence that differs by one or more amino acids from the amino acid sequence of WT human NGAL (SEQ ID NO.1, see sequence of HsNGAL in FIG. 1).

The mutant NGAL proteins of the invention may have one or more "non conservative" changes, wherein a given amino acid is substituted with another amino acid that has different structural or chemical properties. In several embodiments of the invention basic/positively charged lysine, arginine, and/or histidine residues on the surface of the NGAL protein, such as those that interact with megalin, are mutated by substituting these residues with non-basic/non-positively charged residues. These are non-conservative changes. For example, in several embodiments of the invention basic/positively charged lysine (Lys-K), arginine (Arg-R), and/or histidine (His-H), residues, such as those on the surface of the NGAL protein that may be involved in the megalin interaction, are substituted with non-basic/non-positively charged residues such as alanine (Ala-A), asparagine (Asn-N), aspartic acid (Asp-D), cysteine (Cys-C), glutamine (Gln-Q), glutamic acid (glu-E), glycine (Gly-G), isoleucine (Ile-I), leucine (Leu-L), methionine (Met-M), phenylalanine (Phe-F), proline (Pro-P), serine (Ser-S), threonine (thr-T), tryptophan (Trp-W), tyrosine (Tyr-Y), and valine (Val-V). In some embodiments, basic/positively charged lysine, arginine, and/or histidine residues are substituted with negatively charged residues such as aspartic acid (Asp-D) and glutamic acid (Glu-E).

In some embodiments the mutant NGAL proteins of the invention may have one or more "conservative" changes, wherein a given amino acid is substituted for another amino acid that has similar structural or chemical properties. For example, in some embodiments it is desirable to either leave the residues of NGAL that are involved in the siderophore interaction intact or to only make conservative changes at those residues. Various other conservative amino acid substitutions may be made throughout the NGAL protein, such as conservative amino acid substitutions that do not destroy the ability of the NGAL mutants of the invention to transport iron out of the body. One type of conservative amino acid substitution refers to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur containing side chains is cysteine and methionine. Useful conservative amino acids substitution groups are: valine leucine isoleucine, phenylalanine tyrosine, lysine arginine, alanine valine, and asparagine glutamine.

The mutant NGAL proteins of the invention may contain various mutations (including additions, deletions, and substitutions) in addition to the mutations of specific residues set forth herein (below), including, for example, additions to or deletions from the N- and/or C-termini of the NGAL mutants. Any such mutations can be made to the extent that they do not adversely affect the ability of the NGAL mutants to bind to a siderophore, to transport iron, and/or to be excreted in the urine.

In further embodiments, the NGAL mutants of the invention may comprise one or more non-naturally occurring amino acids. Non-natural amino acids, such as those that contain unique side chain functional groups including halogens, unsaturated hydrocarbons, heterocycles, silicon, and organometallic units, can offer advantages in improving the stability of proteins. Many such non-naturally occurring amino acids are known. Such non-naturally occurring amino acids can be used in the NGAL mutants of the invention.

In certain embodiments, the present invention provides NGAL mutants having a certain % identity to WT human NGAL or to some other NGAL mutant. The following terms are used to describe the sequence relationships between two or more polynucleotides or amino acid sequences: "sequence identity," "percentage sequence identity" and "identity." These terms are used in accordance with their usual meaning in the art. Percentage sequence identity is measured with reference to a reference sequence. The term "sequence identity" means that two polynucleotide or amino acid sequences are identical (i.e., on a nucleotide-by-nucleotide basis). The term "percentage of sequence identity" is calculated by comparing two optimally aligned sequences, determining the number of positions at which the identical nucleic acid base or amino acid occurs in both sequences to yield the number of matched positions, dividing the number of matched positions by the total number of positions, and multiplying the result by 100 to yield the percentage of sequence identity.

Thirteen Non-Conserved Positive Surface Residues in NGAL

The NGAL protein contains thirteen basic/positive surface amino acid residues that are not conserved among species, namely residues Lys 15, Lys 46, Lys 50, Lys 59, Lys 62, Lys 73, Lys 74, Lys 75, Lys 98, His 118, Arg 130, Lys 149, and His 165. Data presented in the present application demonstrate that mutations of various combinations of these thirteen amino acid residues results in the generation of NGAL mutants that, like WT NGAL, have the ability to bind to enterochelin-iron but, unlike WT NGAL, are not effectively reabsorbed in the kidney. Such NGAL mutants, when complexed with a siderophore such as enterochelin, can be used to transport excess iron out of the body by facilitating its excretion in the urine. Such NGAL mutants may also have bacteriostatic activity and can be used to treat bacterial infections of the urinary tract.

In one embodiment, the mutant NGAL proteins of the invention comprise, consist of, or consist essentially of amino acid sequences that are based on the amino acid sequence of WT human NGAL, or a fragment thereof, but that contain one or more mutations. In one embodiment, the present invention provides an NGAL mutant having one, two, three, four, five, six, seven, eight, nine, ten, eleven, twelve, or all thirteen of the following amino acid positions mutated as compared to WT human NGAL: Lys 15, Lys 46, Lys 50, Lys 59, Lys 62, Lys 73, Lys 74, Lys 75, Lys 98, His 118, Arg 130, Lys 149, and His 165. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL.

In one embodiment the mutated amino acid residues are deleted. In another embodiment the mutated amino acid residues are substituted with a non-positively charged amino acid (i.e. a non-conservative substitution). In another embodiment the mutated amino acid residues are substituted with a negatively charged amino acid (i.e. a non-conservative substitution). In another embodiment the NGAL mutant may comprise any combination of such mutations, i.e. any combination of deletions, substitutions for non-positively charged amino acids, or substitutions for negatively charged amino acids may be present at any one, two, three, four, five, six, seven, eight nine, ten, eleven, twelve, or all thirteen of the above listed amino acid residues. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one preferred embodiment the present invention provides an NGAL mutant in which Lys (K) 15 is substituted with an uncharged amino acid, including, but not limited to, Ser (S). In one preferred embodiment the present invention provides an NGAL mutant in which Lys (K) 46 is substituted with a negatively charged amino acid, including, but not limited to, Glu (E). In one preferred embodiment the present invention provides an NGAL mutant in which Lys (K) 50 is substituted with an uncharged amino acid, including, but not limited to, Thr (T). In one preferred embodiment the present invention provides an NGAL mutant in which Lys (K) 59 is substituted with an uncharged amino acid, including, but not limited to, Gln (Q). In one preferred embodiment the present invention provides an NGAL mutant in which Lys (K) 62 is substituted with an uncharged amino acid, including, but not limited to, Gly (G). In one preferred embodiment the present invention provides an NGAL mutant in which Lys (K) 73 is substituted with a negatively charged amino acid, including, but not limited to, Asp (D). In one preferred embodiment the present invention provides an NGAL mutant in which Lys (K) 74 is substituted with a negatively charged amino acid, including, but not limited to, Asp (D). In one preferred embodiment the present invention provides an NGAL mutant in which Lys (K) 75 is substituted with an aliphatic amino acid, including, but not limited to, Gly (G). In one preferred embodiment the present invention provides an NGAL mutant in which Lys (K) 98 is substituted with an uncharged amino acid, including, but not limited to, Gln (Q). In one preferred embodiment the present invention provides an NGAL mutant in which His (H) 118 is substituted with a non-polar amino acid, including, but not limited to, Phe (F). In one preferred embodiment the present invention provides an NGAL mutant in which Arg (R) 130 is substituted with an uncharged amino acid, including, but not limited to, Gln (Q). In one preferred embodiment the present invention provides an NGAL mutant in which Lys (K) 149 is substituted with an uncharged amino acid, including, but not limited to, Gln (Q). In one preferred embodiment the present invention provides an NGAL mutant in which His (H) 165 is substituted with an uncharged amino acid, including, but not limited to, Asn (N).

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO.1), or a fragment thereof, wherein one, two, three, four, five, six, seven, eight, nine, ten, eleven, twelve, or all thirteen residues from among Lys 15, Lys 46, Lys 50, Lys 59, Lys 62, Lys 73, Lys 74, Lys 75, Lys 98, His 118, Arg 130, Lys 149, and His 165 is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

Exemplary NGAL mutants of the invention include those that comprise the sequence of mutants K1, K2, K3, K5, I1, I3, F4, F5, and B2 (see Table 2), or that comprise fragments or variants of such sequences. In some embodiments such variants have the amino acids specified in Table 2 at residues 15, 46, 59, 62, 73, 74, 75, 98, 118, 130, 149, and 165, but other amino acid residues can differ from the specified sequences provided that the NGAL mutant is at least 70%, or at least 75%, or at least 80%, or at least 85%, or at least 90%, or at least 95%, or at least 98% identical to the sequence of WT human NGAL (SEQ ID NO.1), or a fragment thereof, and provided that the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and also provided that he NGAL mutant (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K3 NGAL mutant (SEQ ID NO.2), wherein residues 15, 46, 73, 74, 75, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K2 NGAL mutant (SEQ ID NO.3), wherein residues 15, 73, 74, 75, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the 13 NGAL mutant (SEQ ID NO.4), wherein residues 62, 73, 74, 75, and 98 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-cubilin-receptor mediated mechanism, and/or (d) has reduced affinity for the megalin-cubilin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the I1 NGAL mutant (SEQ ID NO.5), wherein residues 15, 73, 74, 75, and 130 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also ((i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K5 NGAL mutant (SEQ ID NO.6), wherein residues 15, 46, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the F4 NGAL mutant (SEQ ID NO.8), wherein residues 15 and 46 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the F5 NGAL mutant (SEQ ID NO.9), wherein residues 15, 46, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the B2 NGAL mutant (SEQ ID NO.10), wherein residues 15, 46, 118, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In another embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of the K1 NGAL mutant (SEQ ID NO.7), wherein residues 15, 46, 59, 98, 118, 130, 149, and 165 each differ from the sequence of WT human NGAL and are each non-positively charged amino acids, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In some embodiments five or more of the thirteen listed amino acid positions are mutated as compared to WT human NGAL. In some embodiments six or more of the thirteen listed amino acid positions are mutated as compared to WT human NGAL. In some embodiments seven or more of the thirteen listed amino acid positions are mutated as compared to WT human NGAL. In some embodiments eight or more of the thirteen listed amino acid positions are mutated as compared to WT human NGAL. In some embodiments nine or more of the thirteen listed amino acid positions are mutated as compared to WT human NGAL. In some embodiments ten or more of the thirteen listed amino acid positions are mutated as compared to WT human NGAL. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments the NGAL mutants described above that have mutations in one or more of the thirteen non-conserved positive/basic surface residues, can also have mutations in one or more of the five conserved positive/based surface residues below, or one or more of the other mutations described in other following sections of this Detailed Description.

Five Conserved Positive/Basic Surface Residues in NGAL

The NGAL protein contains five basic/positive surface amino acid residues that are conserved among human, rat, mouse, chimpanzee, cow, dog, wild boar and rhesus monkey species, namely residues Arg(R) 43, Arg(R) 72, Arg(R) 140, Lys(K) 142, and Lys(K) 157. In one embodiment, the present invention provides an NGAL mutant having one, two, three, four, or all five of these amino acid positions mutated as compared to WT human NGAL. In one embodiment the mutated amino acid residue or residues are deleted. In another embodiment the mutated amino acid residue or residues are substituted with a non-positively charged amino acid (i.e. a non-conservative change). In another embodiment the mutated amino acid residue or residues are substituted with a negatively charged amino acid (i.e. a non-conservative change). In another embodiment the NGAL mutant may comprise any combination of such mutations, i.e. any combination of deletions, substitutions for non-positively charged amino acids, or substitutions for negatively charged amino acids may be provided at one, two, three, four, or five of the above listed amino acid residues.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO.1), or a fragment thereof, wherein one, two, three, four, or all five residues from among (R) 43, Arg(R) 72, Arg(R) 140, Lys(K) 142, and Lys(K) 157 is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant also (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In further embodiments the NGAL mutants described in this section that have mutations in one or more of the five conserved positive/basic surface residues, can also have mutations in one or more of the thirteen non-conserved positive/based surface residues described in the previous section of the Detailed Description, or one or more of the other mutations described in the following sections of this Detailed Description.

Additional Surface Residues in NGAL

The following amino acid residues are located on the surface of the NGAL protein and can play a role in the interaction of the NGAL protein with the megalin protein and/or in the reabsorption of NGAL in the kidney: amino acid residues 1-15, 17-26, 40-50, 57-62, 71-82, 84-89, 96-105, 114-118, 128-131, 134, 140-151, 157-165, and 170-174.

In one embodiment, the mutant NGAL proteins of the invention comprise, consist of, or consist essentially of amino acid sequences that are based on the amino acid sequence of human NGAL, or a fragment thereof, but that contain mutations as at one or more of the individual amino acid residues located at residues 1-15, 17-26, 40-50, 57-62, 71-82, 84-89, 96-105, 114-118, 128-131, 134, 140-151, 157-165, and/or 170-174 of WT human NGAL. In one embodiment one or more of the mutated amino acid residues can be deleted. In another embodiment one or more of the mutated amino acid residues can be substituted with a non-positively charged amino acid, including, but not limited to a negatively charged amino acid. In another embodiment the NGAL mutant may comprise any combination of such mutations, i.e. any combination of deletions, substitutions for non-positively charged amino acids, and/or substitutions for negatively charged amino acids at any one or more of the above listed amino acid residues. Table 2 provides details of all possible mutations of the surface residues of NGAL that are contemplated by the present invention. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

In one embodiment, the present invention provides an NGAL mutant that comprises, consists essentially of, or consists of an amino acid sequence that is at least 70%, or at least 75%, or at least 80%, or at least 85%, or at least 90%, or at least 95%, or at least 98% identical to the sequence of WT human NGAL (SEQ ID NO.1), or a fragment thereof, wherein one or more of the individual amino acid residues located at residues 1-15, 17-26, 40-50, 57-62, 71-82, 84-89, 96-105, 114-118, 128-131, 134, 140-151, 157-165, and/or 170-174 of WT human NGAL is deleted or substituted with a non-positively charged amino acid, such as a negatively charged amino acid, and wherein the NGAL mutant: (a) is excreted in the urine or exhibits a greater level of excretion in the urine than WT human NGAL, and/or (b) is not reabsorbed in the proximal tubule of the kidney or exhibits a lower level of reabsorption in the proximal tubule of the kidney as compared to WT human NGAL, and/or (c) is not a substrate for reabsorption in the kidney by a megalin-cubilin-receptor mediated mechanism, and/or (d) has reduced affinity for the megalin-cubilin-receptor as compared to WT NGAL, and/or (e) has fewer positively charged residues on its solvent accessible surface as compared to WT human NGAL, and wherein the NGAL mutant (i) is able to bind to a siderophore, and/or (ii) is able to bind to a siderophore complexed with iron, and/or (iii) has a preserved three-dimensional structure of the enterochelin binding pocket and/or (iv) has bacteriostatic activity. In preferred embodiments such NGAL mutants are not mutated (i.e. have the same amino acid sequence as WT human NGAL), at one or more, or more preferably all, of the following amino acid residues that are involved in the NGAL-enterochelin interaction: Asparagine 39, Alanine 40, Tyrosine 52, Serine 68, Trptophan 79, Arginine 81, Tyrosine 100, Tyrosine 106, Phenylalanine 123, Lysine 125, Tyrosine 132, Phenylalanine 133, and Lysine 134, or if mutated at these residues only conservative substitutions are made.

Functional Properties of NGAL Mutants

In certain embodiments the mutant NGAL proteins of the invention have certain specified functions. For example, in some embodiments the mutant NGAL proteins of the invention have one or more of the following properties: (a) they are excreted in the urine or exhibit a greater level of excretion in the urine than WT human NGAL, and/or (b) they are not reabsorbed in the proximal tubule of the kidney or exhibit a lower level of reabsorption in the proximal tubule of the kidney than WT human NGAL, and/or (c) they are not a substrate for reabsorption in the kidney by a megalin-cubilin-receptor mediated mechanism. Similarly, in some embodiments the mutant NGAL proteins of the invention have one or more of the following properties: (i) they are able to bind to enterochelin-type siderophores, and/or (ii) they are able to bind to enterochelin-type siderophores complexed with iron, and/or (iii) they have a preserved three-dimensional structure of the enterochelin binding pocket and/or (iv) they have bacteriostatic activity.

Each of the above properties of the mutant NGAL proteins of the invention can be tested for and/or quantified, and in some embodiments the mutant NGAL proteins of the invention have functional properties that fall within a certain numeric range.

Figure 5:
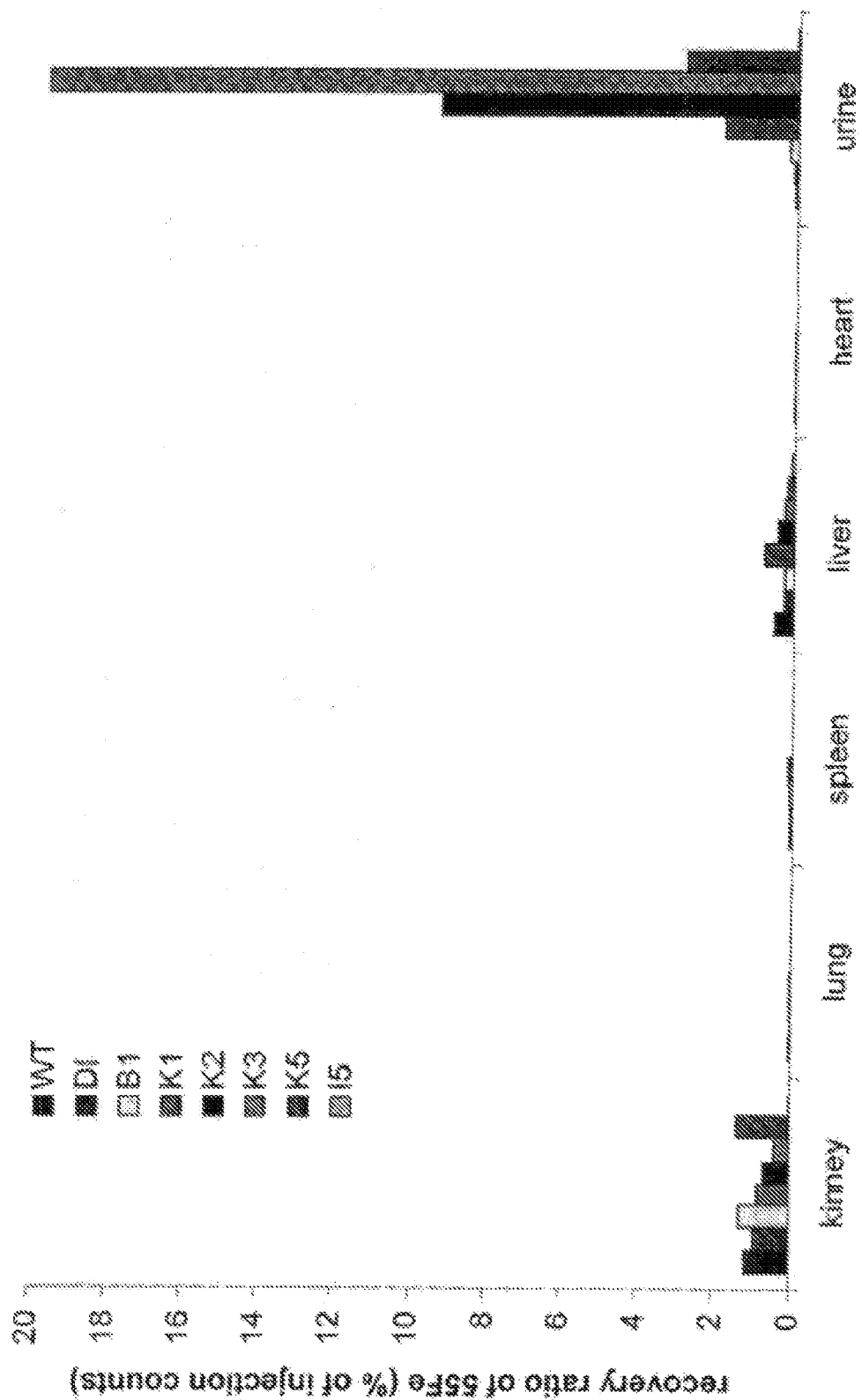
FIG. 5. Percentage recovery of $^{55}Fe^{3+}$ following injection of NGAL mutant proteins complexed with enterochelin and $^{55}Fe^{3+}$. The amount of NGAL-bound Ent-$^{55}Fe^{3+}$ was calculated as percentage of the starting total $^{55}Fe^{3+}$. Recovery in the urine, kidney, lung, spleen, liver, and heart is shown. D1 is SEQ ID NO: 32; B1 is SEQ ID NO: 24; K1 is SEQ ID NO: 7; K2 is SEQ ID NO: 3; K3 is SEQ ID NO: 2; K5 is SEQ ID NO: 6; I5 is SEQ ID NO: 45.

For example, in some embodiments the mutant NGAL proteins of the invention are excreted in the urine or exhibit a greater level of excretion in the urine than WT human NGAL. Excretion of the mutant NGAL proteins of the invention can be detected and quantified, for example using the methods described in the Examples section of this application. For example the amount of the mutant NGAL protein present in the urine a given time after its is administered to a subject, such as a mouse or a human subject, can be measured and can be expressed as a percentage of the total amount administered (see Examples and Table 1) to give a % accumulation in the urine. The % accumulation in the urine of a given NGAL mutant can be compared to that of other mutants or of WT NGAL. NGAL or an NGAL mutant or siderophore complex thereof can be radiolabeled (e.g. with radioactive iron) or labeled with some other detectable moiety in order to facilitate its detection and quantification. In some embodiments the present invention provides that the mutant NGAL proteins of the invention exhibit a greater level of excretion in the urine than does WT human NGAL. For example, the NGAL mutants can have a 6-fold, 7-fold, 8-fold, 9-fold, 10-fold, 15-fold, 20-fold, 25-fold, 30-fold, 40-fold, 50-fold, 100-fold or higher level of excretion in the urine than WT human NGAL. As seen in FIG. 5, WT NGAL can have a % accumulation in the urine (measured as a % of the amount administered intraperitoneally) of less than 0.2%. In contrast, as can be seen from FIG. 3, FIG. 5, and Table 1, the NGAL mutants of the invention can have a % accumulation in the urine (measured as a % of the amount administered intraperitoneally 3 hours after administration) of greater than 1%, or greater than 2%, or greater than 3%, or greater than 4%, or greater than 5%, or greater than 6%, or greater than 7%, or greater than 8%, or greater than 9%, or greater than 10%, or greater than 15%, or greater than 20%, or more.

In some embodiments the mutant NGAL proteins of the invention are able to bind to siderophores, such as enterochelin, and/or they are able to bind to siderophores complexed with iron. The ability of the NGAL mutants of the invention to bind to siderophores and siderophore-iron complexes can be tested and/or quantified, for example using the methods described in the Examples section of this application. For example NGAL (including the NGAL mutants of the invention) and siderophore molecules such as enterochelin and iron associate with each other in a 1:1:1 molar ratio and NGAL (including the NGAL mutants of the invention) and siderophore molecules such as catechol and iron associate with each other in a 1:3:1 molar ratio. Accordingly using a radiolabelled form of iron the binding of NGAL to siderophore molecules and iron can be measured or estimated by examining the % of radiolabelled iron that is retained by a given NGAL protein. The % of iron (iron-siderophore) that is retained can be compared between NGAL mutants or between an NGAL mutant and WT NGAL. In some embodiments the present invention provides that the mutant NGAL proteins of the invention exhibit a similar % of iron (iron-siderophore) retention as compared to WT NGAL. In some embodiments the present invention provides that the mutant NGAL proteins of the invention exhibit a higher % of iron (iron-siderophore) retention as compared to WT NGAL, such as a 1.5-fold, 2-fold, 2.5-fold or greater-fold higher % of iron (iron-siderophore) retention. In some embodiments, the mutant NGAL proteins of the invention exhibit a % iron (iron-siderophore) retention of about 20% or more, or about 30% or more, or about 40% or more.

In some embodiments the mutant NGAL proteins of the invention have anti-bacterial activity. Antibacterial activity of the NGAL mutants of the invention can be tested and/or quantified, for example using standard methodologies known in the art, for example by culturing bacteria in the presence of the NGAL mutants and assessing the effect of the NGAL mutants on bacterial growth, survival, numbers, etc. in comparison to control conditions in which no NGAL mutant is present.

In one embodiment, Ngal mutants bypass megalin. In another embodiment, Ngal mutants bind Ent:iron. Thus, the Ngal mutants of the invention comprise a therapeutic that can safely excrete NTBI in the urine.

Non-NGAL Lipocalins

In addition to mutants of NGAL, the present invention also contemplates that mutants of other lipocalins can be made that, like the NGAL mutants described herein, have the ability to bind to siderophore-iron complexes but that are not reabsorbed in the kidney. It is expected that such lipocalin mutants could be used similarly to the NGAL mutants described herein to traffic iron out of the body and could thus be used in the treatment of iron overload disorders. It is also expected that such lipocalin mutants could also be used to treat bacterial infections of the urinary tract.

There are about 20 known proteins in the lipocalin family. Any lipocalin protein, or homolog, variant, derivative, fragment, or mutant thereof, that binds to a siderophore-iron complex can be mutated in order to provide a lipocalin mutant of the invention. Examples of lipocalins that can be used in accordance with the present invention include, but are not limited to, retinol binding protein, lipocalin allergen, aphrodisin, alpha microglobulin, prostaglandin D synthase, beta-lactoglobulin, bilin-binding protein, the nitrophorins, lipocalin 1, lipocalin 12, and lipocalin 13.

Siderophores

Siderophores are high affinity iron (e.g. $Fe^{3+}$) binding compounds. The vast majority of siderophores known are produced by bacteria. Bacteria release siderophores into the surrounding environment for the purpose of scavenging or chelating iron and transporting the iron to the bacteria—a process necessary for survival of bacteria. Siderophores that are known in the art include, but are not limited to heme, enterochelin, TRENCAM, MECAM, TRENCAM-3,2-HOPO, parabactin, carboxymycobactin, fusigen, triacetylfusarinine, feriichrome, coprogen, rhodotorulic acid, ornibactin, exochelin, ferrioxamine, desferrioxamine B, aerobactin, ferrichrome, rhizoferrin, pyochelin, pyoverdin. The structures of these compounds are disclosed in Holmes et al., Structure, 2005, 13:29-41 and Flo et al., Nature, 2004, 432: 917-921, the contents of which are hereby incorporated by reference.

Several of the above siderophores are known to bind to lipocalins, including NGAL, and complexes of these siderophores and lipocalins are known to be able to sequester iron (see for example, Holmes et al., Structure, 2005, 13:29-41 and Flo et al., Nature, 2004, 432: 917-921; Goetz et al, Molecular Cell, 2002, 10: 1033-1043 and Mori, et al., "Endocytic delivery of lipocalin-siderophore-iron complex rescues the kidney from ischemia-reperfusion injury." J. Clin Invest., 2005, 115, 610-621). The mutant NGAL proteins of the invention can also form complexes with siderophores and can thereby chelate and transport iron.

In some aspects the present invention provides complexes of a mutant NGAL protein of the invention and a siderophore, including, but not limited to, the siderophores listed herein. In preferred aspects the siderophore is selected from the group consisting of enterochelin, pyrogallol, carboxymycobactin, catechol, and variants or derivatives thereof. Any variant or derivative of such siderophores that retains the ability to bind to iron (ideally in a pH insensitive manner) and that retains the ability to bind to NGAL and/or one or more of the NGAL mutants of the invention may be used.

Manufacture of Mutant NGAL Proteins and Complexes with Siderophores

The mutant NGAL proteins of the invention can be manufactured by any suitable method known in the art for manufacture of protein drugs. For example the mutant NGAL proteins can be made using standard techniques known for the production of recombinant proteins, for example by delivering to a cell, such as a bacterial cell or a mammalian cell, an expression vector containing a nucleotide sequence that encodes an NGAL mutant under the control of a suitable promoter, and culturing the cell under conditions in which the protein will be expressed. Methods for the large scale culture, isolation, and purification of recombinant proteins are well known in the art and can be used in the manufacture of the NGAL mutants of the present invention. Similarly, methods of producing peptides and proteins synthetically are known in the art and can be used in the manufacture of the NGAL mutants of the present invention.

In certain embodiments, the present invention provides fusion proteins comprising the NGAL mutants of the invention and one or more additional "tags". Such additional tags can be fused to the N- or C-terminus of the NGAL mutants, or can in some instances be added at an internal location to the extent that the inclusion of the tag does not adversely affect the function of the NGAL mutant. Suitable tags include, but are not limited to glutathione-S-transferase (GST), poly-histidine (His), alkaline phosphatase (AP), horseradish peroxidase (HRP), and green fluorescent protein (GFP). Other suitable tags will also be apparent to those skilled in the art. The tags may be useful for several applications, including to assist in the isolation and/or purification of the NGAL mutants and/or to facilitate their detection.

Many chemical modifications of proteins are known in the art to be useful for improving the properties of protein-based drugs and such modifications can be used in accordance with the present invention to improve the stability and reduce the immunogenicity of the mutant NGAL proteins of the invention for therapeutic applications. For example, it is well known in the art that the process of covalent attachment of polyethylene glycol polymer chains to another molecule (i.e. PEGylation) can "mask" a proteinaceous agent from the host's immune system, and also increase the hydrodynamic size (size in solution), prolongs the circulatory half-life, and improve water solubility of protein-based drugs. Various other chemical modifications are also known and used in the art and can be used in conjunction with the mutant NGAL proteins of the invention.

Complexes containing a mutant NGAL protein of the invention and a siderophore, such as enterochelin or a derivative or variant thereof, can readily be prepared used standard methodologies known in the art, such as those provided in the Examples section of this application. For example, an NGAL-siderophore complex can be prepared by mixing NGAL (including mutant NGAL) and a siderophore together in a molar ratio of 1:1 (e.g. Ent) or 1:3 (e.g. catechol). The mixture can be incubated at room temperature for a suitable time, e.g. 30 minutes, to allow for complex formation. Unbound siderophore can then be removed/separated from the bound siderophore-NGAL complexes using standard separation techniques, such as centrifugation based techniques, filter-based techniques, or other size-based separation techniques.

Methods of Treatment—Iron Overload

In one embodiment, the mutant NGAL proteins of the invention, and complexes and compositions comprising such mutant NGAL proteins, can be used to treat conditions, diseases, or disorders associated with excessive iron levels or iron overload. In particular, complexes of the mutant NGAL proteins of the invention with a siderophore, such as enterochelin, and compositions comprising such complexes, can be used to chelate iron in the body and facilitate its excretion in the urine.

Large amounts of free iron in the bloodstream can lead to cell damage, especially in the liver, heart and endocrine glands. The causes of excess iron may be genetic, for example the iron excess may be caused by a genetic condition such as hemochromatosis type 1 (classical hemochromatosis), hemochromatosis type 2A or 2B (juvenile hemochromatosis), hemochromatosis type 3, hemochromatosis type 4 (African iron overload), neonatal hemochromatosis, aceruloplasminemia, or congenital atransferrinemia. Examples of non-genetic causes of iron excess include dietary iron overload, transfusional iron overload (due to a blood transfusion given to patients with thalassaemia or other congenital hematological disorders), hemodialysis, chronic liver disease (such as hepatitis C, cirrhosis, non-alcoholic steatohepatitis), porphyria cutanea tarda, post-portacaval shunting, dysmetabolic overload syndrome, iron tablet overdose (such as that caused by consumption by children of iron tablets intended for adults), or any other cause of acute or chronic iron overload.

The two common iron-chelating agents available for the treatment of iron overload are deferoxamine (DFO) and deferiprone (oral DFO). Due to its high cost and need for parenteral administration, the standard iron chelator deferoxamine is not used in many individuals with acute and/or chronic iron poisoning. Deferoxamine must be administered parenterally, usually as a continuous subcutaneous infusion over a 12-hour period, front three to seven times a week. Treatment is time consuming and can be painful. As a result compliance is often poor. Side-effects include local skin reactions, hearing loss, nephrotoxicity, pulmonary toxicity, growth retardation and infection. Deferiprone is the only orally active iron-chelating drug to be used therapeutically in conditions of transfusional iron overload. It is indicated as a second-line treatment in patients with thalassaemia major, for whom deferoxamine therapy is contraindicated, or in patients with serious toxicity to deferoxamine therapy. Deferiprone is an oral iron-chelating agent which removes iron from the heart, the target organ of iron toxicity and mortality in iron-loaded thalassaemia patients. However, although deferiprone offers the advantage of oral administration, it is associated with significant toxicity and there are questions about its long-term safety and efficacy. It is recommended to be used in patients who are unable to use desferrioxamine because of adverse effects, allergy, or lack of effectiveness. Deferiprone is associated with serious safety issues include genotoxicity, neutropenia and agranulocytosis. Weekly monitoring of neutrophils is recommended. Gastrointestinal and joint problems can occur and liver toxicity has been reported. Therefore, there is clearly a need for alternative convenient, safe, and effective iron chelation therapies, such as those provided by the present invention.

The mutant NGAL proteins of the invention, and in particular complexes thereof with siderophores, can be used to chelate free iron and clear the excess iron from the body via the kidneys, for example to reduce toxic circulating levels of iron to below toxic levels.

Methods of Treatment—Bacterial Infections of the Urinary Tract

WT NGAL is known to have bacteriostatic activity, in part due to its ability to tightly bind to bacterial siderophores, leading to depletion of bacterial iron and inhibition of bacterial growth (Goetz et al., Mol. Cell. (2002), 10(5) 1033-1043). The mutant NGAL proteins of the invention, like WT NGAL, have the ability to bind to bacterial siderophores, and thus can have anti-bacterial activity. Furthermore, because the mutant NGAL proteins of the invention are not reabsorbed by the kidney and accumulate in the urine, they are particularly well-suited to use in the treatment of bacterial infections of the urinary tract.

Pharmaceutical Compositions & Administration

The present invention also provides pharmaceutical compositions, formulations, kits, and medical devices that comprise the mutant NGAL proteins described herein, and complexes thereof with siderophores, and which may be useful to treat various diseases, disorders, and conditions, including iron overload and bacterial infections. Pharmaceutical formulations include those suitable for oral or parenteral (including intramuscular, subcutaneous and intravenous) administration. Examples of medical devices provided by the invention include, but are not limited to, beads, filters, shunts, stents, and extracorporeal loops which are coated with or otherwise contain a mutant NGAL or complexes thereof, as described herein, such that the device is implanted in or otherwise administered to a subject in a manner which permits the mutant NGAL or complexes thereof to chelate or absorb excess iron in the subject.

Administration of a therapeutically effective amount of the mutant NGAL proteins, and complexes thereof can be accomplished via any mode of administration suitable for therapeutic agents. One of skill in the art can readily select mode of administration without undue experimentation. Suitable modes may include systemic or local administration such as oral, nasal, parenteral, transdermal, subcutaneous, vaginal, buccal, rectal, topical, intravenous (both bolus and infusion), intraperitoneal, or intramuscular administration modes. In preferred embodiments, oral or intravenous administration is used. In other preferred embodiments, the compositions of the invention are administered directly to the desired site of action, such as for example, the kidney, for example by local injection or local infusion or by use of (e.g. conjugation to) agents useful for targeting proteins or pharmaceuticals to specific tissues, such as antibodies etc.

Depending on the intended mode of administration, the mutant NGAL proteins and complexes of the invention, in a therapeutically effective amount, may be in solid, semi-solid or liquid dosage form, such as, for example, injectables, tablets, suppositories, pills, time-release capsules, elixirs, tinctures, emulsions, syrups, powders, liquids, suspensions, or the like. In one embodiment the mutant NGAL proteins and complexes of the invention may be formulated in unit dosage forms, consistent with conventional pharmaceutical practices. Liquid, particularly injectable, compositions can, for example, be prepared by dissolution or dispersion. For example, mutant NGAL proteins and complexes of the invention can be admixed with a pharmaceutically acceptable solvent such as, for example, water, saline, aqueous dextrose, glycerol, ethanol, and the like, to thereby form an injectable isotonic solution or suspension.

Parental injectable administration can be used for subcutaneous, intramuscular or intravenous injections and infusions. Injectables can be prepared in conventional forms, either as liquid solutions or suspensions or solid forms suitable for dissolving in liquid prior to injection. One embodiment, for parenteral administration, employs the implantation of a slow-release or sustained-released system, according to U.S. Pat. No. 3,710,795, incorporated herein by reference.

The mutant NGAL proteins and complexes of the invention can be sterilized and may contain any suitable adjuvants, preservatives, stabilizers, wetting agents, emulsifying agents, solution promoters, salts (e.g. for regulating the osmotic pressure), pH buffering agents, and/or other pharmaceutically acceptable substances, including, but not limited to, sodium acetate or triethanolamine oleate. In addition, the compositions of the invention may also contain other therapeutically useful substances, such as, for example, other iron chelators or other agents useful in the treatment of iron overload, or other agents useful in the treatment of any of the conditions described herein.

The compositions of the invention can be prepared according to conventional mixing, granulating or coating methods, respectively, and the present pharmaceutical compositions can contain from about 0.1% to about 99%, preferably from about 1% to about 70% of the compound or composition of the invention by weight or volume.

The dose and dosage regimen to be used can be determined in accordance with a variety of factors including the species, age, weight, sex and medical condition of the subject; the severity of the condition; the route of administration; the renal or hepatic function of the subject; and the particular mutant or complex employed. A person skilled in the art can readily determine and/or prescribe an effective amount of a mutant or complex of the invention useful for treating or preventing a condition, for example, taking into account the factors described above. Dosage strategies are also provided in L. S. Goodman, et al., The Pharmacological Basis of Therapeutics, 201-26 (5th ed.1975), which is herein incorporated by reference in its entirety. In one embodiment, compositions of the invention are administered such that the NGAL component is administered at a dose range of about 1 to about 100 mg/kg body weight, and typically at a dosage of about 1 to about 10 mg/kg body weight is administered at a dose that results in a concentration in the range of about 0.1 ng/ml to about 100 ng/ml, e.g., in the range of about 1.0 ng/ml to about 20 ng/ml, in the blood. The amount of a siderophore component of a composition of the invention will be chosen accordingly, such that the desired stoichiometry, e.g. 1:1 or 1:3 binding with the mutant NGAL protein, is achieved.

In addition to the above methods of treatment, the mutant NGAL protein—siderophore complexes of the invention may be useful to chelate and/or remove iron from samples, wherein the samples are not in a subject's body. Thus, in one embodiment, the present invention provides a method for removing iron from a fluid, the method comprising admixing the fluid with a mutant NGAL protein—siderophore complex for a period of time sufficient for iron in the sample to bind to the mutant NGAL protein—siderophore complexes, wherein the mutant NGAL protein—siderophore complex can chelate iron from the sample. In one embodiment, the mutant NGAL protein—siderophore complexes having iron bound thereto may then be removed from the sample. In preferred embodiments, the sample is a biological fluid, such as blood, serum, plasma, or urine. In certain embodiments the mutant NGAL protein—siderophore complexes are admixed with the sample outside the body, e.g. in an extracorporeal device, and the sample is then delivered to or returned to the body. For example, such methods can be used to chelate and/or remove excess iron in blood samples for transfusion, or in a dialysis procedure. For example, blood or another bodily fluid from a subject may be removed from the body, treated with a compound or composition of the invention to chelate or remove excess iron, and then returned to the subject.

EXAMPLES

Example 1

Mutant NGAL Proteins and their Use as Therapeutic Iron Chelators and as Antimicrobial Agents Lipocalin 2 (Lcn2), also called Neutrophil Gelatinase-Associated Lipocalin (NGAL) is a protein that binds to iron with high affinity. To bind iron, NGAL binds a cofactor called a siderophore produced by bacteria (Binding constant $K_m=0.41\times10^{-9}$ M for the NGAL:enterochelin-iron interaction; $K_m=10^{-49}$ M for the enterochelin (enterobactin):iron interaction) or catechol containing compounds ($K_m=0.4\pm10^{-9}$ M for catechol-iron; $K_m=10^{-45.9}$ M for the catechol:iron interaction) produced by a combination of bacterial and mammalian enzymes. NGAL is also a secretory protein that is markedly upregulated by bacterial infection and acute kidney injury and is secreted into the blood and urine. During bacterial infection, NGAL sequesters iron from bacteria by binding enterochelin-iron, resulting in the inhibition of bacterial growth.

Serum NGAL with bound enterochelin:Fe is filtered by the glomerulus in the kidney, but then the majority of it is retained (reabsorbed) by kidney where it is degraded. Very little NGAL escapes to the urine and is excreted. For example, as demonstrated by recent research, when NGAL is injected intraperitoneally, more than 70% of the WT NGAL accumulates in kidney while less than 0.1% is found in the urine after 3 hours.

The capture and retention of serum NGAL in the kidney is achieved by the absorption of NGAL by megalin, a multi-ligand receptor also called low-density lipoprotein receptor-related protein 2 (LRP2). Megalin is located at the apical plasma membrane of proximal tubular epithelial cells where it contacts the glomerular filtrate. Megalin associates with cubilin. NGAL can transport iron by using cofactors such as enterochelin or catechol and deliver the iron specifically to the kidney.

Amnionless is another protein associated with the the megalin-cubulin-receptor complex. In one embodiment, NGAL interacts with megalin, cubilin, amnionless, or a combination thereof. For additional information on the amnionless protein, see Kozyraki R, Gofflot F, (2007) Curr Pharm Des. 13(29):3038-46 and Nielsen R, Christensen E I., (2010) Pediatr Nephrol., 25(5):813-22, both of which are incorporated by reference in their entireties.

Mutant NGAL as a Therapeutic Iron Chelator and Antimicrobial Agent

The molecular cutoff for glomerular filtration is about 70 kD. Recombinant or native NGAL protein with molecular weights of about 20.5 kD and 23-25 kD respectively can be filtered in the glomerulus, but is then efficiently reabsorbed into the proximal epithelia by megalin and/or by a megalin associated complex which includes cubilin. Megalin has a binding affinity for apo- and iron-loaded NGAL of about 60 nM (Hvidberg, et al., FEBS Letters, 2005, 579: 773-777)). Megalin is a multi-ligand, endocytic receptor, responsible for reabsorption of many proteins including NGAL, apoE, lipoprotein lipase, lactoferrin, approtinin, etc., after glomerular filtration (Christensen and Birn, Nature Reviews-Molecular Cell Biology, 2002, 3: 258-2682002). Electrostatic interactions between megalin's acidic regions of "type A repeats" in megalin protein and basic regions of ligands are involved in ligand-receptor recognition i.e. megalin recognizes positively charged surfaces of ligand proteins (Moestrup and Verrost, Annual Reviews of Nutrition, 2001, 21: 407-428. 2001). Some basic amino acid residues on the surface of human NGAL protein can therefore be involved in its high binding affinity to megalin, and mutation of these basic residues can disrupt the electrostatic interactions between NGAL and megalin while preserving the binding affinity for enterochelin-iron in its interior clayx. The disabled interaction between mutant NGAL and megalin can allow mutant NGAL:enterocalin:iron or apo-mutant NGAL to be filtered into the urine without being reabsorbed from the filtrate after glomerular filtration. In the former case, where enterochelin is present in the mutant NGAL complex, it can absorb iron from the blood and traffic it into the urine. This can allow removal of iron from the subject (e.g. animal or human) associated with the siderophore-iron. Alternatively, in the case of the mutant apo-NGAL, it can lead to an accumulation of NGAL in the urine which can inhibit bacterial growth in the urinary tract.

The mutant NGAL proteins of the invention have at least two potential applications in clinical therapeutics.

Firstly, the mutant NGAL proteins can be used as efficient iron chelators to remove excess iron from subjects, such as human subjects, with iron overload disorders. Iron overload patients (e.g. due to hemachromatosis, sickle cell disease, thalassemia, multiple transfusion of red blood cells or other biological products) are administered mutant NGAL bound to iron-free siderophore, such as enterochelin, by intravenous infusion. Enterochelin chelates serum iron to form an NGAL-enterochelin-iron complex. This complex is mostly transported to the kidney and subsequently filtered by glomerulus. It remains in the glomerular filtrate without being reabsorbed due to its inability to bind megalin in the proximal tubular epithelial cells. It then appears in the urine and is ultimately excreted together with the iron that it binds. Mutant NGAL can be an efficient tool to remove excessive iron from iron overloaded human subjects. The molar ratio for NGAL binding to enterochelin and iron is 1:1:1. If 10 g of mutant apo-NGAL, which equals about 500 μmoles, is given to an iron overloaded patient, about 500 μmoles or about 27.9 mg of iron can theoretically bind mutant NGAL and enterochelin and be delivered into the urine for excretion (assuming accumulation of mutant NGAL protein in urine is 100%). This is a very efficient way to remove excessive iron from a human patient with iron overload given that the human only loses 1-2 mg iron per day mainly via the shedding of intestinal cells and dead skin cells, and only gains 1-2 mg per day from food.

Secondly, the mutant NGAL protein can be used as an anti-microbial to treat patients with a urinary tract infection (UTI). Mutant apo-NGAL is given to human subjects with a UTI by infusion. The mutant NGAL is transported to the kidney and filtered into the urine without reabsorption due to its loss of binding affinity for megalin. Once inside the urine, the mutant apo-NGAL protein binds siderophores of UTI bacteria (e.g. enterochelin) and results in the inhibition of their growth.

Experimental Design and Experimental Procedures
Cloning of Human NGAL

Human NGAL cDNA (Ganbank accession number: NM 005564) is obtained from Open Biosystems, and the open reading frame encoding the secreted NGAL protein is PCR-amplified by using a PfuUltra™ DNA polymerase (Stratagene), and cloned into a pGEX-4T-3 plasmid vector (GE Healthcare) for site-directed mutagenesis.

Structure of Human NGAL Protein

Figure 4A:
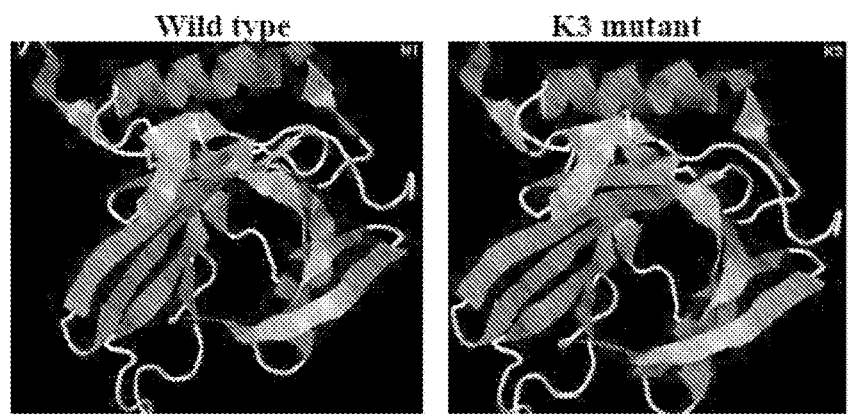
FIGS. 4A-4B. Comparison of structures of wild-type NGAL and the K3 mutant NGAL protein.

Based on the structure of the human NGAL protein, amino acid residues, especially basic residues (arginine, lysine and histidine), on the surface of the protein can mediate the electrostatic interaction with megalin for high affinity binding (FIG. 1 and FIG. 4A).

Designation of NGAL Mutants

There are five basic amino acid residues on the surface of NGAL protein which are conserved (R43, 72, 140, and K142, 157) among different mammalian species including human, mouse, rat, Chimpanzee, bovine, dog, wild boar, and Rhesus Monkey, while there are 13 non-conserved basic residues (R130; K15, 46, 50, 59, 62, 73, 74, 75, 97, 149; H118, 165). These basic residues can be mutated to other non-basic residues.

Generation of NGAL Mutants

A variety of different amino acid residues on the surface of NGAL protein were mutated by using a QuikChange™ Site-Directed Lightning Multi Mutagenesis Kit (Stratagene), and this resulted in the generation of many mutants with mutations at different sites of the NGAL protein. 57 NGAL mutants were made as shown in Table 2, SEQ ID NOS:2-10, 21-68, 247-251.

Production of NGAL Protein

Wild-type and mutant plasmid constructs are electroporated into BL21 E. coli (GE Healthcare), and expression of wild-type and mutant apo-NGAL proteins are induced by the addition of IPTG to a final concentration of 0.2 mM for 5 hours, and subsequently purified by a combination of GST-based pull-down and gel filtration in a FPLC system with a Sepharose™ column.

Binding Affinity of Mutant NGAL for Enterochelin and Iron

The NGAL mutant proteins are examined for their ability to bind enterochelin and iron by using a radioactive form of iron, $^{55}Fe^{3+}$. The binding affinity of NGAL for enterochelin and $^{55}Fe^{3+}$ was estimated by examining the percentage of $^{55}Fe^{3+}$ which was retained by mutant and wild type NGAL proteins, and the wild-type NGAL protein can be used as a positive control.

Preparation of NGAL-Enterochelin-Iron Complex

The NGAL-enterochelin-iron complex is prepared by mixing NGAL protein, enterochelin and $^{55}Fe^{3+}$ together in a molar ratio of 1:1:1 (4 nmole each). The mixture is incubated at RT for 30 minutes, and washed in a 10 K Microcon™ by centrifugation 4 times at 7000 rpm for 5 minutes to remove the unbound enterochelin and $^{55}Fe^{3+}$, and the NGAL-enterochelin-$^{55}Fe^{3+}$ complex is retained in the Microcon™.

Screening of NGAL Mutants in Mice

There is 76% amino acid identity and 87% amino acid similarity between human mouse megalin proteins, indicating that they likely have very similar binding properties. In the present experiments the binding of human NGAL protein to mouse megalin was tested. Due to the high degree of amino acid identity and similarity between human and mouse megalin protein, the mouse system provides a useful model to screen mutant NGAL proteins for their ability to escape megalin-cubilin-dependent renal reabsorption and ultimately to be delivered into urine.

The radiolabelled NGAL-enterocalin-$^{55}Fe^{3+}$ complex is intraperitoneally injected into female C57BL/6 mice (4 weeks), and urine is collected in metabolic cages. After urine collection for 3 hours, the mice are sacrificed and kidneys and liver are collected, weighed and solubilized in a solution of 0.5M NaOH and 1% SDS at 70° C. overnight. The radioactivity in urine, kidney and liver is examined in a scintillation counter, and the accumulation of the NGAL-enterochelin-iron complex will be calculated as the percentage of total injected complex.

Experimental Results

Figure 3A:
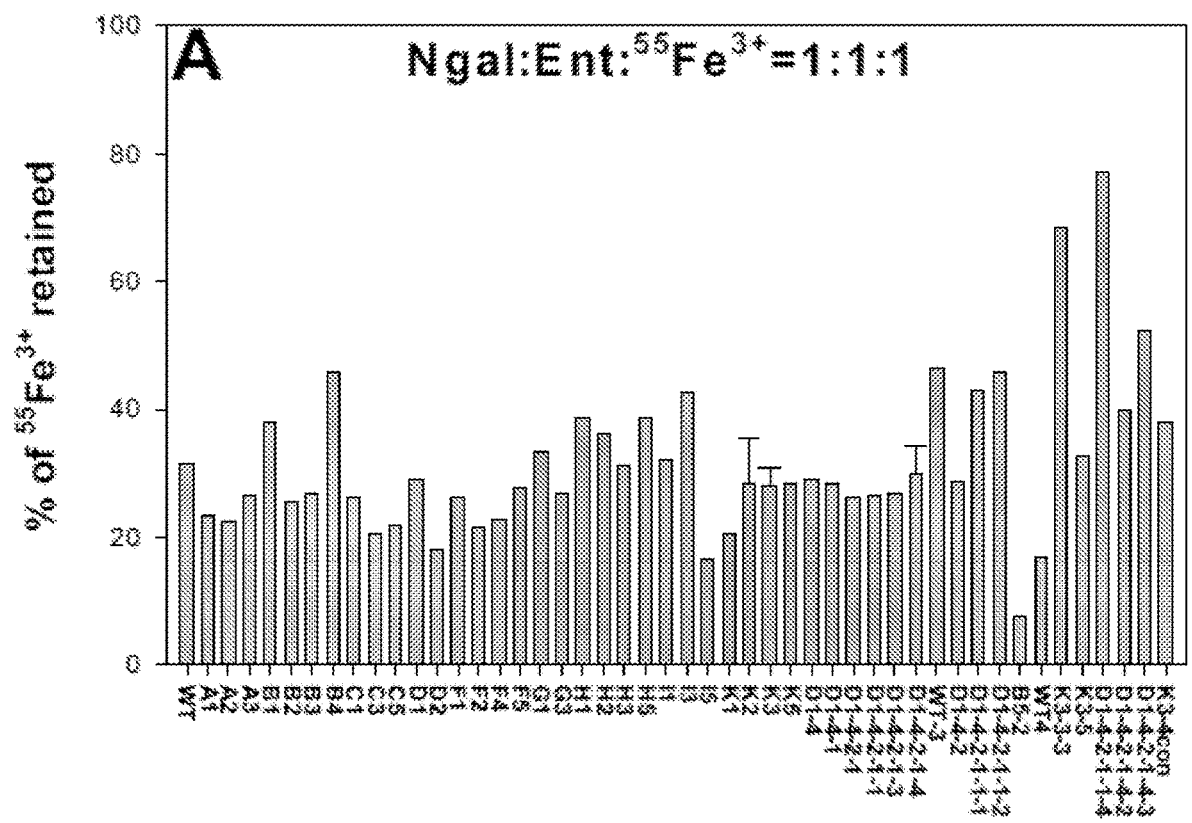
FIGS. 3A-3D. Screening for NGAL mutants exhibiting specific accumulation in urine.
Figure 3B:
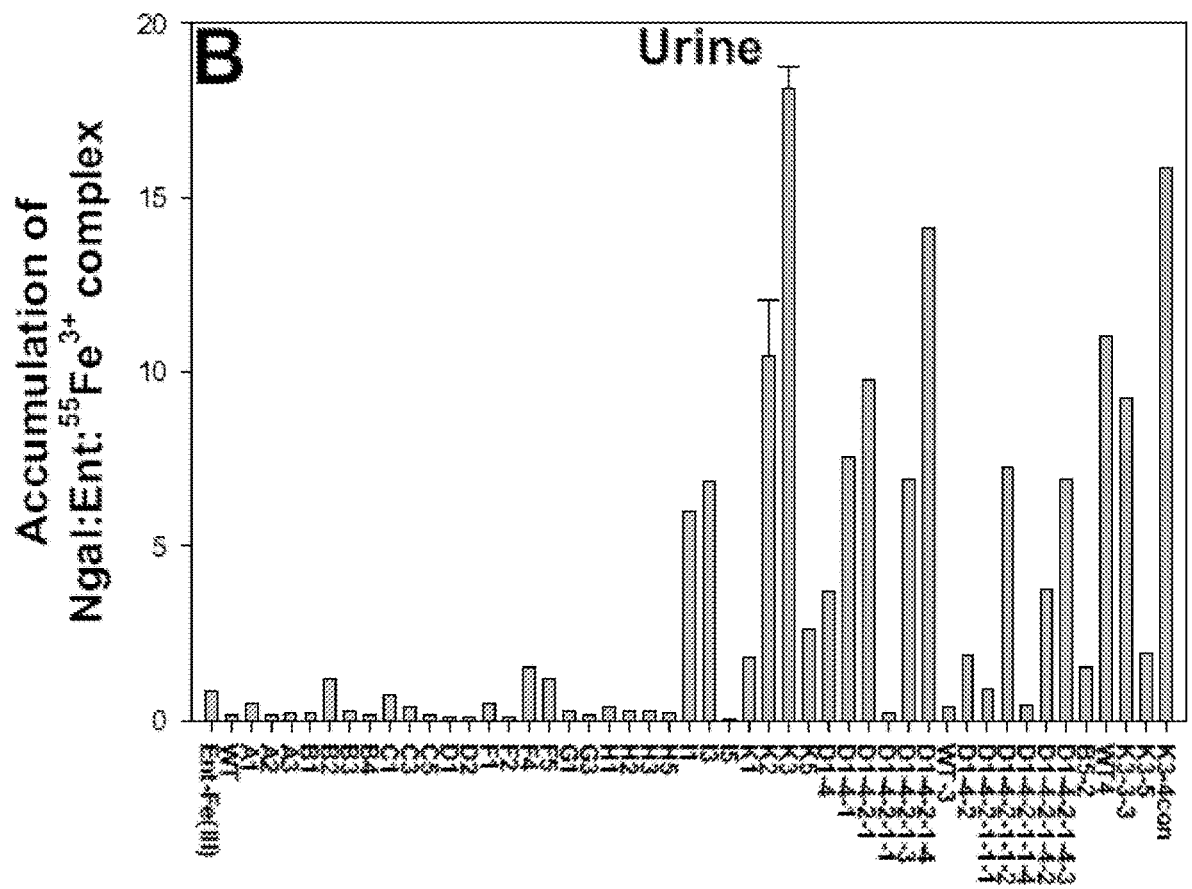
Figure 3C:
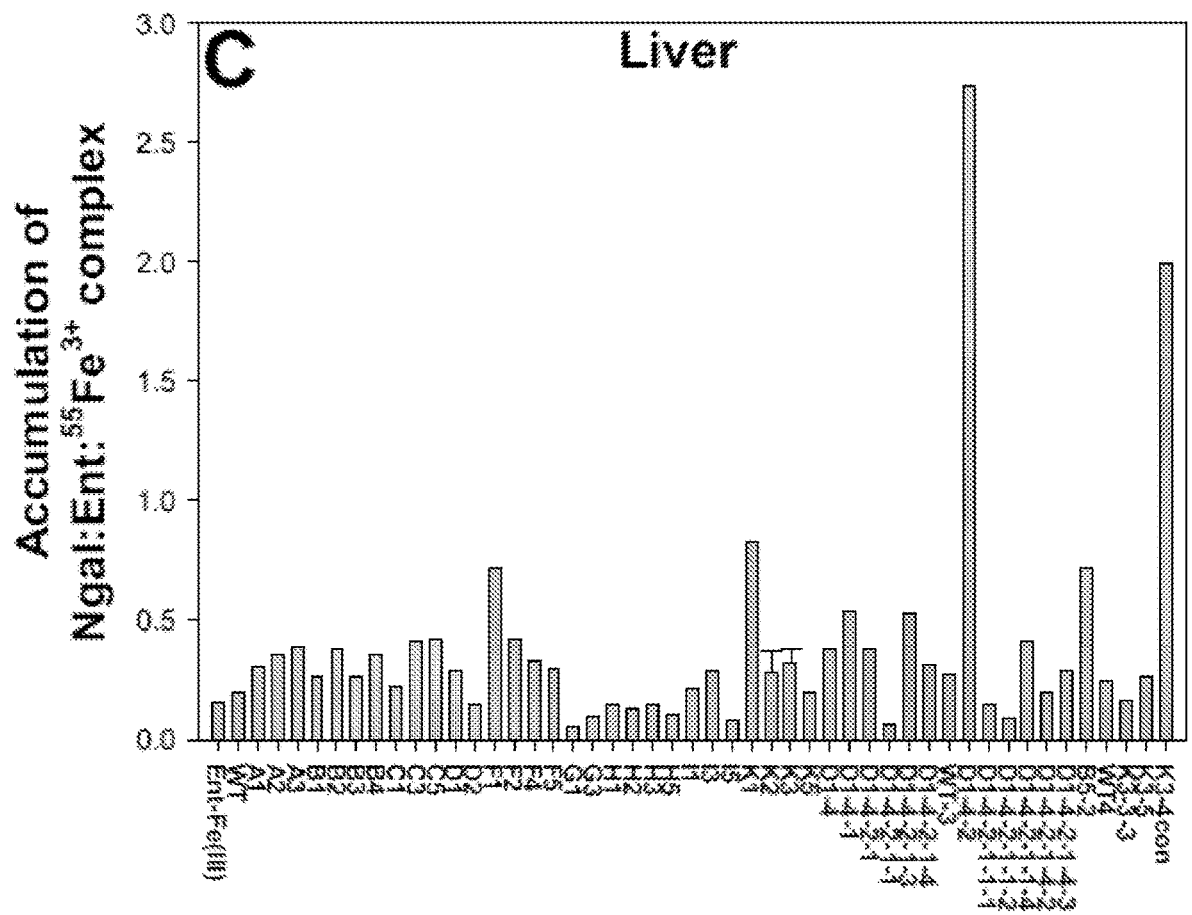
Figure 3D:
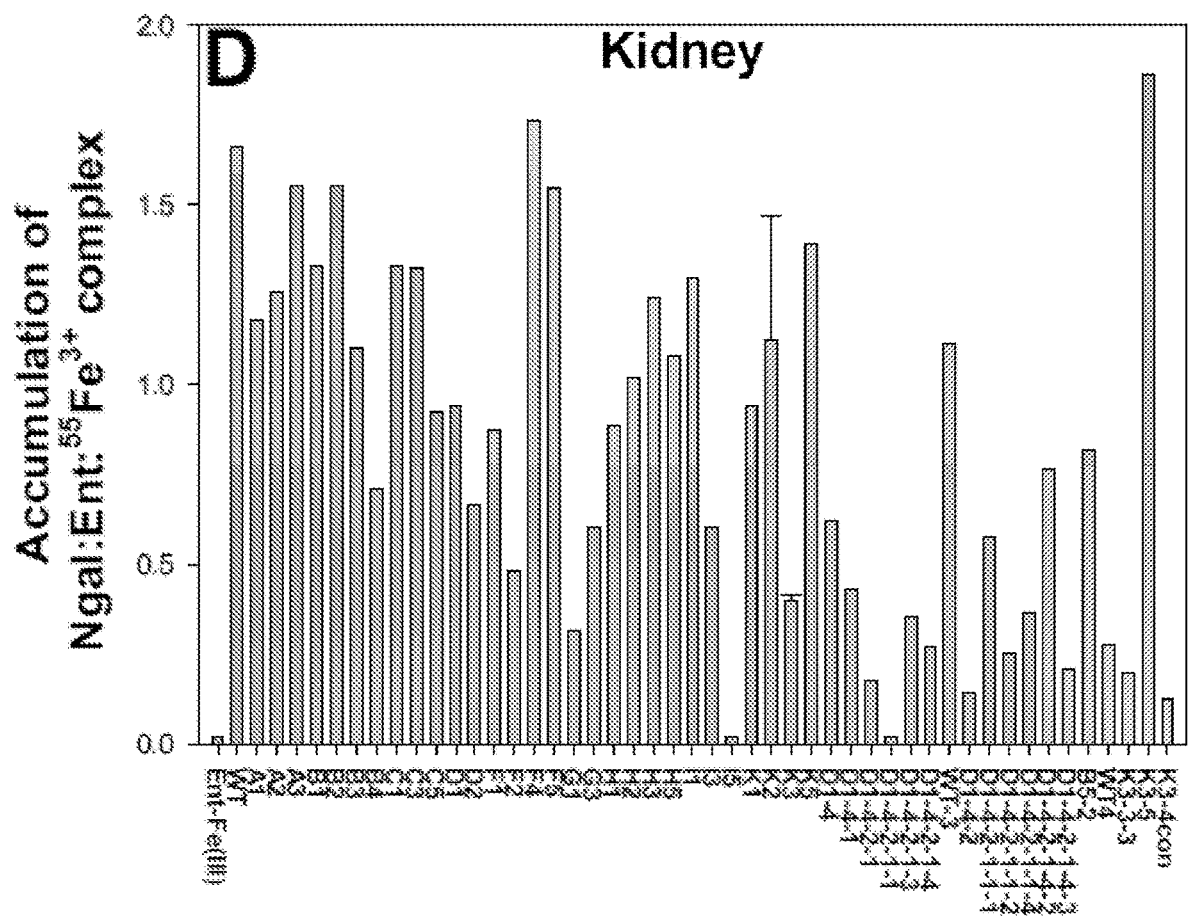

57 NGAL mutants were generated (Table 2; SEQ ID NOS:2-10, 21-68, 247-251). Twenty nine mutant apo-proteins were produced in BL21 E. coli, and were examined for their binding affinity to enterochelin and trafficking in C57B6L/6 mice after intraperitoneal (i.p.) injection. As shown in FIG. 3A, all mutant human NGAL proteins retained 16.7% to 45.7% of total iron after incubation with enterochelin-iron in a molar ratio of 1:1:1 (4 nmole each) for 30 minutes at room temperature, indicating their preserved binding affinity for enterochelin-iron (high amounts of enterochelin will increase loading of NGAL).

When administered by i.p. injection, six mutant NGAL-enterochelin-$^{55}Fe^{3+}$ complexes showed a markedly increased accumulation in urine compared with wild-type NGAL complex (mutants K3, K2, I3, I1, K5, and K1). Decreased accumulation in liver and kidney after 3 hours (FIG. 3B, C, D; Table 1) was also seen. There were 6%, 6.9%, 1.9%, 9.3%, 19.6% and 2.9% of I1, I3, K1, K2, K3 and K5 mutant NGAL complexes which were delivered to urine after 3 hours, respectively, while there were only 0.18%, 0.13%, 0.26%, 0.1%, 0.11%, 0.17%, 0.27% and 0.05% of A2, B4, C3, D1, F2, G3, H2 and I5 mutant NGAL complexes in urine.

Figure 4B:
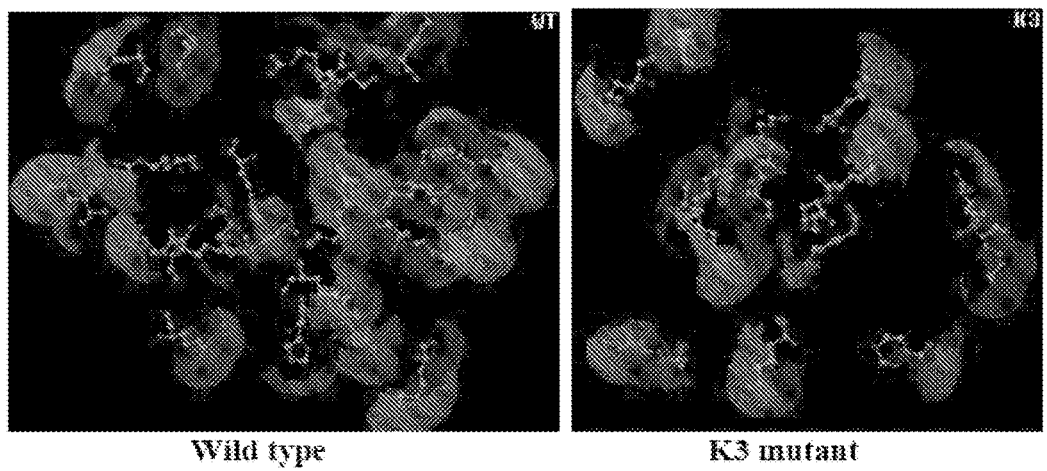

Using the crystal structure of wild-type NGAL (PDB accession number: 1ng1A) as substrate, the structure of K3 mutant protein was predicted by using Swissmodel (www.swissmodel.expasy.org). As shown in FIG. 4A, the predicted 3D structure of K3 mutant protein contains a similar pocket as the wild type protein, supporting our finding that affinity for enterochelin-iron is preserved. However, K3 mutant protein exhibited fewer positive amino acids on the solvent accessible surface than wild-type NGAL protein (FIG. 4B), consistent with its decreased ability for electrostatic interaction with megalin, and increased accumulation in urine once introduced into mice.

TABLE 1

Binding of mutant Ngal proteins to enterochelin-$^{55}Fe^{3+}$ and accumulation of mutant Ngal-enterochelin-$^{55}Fe^{3+}$ in urine, kidney and liver 3 hours after i.p. injection into C57BL/6 mice.

| Ngal Mutants | Enterocalin-iron Binding (%) | Accumulation 3 hours after i.p. injection (%) | | |
|---|---|---|---|---|
| | | Urine | Kidney | Liver |
| A1 | 23.4 | 0.55 | 0.32 | 1.10 |
| A2 | 22.6 | 0.18 | 0.37 | 1.11 |
| A3 | 26.6 | 0.23 | 0.39 | 1.52 |
| B1 | 20.7 | 0.22 | 0.26 | 1.30 |
| B2 | 25.7 | 1.22 | 0.34 | 1.27 |
| B3 | 26.9 | 0.30 | 0.26 | 1.01 |
| B4 | 45.7 | 0.13 | 0.32 | 0.71 |
| C1 | 26.2 | 0.72 | 0.21 | 1.15 |
| C3 | 20.6 | 0.44 | 0.33 | 1.22 |
| C5 | 21.9 | 0.26 | 0.44 | 0.85 |
| D1 | 29.1 | 0.10 | 0.26 | 0.94 |
| D2 | 18.1 | 0.11 | 0.16 | 0.60 |
| F1 | 26.1 | 0.51 | 0.69 | 0.79 |
| F2 | 21.5 | 0.11 | 0.40 | 0.51 |
| F4 | 22.8 | 1.65 | 0.43 | 1.68 |
| F5 | 27.7 | 1.23 | 0.29 | 1.61 |

TABLE 1-continued

Binding of mutant Ngal proteins to enterochelin-$^{55}$Fe$^{3+}$ and accumulation of mutant Ngal-enterochelin-$^{55}$Fe$^{3+}$ in urine, kidney and liver 3 hours after i.p. injection into C57BL/6 mice.

| Ngal Mutants | Enterocalin-iron Binding (%) | Accumulation 3 hours after i.p. injection (%) | | |
|---|---|---|---|---|
| | | Urine | Kidney | Liver |
| G1 | 33.5 | 0.28 | 0.05 | 0.33 |
| G3 | 26.9 | 0.17 | 0.58 | 0.30 |
| H1 | 38.7 | 0.37 | 0.15 | 0.89 |
| H2 | 36.1 | 0.27 | 0.12 | 1.06 |
| H3 | 31.1 | 0.30 | 0.15 | 1.25 |
| H5 | 38.6 | 0.24 | 0.09 | 1.07 |
| I1 | 32.1 | 6.00 | 0.20 | 1.21 |
| I3 | 42.8 | 6.90 | 0.27 | 0.55 |
| I5 | 16.7 | 0.05 | 0.10 | 0.02 |
| K1 | 21.2 | 1.90 | 0.76 | 0.82 |
| K2 | 31.4 | 9.60 | 0.43 | 0.68 |
| K3 | 22.9 | 19.60 | 0.27 | 0.40 |
| K5 | 28.4 | 2.90 | 0.18 | 1.37 |

Example 2

The superscripted numbers in this Example refer to the numbered references in the list of references that follows this Example. Ngal mutants "K numbers 1-8" represent actual Mutants K1, K2, D1-4-2-1-1, K5, D1-4-2-1-1-4, K3, WT-3 and WT4. The sequences of the mutants are provided herein in Table 2.

The transport of iron poses a significant problem because free ferric iron is insoluble (<10-18 M) in aerobic solutions at physiologic pH, while upon solubilization by some chelators, a reactive form of iron is created that can produce toxic oxygen species. Specialized mechanisms are consequently required to traffic iron and these specialized mechanisms are found in proteins which utilize conserved motifs to directly bind iron (transferrin and ferritin) or utilize embedded cofactors. While extracellular iron transport is largely mediated by transferrin, mice carrying deletions of these genes displayed surprisingly limited phenotypes (Barasch, Developmental Cell, 2009). It was found that a member of the lipocalin superfamily called Ngal acted as a high affinity iron carrier (Barasch, Molecular Cell, 2002) when binding a family of novel cofactors called the catechols or related bacterial siderophores constructed from catechol. In the presence of iron, formation of the Ngal:siderophore:FeIII complex occurred at subnanomolar affinity (Barasch, Nature Chemical Biology, 2010) forming a bright red protein, which was stable for many days in solution and stable in vivo for transport of its tightly bound iron. Ngal is expressed in vivo, but a number of "damage" stimuli raise its concentration by orders of magnitude. Thereafter, Ngal traffics in the serum and is thought to be captured by the kidney receptor megalin, where Ngal clears the siderophore:Fe complex. While a great deal is known about the metabolism of the urinary form of Ngal (it is expressed from the distal nephron and is excreted in the urine as a full length protein), much less is known about this clearance system and the role of the megalin receptor, which is the only confirmed receptor for Ngal. To study this process in depth a conditional mutant of megalin can be examined. Also, for studies in wild type mice a series of Ngal mutants can be tested. Some such mutants bypass the proximal tubule where megalin is located, resulting in their presence in the urine. These mutants can still bind to siderophore:FeIII at high affinity (and produce red colored proteins), and can definitely excrete iron, likely in a redox inactive manner. Indeed, rather than donate iron to micro-organisms, which is a major concern for small molecule chelators, the Ngal:siderophore:Fe complexes sequester iron from bacteria. The hypothesis that megalin is the key recycling receptor for Ngal can be tested. It is expected that when the megalin-Ngal complex is inhibited, Ngal can carry tightly bound iron in the urine, hence serving as a safe therapeutic for the common syndromes of iron overload diseases.

Iron overload diseases are common occurrences in clinical medicine, and their therapies have proved toxic to many cell lineages as well as inductive of bacterial growth. Iron overload is a common sequela of blood transfusions, but it is well known in hepatitis, chronic kidney disease as well as in common hereditary diseases such as hemachromatosis. The present invention involves the discovery of an iron trafficking pathway based on the protein Ngal, which is massively expressed in the human in different types of tissue damage. Our studies in Ngal metabolism provide proof of concept that Ngal can be used as a safe therapeutic iron chelator.

Iron is specifically bound by transferrin in circulation, which preserves its bioavailability and prevents its redox toxicity. However, non-transferrin-bound iron (NTBI) appears in patients with a variety of diseases' including both genetic causes and the non-genetic causes. NTBI damages liver[4-7], heart[8-12], endocrine glands[13-18] and kidney[9-21] and severe overload can be fatal[22,23] by catalyzing reactive oxygen species (ROS) via the Haber-Weiss and Fenton reactions[24-25].

To date, two small molecules, deferoxamine (DFO) and deferiprone are available for the chelation of NTBI and the treatment of iron overload[26-28]. However, these molecules demonstrate significant toxicity. DFO causes skin reactions, hearing loss, renal and pulmonary toxicity, and most interestingly fungal infection[29-32], which results because DFO (which is a derivative of a fungal "siderophore") can deliver iron to pathogens[32]. Deferiprone is also associated with genotoxicity, neutropenia and agranulocytosis and kidney disease[33,34]. Hence, new agents are required for non-toxic NTBI excretion, that do not deliver iron to microorganisms.

The present invention utilizes an endogenous mechanism of iron transport (*Molecular Cell*, 2002; *Nature N&V*, 2005; *Nature Chemical Biology*, 2010)[35-38], which is manipulated to safely export iron from the body. The carrier is called Neutrophil Gelatinase-Associated Lipocalin (Ngal). The present invention involves Ngal mutants which allow Ngal to be safely excreted in urine, still tightly binding its iron.

Ngal is a small iron carrier protein (22KDa) which is markedly expressed in the serum and in the urine when a human or an animal is exposed to a stimulus which typically causes acute kidney injury (AKI: *JASN*, 2003; *JCI*, 2005; *Lancet*, 2005; *Ann Int Med*, 2008)[39-42]. As a result, the protein is now well known as a "biomarker" of AKI, with well over 100 papers confirming its robust expression, yet only a few labs study its biology. We have found that once Ngal is expressed, it is rapidly secreted into circulation, where it can capture iron by binding cofactors such as endogenous catechols or related catecholate-type siderophores (Enterochelin, Ent)[36] which are synthesized by bacteria to capture iron (See FIG. 6A-6B). Hence, Ngal interrupts the nutrient supply of iron for bacteria, providing bacteriostasis.

Figure 7:
FIG. 7. Clearance of Ngal by the proximal tubule. Fl-Ngal was introduced into the peritoneum, and after 1 hour the kidney harvested. Ngal was localized to proximal tubule lysosomes.

Ngal complexes are stable for transport, and they are filtered by the glomerulus and captured by the proximal tubule (FIG. 7), where Ngal is degraded and iron is released for recycling[38]. Ngal is thought to be endocytosed by megalin in proximal tubule cells and a direct interaction between Ngal-megalin has been characterized using surface plasmon resonance (SPR/Biacore™)[43]. The present invention involves Ngal mutants that may bypass megalin, yet still bind Ent:iron, hence providing a therapeutic that can safely excrete NTBI in the urine.

Evaluation of the Ngal-Megalin Interaction Using Ngal Mutants

Since megalin may be the major receptor mediating the reabsorption of filtered Ngal[43], 40 mutant Ngal proteins were produced, some of which are believed to target the Ngal-megalin interaction. The megalin hypothesis can be tested using one of these mutants (K6, i.e., K3) and its optimized derivatives, which partially bypass the proximal tubule and appear in the urine. This mutant can be used to study protein interactions, and cellular, and organ capture in wild type mice and in conditional megalin knockouts, to confirm that the interruption of megalin permits the excretion of iron. Additional mutants can also be tested using this system.

Evaluation of the Ngal:Ent:$Fe^{III}$ Interaction in Ngal Mutants

Figure 8:
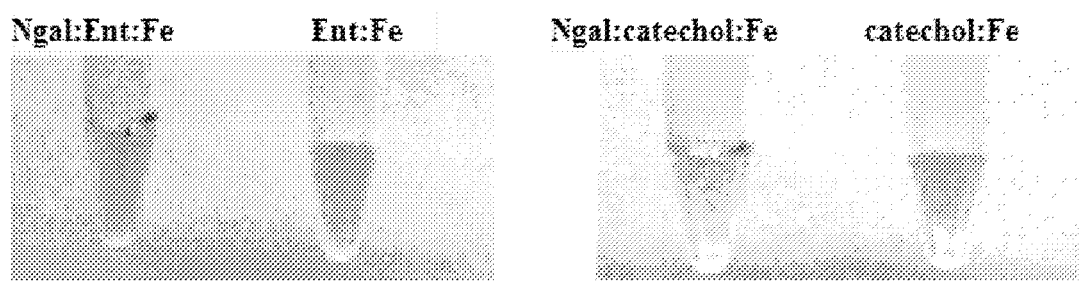
FIG. 8. While ligand-metal charge-transfers between Ent and Fe3+ (lmax=498 nm) were not modified by the addition of Ngal protein (note red coloration in 2 left tubes), catechol:Fe3+ converted from a FeL complex (blue, lmax=575 nm) to a FeL3 complex (red, lmax=498 nm) when bound to Ngal (right tubes) and produced an identical spectrum as Ent:Fe.

Ngal contains a central calyx where, when Ent:$Fe^{III}$ is bound, a bright red protein[35] is produced (FIG. 8). Ngal mutants, engineered to reduce their interactions with megalin, were also brightly red colored when mixed with Ent:$Fe^{III}$, indicating retention of ligand affinity. The Ngal complexes can be quantitatively analyzed using Flourescence Quenching techniques and X-Ray Crystallography.

Safe Excretion of Iron by the Delivery of Mutant NGAL: Ent:$Fe^{III}$

K6 (i.e., K3) and optimized mutants can be administered to mice to test NTBI chelation and urinary excretion of $Fe^{III}$ in murine models of hereditary ($HFE^{-/-}$)[44,45] and acquired hemochromatosis[44]. Efficacy can be evaluated by measuring the depletion of NTBI from serum and liver, and toxicity can be ruled out by measuring oxidative stress and the expression of endogenous Ngal, which we previously discovered, indicates the onset of kidney damage.

Significance Iron overloaded patients demonstrate elevated serum transferrin saturation (>50%) and elevated serum ferritin levels (>1000 μg/L)[1-3]. They also demonstrate non-transferrin-bound iron in circulation (NTBI, e.g. 0.9-12.8 μmol/L in thalassemic sera; 4-16.3 μM in hereditary hemachromatosis (HH) sera[2]), as well as a labile iron pool (LIP) within cells[46]. These abnormal pools of iron participate in Haber-Weiss and Fenton reactions which oxidize lipids and proteins and mutate nucleotides by forming hydroxyl, ferryl, or perferryl species[24-25,47]. Ultimately, cell death is found in a variety of sensitive organs, including liver (fibrosis/cirrhosis and hepatocellular carcinoma)[4-7], heart (congestive cardiomyopathy)[8-12], kidney (necrosis and apoptosis of proximal tubular cells)[19-21] and endocrine glands (diabetes, hypothyroidism, and hypogonadism)[13-18].

In general there are two types of iron overload disorders, hereditary hemachromatosis (HH) and acquired hemochromatosis (AH). HH is caused by loss of function of genes associated with the regulation of iron metabolism, such as HFE (type 1 HH), HJV (type 2A HH), HAMP (type 2B HH), TfR2 (type 3 HH), SLC40A1 (type 4 HH), CP (aceruloplasminaemia), TF (hypotransferrinaemia)[3,48]. In the most common entity, Type I HFE C282Y allele, 28% of males were iron overloaded[49]. AH in contrast is caused by blood transfusions, thalassaemia major, sideroblastic and hemolytic anemias, dietary iron overload, chronic kidney and liver diseases due to hepatitis C or alcohol or porphyria[3,44,48]. The 5 million blood transfusions, >15 million units/yr in the US are the most common cause of AH[50]. Blood transfusions cause iron overload because while the human loses 1-2 mg iron per day, each unit of blood contains 250 mg of iron and clear evidence of toxicity appears after 20 transfusions[51-53]. Chronic kidney diseases can also produce a syndrome of excess iron deposition in the proximal tubule and in the urinary space. Iron is deposited in the kidney cortex in HIV associated nephropathy[54] as well as in other forms of nephrotic syndrome[55]. Urinary iron is also a common finding in AKI of various etiologies including hemoglobinuria and myoglobinuria[56], chemotherapy (cis-platin[57]; doxorubicin[58]), ischemia-reperfusion[59,60] and transplant ischemia[61]. It is believed that the release of iron into the urine is a critical step in cell damage[62-69]. In sum, both HH and AH patients suffer organ damage without iron chelation therapy[22,23].

Figure 9:
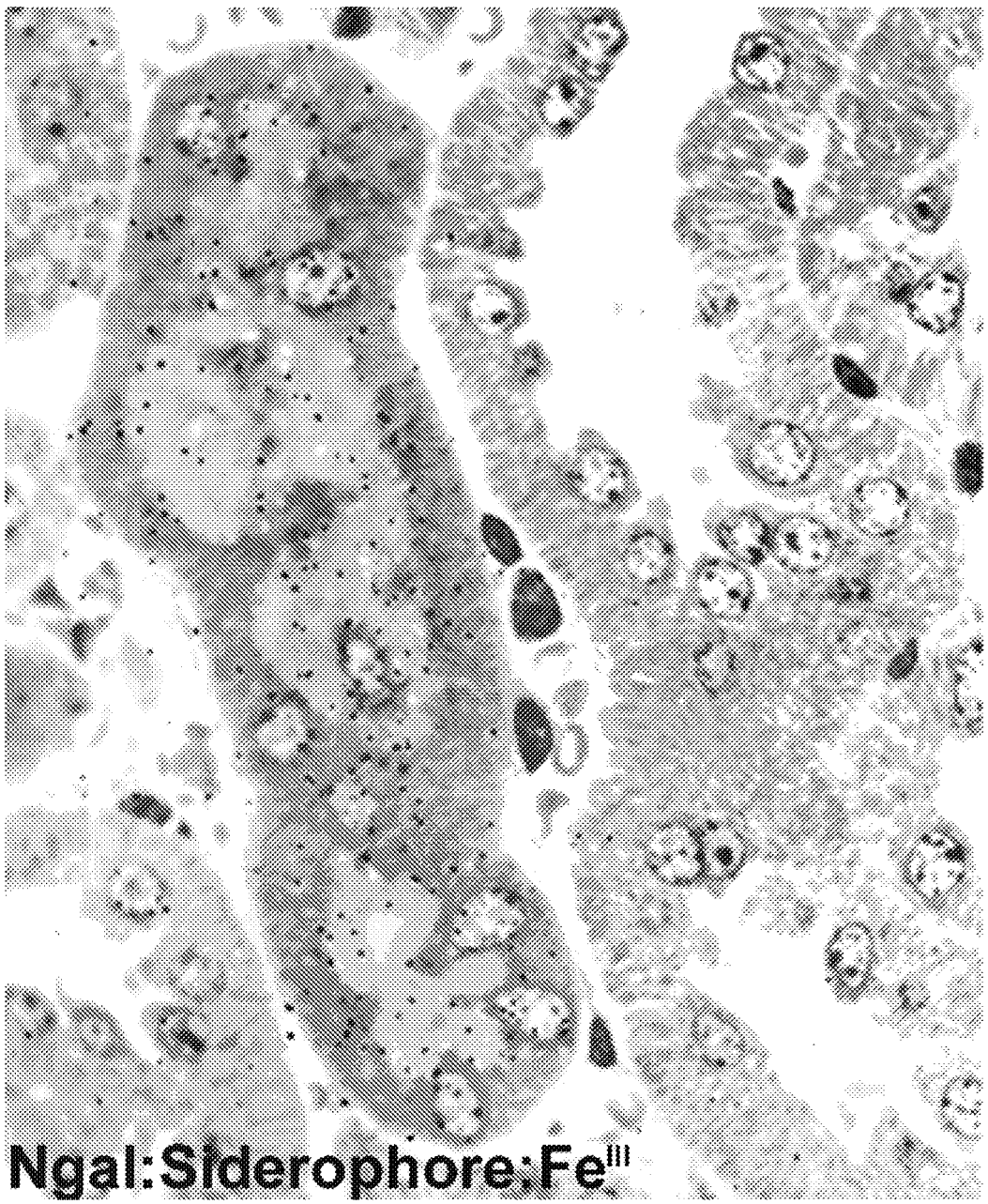
FIG. 9. Trafficking of 55Fe bound to Ngal through the serum to the kidney was visualized by radioautography. Note the black silver grains in proximal tubules but not in distal nephrons after introduction of Ngal:Ent:55Fe or Ngal:catechol:55Fe.
Figure 10:
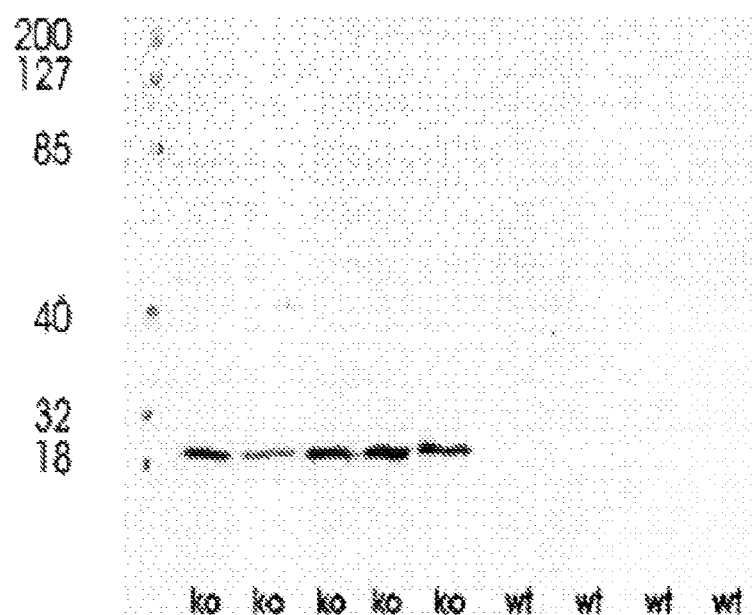
FIG. 10. Urine was collected from both wild type and megalin deleted mice. Ngal was detected by immunoblot using polyclonal anti-mouse Ngal antibodies.
Figure 11:
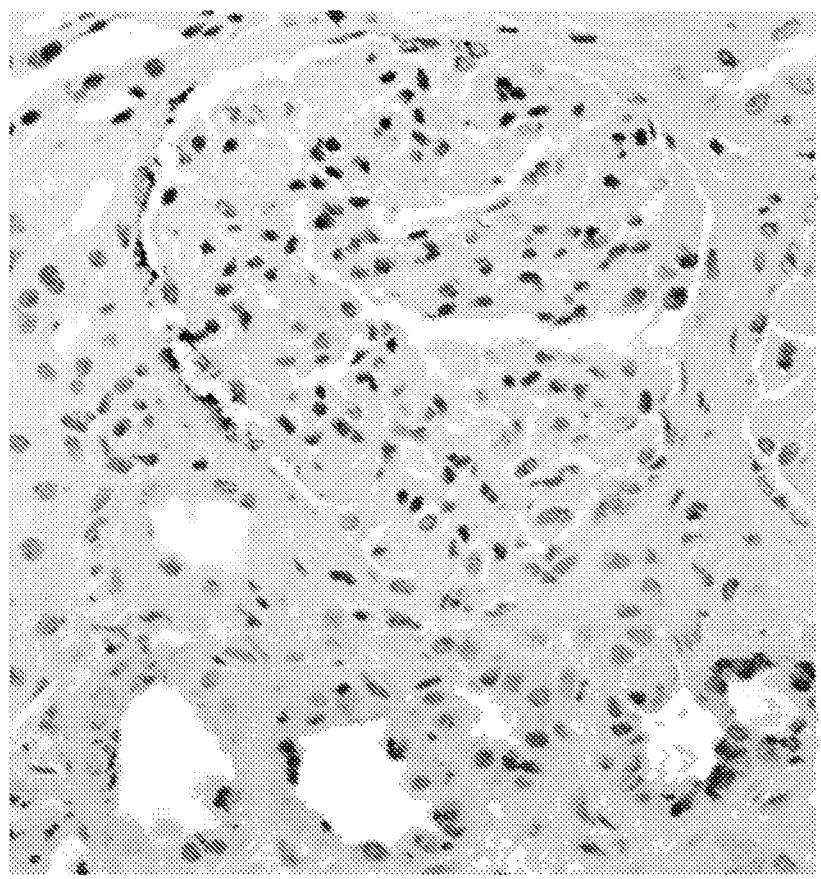
FIG. 11. Human kidney biopsy for AKI stained with anti-Ngal antibodies. Note the association of NGAL with Bowman's Capsule and with the proximal tubule (red-brown staining) apical endosomes.
Figure 12:
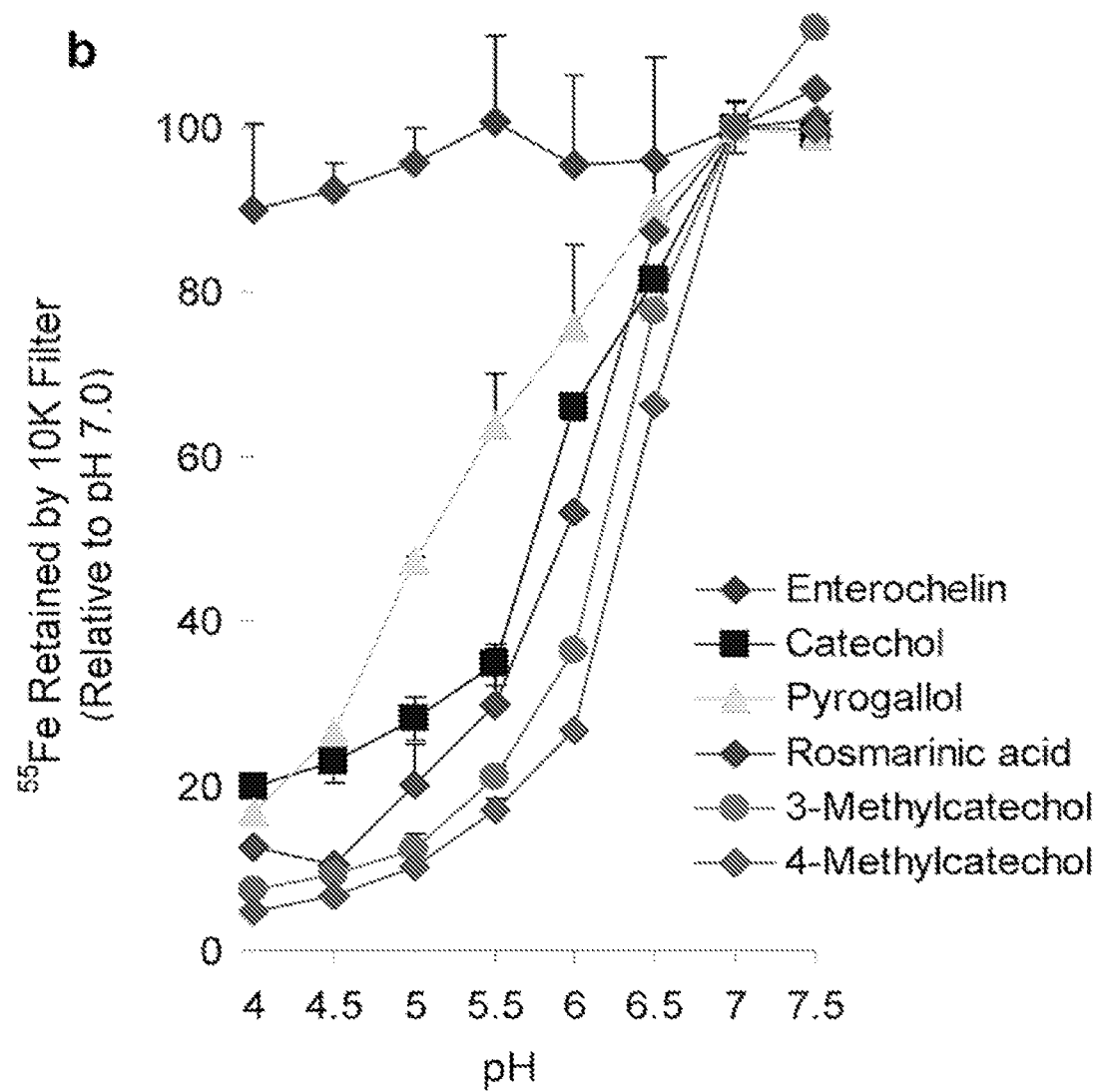
FIG. 12. Release of ligands from Ngal as a result of acidification. Low pH released 55Fe from Ngal:catechol:FeIII complexes but not from Ngal:Ent:FeIII. FeIII loading at pH 7.0 was defined as 100% of the assay. Catechol differed significantly from Ent (P=0.00012).

Two iron-chelating chemicals are currently in clinical use[26-28], but both are limited by toxicity and long-term safety concerns (e.g. "Deferasirox: Uncertain future following renal failure fatalities, agranulocytosis and other toxicities. Expert Opin Drug Saf. 2007 6:235-9)[29-34]. The present invention provides a novel strategy which takes advantage of the endogenous mechanisms of iron trafficking which is manipulated to develop a highly efficient, non-toxic iron chelator for the treatment of iron overload. Ngal is well suited to this approach because of the following characteristics. Ngal was first identified as an iron carrier and growth factor in kidney cells[35]. Second, Ngal binds iron (FIG. 6A-6B) by using bacterial siderophores (such as enterochelin [Ent] from Gram-negative bacteria, bacillibactin from Gram-positive bacteria and carboxymycobactins from mycobacteria[36,70]) or alternatively endogenous catechols found in mammals[38]. Ent and catechols have extremely high affinity for iron ($K_d=10^{-49}$ M and $10^{-45.9}$ M, respectively)[71,72], and Ngal strongly binds Ent:Fe and catechol:Fe ($K_d=0.4$ nM)[36,38], which allows these complexes to sequester iron. In fact, the chelation of bacterial siderophores by Ngal is a critical aspect of the innate immune response, given that the $Ngal^{-/-}$ mice do not clear bacterial inocula[37]. These data stand in contrast to the high affinity iron chelator DFO ($K_d=10^{-30}$ M)[73] which can deliver its iron to *Rhizopus* and induce fatal MucorMycosis[32]. Third, binding of iron to Ngal limited its reactivity as demonstrated by the suppression of phenanthroline and 3'-(p-hydroxyphenyl) fluorescein (HPF) tests of reactive $Fe^{2+}$; in other words, binding to Ngal blocked the Fenton reaction[38]. Fourth, Ngal can load with iron in vivo when it was presented with Ent:$^{55}$Fe or Catechol:$^{55}$Fe; the Ngal complex can then be recovered from the serum five minutes later. Fourth, Ngal loaded with iron traveled through the circulation and targeted the mouse kidney, as demonstrated by radioautography[38,40] (FIG. 9). This process most likely involved glomerular filtration of the Ngal complex, followed by megalin-mediated endocytosis at the apical membrane of the proximal tubule[43] since we found Ngal in the urine of megalin knock-out mice[74] (FIG. 10), and since Surface Plasmon Resonance Analysis (Biacore™) showed that Ngal and megalin interacted directly ($K_d=60$ nM[43]). Fifth, the same process was ongoing in humans, since Ngal was visualized in lysosomes of the proximal tubule of patients with AKI (FIG. 11). Sixth, Ent had a very high affinity for Ngal even in the absence of iron ($K_d=3.57$ nM)[75], while catechol itself bound to Ngal with poor affinity ($K_d=200\pm6$ nM)[38] meaning that Ent was even a better candidate for iron capture and transport than catechol. Finally, the Ngal:Ent:$Fe^{III}$ complex was pH insensitive, failing to dissociate even at pH 4.0, while Ngal:catechol:$Fe^{III}$ complexes were stable until pH6.5, but acidification progressively reversed catechol-dependent fluorescence quenching and resulted in the dissociation of iron by pH 6.0 (FIG. 12)[38]. Hence, because of its stability at acidic pH, Ngal:Ent:Fe$^{III}$ is not expected to dissociate in acidified urine.

In summary, Ngal:catechol/Ent can chelate NTBI in the circulation with high affinity and clear iron in the kidney. This pathway is active in humans in vivo and potentially traffics large amounts of Ngal and iron: if the GFR is 140 L/Day and the concentration of serum Ngal is 20 ng/ml, 2.8 mg/day of NGAL (0.14 μmole) and 8 μg iron are recycled in the proximal tubule, but in the setting of ischemia, renal failure, sepsis, the level of Ngal rises 100-1000 fold, meaning a very substantial mechanism of clearance may be ongoing (depending on the residual GFR). Therefore, to understand the capture of iron in the kidney and to create a new therapy, we have decided to disrupt the reabsorption of Ngal.

Innovation: A. The first area of innovation has to do with the treatment of iron overload diseases which for too long has relied on toxic chelators[29,34]. The present invention provides a strategy to develop high-efficacy, non-toxic NTBI chelators. This strategy has many advantages over current iron chelators in that (1) Ngal provides an endogenous pathway for delivering iron to the kidney[35,36,38,39]; (2) Ngal:Ent has higher affinity for iron than any other known substance[71,72]; (3) Ngal:Ent:Fe$^{III}$ is redox inactive[38]; (4) Ngal:Ent:Fe$^{III}$ is stable in acidified urine[38] and hence (5) may chelate urinary iron, perhaps alleviating damage in certain renal diseases. A second area of innovation is a description of the metabolism of Ngal-iron. A bioluminescent mouse can be used to compare the timing and intensity of Ngal gene expression in the kidney and in the urine, which has provided a clear understanding of the biosynthesis and excretion of this pool (Paragas et al, In Review). Ngal mutants can directly test the role of megalin in wild type mice and provide complimentary data for the analysis of megalin defective mice. This approach can also test the notion that a second NGAL receptor (24p3R)[76] may be present in the nephron.

Evaluation of the Ngal-Megalin Interaction by the Generation of Ngal Mutants

Figure 13:
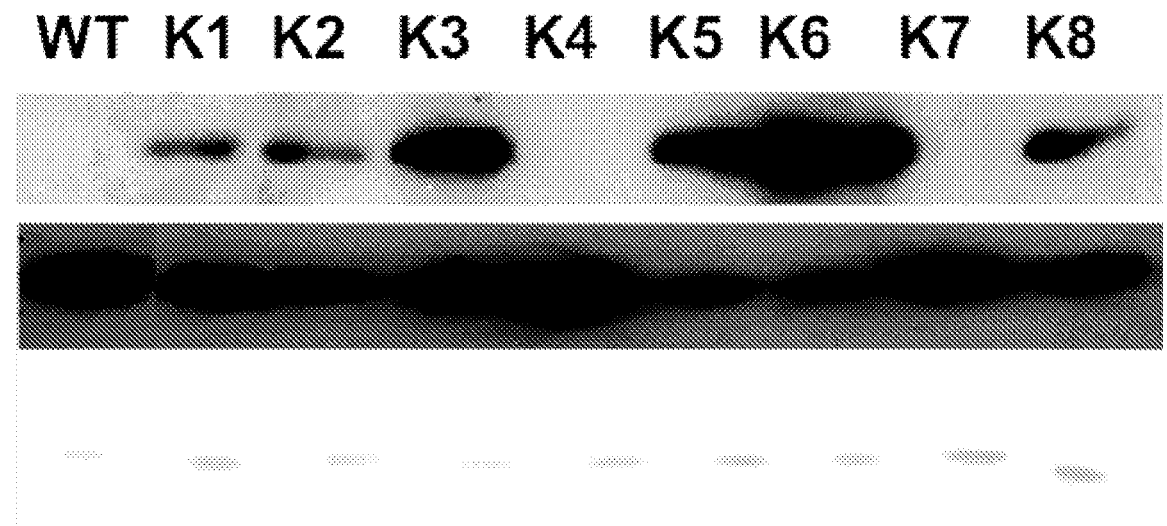
FIG. 13. Top Urine Immunodetection by Western Blot of WT and mutant Ngal species in the urine 3 hrs after i.p. injection (80 micrograms). Middle Starting Material shows immunoblot of purified WT and Mutant Ngal proteins (100 ng) and Bottom SDS-Page and Coomassie stain of each mutant. The designations "WT" and "K numbers 1-8" represent Wild Type and actual Mutants K1, K2, D1-4-2-1-1, K5, D1-4-2-1-1-4, K3, WT-3 and WT4.

Megalin is thought to bind its ligands using a series of electrostatic interactions between megalin's negatively-charged ligand-binding domains and the positively-charged surface-domains of the ligand[77]. Consequently, by mutating Ngal's positively charged surface residues the megalin-Ngal interaction can be disrupted. Surface domains of human Ngal were identified based on its crystal structure (R. Strong; PDB no. 1L6M) using the software Pymol[78]. The surface domains contained 18 positively charged amino acids (Lys 15, Lys 46, Lys 50, Lys 59, Lys 62, Lys 73, Lys 74, Lys 75, Lys 98, His 118, Arg 130, Lys 149, and His 165, R43, 72, 140, and K142, 157), 5 of which were conserved in mammalians[36], and these residues were chosen for site-directed mutagenesis. The human Ngal ORF (without signal peptide sequence) was cloned into pGEX-4T-3 bacterial expression plasmid (Amersham) to generate a GST-Ngal fusion to create a template for mutagenesis. The conserved positively charged surface residues were then mutated to alanine. Non-conserved amino acids were mutated to non-positively charged residues which occupied the same position in non-human Ngal proteins. For mutagenesis a single or a combined strategy with the QuikChange™ Site-Directed Mutagenesis kit (Stratagene) was used, producing 40 Ngal mutant clones. Wild-type and mutant Ngal proteins were then produced in BL21 *E. coli* by induction with 0.2 mM IPTG, and purification by GST-based affinity isolation and gel filtration chromatography using our established protocols[35,38]. We then functionally screened these Ngal proteins by introducing them (80 μg/400 μl) into C57BL/6 mice (4 weeks) to identify which mutants could bypass renal absorption and appear in urine within 3 hrs. Ngal mutants K1, K2, K3, K5, K6 (i.e., K3), and K8 were detected in the urine by SDS-PAGE as well as by immunoblot using a human Ngal-specific antibody developed in rat (R&D System) (recombinant Ngal=21 KDa; endogenous Ngal=25 KDa), suggesting that the mutations resulted in loss of affinity for the recycling receptors on the apical plasma membrane of proximal tubular epithelia. In contrast, wild-type, K4 and K7 mutants could not be detected in the urine and consequently were most likely reabsorbed (FIG. 13). These data provide valuable information about the Ngal-megalin interaction because they test whether variations in Ngal reabsorption may be ascribed to variations in the megalin-Ngal interaction, providing insight into the mechanisms of clearance of serum Ngal, and allowing the optimization of mutants to excrete iron.

Structural Basis for NGAL-Megalin Interaction

Interactions with Megalin

The interaction between wild-type human Ngal (ligand-free) and chip-coupled megalin ($K_d$=~60 nM)[43] purified from human kidney cortex was previously analyzed by $\alpha_2$-macroglobulin-affinity chromatography[79]. Biacore™ T100 technology can be used to compare wild type and K6 (i.e., K3) (or other mutant) interactions with megalin. Whether ligand-binding influences Ngal-Megalin interaction can also be tested by using bacterial siderophores and catechol ligands. Data can be calculated with BIAevaluation 4.1 software (Biacore™), globally fitting data to derive kinetic and equilibrium parameters. A range of coupling and regeneration conditions can also be used, though antibody-capture often provides the cleanest data.

Megalin Mediated Endocytosis

Classical megalin-expressing cell models can be used to investigate megalin-binding and endocytosis. Such cells include HK-2[90] and Brown Norway rat yolk sac epithelia[43]. Rat yolk sac cells are important because megalin is the only receptor which mediates endocytosis of human Ngal in these cells, since uptake was completely abolished with anti-megalin antibodies[43] (the neutralizing antibodies proved more effective than megalin shRNA). Wild-type and K6 ((i.e., K3) mutant proteins (and other mutants) can be labeled with fluorescent probes (Alexa Fluor™ 488, Molecular Probes) cleaned-up by gel filtration (GE Biotech, PD10) and dialysis (Pierce 10K cassette)[35,43] in order to study their rate of uptake (50 μg/ml in serum-free DMEM for 0.5-6 hours) in the presence or absence of anti-human or anti-rat megalin antibodies (Santa Cruz; 200 μg/ml)[43] which were previously shown to block uptake of wild type human Ngal in BN cells[43]. Endocytosis of Ngal can be measured both by using a Zeiss LSM510-META inverted confocal laser scanning microscope and immunoblots of cell extracts to detect the presence of human Ngal. These experiments can determine whether the failure to capture K6 (i.e, K3) (or other mutants) can be ascribed to defective Ngal-megalin interactions and if the affinity defect or the endocytosis defect is truly partial. If so, then additional mutations can be provided to disrupt the remaining interactions with megalin. The remaining positively charged surface residues in K6 (i.e, K3) (or other mutants) can be mutated using a single or combinational approach as above, and then reiteratively tested using the Biacore™ assays and the cellular uptake assays. As a result of these mutations, the role in megalin in Ngal capture and Ngal's megalin binding domain can be defined. Additionally optimized mutants can be generated.

Alternative Receptors

Our data (FIGS. 9 and 13) and a previously published report[43] suggests that megalin is an essential receptor for Ngal. However, there may be non-megalin receptor(s) in the proximal tubule. The main candidate is 24p3R (SLC22A17), which is found throughout the kidney and shown to mediate Ngal endocytosis[76], but its function is not yet confirmed. Stably transfected HEK293 cells over-expressing human 24p3R can be generated, and the uptake of Alexa Fluor™-488 labeled wild-type and K6 (i.e, K3) mutant Ngal and Ngal:Ent:Fe$^{III}$ can be determined, for example by using confocal microscopy and immunoblots. If 24p3R stimulates the uptake of wild-type Ngal, it can be a receptor for Ngal, and the K6 (i.e., K3) mutant (and other mutants) may show defective interactions with this receptor.

Distribution of Ngal Mutants In Vivo

A further test of the Ngal-megalin interaction can be performed using a megalin conditional knockout murine model[91], in which megalin is deleted in the proximal tubular epithelia using floxed-megalin mice and gGT-Cre which specifically deletes genes in 80% of cells in the S3 segment of the proximal tubule[92]. According to TE Willnow[91], these conditionally deleted mice are viable and fertile. The efficiency of the megalin deletion can be confirmed by immunohistochemical staining with anti-megalin antibodies. If the deletion is complete, megalin$^{f/f}$ mice can be bred with megalin$^{f/+}$ gGT-Cre mice to generate megalin$^{f/f}$:gGT-Cre mice (25%) and littermate controls megalin$^{f/f}$ (25%), megalin$^{f/+}$:gGT-Cre (25%) and megalin$^{f/+}$ (25%). The megalin deleted mice (n=12) can be identified by PCR-genotyping the floxed allele and the gGT-cre recombinase. Alexa Fluor™-488- or rhodamine labeled wild-type or K6 (i.e, K3) mutants (two different labels to avoid the contribution of negative (Alexa Fluor™-488) or positive (Rhodamine) charges) can be tested by i.p. injection into 4 week old mice and their trafficking analyzed by using a Zeiss LSM510-META inverted confocal laser scanning microscope and immunoblots with anti-human antibodies. Since megalin expression is limited to proximal kidney epithelia, parathyroid cells, epididymal epithelial cells, type II pneumocytes, mammary epithelial and thyroid follicular cells, the distribution of both wt and mutant Ngal in wt and knockout mice can be investigarted to explore the Ngal-megalin interaction in vivo. If the capture of wt Ngal by the proximal tubule is abolished in the conditional megalin-ko kidney, and Ngal is excreted (similar to FIG. 10), megalin is likely the only Ngal receptor in the kidney and the proposed receptor 24p3R is non-essential. If this is the case, then the distribution of wt Ngal should also correlate with the distribution of megalin in different tissues. Moreover, if Ngal mutants such as K6 (i.e, K3) have poor affinity for megalin, their escape in the urine can be directly explained. On the other hand, if wt Ngal is captured in the megalin knockout proximal tubule and by cells of the body where megalin is not expressed, then alternative receptor(s) are expected. In this case, the excretion of mutant Ngal may be the result of loss-of-affinity not only for megalin, but for non-megalin receptors.

Evaluation of the Ngal:Ent:Fe$^{III}$ Interaction in Ngal Mutants

Figure 14:
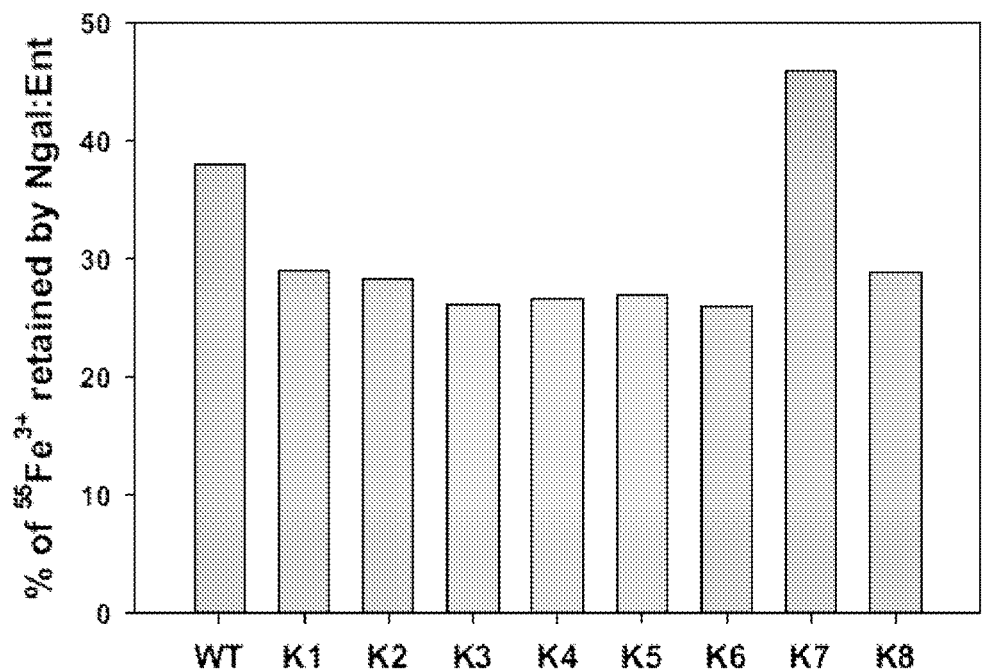
FIG. 14. 55Fe3+ retaining activity of wild-type and mutant Ngal:Ent. The designations "WT" and "K numbers 1-8" represent Wild Type and actual Mutants K1, K2, D1-4-2-1-1, K5, D1-4-2-1-1-4, K3, WT-3 and WT4.
Figure 15A:
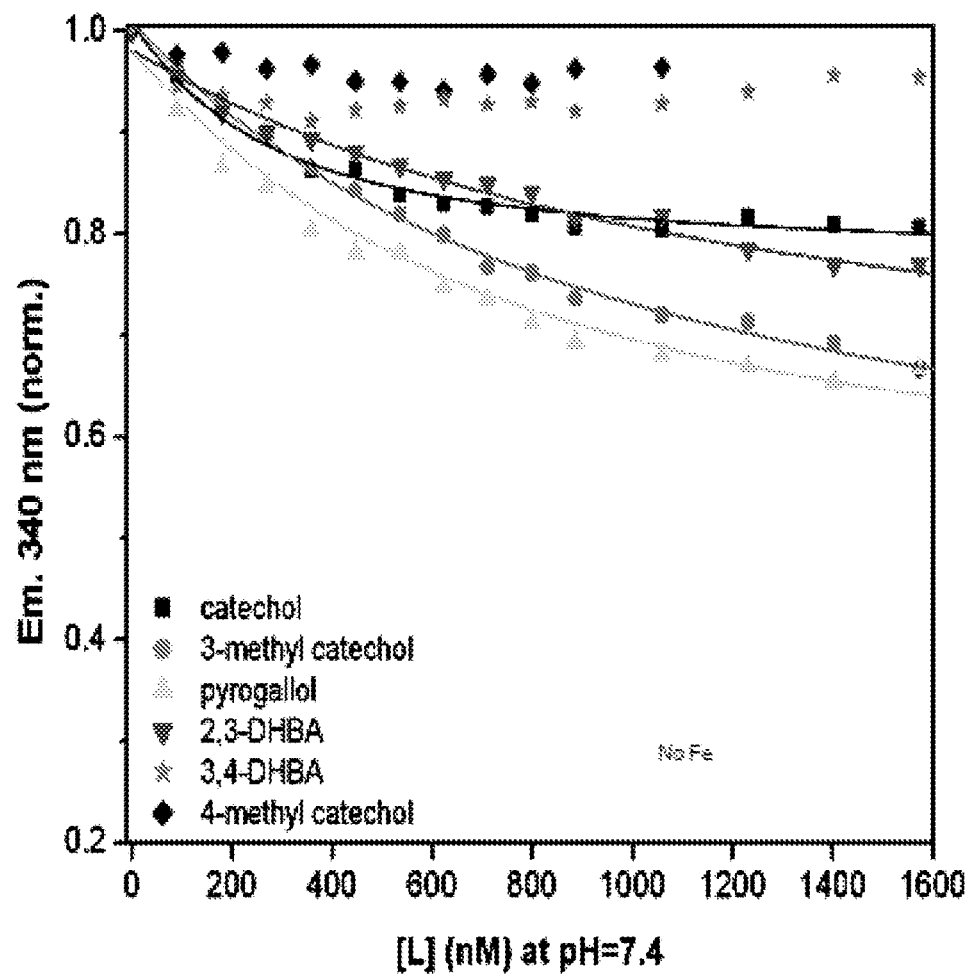
FIGS. 15A-15B. Determination of the affinity of siderophore:iron in complex with wild type Ngal.
Figure 15B:
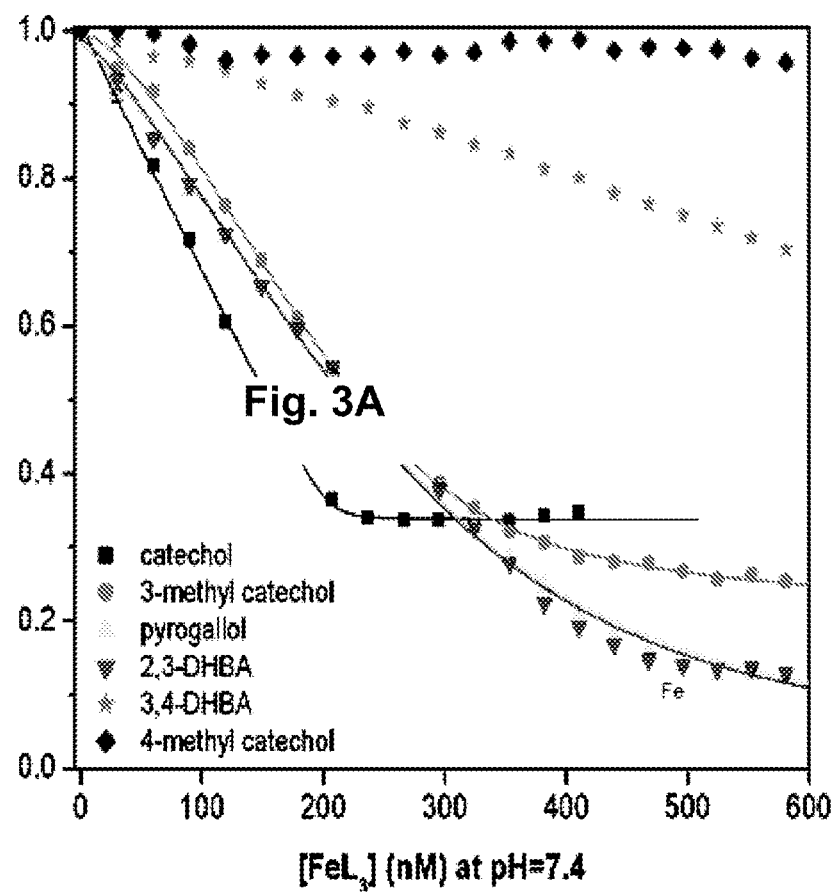

Ngal specifically binds Ent:Fe$^{III}$ and Ent with high affinities (0.4 nM and 3.57 nM, respectively)[36,75], and it fails to release bound iron even at low pH[38]. Ngal sequestered iron no longer participates in chemical reactions and the complex is stable for transport in circulation. Whether loss-of-"reabsorption" mutants still have the capacity to bind ferric siderophores at high affinity can be tested. Initial data shows that the mutants retain iron in the presence of Ent (FIG. 14) and demonstrates a distinct red coloration. The K6 (i.e., K3) Ngal:Ent interaction can be quantified and the structural effects of the introduced mutations can be determined.

Quantitative Measurement of Ent:Fe$^{III}$ Binding by Ngal

A fluorescence quenching (FQ) strategy (Nature Chemical Biology, 2010[38], FIG. 10) can be utilized to quantify the spectrum of Ngal and Ngal mutant:ferric siderophore interactions[93-98] to derive affinity measurements for Ent binding. Excitation $\lambda_{exc}$=281 nm and emission $\lambda_{em}$=340 nm data can be collected from 100 nM K6 (i.e., K3) Ngal mutant protein solutions (with 32 µg/mL ubiquitin and 5% DMSO), exposed to Ent:Fe. The pH sensitivity of the complex can be determined by incrementally adjusting the solution's pH until the fluorescence signal stabilizes. The data can be examined using nonlinear regression analysis using a one-site binding model (DYNAFIT)[99]. Control experiments can be performed to ensure protein stability. Alternative techniques include SPR and isothermal titration calorimetry (e.g. from the Strong group[86]).

Structural Basis for the Formation of Mutant Ngal:Ent:Fe$^{III}$

In order to confirm that mutations introduced to disable megalin binding do not interfere with ferric siderophore ligand recognition, the structure of K6 (i.e., K3)±Ent:Fe$^{III}$ can be determined by X-Ray Crystallography. Over 20 Ngal crystal structures, including human, murine and mutant forms, ±N-linked CHO, both empty and bound to a series of natural siderophores or synthetic analogs have been determined previously[36,38,93,99,100]. Since the K6 (i.e., K3) mutations affect crystal contacts in all the known Ngal crystal forms, this can be approached as a de novo structure determination. For crystallization, the protein can be highly purified by GST chromatography, followed by gel filtration and ion exchange chromatography, with purity and monodispersivity determined by reduced/non-reduced PAGE and mass-spectroscopy with concurrent static/dynamic light scattering (SLS/DLS). Monodispersed protein preparations can be screened for crystallizability using sub-microliter robotics and commercially-available factorial screens. Preliminary crystals can be optimized in conventional crystallization formats using established methodologies that catalyze crystallization. Alternatively, the protein can be more stringently purified or complexed with Fabs (the structure of a murine Ngal:Fab complex [crystallized from 20% PEG 4000 and 10% isopropanol, pH=7.0; space group: P2$_1$2$_1$2$_1$, a=37.9 Å, b=69.4 Å, c=117.6 Å; d$_{min}$=2.15 Å, R$_{merge}$=0.04] was determined—a panel of over 16 anti-human Ngal antibody Fabs can be used for co-crystallization). Diffraction data can be collected. Data can be reduced with any of a variety of available software packages and can be phased by direct difference Fourier (for isomorphous crystals), molecular replacement (MR), MAD (generally using selenomethionine) or MIRAS (using any of a variety of derivatization strategies). These data can quantitatively characterize Ngal:Ent interactions, indicating whether K6 (i.e., K3) (or other mutants) have retained affinity for Ent:Fe$^{III}$. These studies can show that the introduced mutations impair ligand binding, and the structures can be used to engineer additional mutations.

Safe Excretion of Iron by the Delivery of Mutant NGAL:Ent:Fe$^{III}$

Figure 16:
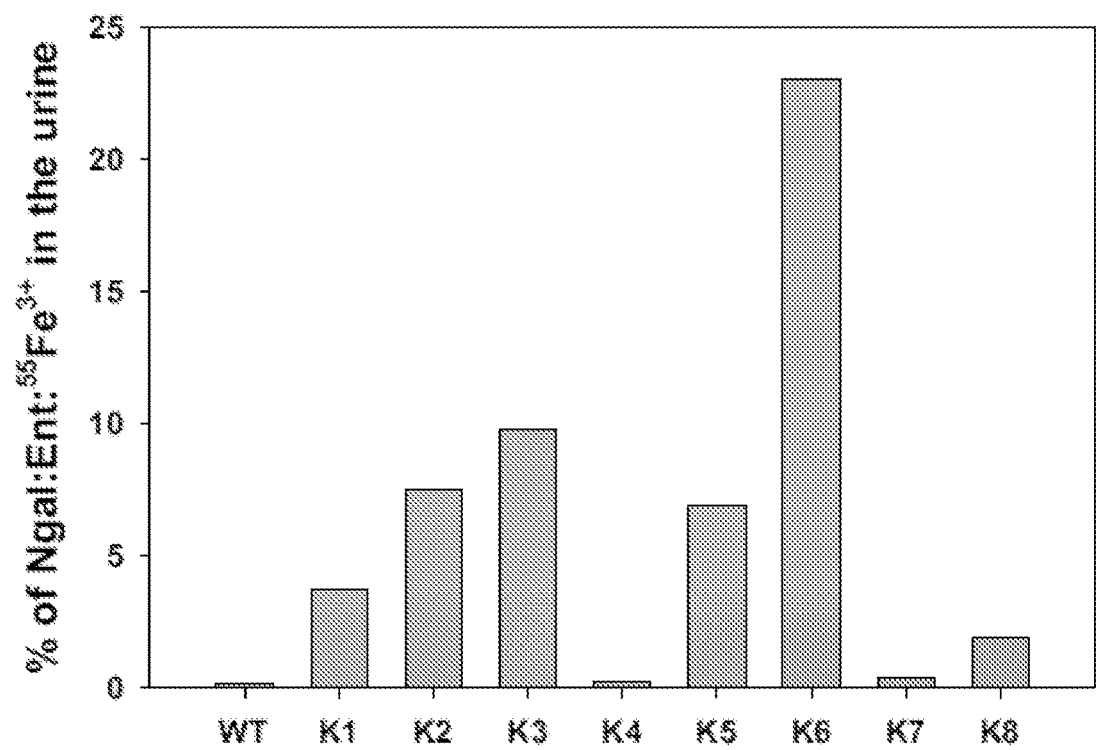
FIG. 16. Analysis of 55Fe3+ which was delivered by wild-type or mutant Ngal:Ent into mouse urine. The designations "WT" and "K numbers 1-8" represent Wild Type and actual Mutants K1, K2, D1-4-2-1-1, K5, D1-4-2-1-1-4, K3, WT-3 and WT4.

To test whether K6 (i.e, K3) Ngal:Ent can efficiently chelate and deliver NTBI to the urine through the kidney, the K6 (i.e, K3):Ent:$^{55}$Fe$^{III}$ complex (80 µg) was introduced into mice (4 weeks), and collected the urine for 3 hrs in metabolic cages. As shown in FIG. 16, 23% of the injected K6 (i.e., K3)-$^{55}$Fe$^{III}$ complex was delivered to the urine, paralleling the percentage of K6 (i.e, K3) protein found in the urine (FIG. 13), while less than 0.1% of the wild type injectate was excreted. Only trace amounts of $^{55}$Fe$^{III}$ accumulated in the liver (<1%), indicating that once iron was chelated by K6 (i.e, K3):Ent, it was mainly delivered to the kidney and the urine. Based on these results, it can be tested whether K6 (i.e, K3):Ent can capture, chelate, traffic and remove endogenous NTBI.

Chelation and Excretion of NTBI by K6 (i.e., K3):Ent in Murine Models of Hemochromatosis Establishment and Evaluation of Mouse Models A mouse model of Type 1 hereditary hemochromatosis lacking the Hfe gene is available from the Jackson Labs (Stock #: 003812). These mice develop organ iron overload 12 weeks after weaning[101]. A mouse model of acquired hemochromatosis can be established as reported previously[101]. This mouse model of transfusion mediated iron overload was made by transfusing stored (14 days at 4° C.) mouse RBC (200 or 4004 at 17.0-17.5 g/dL hemoglobin) into a recipient via the retro-orbital plexus of isoflurane-anesthetized mice, which is the equivalent of transfusing a human with 1-2 units of RBC. Briefly, the RBCs are obtained from 30-50 C57BL/6 mice in CPDA-1 solution (Baxter), leukoreduced using a Neonatal High-Efficiency Leukocyte Reduction Filter (Purecell Neo) and then concentrated by centrifugation to a final hemoglobin level of 17 g/dL, as determined by Drabkin assays (Ricca)[102] and the optical density (540 nm) compared with the Count-a-Part Cyanmethemoglob-in Standards (Diagnostic Technology)[101]. Residual leukocytes are counted by cytometry (LeucoCOUNT™; BD)[101]. NTBI was previously observed in both HFE$^{-/-}$ (~3.7 µM)[103] and RBC transfused (~2.5 µM) mice[101]. NTBI can be measured in these models using a standard nitrilotriacetic acid (NTA) ultrafiltration assay[101]. This can be done by incubating heparinized plasma (90 µL) with NTA (800 mM, pH 7.0) and then preparing a 30 K ultrafiltrate (NanoSep™, 30-kDa cutoff, polysulfone type) and measuring NTBI with ferrozine[104]. Total organ iron can be determined using a procedure which involves desiccation at 65° C., followed by acidification and detection of NTBI with a chromogen (1.6 mM bathophenanthroline)[105]. Hemoglobinemia can be detected spectrophotometrically using a PowerWave XS spectrophotometer (BioTek)[101]. Intracellular iron accumulation in the liver and spleen can be detected in paraffin sections with Perl's reagent which reveals blue granules[54] and in sections with co-immunostaining to detect macrophages with anti-mouse F4/80 antibody (eBioscience) and ABC and DAB kits (Vector Laboratories)[101].

As reported previously, a number of cytokines/chemokines, especially interleukin-6 (IL-6), monocyte chemoattractant protein-1 (MCP-1), macrophage inhibitory protein-1β (MIP-1β), and keratinocyte-derived chemokine/CXCL1 (KC/CXCL1) are increased in the plasma 2 hrs after transfusion of old stored RBC[101]. Hence, these cytokines can be measured as markers of iron overload and as a measure of treatment efficacy of Ngal. The cytokines/chemokines can be quantified using the Cytometric Bead Array Mouse Flex Kit (BD Biosciences) and plasma with a FACSCalibur cytometer (BD Biosciences) equipped with FlowJo software[101].

Treatment of Iron Overload with K6 (i.e., K3)::Ent and Evaluation of Treatment Efficacy.

The K6 (i.e., K3):Ent complex can be introduced into HFE$^{-/-}$ or RBC transfused mice by intravenous infusion with a micro-osmotic pump (ALZET®). For HFE$^{-/-}$ mice, the dose of K6 (i.e., K3):Ent can be 17.9 mg K6 (i.e., K3):Ent for 12 hours, 3 times a week for 4 weeks. This dose is based on the following calculation: For HFE$^{-/-}$ mice, NTBI is ~3.7 µM and blood volume is ~1.6 ml; to maximize iron chelation and removal, equal moles of Ngal:Ent should be continually present in circulation for a 12 hour treatment with the consideration of Ngal's half life of 10 min, or approximately ~0.85 µmoles (~17.9 mg) of Ngal:Ent are theoretically required over 12-hours. Similarly, for the transfusion mice the dose is ~0.58 µmoles (~12 mg) of Ngal:Ent over 12 hours in a single treatment period. Apo-K6 (i.e., K3) is as a negative control because it does not bind iron and associated endogenous catechols would dissociate. Wt Ngal is also a useful control because it is captured by megalin, and it does not traffic iron into the urine.

The efficacy of treatment can be evaluated by the measurement of serum and urinary iron, iron concentration in the liver, spleen and kidney, intracellular iron accumulation in macrophages and hepatocytes, and cytokines/chemokines in the plasma of K6 (i.e., K3):Ent-vs K6 (i.e, K3)- or Wt-treated mice as described above. K6 (i.e, K3) Ngal can be detected in urine by immunoblot with anti-human antibodies. Preliminary data suggests that K6 (i.e, K3) will appear in the urine, and that K6 (i.e, K3):Ent will markedly diminish serum NTBI, decrease the iron content of HFE$^{-/-}$ mice and transfusion overload, and additionally normalize the levels of cytokines/chemokines in old-RBC transfusions.

Effect of K6 (i.e, K3):Ent Treatment on Iron-Mediated Cell Damage

Measurement of Redox Activity in the Kidney Peroxidized lipids are a marker of iron catalyzed oxidant stress, which are measured by malondialdehyde. The renal cortex of mice subjected to K6 (i.e, K3) treatment is separated from the medulla, homogenized[106,107] and treated with TCA and thiobarbituric acid and the supernatant read at 535 nm. Malondialdehyde, expressed in nmoles, is calculated using a molar extinction coefficient of $1.56 \times 10^5$ M$^{-1}$ cm$^{-1}$ at 535 nm. An additional measurement of kidney damage during the treatment with K6 (i.e, K3) is the detection of endogenous mouse uNgal (25KDa) with mouse antibody (R&D system). Ngal is expressed within 3 hrs of damage by stimuli that cause AKI including radical attack, and here we will measure uNgal in the different treatment groups.

Measurement of Free Iron and Redox Activity in Mouse Urine

Figure 17:
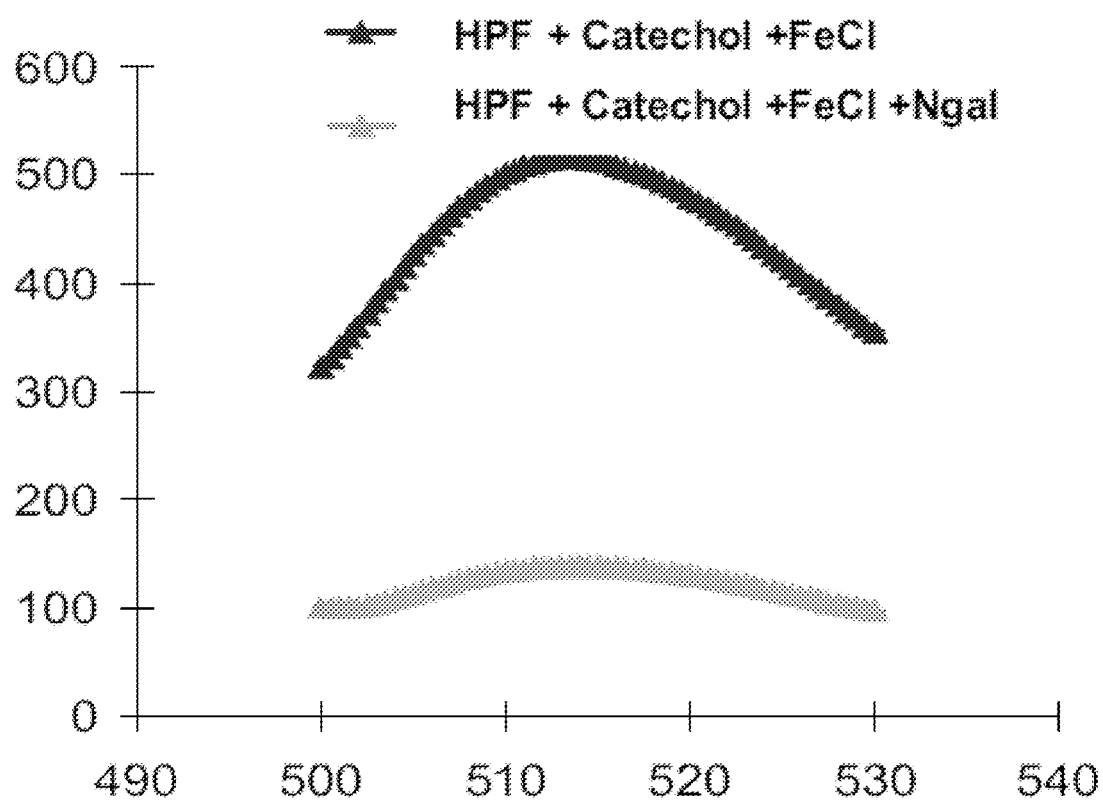
FIG. 17. Ngal effectively chelates FeIII. Conversion of HPF to fluorescein (Ex 490 nm, Em 515 nm) was detected in the presence of catechol, ironIII and H2O2 (black line), but the addition of Ngal blocked this reaction (grey line); P<10-5.
Figure 18:
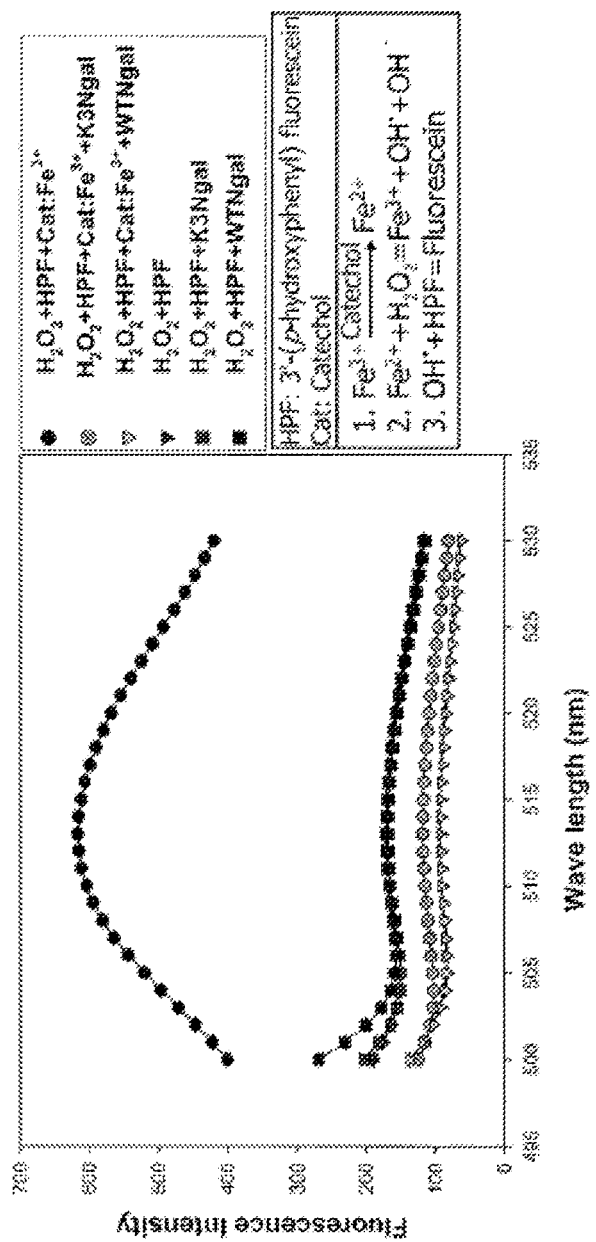
FIG. 18. K3 Ngal mutant inhibits the Redox Activity of Iron. Oxidative radicals produced by Fe(III), catechol and H2O2 was detected by a fluorescent probe, 3'-(p-hydroxyphenyl) fluorescein (HPF), and the production of the Oxidative radicals was completely inhibited by wild-type (WT) and K3 Ngal proteins.
Figure 20:
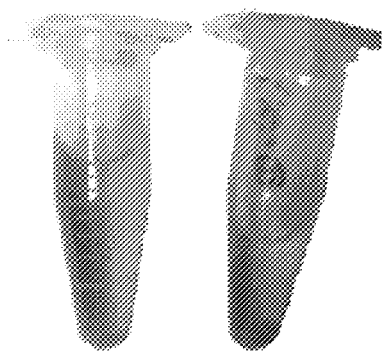
FIG. 20. Left tube shows that NGAL binds Catechol:Fe found in the urine, generating a bright red color. The tube contains the K3 mutant form of NGAL which can bypass the proximal tubule and deliver Iron or Apo-NGAL to the urine. Right tube: Apo-Ngal. These data show that the K3 NGAL is capable of binding to siderophores such as Ent:Fe and therefore are predicted to transport iron from the blood into the urine.

The data presented herein suggests that the iron will be tightly bound to K6 (Le, K3) Ngal and redox inactive even in the acidic urine. This can be tested using the classic spectrophotometric bleomycin test of Gutteridge[57] to measure urinary "catalytic" iron in mice treated with K6 (i.e, K3), K6 (i.e, K3):Ent and wild type Ngal. Urine is collected in Chelex-treated, pyrogen-free water and an ultrafiltrate created using a Microcon™ (10K, Millipore) measured with the bleomycin assays. A standard curve is prepared with urine spiked with FeCl$_3$ and bleomycin-detectable iron recorded per mg creatinine (Abcam). A second strategy to measure redox activity can also be used—the iron mediated generation of hydroxyl radicals can be detected by the conversion of 3'-(p-hydroxyphenyl) fluorescein (HPF; Invitrogen) to fluorescein in the presence of ascorbic acid[94] (Ex 490 nm, Em 515 nm). As shown in FIGS. 17 and 18, wild type Ngal quenched the activity of catechol:Fe$^{III}$—urine from mice treated with K6 (i.e, K3), K6 (i.e, K3):Ent and Wt Ngal:Ent is tested. A positive control is Ent/catechol:Fe$^{III}$ followed by K6 (i.e, K3) which inhibits the production of superoxide radicals.

Vertebrate Animals

In Vivo Characterization of Ngal-Mediated Iron Chelation and Trafficking:

Adult female and male mice (C57BL/6) are the principal source of experimental tissues for studying the regulation of iron metabolism. We have used adult tissues from these mice for many years to discover how Ngal mediates iron trafficking (Bao et al Nat Chem Biol, 2010). Both male and female adults are used in vivo to characterize the Ngal-mediated iron transport to different tissues (e.g. liver, heart, lung, kidney, spleen, pancreas, brain) and urine (Bao et al Nat Chem Biol, in press, 2010). Animals of all ages and both sexes will be used.

Mouse is a standard model for studying the regulation of iron delivery and metabolism dating back to the 1950's, and many murine models of iron overload diseases such as HFE-/- mice have been established and utilized to study the pathogenesis of these diseases and potential therapeutic treatments. Further, use of mice carrying gene knockouts is a standard of the field which has yielded most of the insights to date in the functions of genes required for iron delivery and metabolism such as megalin which is required for transferrin- and Ngal-bound iron reabsorption in the kidney. There are no alternatives to the use of these mouse models because no other animal models of other species are available and studies based on cultured cell lines can not reflect the in vivo mechanism of iron delivery and metabolism. Hence, these murine models will be used to investigate the in vivo mechanism of Ngal-mediated iron delivery to various tissues and urine.

Based on data on the difference of the ability of the intraperitoneally injected wild-type and K6 (i.e, K3) mutant Ngal proteins to bypass the kidney and enter the urine, we estimated the number of mice (sample size) which are required for the experiments by using Power Analysis with parameters of $p<0.05$ and Power=0.8 and a Biomath program (www.biomath.info/power/ttest.htm), and 6 mice are suggested in each of the groups to achieve statistic significance (t-test on group means). According to the calculation, for each experimental category (control K6 (i.e, K3), K6 (i.e, K3):Ent, Wt:Ent) we will need 6 wild-type mice, 6 megalinf/f; GgT-cre+ mice, 6 HFE-/- mice (total=54 mice). To generate these mice, 10 mating cage, each containing 1 male and 2 females will be used (2 cages for the generation of megalinf/f, 2 cages for GgT-cre/megalinf/+, 2 cages for megalinf/f GgT-cre+, and 2 cages for homozygous HFE-/-). Similarly, for the RBC transfusions we will need 18 mice to test Ngal proteins and, in order to collect plasma from cardiac puncture, we will need 50 wild type mice to blood bank the RBC for transfusion.

No surgical procedures are planned. Genotyping: In the case of animals carrying gene knockouts (e.g. Megalinf/f, GgT-cre+, HFE-/-) genotyping is necessary. The animal is genotyped at 14 days by snipping a 2-3 mm of tail dabbing the wound with lidocaine. Pressure is applied to control blood loss/

Euthanasia is performed through CO2 narcosis and cervical dislocation. Following CO2 narcosis the chest cavity is opened to assure death of the animal, and the feti are removed.

REFERENCE LIST

1. Hershko, C., and Peto, T. E. Non-transferrin plasma iron. Br. J. Haematol. 66: 149-151, 1987.
2. Breuer, W., Ronson, A., Slotki, I. N., Abramov, A., Hershko, C., and Cabantchik, Z. I. The assessment of serum nontransferrin-bound iron in chelation therapy and iron supplementation. Blood. 95: 2975-2982, 2000.
3. Andrews, N.C. Iron metabolism: Iron Deficiency and Iron Overload. Annu. Rev. Genomics Hum. Genet. 1:75-98, 2000.
4. Thakerngpol, K., Fucharoen, S., Boonyaphipat, P., Srisook, K., Sahaphong, S., Vathanophas, V., and Stitnimankarn, T. Liver injury due to iron overload in thalassemia: histopathologic and ultrastructural studies. Biometals. 9: 177-183, 1996.
5. Conte, D., Piperno, A., Mandelli, C., et al. Clinical, biochemical and histological features of primary haemochromatosis: a report of 67 cases. Liver. 6: 310-315, 1986.
6. Tsukamoto, H., Home, W., Kamimura, S., Niemela, O., Parkkila, S., Yla-Herttuala, S., and Brittenham, G. M. Experimental liver cirrhosis induced by alcohol and iron. J. Clin. Invest. 96: 620-630, 1995.
7. Berdoukas, V., Bohane, T., Tobias, V., et al. Liver iron concentration and fibrosis in a cohort of transfusion-dependent patients on long-term desferrioxamine therapy. Hematol. J. 5: 572-578, 2004.
8. Liu, P., and Olivieri, N. Iron overload cardiomyopathies: new insights into an old disease. Cardiovasc. Drugs. Ther. 8: 101-110, 1994.
9. Buja, L. M., and Roberts, W. C. Iron in the heart. Etiology and clinical significance. Am. J. Med. 51: 209-221, 1971.
10. Schwartz, K. A., Li, Z., Schwartz, D. E., et al. Earliest cardiac toxicity induced by iron overload selectively inhibits electrical conduction. J. Appl. Physiol. 93: 746-751, 2002.
11. Oudit, G. Y., Trivieri, M. G., Khaper, N., Liu, P. P., and Backx, P. H. Role of L-type Ca2+ channels in iron transport and iron-overload cardiomyopathy. J. Mol. Med. 84: 349-364, 2006.
12. Oudit, G. Y., Sun, H., Trivieri, M. G., Koch, S. E., Dawood, F., Ackerley, C., Yazdanpanah, M., Wilson, G. J., Schwartz, A., Liu, P. P., and Backx, P. H. L-type $Ca^{2+}$ channels provide a major pathway for iron entry into cardiomyocytes in iron-overload cardiomyopathy. Nat. Med. 9: 1187-1194, 2003.
13. Andrews, N. C. Disorders of iron metabolism. N. Engl. J. Med. 341: 1986-1995, 1999.
14. Argyropoulou, M. I., and Astrakas, L. MRI evaluation of tissue iron burden in patients with beta-thalassaemia major. Pediatr. Radiol. 37: 1191-1200, 2007.
15. Argyropoulou, M. I., Kiortsis, D. N., Astrakas, L., Metafratzi, Z., Chalissos, N., Efremidis, S. C. Liver, bone marrow, pancreas and pituitary gland iron overload in young and adult thalassemic patients: a T2 relaxometry study. Eur. Radiol. 17: 3025-3030, 2007.
16. Cunningham, M. J., Macklin, E. A., Neufeld, E. J., and Cohen, A. R. Complications of beta-thalassemia major in North America. Blood. 104: 34-39, 2004.
17. Fung, E., Harmatz, P. R., Lee, P. D., Milet, M., Bellevue, R., Jeng, M. R., Kalinyak, K. A., Hudes, M., Bhatia, S., and Vichinsky, E. P. Increased prevalence of iron-overload associated endocrinopathy in thalassaemia versus sickle-cell disease. Br. J. Haematol. 135: 574-582, 2006.
18. Kattamis, C., and Kattamis, A. C. Management of thalassemias: growth and development, hormone substitution, vitamin supplementation, and vaccination. Semin. Hematol. 32: 269-279, 1995.
19. Eschbach, J. W., and Adamson, J. W. Iron overload in renal failure patients: Changes since the introduction of erythropoietin therapy. Kidney Int. 55: S35-S43, 1999.

20. Lorenz, M., Kletzmayr, J., Huber, A., Hörl, A. H., Sunder-Plassmann, G., and Födinger, M. Iron overload in kidney transplants: Prospective analysis of biochemical and genetic markers. Kidney Int. 67, 691-697, 2005.
21. Mandalunis, P. M., and Ubios, A. M. Experimental Renal Failure and Iron Overload: A Histomorphometric Study in Rat Tibia. Toxicol. Pathol. 33; 398-403, 2005.
22. Karnon, J., Zeuner, D., Brown, J., Ades, A. E., Wonke, B., and Modell, B. Lifetime treatment costs of beta-thalassaemia major. Clin. Lab. Haematol. 21: 377-385, 1999.
23. Darbari, D. S., Kple-Faget, P., Kwagyan, J., Rana, S., Gordeuk, V. R., and Castro, O. Circumstances of death in adult sickle cell disease patients. Am. J. Hematol. 81: 858-863, 2006.
24. McCord, J. M. Oxygen-derived free radicals in postischemic tissue injury. N. Engl. J. Med. 312: 159-163, 1985.
25. Meneghini, R. Iron homeostasis, oxidative stress, and DNA damage. Free Radic. Biol. Med. 23: 783-792, 1997.
26. Kalinowski, D. S., and Richardson, D. R. The Evolution of Iron Chelators for the Treatment of Iron Overload Disease and Cancer. Pharmacol. Rev. 57: 547-583, 2005.
27. Cohen, A. R. New Advances in Iron Chelation Therapy. Hematology-American Hematology Society Hematology Education Program. 42-47, 2006.
28. Hoffbrand, A. V., Cohen, A., and Hershko, C. Role of deferiprone in chelation therapy for transfusional iron overload. Blood 102: 17-24, 2003.
29. Bosque, M. A., Domingo, J. L., and Corbella, J. Assessment of the developmental toxicity of deferoxamine in mice. Arch. Toxicol. 69: 467-471, 1995.
30. Oliveri, N. F., Buncic, J. R., Chew, E., Galant, T., Harrison R. V., Keenan, N., Logan, W., Mitchell, D., Rici, G., Skarf, B., Taylor, M., and Freedman, M. H. Visual and auditory neurotoxicity in patients receiving subcutaneous deferoxamine infusions. N. Engl. J. Med. 314: 869-873, 1986.
31. Boelaert, J. R., and de Locht, M. Side-effects of desferrioxamine in dialysis patients. Nephrol Dial Transplant. 8: S43-S46, 1993.
32. Windus D W, Stokes T J, Julian B A, Fenves A Z. Fatal Rhizopus infections in hemodialysis patients receiving deferoxamine. Ann. Intern. Med. 107: 678-80, 1987.
33. Kowdley, K. V., and Kapla, M. M. Iron-chelation therapy with oral deferiprone—Toxicity or Lack of Efficacy? N. Engl. J. Med. 339: 468-469, 1998.
34. Kontoghiorghes, G. J. "Deferasirox: Uncertain future following renal failure fatalities, agranulocytosis and other toxicities. Expert. Opin. Drug. Saf. 6:235-239, 2007.
35. Yang, J., Goetz, D., Li, J. Y., Wang, W., Mori, K., Setlik, D., Du, T., Erdjument-Bromage, H., Tempst, P., Strong R., and Barasch, J. An iron delivery pathway mediated by a lipocalin. Mol. cell, 10: 1045-56, 2002.
36. Goetz, D. H., Holmes, M. A., Borregaard, N., Bluhm, M. E., Raymond, K. N., and Strong, R. K. The neutrophil lipocalin NGAL is a bacteriostatic agent that interferes with siderophore-mediated iron acquisition. Mol. cell, 10: 1033-1043, 2002.
37. Flo, T. H., Smith, K. D., Sato, S., Rodriguez, D. J., Holmes, M. A., and Strong, R. K., Akira, S., and Aderem, A. Lipocalin 2 mediates an innate immune response to bacterial infection by sequestrating iron. Nature, 432: 917-921, 2004.
38. Bao, G., Clifton, M., Hoette, T. M., Mori, K., Deng, S. X., Qiu, A., Viltard, M., Williams, D., Paragas, N., Leete, T., Kulkarni, R., Li, X., Lee, B., Kalandadze, A., Ratner, A. J., Pizarro, J. C., Schmidt-Ott, K., Landry, D. W., Raymond, K. N., Strong, R. K., and Barasch, J. Iron Traffics in Circulation Bound to a Siderocalin (Ngal)-Catechol Complex. Nat. Chem. Biol. in press, 2010.
39. Mishra, J., Ma, Q., Prada, A., Mitsnefes, M., Zahedi, K., Yang, J., Barasch, J., and Devarajan, P. Identification of neutrophil gelatinase-associated lipocalin as a novel early urinary biomarker for ischemic renal injury. J. Am. Soc. Nephrol. 14: 2534-43, 2003.
40. Mori, K., Lee, H. T., Rapoport, D., Drexler, I. R., Foster, K., Yang, J., Schmidt-Ott, K. M., Chen, X., Li, J. Y., Weiss, S., Mishra, J., Cheema, F. H., Markowitz, G., Suganami, T., Sawai, K., Mukoyama, M., Kunis, C., D'Agati, V., Devarajan, P., and Barasch, J. Endocytic delivery of lipocalin-siderophore-iron complex rescues the kidney from ischemia-reperfusion injury. J. Clin. Invest. 115: 610-621, 2005.
41. Mishra, J., Dent, C., Tarabishi, R., Mitsnefes, M. M., Ma, Q., Kelly, C., Ruff, S. M., Zahedi, K., Shao, M., Bean, J., Mori, K., Barasch, J., and Devarajan, P. Neutrophil gelatinase-associated lipocalin (NGAL) as a biomarker for acute renal injury after cardiac surgery. Lancet. 365: 1231-1238, 2005.
42. Nickolas, T. L., O'Rourke, M. J., Yang, J., Sise, M. E., Canetta, P. A., Barasch, N., Buchen, C., Khan, F., Mori, K., Giglio, J., Devarajan, P., and Barasch, J. Sensitivity and specificity of a single emergency department measurement of urinary neutrophil gelatinase-associated lipocalin for diagnosing acute kidney injury. Ann. Intern. Med. 148: 810-9, 2008.
43. Hvidberg, V., Jacobsen, C., Strong, R. K., Cowland, J. B., Moestrup, S. K., and Borregaar, N. The endocytic receptor megalin binds the iron transporting neutrophil-gelatinase-associated lipocalin with high affinity and mediates its cellular uptake, FEBS Letters 579: 773-777, 2005.
44. Andrews, N.C. Iron homeostasis: insights from genetics and animal models. Nat. Rev. 1: 208-217, 2000.
45. Bahram, S., Gilfillan, S., Kuhn, L. C., Moret, R., Schulze, J. B., Lebeau, A., and Schumann, K. Experimental hemochromatosis due to MHC class I HFE deficiency: immune status and iron metabolism. Proc. Natl. Acad. Sci. USA. 96: 13312-13317, 1999.
46. Borwein, S., Ghent, C. N., and Valberg, L. S. Diagnostic efficacy of screening tests for hereditary hemochromatosis. Cen. Med. Assoc. 131: 895-901, 1984.
47. Halliwell, B., and Gutteridge, J. M. Role of free radicals and catalytic metal ions in human disease: an overview. Methods Enzymol. 186: 1-85, 1990.
48. Trinder, D., Fox, C., Vautier, G., and Olynyk, J. K. Molecular pathogenesis of iron overload, Gut 51: 290-295, 2002.
49. Allen, K. J., Gurrin, L. C., Constantine, C. C., Osborne, N. J., Delatycki, M. B., Nicoll, A. J., McLaren, C. E., Bahlo, M., Nisselle, A. E., Vulpe, C. D., Anderson, G. J., Southey, M. C., Giles, G. G., English, D. R., Hopper, J. L., Olynyk, J. K., Powell, L. W., and Gertig, D. M. Iron-overload-related disease in HFE hereditary hemochromatosis. N. Engl. J. Med. 358: 221-230, 2008.
50. Landro, L. New rules may shrink ranks of blood donors. Wall Street Journal. 2007-01-10.
51. Bennett, J. M. (ed). The Myelodysplastic Syndromes: Pathobiology and Clinical Management. New York: Marcel Dekker, Inc. 2002.
52. Iron Disorders Institute, Inc. Transfusion-dependent iron overload. idInsight. Greenville, S.C.

53. Schafer, A., Cheron, R. G., Dluhy, R., Cooper, B., Gleason, R E., Soeldner, J. S., and Bunn, H. F. Clinical consequences of acquired transfusional iron overload in adults. N. Engl. J. Med. 304: 319-324, 1981.
54. Paragas, N., Nickolas, T. L., Wyatt, C., Forster, C. S., Sise, M., Morgello, S., Jagla, B., Buchen, C., Stella, P., Sanna-Cherchi, S., Carnevali, M. L., Maffei, S., Bovino, A., Argentiero, L., Magnano, A., Devarajan, P., Schmidt-Ott, K. M., Allegri, L., Klotman, P., D'Agati, V., Gharavi, A. G., and Barasch, J. Urinary NGAL marks cystic disease in HIV-associated nephropathy. J. Am. Soc. Nephrol. 20: 1687-1692, 2009.
55. Alfrey, A. Toxicity of tubule fluid iron in nephrotic syndrome. Am. J. Physiol. 263: F637-641, 1992.
56. Baliga, R., Zhang, Z., Baliga, M., and Shah, S. V. Evidence for cytochrome P-450 as a source of catalytic iron in myoglobinuric acute renal failure. Kidney Int. 49: 362-369, 1996.
57. Baliga, R., Zhang, Z., Baliga, M., Ueda, N., and Shah, S. V. In vitro and in vivo evidence suggesting a role for iron in cisplatin-induced nephrotoxicity. Kidney Int. 53: 394-401, 1998.
58. Saad, S. Y., Najjar, T. A., and Al-Rikabi, A. C. The preventive role of deferoxamine against acute doxorubicin-induced cardiac, renal and hepatic toxicity in rats. Pharmacol. Res. 43: 211-218, 2001.
59. Paller, M. S., and Jacob, H. S. Cytochrome P-450 mediates tissue-damaging hydroxyl radical formation during reoxygenation of the kidney. Proc. Natl. Acad. Sci. USA. 91: 7002-7006, 1994.
60. Baliga, R., Ueda, N., and Shah, S. V. Increase in bleomycin-detectable iron in ischaemia/reperfusion injury to rat kidneys. Biochem. J. 291: 901-905, 1993.
61. Baron, P., Gomez-Marin, O., Casas, C., Heil, J., Will, N., Condie, R., Burke, B., Najarian, J. S., and Sutherland, D. E. Renal preservation after warm ischemia using oxygen free radical scavengers to prevent reperfusion injury. J. Surg. Res. 51: 60-65. 1991.
62. Wu, Z. L., and Paller, M. S. Iron loading enhances susceptibility to renal ischemia in rats. Ren. Fail. 16: 471-480, 1994.
63. Baliga, R., Zhang, Z., Baliga, M., Ueda, N., and Shah, S. V. In vitro and in vivo evidence suggesting a role for iron in cisplatin-induced nephrotoxicity. Kidney Int. 53: 394-401, 1998.
64. Walker, P. D., and Shah, S. V. Evidence suggesting a role for hydroxyl radical in gentamicin-induced acute renal failure in rats. J. Clin. Invest. 81: 334-341, 1988.
65. Paller, M. S., and Hedlund, B. E. Role of iron in postischemic renal injury in the rat. Kidney Int. 34: 474-480, 1988.
66. Paller, M. S., and Hedlund, B. E. Extracellular iron chelators protect kidney cells from hypoxia/reoxygenation. Free Radic. Biol. Med. 17: 597-603, 1994.
67. de Vries, B., Walter, S. J., von Bonsdorff, L., Wolfs, T. G., van Heurn, L. W., Parkkinen, J., and Buurman, W. A. Reduction of circulating redox-active iron by apotransferrin protects against renal ischemia-reperfusion injury. Transplantation, 77: 669-675, 2004.
68. Zager, R. A., Burkhart, K. M., Conrad, D. S., and Gmur, D. J. Iron, heme oxygenase, and glutathione:effect on myohemoglobinuric proximal tubular injury. Kidney Int. 48: 1624-1634, 1995.
69. Paller, M. S., and Hedlund, B. E. Extracellular iron chelators protect kidney cells from hypoxia/reoxygenation. Free Radic. Biol. Med. 17: 597-603, 1994.
70. Holmes, M. A., Paulsene, W., Jide, X., Ratledge, C., and Strong, R. K. Siderocalin (Lcn 2) also binds carboxymycobactins, potentially defending against mycobacterial infections through iron sequestration. Structure 13: 29-41, 2005.
71. Loomis, L. D., and Raymond, K. N. Solution Equilibria of Enterobactin and Metal-Enterobactin Complexes. Inorg. Chem. 30: 906-911, 1991.
72. Jewett, S. L., Eggling, S., and Geller, L. Novel method to examine the formation of unstable 2:1 and 3:1 complexes of catecholamines and iron(III), J. Inorg. Biochem. 66: 165-173, 1997.
73. Keberle, H. The biochemistry of desferrioxamine and its relation to iron metabolism. Ann. N. Y. Acad. Sci. 119: 758-768, 1964.
74. Leheste, J. R. et al. Megalin knockout mice as an animal model of low molecular weight proteinuria. Am. J. Pathol. 155: 1361-1370, 1999.
75. Abergel, R. J., Wilson, M. K., Arceneaux, J. E. L, Hoette, T. M., Strong, R. K., Byers, B. R., and Raymond, K. N. Anthrax pathogen evades the mammalian immune system through stealth siderophore production. PNAS 103: 18499-18503, 2006.
76. Devireddy, L. R., Gazin, C., Zhu, X., and Green, M. R. A cell-surface receptor for lipocalin 24p3 selectively mediates apoptosis and iron uptake. Cell. 123: 1293-305, 2005.
77. Moestrup, S. K., and Verroust, P. J. Megalin- and cubilin-mediated endocytosis of protein-bound vitamins, lipids, and hormones in polarized epithelia. Annu. Rev. Nutr. 21: 407-428, 2001.
78. Liang, M. P., Banatao, D. R., Klein, T. E., Brutlag, D. L., and Altman, R. B. WebFEATURE: An interactive web tool for identifying and visualizing functional sites on macromolecular structures. Nucleic Acids Res. 31: 3324-3327, 2003.
79. Moestrup, S. K. and Gliemann, J. Analysis of ligand recognition by the purified alpha 2-macroglobulin receptor (low density lipoprotein receptor-related protein). Evidence that high affinity of alpha 2-macroglobulin-proteinase complex is achieved by binding to adjacent receptors. J. Biol. Chem. 266: 14011-14017, 1991.
80. Kaiser, B. K., Barahmand-Pour, F., Paulsene, W., Medley, S., Geraghty, D. E., and Strong, R. K., Interactions between NKG2x immunoreceptors and HLA-E ligands display overlapping affinities and thermodynamics. J. Immunol. 174: 2878-2884, 2005.
81. Li, P., McDermott, G., and Strong, R. K., Crystal structures of RAE-1beta and its complex with the activating immunoreceptor NKG2D. Immunity, 16: 77-86, 2002.
82. Li, P., Morris, D. L., Willcox, B. E., Steinle, A., Spies, T., and Strong, R. K., Complex Structure of the Activating Immunoreceptor NKG2D and its MHC Class I-like Ligand MICA. Nature Immunol. 2: 443-451, 2001.
83. McBeth, C., Seamons, A., Pizarro, J. C., Fleishman, S. J., Baker, D., Kortemme, T., Goverman, J. M., and Strong, R. K., A new twist in TCR diversity revealed by a forbidden alphabeta TCR. J. Mol. Biol. 375: 1306-1319, 2008.
84. McFarland, B. J., and Strong, R. K. Thermodynamic analysis of degenerate recognition by the NKG2D immunoreceptor: not induced fit but rigid adaptation. Immunity 19: 803-812, 2003.

85. Vigdorovich, V., Strong, R. K., and Miller, A. D., Expression and characterization of a soluble, active form of the jaagsiekte sheep retrovirus receptor, Hya12. J. Virol. 79: 79-86, 2005.

86. Xu, H., Song, L., Kim, M., Holmes, M. A., Kraft, Z., Sellhorn, G., Reinherz, E. L., Stamatatos, L., and Strong, R. K. Interactions between lipids and human anti-HIV antibody 4E10 can be reduced without ablating neutralizing activity. J. Virol. 84: 1076-1088, 2010.

87. Correia, B. E., Ban, Y. E. A., Holmes, M. A., Xu, H., Ellingson, K., Kraft, Z., Carrico, C., Boni, E., Sather, N., Zenobia, C., Burke, K. Y., Bradley-Hewitt, T., Bruhn-Johannsen, J. F., Kalyuzhniy, O., Baker, D., Strong, R. K., Stamatatos, L., and Schief, W. R. Computational design of epitope-scaffolds allows induction of antibodies specific for a poorly immunogenic HIV vaccine epitope. Structure, in press, 2010.

88. Strong, R. K., Bratt, T., Cowland, J. B., Borregaard, N., Wiberg, F. C., and Ewald, A. J., Expression, purification, crystallization and crystallographic characterization of dimeric and monomeric human neutrophil gelatinase associated lipocalin (NGAL). Acta Cryst. D54: 93-95, 1998.

89. Bauer, S., Willie, S. T., Spies, T., and Strong, R. K. Expression, purification, crystallization and crystallographic characterization of the human MHC class I related protein MICA. Acta Cryst.D54: 451-453, 1998.

90. Ryan, M. J., et al. HK-2: an immortalized proximal tubule epithelial cell line from normal adult human kidney. Kidney Int. 45: 48-57, 1994.

91. Leheste, J. R., Melsen, F., Wellner, M., Jansen, P., Schlichting, U., Renner-Muller, I., Andreassen, T. T., Wolf, E., Bachmann, S., Nykjaer, A., and Willnow, T. E. Hypocalcemia and osteopathy in mice with kidney-specific megalin gene defect. FASEB J. 17: 247-249, 2003.

92. Dworniczak, B., Skryabin, B., Tchinda, J., Heuck, S., Seesing, F. J., Metzger, D., Chambon, P., Horst, J., Pennekamp, P. Inducible Cre/loxP Recombination in the Mouse Proximal Tubule. Nephron Experimental Nephrology, 106: e11-e20, 2007.

93. Abergel, R. J., Clifton, M. C., Pizarro, J. C., Warner, J. A., Shuh, D. K., Strong, R. K., and Raymond, K. N., The siderocalin/enterobactin interaction: a link between mammalian immunity and bacterial iron transport. J. Am. Chem. Soc. 130: 11524-34, 2008.

94. Abergel, R. J., Moore, E. G., Strong, R. K., and Raymond, K. N., Microbial evasion of the immune system: structural modifications of enterobactin impair siderocalin recognition. J. Am. Chem. Soc. 128: 10998-9, 2006.

95. Abergel, R. J., Wilson, M. K., Arceneaux, J. E., Hoette, T. M., Strong, R. K., Byers, B. R., and Raymond, K. N. Anthrax pathogen evades the mammalian immune system through stealth siderophore production. Proc. Natl. Acad. Sci. USA 103: 18499-503, 2006.

96. Fischbach, M. A., Lin, H., Zhou, L., Yu, Y., Abergel, R. J., Liu, D. R., Raymond, K. N., Wanner, B. L., Strong, R. K., Walsh, C. T., Aderem, A., and Smith, K. D. The pathogen-associated iroA gene cluster mediates bacterial evasion of lipocalin 2. Proc. Natl. Acad. Sci. USA 103: 16502-7, 2006.

97. Hoette, T. M., Abergel, R. J., Xu, J., Strong, R. K., and Raymond, K. N. The role of electrostatics in siderophore recognition by the immunoprotein Siderocalin. J. Am. Chem. Soc. 130: 17584-92, 2008.

98. Goetz, D. H., Willie, S. T., Armen, R. S., Bratt, T., Borregaard, N., and Strong, R. K. Ligand preference inferred from the structure of neutrophil gelatinase associated lipocalin. Biochemistry, 39: 1935-41, 2000.

99. Kerjaschkit, D., Orlando, R. A., Farquhar, M. G., and Kuzmic, P. Program DYNAFIT for the analysis of enzyme kinetic data: application to HIV proteinase. Anal. Biochem. 237: 260-273, 1996.

100. Holmes, M. A., Paulsene, W., Jide, X., Ratledge, C., and Strong, R. K. Siderocalin (Lcn 2) Also Binds Carboxymycobactins, Potentially Defending against Mycobacterial Infections through Iron Sequestration. Structure, 13: 29-41, 2005.

101. Hod, E. A., Zhang, N., Sokol, S. A., Wojczyk, B. S., Francis, R. O., Ansaldi, D., Francis, K. P., Della-Latta, P., Whittier, S., Sheth, S., Hendrickson, J. E., Zimring, J. C., Brittenham, G. M., and Spitalnik, S. L. Transfusion of red blood cells after prolonged storage produces harmful effects that are mediated by iron and inflammation. Blood. 115: 4284-4292, 2010.

102. Moore, G. L., Ledford, M. E., and Merydith, A. A micromodification of the Drabkin hemoglobin assay for measuring plasma hemoglobin in the range of 5 to 2000 mg/dl. Biochem. Med. 26: 167-173, 1981.

103. Anita, C., Chua, G., Olynyk, J. K., Leedman, P. J., and Trinder, D. Nontransferrin-bound iron uptake by hepatocytes is increased in the Hfe knockout mouse model of hereditary hemochromatosis. Blood. 104: 1519-1525, 2004.

104. Evans, R. W., Rafique, R., Zarea, A., et al. Nature of non-transferrin-bound iron: studies on iron citrate complexes and thalassemic sera. J. Biol. Inorg. Chem. 13: 57-74, 2008.

105. Overmoyer, B. A., McLaren, C. E., and Brittenham, G. M. Uniformity of liver density and nonheme (storage) iron distribution. Arch. Pathol. Lab. Med. 111: 549-554, 1987.

106. Walker, P. D., and Shah, S. V gentamicin-induced acute renal failure in rats. J. Clin. Invest. 81: 334-341, 1988.

107. Paller, M. S., and Hedlund, B. E. Role of iron in postischemic renal injury in the rat. Kidney Int. 34: 474-480. Evidence suggesting a role for hydroxyl radical in, 1998.

Table 2 shows a listing of amino acid sequences, and the amino acid sequences of mutant NGAL proteins. Mutant NGAL proteins which were generated are shown as SEQ ID NOS: 2-10; 21-68; 247-251. Table 2 also shows putative mutant NGAL proteins having substitutions to non-positively charged amino acids at all positions on NGAL (SEQ ID NOS: 69-246, including all surface residues on NGAL, which surface residues are inclusive of positions 1-15 (SEQ ID NOS: 69-83), positions 17-26 (SEQ ID NOS: 85-94), positions 40-50 (SEQ ID NOS: 108-118), positions 57-62 (SEQ ID NOS: 125-130), positions 71-82 (SEQ ID NOS: 139-150), positions 84-89 (SEQ ID NOS: 152-157), positions 96-105 (SEQ ID NOS: 164-173), positions 114-118 (SEQ ID NOS: 182-186), positions 128-131 (SEQ ID NOS: 196-199), position 134 (SEQ ID NO: 202), positions 140-151 (SEQ ID NOS: 208-219), positions 157-165 (SEQ ID NOS: 225-233), positions 170-174 (SEQ ID NOS: 238-242). The amino acid sequence of the K3Cys protein is depicted in SEQ ID NO:252.

| SEQ ID NO | Name | Sequence |
|---|---|---|
| SEQ ID NO: 1 | WT NGAL | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 2 | K-3 | QDSTSDLIPAPPLSSVPLQQNFQDNQFQGKWYVVGLAGNAILREDKDP<br>QKMYATIYELKEDKSYNVTSVLFRDDGCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 3 | K-2 | QDSTSDLIPAPPLSSVPLQQNFQDNQFQGKWYVVGLAGNAILREDKDP<br>QKMYATIYELKEDKSYNVTSVLFRDDGCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 4 | I-3 | QDSTSDLIPAPPLSKVPLQQNFQDNQFQGKWYVVGLAGNAILREDKDP<br>QKMYATIYELKEDSYNVTSVLFRDDGCDYWIRTFVPGCQPGEFTLGN<br>IQSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 5 | I-1 | QDSTSDLIPAPPLSSVPLQQNFQDNQFQGKWYVVGLAGNAILREDKDP<br>QKMYATIYELKEDKSYNVTSVLFRDDGCDYWIRTFVPGCQPGEFTLGN<br>IKSYPGLTSYLVRVVSTNYNQHAMVFFKKVSQNQEYFKITLYGRTKEL<br>TSELKENFIRFSKSLGLPENHIVFPVPIDQCIDG |
| SEQ ID NO: 6 | K-5 | QDSTSDLIPAPPLSSVPLQQNFQDNQFQGKWYVVGLAGNAILREDEDP<br>QKMYATIYELKEDKSYNVTSVLFRKKKCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 7 | K-1 | QDSTSDLIPAPPLSSVPLQQNFQDNQFQGKWYVVGLAGNAILREDEDP<br>QKMYATIYELQEDKSYNVTSVLFRKKKCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 8 | F-4 | QDSTSDLIPAPPLSSVPLQQNFQDNQFQGKWYVVGLAGNAILREDEDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELQENFIRFSKSLGLPENNIVFPVPIDQCIDG |
| SEQ ID NO: 9 | F-5 | QDSTSDLIPAPPLSSVPLQQNFQDNQFQGKWYVVGLAGNAILREDEDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELQENFIRFSKSLGLPENNIVFPVPIDQCIDG |
| SEQ ID NO: 10 | B-2 | QDSTSDLIPAPPLSSVPLQQNFQDNQFQGKWYVVGLAGNAILREDEDP<br>QKMYATIYELKEDKSYNVTSVLFRKKKCDYWIRTFVPGCQPGEFTLGN<br>IKSYPGLTSYLVRVVSTNYNQFAMVFFKKVSQNREYFKITLYGRTKEL<br>TSELKENFIRFSKSLGLPENNIVFPVPIDQCIDG |
| SEQ ID NO: 11 | EcNGAL | RDPAPKLIPAPPLDRVPLQPDFKDDQFQGKWYVVGVAGNAFKKEEQGQ<br>FTMYTTTYELKEDHSYNVTSILLRDQNCDHWIRTFIPSSQPGQFNLGD<br>IKRYFGVQSYIVRVADTDYNQFAIVFFRKVYKNQEYFKTTLYRRTKEL<br>TPELREKFISFAKSLGLTDDHIIFPVPIDQCIDEE |
| SEQ ID NO: 12 | CfNGAL | QDSTPSLIPAPPPLKVPLQPDFQHDQFQGKWYVIGIAGNILKKEGHGQ<br>LKMYTTTYELKDDQSYNVTSTLLRNERCDYWNRDFVPSFQPGQFSLGD<br>IQLYPGVQSYLVQVVATNYNQYALVYFPRKVYKSQEYFKITLYGRTKEL<br>PLELKKEFIRFAKSIGLTEDHIIFPVPIDQCIDE |
| SEQ ID NO: 13 | SsNGAL | QGTIPNWIPAPPLSKVPLQPNFQADQFQGKWYVVGLAGNAVKKEEQGR<br>FKMYTTTYELKEDGSYNVISTLLRGQLCDNWIRTFVPSLQPGQFKLGD<br>IKKYSGLQSYVRVVSTNYSQFAIVFFKKVSNNQEYFKTTLYGRTKVL<br>SPELKENFVRFAKSLGLSDDNIIFPVAIDQCIDGQ |
| SEQ ID NO: 14 | PtNGAL | QDSTSDLIPAPPLSKVPLQQNFQDNQFQGKWYVVGLAGNAILREDKDP<br>QKMYATIYELKEDKSYNVTSVLFRKKKCDYWIRTFVPGRQPGEFTLGN<br>IKSYPGLTSYLVRVVSTNYNQHAMVFFKKVSQNREYFKITLYGRTKEL<br>TSELQENFIRFSKSLGLPENHIVFPVPIDQCIDG |
| SEQ ID NO: 15 | MamNGAL | QDSSSDLIPAPPLSKVPLQQNFQDNQFQGKWYVVGLSGNAVGRKDEAP<br>LKMYATIYELKEDKSYNVTSILFRKEKCDYWIRTFVPGSQPGEFTLGN<br>IQNHPGLTSYVRVVSTNYKQYAMVFFKKVSQNKEYFKITLYGRTKEL<br>TSELKENFIRFSKSLGLPENHIVFSVPIDQCING |

| SEQ ID NO | Name | Sequence |
|---|---|---|
| SEQ ID NO: 16 | BtNGAL | RSSSSRLLRAPPLSRIPLQPNFQADQFQGKWYTVGVAGNAIKKEEQDP LKMYSSNYELKEDGSYNVTSILLKDDLCDYWIRTFVPSSQPGQFTLGN IKSYRGIRSYTVRVVNTDYNQFAIVYFKKVQRKKTYFKITLYGRTKEL TPEVRENFINFAKSLGLTDDHIVFTVPIDRCIDDQ |
| SEQ ID NO: 17 | MmNGAL | QDSTQNLIPAPSLLTVPLQPDFRSDQFRGRWYVVGLAGNAVQKKTEGS FTMYSTIYELQENNSYNVTSILVRDQDQGCRYWIRTFVPSSRAGQFTL GNMHRYPQVQSYNVQVATTDYNQFAMVFFRKTSENKQYFKITLYGRTK ELSPELKERFTRFAKSLGLKDDNIIFSVPTDQCIDN |
| SEQ ID NO: 18 | RnNGAL | QDSTQNLIPAPPLISVPLQPGFWTERFQGRWFVVGLAGNAVQKERQSR FTMYSTIYELQEDNSYNVTSILVRGQGCRYWIRTFVPSSRPGQFTLGN IHSYPQIQSYDVQVADTDYDQFAMVFFQKTSENKQYFKVTLYGRTKGL SDELKERFVSFAKSLGLKDNNIVFSVPTDQCIDN |
| SEQ ID NO: 19 | HsMegalin | MDRGPAAVACTLLLALVACLAPASGQECDSAHFRCGSGHCIPADWRCD GTKDCSDDADEIGCAVVTCQQGYFKCQSEGQCIPNSWVCDQDQDCDDG SDERQDCSQSTCSSHQITCSNGQCIPSEYRCDHVRDCPDGADENDCQY PTCEQLTCDNGACYNTSQKCDWKVDCRDSSDEINCTEICLHNEFSCGN GECIPRAYVCDHDNDCQDGSDEHACNYPTCGGYQFTCPSGRCIYQNWV CDGEDDCKDNGDEDGCESGPHDVHKCSPREWSCPESGRCISIYKVCDG ILDCPGREDENNTSTGKYCSMTLCSALNCQYQCHETPYGGACFCPPGY IINHNDSRTCVEFDDCQIWGICDQKCESRPGRHLCHCEEGYILERGQY CKANDSFGEASIIFSNGRDLLIGDIHGRSFRILVESQNRGVAVGVAPH YHLQRVFWTDTVQNKVFSVDINGLNIQEVLNVSVETPENLAVDWVNNK IYLVETKVNRIDMVNLDGSYRVTLITENLGHPRGIAVDPTVGYLFFSD WESLSGEPKLERAFMDGSNRKDLVKTKLGWPAGVTLDMISKRVYWVDS RFDYIETVTYDGIQRKTVVHGGSLIPHPFGVSLFEGQVFFTDWTKMAV LKANKFTETNPQVYYQASLRPYGVTVYHSLRQPYATNPCKDNNGGCEQ VCVLSHRTDNDGLGFRCKCTFGFQLDTDERHCIAVQNFLIFSSQVAIR GIPFTLSTQEDVMVPVSGNPSFFVGIDFDAQDSTIFFSDMSKHMIFKQ KIDGTGREILAANRVENVESLAFDWISKNLYWTDSHYKSISVMRLADK TRRTVVQYLNNPRSVVVHPFAGYLFFTDWFRPAKIMRAWSDGSHLLPV INTTLGWPNGLAIDWAASRLYWVDAYFDKIEHSTFDGLDRRRLGHIEQ MTHPFGLAIFGEHLFFTDWRLGAIIRVRKADGGEMTVIRSGIAYILHL KSYDVNIQTGSNACNQPTHPNGDCSHFCFPVPNFQRVCGCPYGMRLAS NHLTCEGDPTNEPPTEQCGLFSFPCKNGRCVPNYYLCDGVDDCHDNSD EQLCGTLNNTCSSSAFTCGHGECIPAHWRCDKRNDCVDGSDEHNCPTH APASCLDTQYTCDNHQCISKNWVCDTDNDCGDGSDEKNCNSTETCQPS QFNCPNHRCIDLSFVCDGDKDCVDGSDEVGCVLNCTASQFKCASGDKC IGVTNRCDGVFDCSDNSDEAGCPTRPPGMCHSDEFQCQEDGICIPNFW ECDGHPDCLYGSDEHNACVPKTCPSSYFHCDNGNCIHRAWLCDRDNDC GDMSDEKDCPTQPFRCPSWQWQCLGHNICVNLSVVCDGIFDCPNGTDE SPLCNGNSCSDFNGGCTHECVQEPFGAKCLCPLGFLLANDSKTCEDID ECDILGSCSQHCYNMRGSFRCSCDTGYMLESDGRTCKVTASESLLLLV ASQNKIIADSVTSQVHNIYSLVENGSYIVAVDFDSIGRIFWSDATQG KTWSAFQNGTDRRVVFDSSIILTETIAIDWVGRNLYWTDYALETIEVS KIDGSHRTVLISKNLTNPRGLALDPRMNEHLLFWSDWGHHPRIERASM DGSMRTVIVQDKIFWPCGLTIDYPNRLLYFMDSYLDYMDFCDYNGHHR RQVIASDLIIRHPYALTLFEDSVYWTDRATRRVMRANKWHGGNQSVVM YNIQWPLGIVAVHPSKQPNSVNPCAFSRCSHLCLLSSQGPHFYSCVCP SGWSLSPDLLNCLRDDQPFLITVRQHIIFGISLNPEVKSNDAMVPIAG IQNGLDVEFDDAEQYIYWVENPGEIHRVKTDGTNRTVFASISMVGPSM NLALDWISRNLYSTNPRTQSIEVLTLHGDIRYRKTLIANDGTALGVGF PIGITVDPARGKLYWSDQGTDSGVPAKIASANMDGTSVKTLFTGNLEH LECVTLDIEEQKLYWAVTGRGVIERGNVDGTDRMILVHQLSHPWGIAV HDSFLYYTDEQYEVIERVDKATGANKIVLRDNVPNLRGLQVYHRRNAA ESSNGCSNNMNACQQICLPVPGGLFSCACATGFKLNPDNRSCSPYNSF IVVSMLSAIRGFSLELSDHSETMVPVAGQGRNALHVDVDVSSGFIYWC DFSSSVASDNAIRRIKPDGSSLMNIVTHGIGENGVRGIAVDWVAGNLY FTNAFVSETLIEVLRINTTYRRVLLKVTVDMPRHIVVDPKNRYLFWAD YGQRPKIERSFLDCTNRTVLVSEGIVTPRGLAVDRSDGYVYWVDDSLD IIARIRINGENSEVIRYGSRYPTPYGITVFENSIIWVDRNLKKIFQAS KEPENTEPPTVIRDNINWLRDVTIFDKQVQPRSPAEVNNNPCLENNGG CSHLCFALPGLHTPKCDCAFGTLQSDGKNCAISTENFLIFALSNSLRS LHLDPENHSPPFQTINVERTVMSLDYDSVSDRIYFTQNLASGVGQISY ATLSSGIHTPFVIASGIGTADGIAFDWITRRIYYSDYLNQMINSMAED GSNRTVIARVPKPRAIVLDPCQGYLYWADWDTHAKIERATLGGNFRVP IVNSSLVMPSGLTLDYEEDLLYWVDASLQRIERSTLTGVDREVIVNAA VHAFGLTLGYQYIYWTDLYTQRIYRANKYDGSGQIAMTTNLLSQPRGI NTVVKNQKQQCNNPCEQFNGGCSHICAPGPNGAECQCPHEGNWYLANN RKHCIVDNGERCGASSFTCSNGRCISEEWKCDNDNCGDGSDEMESVC ALHTCSPTAFTCANGRCVQYSRCDYYNDCGDGSDEAGCLFRDCNATT EFMCNNRRCIPREFICNGVDNCHDNNTSDEKNCPDRTCQSGYTKCHNS NICIPRVYLCDGDNDCGDNSDENPTYCTTHTCSSSEFQCASGRCIPQH |

| SEQ ID NO | Name | Sequence |
| --- | --- | --- |
| | | WYCDQETDCFDASDEPASCGHSERTCLADEFKCDGGRCIPSEWICDGD
NDCGDMSDEDKRHQCQNQNCSDSEFLCVNDRPPDRRCIPQSWVCDGDV
DCTDGYDENQNCTRRTCSENEFTCGYGLCIPKIFRCDRHNDCGDYSDE
RGCLYQTCQQNQFTCQNGRCISKTFVCDEDNDCGDGSDELMHLCHTPE
PTCPPHEFKCDNGRCIEMMKLCNHLDDCLDNSDEKGCGINECHDPSIS
GCDHNCTDTLTSFYCSCRPGYKLMSDKRTCVDIDECTEMPFVCSQKCE
NVIGSYICKCAPGYLREPDGKTCRQNSNIEPYLIFSNRYYLRNLTIDG
YFYSLILEGLDNVVALDFDRVEKRLYWIDTQRQVIERMFLNKTNKETI
INHRLPAAESLAVDWVSRKLYWLDARLDGLFVSDLNGGHRRMLAQHCV
DANNTFCFDNPRGLALHPQYGYLYWADWGHRAYIGRVGMDGTNKSVII
STKLEWPNGITIDYTNDLLYWADAHLGYIEYSDLEGHHRHTVYDGALP
HPFAITIFEDTIYWTDWNTRTVEKGNKYDGSNRQTLVNTTHRPFDIHV
YHPYRQPIVSNPCGTNNGGCSHLCLIKPGGKGFTCECPDDFRTLQLSG
STYCMPMCSSTQFLCANNEKCIPIWWKCDGQKDCSDGSDELALCPQRF
CRLGQFQCSDGNCTSPQTLCNAHQNCPDGSDEDRLLCENHHCDSNEWQ
CANKRCIPESWQCDTFNDCEDNSDEDSSHCASRTCRPGQFRCANGRCI
PQAWKCDVDNDCGDHSDEPIEECMSSAHLCDNFTEFSCKTNYRCIPKW
AVCNGVDDCRDNSDEQGCEERTCHPVGDFRCKNHHCIPLRWQCDGQND
CGDNSDEENCAPRECTESEFRCVNQQCIPSRWICDHYNDCGDNSDERD
CEMRTCHPEYFQCTSGHCVHSELKCDGSADCLDASDEADCPTRFPDGA
YCQATMFECKNHVCIPPYWKCDGDDDCGDGSDEELHLCLDVPCNSPNR
FRCDNNRCIYSHEVCNGVDDCGDGTDETEEHCRKPTPKPCTEYEYKCG
NGHCIPHDNVCDDADDCGDWSDELGCNKGKERTCAENICEQNCTQLNE
GGFICSCTAGFETNVFDRTSCLDINECEQFGTCPQHCRNTKGSYECVC
ADGFTSMSDRPGKRCAAEGSSPLLLLPDNVRIRKYNLSSERFSEYLQD
EEYIQAVDYDWDPKDIGLSVVYYTVRGEGSRFGAIKRAYIPNFESGRN
NLVQEVDLKLKYVMQPDGIAVDWVGRHIYWSDVKNKRIEVAKLDGRYR
KWLISTDLDQPAAIAVNPKLGLMFWTDWGKEPKIESAWMNGEDRNILV
FEDLGWPTGLSIDYLNNDRIYWSDFKEDVIETIKYDGTDRRVIAKEAM
NPYSLDIFEDQLYWISKEKGEVWKQNKFGQGKKEKTLVVNPWLTQVRI
FHQLRYNKSVPNLCKQICSHLCLLRPGGYSCACPQGSSFIEGSTTECD
AAIELPINLPPPCRCMHGGNCYFDETDLPKCKCPSGYTGKYCEMAFSK
GISPGTTAVAVLLTILLIVVIGALAIAGFFHYRRTGSLLPALPKLPSL
SSLVKPSENGNGVTFRSGADLNMDIGVSGFGPETAIDRSMAMSEDFVM
EMGKQPIIFENPMYSARDSAVKVVQPIQVTVSENVDNKNYGSPINPSE
IVPETNPTSPAADGTQVTKWNLFKRKSKQTTNFENPIYAQMENEQKES
VAATPPPSPSLPAKPKPPSRRDPTPTYSATEDTFKDTANLVKEDSEV |
| SEQ ID NO: 20 | MmMegalin | MERGAAAAAWMLLLAIAACLAPVSGQECGSGNFRCDNGYCIPASWRCD
GTRDCLDDTDEIGCPPRSCGSGFFLCPAEGTCIPSSWVCDQDKDCSDG
ADEQQNCPGTTCSSQQLTCSNGQCVPIEYRCDHVSDCPDGSDERNCYY
PTCDQLTCANGACYNTSQKCDHKVDCRDSSDEANCTTLCSQKEFQCGS
GECILRAYVCDHDNDCEDNSDEHNCNYDTCGGHQFTCSNGQCINQNWV
CDGDDDCQDSGDEDGCESNQRHHTCYPREWACPGSGRCISMDKVCDGV
PDCPEGEDENNATSGRYCGTGLCSILNCEYQCHQTPYGGECFCPPGHI
INSNDSRTCIDFDDCQIWGICDQKCESRQGRHQCLCEEGYILERGQHC
KSNDSFSAASIIFSNGRDLLVGDLHGRNFRILAESKNRGIVMGVDFHY
QKHRVFWTDPMQAKVFSTDINGLNTQEILNVSIDAPENLAVDWINNKL
YLVETRVNRIDVVNLEGNQRVTLITENLGHPRGIALDPTVGYLFFSDW
GSLSGQPKVERAFMDGSNRKDLVTTKLGWPAGITLDLVSKRVYWVDSR
YDYIETVTYDGIQRKTVARGGSLVPHPFGISLFEEHVFFTDWTKMAVM
KANKFTDTNPQVYHQSSLTPFGVTVYHALRQPNATNPCGNNNGGCAQI
CVLSHRTDNGGLGYRCKCEFGFELDADEHHCVAVKNFLLFSSQTAVRG
IPFTLSTQEDVMVPVTGSPSFFVGIDFDAQHSTIFYSDLSKNIIYQQK
IDGTGKEVITANRLQNVECLSFDWISRNLYWTDGGSKSVTVMKLADKS
RRQIISNLNNPRSIVVHPAAGYMFLSDWFRPAKIMRAWSDGSHLMPIV
NTSLGWPNGLAIDWSTSRLYWVDAFFDKIEHSNLDGLDRKRLGHVDQM
THPFGLTVFKDNVFLTDWRLGAIIRVRKSDGGDMTVVRRGISSIMHVK
AYDADLQTGTNYCSQTTHPNGDCSHFCFPVPNFQRVCGCPYGMKLQRD
QMTCEGDPAREPPTQQCGSSSFPCNNGKCVPSIFRCDGVDDCHDNSDE
HQCGALNNTCSSSAFTCVHGGQCIPGQWRCDKQNDCLDGSDEQNCPTR
SPSSTCPPTSFTCDNHMCIPKEWVCDTDNDCSDGSDEKNCQASGTCHP
TQFRCPDHRCISPLYVCDGDKDCVDGSDEAGCVLNCTSSQFKCADGSS
CINSRYRCDGVYDCKDNSDEAGCPTRPPGMCHPDEFQCQGDGTCIPNT
WECDGHPDCIQGSDEHNGCVPKTCSPSHFLCDNGNCIYNSWVCDGDND
CRDMSDEKDCPTQPFHCPSSQWQCPGYSICVNLSALCDGVFDCPNGTD
ESPLCNQDSCLHFNGGCTHRCIQGPFGATCVCPIGYQLANDTKTCEDV
NECDIPGFCSQHCVNMRGSFRCACDPEYTLESDGRTCKVTASENLLLV
VASRDKIIMDNITAHTHNIYSLVQDVSFVVALDFDSVTGRVFWSDLLE
GKTWSAFQNGTDKRVVHDSGLSLTEMIAVDWIGRNIYWTDYTLETIEV
SKIDGSHRTVLISKNVTKPRGLALDPRMGDNVMFWSDWGHHPRIERAS
MDGTMRTVIVQEKIYWPCGLSIDYPNRLIYFMDAYLDYIEFCDYDGQN
RRQVIASDLVLHHPHALTLFEDSVFWTDRGTHQVMQANKWHGRNQSVV
MYSVPQPLGIIAIHPSRQPSSPNPCASATCSHLCLLSAQEPRHYSCAC
PSGWNLSDDSVNCVRGDQPFLISVRENVIFGISLDPEVKSNDAMVPIS
GIQHGYDVEFDDSEQFIYWVENPGEIHRVKTDGSNRTAFAPLSLLGSS |

| SEQ ID NO | Name | Sequence |
|---|---|---|
| | | LGLALDWVSRNIYYTTPASRSIEVLTLRGDTRYGKTLITNDGTPLGVG
FPVGIAVDPARGKLYWSDHGTDSGVPAKIASANMDGTSLKILFTGNME
HLEVVTLDIQEQKLYWAVTSRGVIERGNVDGTERMILVHHLAHPWGLV
VHGSFLYYSDEQYEVIERVDKSSGSNKVVFRDNIPYLRGLRVYHHRNA
ADSSNGCSNNPNACQQICLPVPGGMFSCACASGFKLSPDGRSCSPYNS
FIVVSMLPAVRGFSLELSDHSEAMVPVAGQGRNVLHADVDVANGFIYW
CDFSSSVRSSNGIRRIKPNGSNFTNIVTYGIGANGIRGVAVDWVAGNL
YFTNAFVYETLIEVIRINTTYRRVLLKVSVDMPRHIVVDPKHRYLFWA
DYGQKPKIERSFLDCTNRTVLVSEGIVTPRGLAVDHDTGYIYWVDDSL
DIIARIHRDGGESQVVRYGSRYPTPYGITVFGESIIWVDRNLRKVFQA
SKQPGNTDPPTVIRDSINLLRDVTIFDEHVQPLSPAELNNNPCLQSNG
GCSHFCFALPELPTPKCGCAFGTLEDDGKNCATSREDFLIYSLNNSLR
SLHFDPQDHNLPFQAISVEGMAIALDYDRRNNRIFFTQKLNPIRGQIS
YVNLYSGASSPTILLSNIGVTDGIAFDWINRRIYYSDFSNQTINSMAE
DGSNRAVIARVSKPRAIVLDPCRGYMYWTDWGTNAKIERATLGGNFRV
PIVNTSLVWPNGLTLDLETDLLYWADASLQKIERSTLTGSNREVVIST
AFHSFGLTVYGQYIYWTDFYTKKIYRANKYDGSDLIAMTTRLPTQPSG
ISTVVKTQQQQCSNPCDQFNGGCSHICAPGPNGAECQCPHEGSWYLAN
DNKYCVVDTGARCNQFQFTCLNGRCISQDWKCDNDNDCGDGSDELPTV
CAFHTCRSTAFTCANGRCVPYHYRCDFYNDCGDNSDEAGCLFRSCNST
TEFTCSNGRCIPLSYVCNGINNCHDNDTSDEKNCPPITCQPDFAKCQT
TNICVPRAFLCDGDNDCGDGSDENPIYCASHTCRSNEFQCVSPHRCIP
SYWFCDGEADCVDSSDEPDTCGHSLNSCSANQFHCDNGRCISSSWVCD
GDNDCGDMSDEDQRHHCELQNCSSTEFTCINSRPPNRRCIPQHWVCDG
DADCADALDELQNCTMRACSTGEFSCANGRCIRQSFRCDRRNDCGDYS
DERGCSYPPCRDDQFTCQNGQCITKLYVCDEDNDCGDGSDEQEHLCHT
PEPTCPPHQFRCDNGHCIEMGTVCNHVDDCSDNSDEKGCGINECQDSS
ISHCDHNCTDTITSFYCSLPGYKLMSDKRTCVDIDECKETPQLCSQK
CENVIGSYICKCAPGYIREPDGKSCRQNSNIEPYLVFSNRYYIRNLTI
DGTSYSLILQGLGNVVALDFDRVEERLYWIDAEKQIIERMFLNKTNQE
TIISHRLRRAESLAVDWVSRKLYWLDAILDCLFVSDLEGRQRKMLAQH
CVDANNTFCFENPRGIVLHPQRGYVYWADWGDHAYIARIGMDGTNKTV
IISTKIEWPNAITIDYTNDLLYWADAHLGYIEFSDLEGHHRHTVYDGT
LPHPFALTIFEDTVFWTDWNTRTVEKGNKYDGSGRVVLVNTTHKPFDI
HVLHPYRQPIMSNPCATNNGGCSHLCLIKAGGRGETCECPDDFQTVQL
RDRTLCMPMCSSTQFLCGNNEKCIPIWWKCDGQKDCSDGSDESDLCPH
RFCRLGQFQCRDGNCTSPQALCNARQDCADGSDEDRVLCEHHRCEANE
WQCANKRCIPEYWQCDSVDDCLDNSDEDPSHCASRTCRPGQFKCNNGR
CIPQSWKCDVDNCGDYSDEPIHECMTAAYNCDNHTEFSCKTNYRCIP
QWAVCNGFDDCRDNSDEQGCESVPCHPSGDFRCGNHHCIPLRWKCDGI
DDCGDNSDEESCVPRECTESEFRCADQQCIPSRWVCDQENDCGDNSDE
RDCEMKTCHPEHFQCTSGHCVPKALACDGRADCLDASDESACPTRFPN
GTYCPAAMFECKNHVCIQSFWICDGENDCVDGSDEEIHLCFNVPCESP
QRFRCDNSRCIYGHQLCNGVDDCGDGSDEKEEHCRKPTHKPCTDTEYK
CSNGNCVSQHYVCDNVDDCGDLSDETGCNLGENRTCAEKICEQNCTQL
SNGGFICSCRPGFKPSTLDKNSCQDINECEEFGICPQSCRNSKGSYEC
FCVDGFKSMSTHYGERCAADGSPPLLLLPENVRIRKYNISSEKFSEYL
EEEEHIQAIDYDWDPEGIGLSVVYYTVLSQGSQFGAIKRAYLPDFESG
SNNPVREVDLGLKYLMQPDGLAVDWVGRHIYWSDAKSQRIEVATLDGR
YRKWLITTQLDQPAAIAVNPKLGLMFWTDQGKQPKIESAWMNGEHRSV
LASANLGWPNGLSIDYLNGDRIYWSDKEDVIESIKYDGTDRRLIIND
AMKPFSLDIFEDQLYWVAKEKGEVWRQNKFGKGNKEKLLVVNPWLTQV
RIFHQLRYNQSVSNPCKQVCSHLCLLRPGGYSCACPQGSDFVTGSTVE
CDAASELPITMPSPCRCMHGGSCYFDENDLPKCKCSSGYSGEYCEIGL
SRGIPPGTTMALLLTFAMVIIVGALVLVGFFHYRKTGSLLPSLPKLPS
LSSLAKPSENGNGVTFRSGADVNMDIGVSPFGPETIIDRSMAMNEQFV
MEVGKQPVIFENPMYAAKDSTSKVGLAVQGPSVSSQVTVPENVENQNY
GRSIDPSEIVPEPKPASPGADETQGTKWNIFKRKPKQTTNFENPIYAE
MDTEQKEAVAVAPPPSPSLPAKASKRSSTPGYTATEDTFKDTANLVKE
DSDV |
| SEQ ID NO: 21 | A-1 | QDSTSDLIPAPPLSSVPLQQNFQDNQFQGKWYVVGLAGNAILREDKDP
QKMYATIYELKEDKSYNVTSVLFRKKKCDYWIRTFVPGCQPGEFTLGN
IKSYPGLTSYLVRVVSTNYNQHAMVFFKKVSQNREYFKITLYGRTKEL
TSELKENFIRFSKSLGLPENHIVFPVPIDQCIDG |
| SEQ ID NO: 22 | A-2 | QDSTSDLIPAPPLSSVPLQQNFQDNQFQGKWYVVGLAGNAILREDKDP
QKMYATIYELKEDKSYNVTSVLFRKKKCDYWIRTFVPGCQPGEFTLGN
IKSYPGLTSYLVRVVSTNYNQHAMVFFKKVSQNREYFKITLYGQTQEL
TSELKENFIRFSKSLGLPENHIVFPVPIDQCIDG |
| SEQ ID NO: 23 | A-3 | QDSTSDLIPAPPLSKVPLQQNFQDNQFQGKWYVVGLAGNAILQEDKDP
QKMYATIYELKEDKSYNVTSVLFRKKKCDYWIRTFVPGCQPGEFTLGN
IKSYPGLTSYLVRVVSTNYNQHAMVFFKKVSQNREYFKITLYGRTKEL
TSELKENFIRFSKSLGLPENHIVFPVPIDQCIDG |

-continued

| SEQ ID NO | Name | Sequence |
|---|---|---|
| SEQ ID NO: 24 | B-1 | QDSTSDLIPAPPLSKVPLQQNFQDNQFQGKWYVVGLAGNAILREDKDP<br>QKMYATIYELKEDKSYNVTSVLFRKKKCDYWIRTFVPGCPGEFTLGN<br>IQSYPGLTSYLVRVVSTNYNQFAMVFFKKVSQNREYFKITLYGRTKEL<br>TSELKENFIRFSKSLGLPENNIVFPVPIDQCIDG |
| SEQ ID NO: 25 | B-3 | QDSTSDLIPAPPLSKVPLQQNFQDNQFQGKWYVVGLAGNAILREDEDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENNIVFPVPIDQCIDG |
| SEQ ID NO: 26 | B-4 | QDSTSDLIPAPPLSKVPLQQNFQDNQFQGKWYVVGLAGNAILREDEDP<br>QKMYATIYELKEDKSYNVTSVLFRKKKCDYWIRTFVPGCQPGEFTLGN<br>IQSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 27 | B-5 | QDSTSDLIPAPPLSKVPLQQNFQDNQFQGKWYVVGLAGNAILREDEDP<br>QKMYATIYELKEDGSYNVTSVLFRKKKCDYWIRTFVPGCQPGEFTLGN<br>IQSYPGLTSYLVRVVSTNYNQFAMVFFKKVSQNREYFKITLYGRTKEL<br>TSELQENFIRFSKSLGLPENNIVFPVPIDQCIDG |
| SEQ ID NO: 28 | C-1 | QDSTSDLIPAPPLSKVPLQQNFQDNQFQGKWYVVGLAGNAILREDKDP<br>QTMYATIYELKEDKSYNVTSVLFQKKKCDYWIRTFVPGCQPGEFTLGN<br>IKSYPGLTSYLVRVVSTNYNQHAMVFFKKVSQNEYFKITLYGRTKEL<br>TSELQENFIRFSQSLGLPENHIVFPVPIDQCIDG |
| SEQ ID NO: 29 | C-3 | QDSTSDLIPAPPLSSVPLQQNFQDNQFQGKWYVVGLAGNAILREDKDP<br>QTMYATIYELKEDKSYNVTSVLFQKKKCDYWIRTFVPGCQPGEFTLGN<br>IKSYPGLTSYLVRVVSTNYNQHAMVFFKKVSQNREYFKITLYGRTKEL<br>TSELQENFIRFSQSLGLPENHIVFPVPIDQCIDG |
| SEQ ID NO: 30 | C-4 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNQEYFKITLYGRTKEL<br>TSELKENFIRFSQSLGLPENHIVFPVPIDQCIDG |
| SEQ ID NO: 31 | C-5 | QDSTSDLIPAPPLSKVPLQQNFQDNQFQGKWYVVGLAGNAILREDKDP<br>QKMYATIYELKEDKSYNVTSVLFQKKKCDYWIRTFVPGCQPGEFTLGN<br>IKSYPGLTSYLVRVVSTNYNQHAMVFFKKVSQNREYFKITLYGRTKEL<br>TSELKENFIRFSQSLGLPENHIVFPVPIDQCIDG |
| SEQ ID NO: 32 | D-1 | QDSTSDLIPAPPLSKVPLQQNFQDNQFQGKWYVVGLAGNAILREDKDP<br>QKMYATIYELKEDKSYNVTSVLFRDDGCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 33 | D-2 | QDSTSDLIPAPPLSKVPLQQNFQDNQFQGKWYVVGLAGNAILREDKDP<br>QKMYATIYELKEDGSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 34 | E-2 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSKSLGLPENHIVFPVPIDQCIDG |
| SEQ ID NO: 35 | F-1 | QDSTSDLIPAPPLSSVPLQQNFQDNQFQGKWYVVGLAGNAILREDEDP<br>QKMYATIYELQEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 36 | F-2 | QDSTSDLIPAPPLSKVPLQQNFQDNQFQGKWYVVGLAGNAILREDEDP<br>QKMYATIYELQEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 37 | G-1 | QDSTSDLIPAPPLSSVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELQENFIRFSKSLGLPENHIVFPVPIDQCIDG |
| SEQ ID NO: 38 | G-2 | QDSTSDLIPAPPLSKVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSKSLGLPENHIVFPVPIDQCIDG |

| SEQ ID NO | Name | Sequence |
|---|---|---|
| SEQ ID NO: 39 | G-3 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSQSLGLPENHIVFPVPIDQCIDG |
| SEQ ID NO: 40 | H-1 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLPENNIVFPVPIDQCIDG |
| SEQ ID NO: 41 | H-2 | QDSTSDLIPAPPLSSVPLQQNFQDNQFQGKWYVVGLAGNAILREDKDP<br>QKMYATIYELKEDKSYNVTSVLFRKKKCDYWIRTFVPGCQPGEFTLGN<br>IQSYPGLTSYLVRVVSTNYNQFAMVFFKKVSQNQEYFKITLYGRTKEL<br>TSELQENFIRFSKSLGLPENNIVFPVPIDQCIDG |
| SEQ ID NO: 42 | H-3 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQFAMVFFKKVSQNREYFKITLYGRTKEL<br>TSELQENFIRFSKSLGLPENNIVFPVPIDQCIDG |
| SEQ ID NO: 43 | H-5 | QDSTSDLIPAPPLSSVPLQQNFQDNQFQGKWYVVGLAGNAILREDKDP<br>QKMYATIYELKEDKSYNVTSVLFRKKKCDYWIRTFVPGCQPGEFTLGN<br>IQSYPGLTSYLVRVVSTNYNQHAMVFFKKVSQNREYFKITLYGRTKEL<br>TSELKENFIRFSKSLGLPENNIVFPVPIDQCIDG |
| SEQ ID NO: 44 | I-4 | QDSTSDLIPAPPLSSVPLQQNFQDNQFQGKWYVVGLAGNAILREDKDP<br>QKMYATIYELKEDKSYNVTSVLFRDDGCDYWIRTFVPGCQPGEFTLGN<br>IQSYPGLTSYLVRVVSTNYNQHAMVFFKKVSQNREYFKITLYGRTKEL<br>TSELKENFIRFSKSLGLPENHIVFPVPIDQCIDG |
| SEQ ID NO: 45 | I-5 | QDSTSDLIPAPPLSSVPLQQNFQDNQFQGKWYVVGLAGNAILREDKDP<br>QKMYATIYELKEDGSYNVTSVLFRDDGCDYWIRTFVPGCQPGEFTLGN<br>IKSYPGLTSYLVRVVSTNYNQHAMVFFKKVSQNQEYFKITLYGRTKEL<br>TSELKENFIRFSKSLGLPENHIVFPVPIDQCIDG |
| SEQ ID NO: 46 | L-1 | QDSTSDLIPAPPLSKVPLQQNFQDNQFQGKWYVVGLAGNAILQEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGQTQEL<br>TSELKENFIRFSQSLGLPENHIVFPVPIDQCIDG |
| SEQ ID NO: 47 | L-2 | QDSTSDLIPAPPLSSVPLQQNFQDNQFQGKWYVVGLAGNAILQEDKDP<br>QKMYATIYELKEDKSYNVTSVLFQKKKCDYWIRTFVPGCQPGEFTLGN<br>IKSYPGLTSYLVRVVSTNYNQHAMVFFKKVSQNREYFKITLYGQTQEL<br>TSELKENFIRFSQSLGLPENHIVFPVPIDQCIDG |
| SEQ ID NO: 48 | B-5-1 | QDSTSDLIPAPPLSKVPLAPDFQDNQFQGKWYVVGLAGNAILREDEDP<br>QKMYATIYELKEDGSYNVTSVLFRKKKCDYWIRTFVPGCQPGEFTLGN<br>IQSYPGLTSYLVRVVSTNYNQFAMVFFKKVSQNREYFKITLYGRTKEL<br>TSELQENFIRFSKSLGLPENNIVFPVPIDQCIDG |
| SEQ ID NO: 49 | B-5-2 | QDSTSDLIPAPPLSKVPLAPDFQDNQFQGKWYVVGLAGNAILREDEDP<br>QKMYATIYELAEDGSYNVTSVLFRKKKCDYWIRTFVPGCQPGEFTLGN<br>IQSYPGLTSYLVRVVSTNYNQFAMVFFKKVSQNREYFKITLYGRTKEL<br>TSELQENFIRFSKSLGLPENNIVFPVPIDQCIDG |
| SEQ ID NO: 50 | B-5-5 | QDSTSDLIPAPPLSKVPLQQNFQDNQFQGKWYVVGLAGNAILREDEDP<br>QKMYATIYELKEDGSYNVTSVLFRKKKCDYWIRTFVPGCQPGEFTLGN<br>IQSYPGLTSYLVRVVSTDYNQFAMVFFKKVSQNREYFKITLYGRTKEL<br>TSELQENFIRFSKSLGLPENNIVFPVPIDQCIDG |
| SEQ ID NO: 51 | WT-1 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGATAEL<br>TSELKENFIRFSKSLGLPENHIVFPVPIDQCIDG |
| SEQ ID NO: 52 | WT-3 | QDSTSDLIPAPPLSKVPLQQNFQDNQFQGKWYVVGLAGNAILAEDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGATAEL<br>TSELKENFIRFSASLGLPENHIVFPVPIDQCIDG |
| SEQ ID NO: 53 | WT-4 | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGATAEL<br>TSELKENFIRFSASLGLPENHIVFPVPIDQCIDG |

| SEQ ID NO | Name | Sequence |
|---|---|---|
| SEQ ID NO: 54 | WT-4-1 | QDSTSDLIPAPPLSKVPLQQNFQDNQFQGKWYVVGLAGNAILREDKDP QKMYATIYELKEDKSYNVTSVLFAKKKCDYWIRTFVPGCQPGEFTLGN IKSYPGLTSYLVRVVSTNYNQHAMVFFKKVSQNREYFKITLYGATAEL TSELKENFIRFSASLGLPENHIVFPVPIDQCIDG |
| SEQ ID NO: 55 | WT-4-1-4 | QDSTSDLIPAPPLSKVPLQQNFQDNQFQGKWYVVGLAGNAILAEDKDP QKMYATIYELKEDKSYNVTSVLFAKKKCDYWIRTFVPGCQPGEFTLGN IKSYPGLTSYLVRVVSTNYNQHAMVFFKKVSQNREYFKITLYGATAEL TSELKENFIRFSASLGLPENHIVFPVPIDQCIDG |
| SEQ ID NO: 56 | D1-1 | QDSTSDLIPAPPLSKVPLAPDFQDNQFQGKWYVVGLAGNAILREDKDP QKMYATIYELKEDKSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCIDG |
| SEQ ID NO: 57 | D1-4 | QDSTSDLIPAPPLSKVPLQQNFQDNQFQGKWYVVGLAGNAILREDKDP QKMYATIYELKEDGSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCIDG |
| SEQ ID NO: 58 | D1-4-1 | QDSTSDLIPAPPLSKVPLQQNFQDNQFQGKWYVVGLAGNAILREDKDP QKMYATIYELAEDGSYNVTSVLFRDDGCDYWIRTFVPGCQPGEFTLGN IKSYPGLTSYLVRVVSTNYNQHAMVFFKKVSQNREYFKITLYGRTKEL TSELKENFIRFSKSLGLPEDAIVFPVPIDQCIDG |
| SEQ ID NO: 59 | D1-4-2 | QDSTSDLIPAPPLSKVPLQQNFQDNQFQGKWYVVGLAGNAILREDKDP QKMYATIYELAEDGSYNVTSVLFRDDGCDYWIRTFVPGCQPGEFTLGN IASYPGLTSYLVRVVSTNYNQHAMVFFKKVSQNREYFKITLYGRTKEL TSELKENFIRFSKSLGLPENHIVFPVPIDQCIDG |
| SEQ ID NO: 60 | D1-4-2-1 | QDSTSDLIPAPPLSKVPLQQNFQDNQFQGKWYVVGLAGNAILREDEDP QKMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 61 | D1-4-2-1-1 | QDSTSDLIPAPPLSKVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 62 | D1-4-2-1-3 | QDSTSDLIPAPPLSKVPLQQNFQDNQFQGKWYVVGLAGNAILREDEDP QKMYATIYELAEDGSYNVTSVLFRDDGCDYWIRTFVPGCQPGEFTLGN IASYPGLTSYLVRVVSTDYNQHAMVFFKKVSESAEYFKITLYGRTKEL TSELKENFIRFSKSLGLPENHIVFPVPIDQCIDG |
| SEQ ID NO: 63 | D1-4-2-1-4 | QDSTSDLIPAPPLSKVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTDYNQHAMVFFKKVSESAEYFKITLYGRTKEL TSELKENFIRFSKSLGLPENHIVFPVPIDQCIDG |
| SEQ ID NO: 64 | D1-4-2-1-1-1 | QDSTSDLIPAPPLSSVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELAENFIRFSKSLGLPENHIVFPVPIDQCIDG |
| SEQ ID NO: 65 | D1-4-2-1-1-2 | QDSTSDLIPAPPLSKVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELAENFIRFSKSLGLPENHIVFPVPIDQCIDG |
| SEQ ID NO: 66 | D1-4-2-1-1-4 | QDSTSDLIPAPPLSSVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTNYNQHAMVFFKKVSESAEYFKITLYGRTKEL TSELKENFIRFSKSLGLPENHIVFPVPIDQCIDG |
| SEQ ID NO: 67 | K3-4 | QDSTSDLIPAPPLSSVPLQQNFQDNQFQGKWYVVGLAGNAILREDEDP QTMYATIYELKEDKSYNVTSVLFADDGCDYWIRTFVPGCQPGEFTLGN IQSYPGLTSYLVRVVSTNYNQFAMVFFKKVSQNEYFKITLYGRTKEL TSELQENFIRFSKSLGLPENNIVFPVPIDQCIDG |
| SEQ ID NO: 68 | K3-5 | QDSTSDLIPAPPLSSVPLQQNFQDNQFQGKWYVVGLAGNAILREDEDP QKMYATIYELKEDKSYNVTSVLFADDGCDYWIRTFVPGCQPGEFTLGN IQSYPGLTSYLVRVVSTNYNQFAMVFFKKVSQNEYFKITLYGRTKEL TSELQENFIRFSKSLGLPENNIVFPVPIDQCIDG |

| SEQ ID NO | Name | Sequence |
|---|---|---|
| SEQ ID NO: 69 | NGAL Mutant | $X_1$DSTSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_1$ = Q, A, N, D, C, E, G, I, L, M, F, P, S, T, W, Y, V |
| SEQ ID NO: 70 | NGAL Mutant | Q$X_2$STSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_2$ = Q, A, N, D, C, E, G, I, L, M, F, P, S, T, W, Y, V |
| SEQ ID NO: 71 | NGAL Mutant | QD$X_3$TSDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_3$ = Q, A, N, D, C, E, G, I, L, M, F, P, S, T, W, Y, V |
| SEQ ID NO: 72 | NGAL Mutant | QDS$X_4$SDLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_4$ = Q, A, N, D, C, E, G, I, L, M, F, P, S, T, W, Y, V |
| SEQ ID NO: 73 | NGAL Mutant | QDST$X_5$DLIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_5$ = Q, A, N, D, C, E, G, I, L, M, F, P, S, T, W, Y, V |
| SEQ ID NO: 74 | NGAL Mutant | QDSTS$X_6$LIPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_6$ = Q, A, N, D, C, E, G, I, L, M, F, P, S, T, W, Y, V |
| SEQ ID NO: 75 | NGAL Mutant | QDSTSD$X_7$IPAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_7$ = Q, A, N, D, C, E, G, I, L, M, F, P, S, T, W, Y, V |
| SEQ ID NO: 76 | NGAL Mutant | QDSTSDL$X_8$PAPPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_8$ = Q, A, N, D, C, E, G, I, L, M, F, P, S, T, W, Y, V |
| SEQ ID NO: 77 | NGAL Mutant | QDSTSDLI$X_9$APPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_9$ = Q, A, N, D, C, E, G, I, L, M, F, P, S, T, W, Y, V |
| SEQ ID NO: 78 | NGAL Mutant | QDSTSDLIP$X_{10}$PPLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{10}$ = Q, A, N, D, C, E, G, I, L, M, F, P, S, T, W, Y, V |

-continued

| SEQ ID NO | Name | Sequence |
|---|---|---|
| SEQ ID NO: 79 | NGAL Mutant | QDSTSDLIPAX$_{11}$PLSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{11}$ = Q, A, N, D, C, E, G, I, L, M, F, P, S, T, W, Y, V |
| SEQ ID NO: 80 | NGAL Mutant | QDSTSDLIPAPX$_{12}$LSKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{12}$ = Q, A, N, D, C, E, G, I, L, M, F, P, S, T, W, Y, V |
| SEQ ID NO: 81 | NGAL Mutant | QDSTSDLIPAPPX$_{13}$SKVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{13}$ = Q, A, N, D, C, E, G, I, L, M, F, P, S, T, W, Y, V |
| SEQ ID NO: 82 | NGAL Mutant | QDSTSDLIPAPPLX$_{14}$KVPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{14}$ = Q, A, N, D, C, E, G, I, L, M, F, P, S, T, W, Y, V |
| SEQ ID NO: 83 | NGAL Mutant | QDSTSDLIPAPPLSX$_{15}$VPLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{15}$ = Q, A, N, D, C, E, G, I, L, M, F, P, S, T, W, Y, V, K |
| SEQ ID NO: 84 | NGAL Mutant | QDSTSDLIPAPPLSKX$_{16}$PLQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{16}$ = Q, A, N, D, C, E, G, I, L, M, F, P, S, T, W, Y, V |
| SEQ ID NO: 85 | NGAL Mutant | QDSTSDLIPAPPLSKVX$_{17}$LQQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{17}$ = Q, A, N, D, C, E, G, I, L, M, F, P, S, T, W, Y, V |
| SEQ ID NO: 86 | NGAL Mutant | QDSTSDLIPAPPLSKVPX$_{18}$QQNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{18}$ = Q, A, N, D, C, E, G, I, L, M, F, P, S, T, W, Y, V |
| SEQ ID NO: 87 | NGAL Mutant | QDSTSDLIPAPPLSKVPLX$_{19}$QNFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{19}$ = Q, A, N, D, C, E, G, I, L, M, F, P, S, T, W, Y, V |
| SEQ ID NO: 88 | NGAL Mutant | QDSTSDLIPAPPLSKVPLQX$_{20}$NFQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{20}$ = Q, A, N, D, C, E, G, I, L, M, F, P, S, T, W, Y, V |

| SEQ ID NO | Name | Sequence |
|---|---|---|
| SEQ ID NO: 89 | NGAL Mutant | QDSTSDLIPAPPLSKVPLQQX$_{21}$FQDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{21}$ = Q, A, N, D, C, E, G, I, L, M, F, P, S, T, W, Y, V |
| SEQ ID NO: 90 | NGAL Mutant | QDSTSDLIPAPPLSKVPLQQNX$_{22}$QDNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{22}$ = Q, A, N, D, C, E, G, I, L, M, F, P, S, T, W, Y, V |
| SEQ ID NO: 91 | NGAL Mutant | QDSTSDLIPAPPLSKVPLQQNFX$_{23}$DNQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{23}$ = Q, A, N, D, C, E, G, I, L, M, F, P, S, T, W, Y, V |
| SEQ ID NO: 92 | NGAL Mutant | QDSTSDLIPAPPLSKVPLQQNFQX$_{24}$NQFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{24}$ = Q, A, N, D, C, E, G, I, L, M, F, P, S, T, W, Y, V |
| SEQ ID NO: 93 | NGAL Mutant | QDSTSDLIPAPPLSKVPLQQNFQDX$_{25}$QFQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{25}$ = Q, A, N, D, C, E, G, I, L, M, F, P, S, T, W, Y, V |
| SEQ ID NO: 94 | NGAL Mutant | QDSTSDLIPAPPLSKVPLQQNFQDNX$_{26}$FQGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{26}$ = Q, A, N, D, C, E, G, I, L, M, F, P, S, T, W, Y, V |
| SEQ ID NO: 95 | NGAL Mutant | QDSTSDLIPAPPLSKVPLQQNFQDNQX$_{27}$QGKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{27}$ = Q, A, N, D, C, E, G, I, L, M, F, P, S, T, W, Y, V |
| SEQ ID NO: 96 | NGAL Mutant | QDSTSDLIPAPPLSKVPLQQNFQDNQFX$_{28}$GKWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{28}$ = Q, A, N, D, C, E, G, I, L, M, F, P, S, T, W, Y, V |
| SEQ ID NO: 97 | NGAL Mutant | QDSTSDLIPAPPLSKVPLQQNFQDNQFQX$_{29}$KWYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{29}$ = Q, A, N, D, C, E, G, I, L, M, F, P, S, T, W, Y, V |
| SEQ ID NO: 98 | NGAL Mutant | QDSTSDLIPAPPLSKVPLQQNFQDNQFQGX$_{30}$WYVVGLAGNAILREDKD<br>PQKMYATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>X$_{30}$ = Q, A, N, D, C, E, G, I, L, M, F, P, S, T, W, Y, V, K |

| SEQ ID NO | Name | Sequence |
|---|---|---|
| SEQ ID NO: 99 | NGAL Mutant | QDSTSDLIPAPPLSKVPLQQNFQDNQFQGKX$_{31}$YVVGLAGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{31}$ = Q, A, N, D, C, E, G, I, L, M, F, P, S, T, W, Y, V |
| SEQ ID NO: 100 | NGAL Mutant | QDSTSDLIPAPPLSKVPLQQNFQDNQFQGKWX$_{32}$VVGLAGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{32}$ = Q, A, N, D, C, E, G, I, L, M, F, P, S, T, W, Y, V |
| SEQ ID NO: 101 | NGAL Mutant | QDSTSDLIPAPPLSKVPLQQNFQDNQFQGKWYX$_{33}$VGLAGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{33}$ = Q, A, N, D, C, E, G, I, L, M, F, P, S, T, W, Y, V |
| SEQ ID NO: 102 | NGAL Mutant | QDSTSDLIPAPPLSKVPLQQNFQDNQFQGKWYVX$_{34}$GLAGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{34}$ = Q, A, N, D, C, E, G, I, L, M, F, P, S, T, W, Y, V |
| SEQ ID NO: 103 | NGAL Mutant | QDSTSDLIPAPPLSKVPLQQNFQDNQFQGKWYVVX$_{35}$LAGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{35}$ = Q, A, N, D, C, E, G, I, L, M, F, P, S, T, W, Y, V |
| SEQ ID NO: 104 | NGAL Mutant | QDSTSDLIPAPPLSKVPLQQNFQDNQFQGKWYVVGX$_{36}$AGNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{36}$ = Q, A, N, D, C, E, G, I, L, M, F, P, S, T, W, Y, V |
| SEQ ID NO: 105 | NGAL Mutant | QDSTSDLIPAPPLSKVPLQQNFQDNQFQGKWYVVGLX$_{37}$GNAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{37}$ = Q, A, N, D, C, E, G, I, L, M, F, P, S, T, W, Y, V |
| SEQ ID NO: 106 | NGAL Mutant | QDSTSDLIPAPPLSKVPLQQNFQDNQFQGKWYVVGLAX$_{38}$NAILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{38}$ = Q, A, N, D, C, E, G, I, L, M, F, P, S, T, W, Y, V |
| SEQ ID NO: 107 | NGAL Mutant | QDSTSDLIPAPPLSKVPLQQNFQDNQFQGKWYVVGLAGX$_{39}$AILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{39}$ = Q, A, N, D, C, E, G, I, L, M, F, P, S, T, W, Y, V |
| SEQ ID NO: 108 | NGAL Mutant | QDSTSDLIPAPPLSKVPLQQNFQDNQFQGKWYVVGLAGNX$_{40}$ILREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{40}$ = Q, A, N, D, C, E, G, I, L, M, F, P, S, T, W, Y, V |

| SEQ ID NO | Name | Sequence |
| --- | --- | --- |
| SEQ ID NO: 109 | NGAL Mutant | QDSTSDLIPAPPLSKVPLQQNFQDNQFQGKWYVVGLAGNAX$_{41}$LREDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{41}$ = Q, A, N, D, C, E, G, I, L, M, F, P, S, T, W, Y, V |
| SEQ ID NO: 110 | NGAL Mutant | QDSTSDLIPAPPLSKVPLQQNFQDNQFQGKWYVVGLAGNAIX$_{42}$REDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{42}$ = Q, A, N, D, C, E, G, I, L, M, F, P, S, T, W, Y, V |
| SEQ ID NO: 111 | NGAL Mutant | QDSTSDLIPAPPLSKVPLQQNFQDNQFQGKWYVVGLAGNAILX$_{43}$EDKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{43}$ = Q, A, N, D, C, E, G, I, L, M, F, P, S, T, W, Y, V, R |
| SEQ ID NO: 112 | NGAL Mutant | QDSTSDLIPAPPLSKVPLQQNFQDNQFQGKWYVVGLAGNAILRX$_{44}$DKD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{44}$ = Q, A, N, D, C, E, G, I, L, M, F, P, S, T, W, Y, V |
| SEQ ID NO: 113 | NGAL Mutant | QDSTSDLIPAPPLSKVPLQQNFQDNQFQGKWYVVGLAGNAILREX$_{45}$KD PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{45}$ = Q, A, N, D, C, E, G, I, L, M, F, P, S, T, W, Y, V |
| SEQ ID NO: 114 | NGAL Mutant | QDSTSDLIPAPPLSKVPLQQNFQDNQFQGKWYVVGLAGNAILREDX$_{46}$D PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{46}$ = Q, A, N, D, C, E, G, I, L, M, F, P, S, T, W, Y, V, K |
| SEQ ID NO: 115 | NGAL Mutant | QDSTSDLIPAPPLSKVPLQQNFQDNQFQGKWYVVGLAGNAILREDKX$_{47}$ PQKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{47}$ = Q, A, N, D, C, E, G, I, L, M, F, P, S, T, W, Y, V |
| SEQ ID NO: 116 | NGAL Mutant | QDSTSDLIPAPPLSKVPLQQNFQDNQFQGKWYVVGLAGNAILREDKD X$_{48}$QKMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{48}$ = Q, A, N, D, C, E, G, I, L, M, F, P, S, T, W, Y, V |
| SEQ ID NO: 117 | NGAL Mutant | QDSTSDLIPAPPLSKVPLQQNFQDNQFQGKWYVVGLAGNAILREDKDP X$_{49}$KMYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{49}$ = Q, A, N, D, C, E, G, I, L, M, F, P, S, T, W, Y, V |
| SEQ ID NO: 118 | NGAL Mutant | QDSTSDLIPAPPLSKVPLQQNFQDNQFQGKWYVVGLAGNAILREDKDP QX$_{50}$MYATIYELKEDKSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{50}$ = Q, A, N, D, C, E, G, I, L, M, F, P, S, T, W, Y, V, K |

-continued

| SEQ ID NO | Name | Sequence |
|---|---|---|
| SEQ ID NO: 119 | NGAL Mutant | QDSTSDLIPAPPLSKVPLQQNFQDNQFQGKWYVVGLAGNAILREDKDP<br>QKX$_{51}$YATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{51}$ = Q, A, N, D, C, E, G, I, L, M, F, P, S, T, W, Y, V |
| SEQ ID NO: 120 | NGAL Mutant | QDSTSDLIPAPPLSKVPLQQNFQDNQFQGKWYVVGLAGNAILREDKDP<br>QKMX$_{52}$ATIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{52}$ = Q, A, N, D, C, E, G, I, L, M, F, P, S, T, W, Y, V |
| SEQ ID NO: 121 | NGAL Mutant | QDSTSDLIPAPPLSKVPLQQNFQDNQFQGKWYVVGLAGNAILREDKDP<br>QKMYX$_{53}$TIYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{53}$ = Q, A, N, D, C, E, G, I, L, M, F, P, S, T, W, Y, V |
| SEQ ID NO: 122 | NGAL Mutant | QDSTSDLIPAPPLSKVPLQQNFQDNQFQGKWYVVGLAGNAILREDKDP<br>QKMYAX$_{54}$IYELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{54}$ = Q, A, N, D, C, E, G, I, L, M, F, P, S, T, W, Y, V |
| SEQ ID NO: 123 | NGAL Mutant | QDSTSDLIPAPPLSKVPLQQNFQDNQFQGKWYVVGLAGNAILREDKDP<br>QKMYATX$_{55}$YELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{55}$ = Q, A, N, D, C, E, G, I, L, M, F, P, S, T, W, Y, V |
| SEQ ID NO: 124 | NGAL Mutant | QDSTSDLIPAPPLSKVPLQQNFQDNQFQGKWYVVGLAGNAILREDKDP<br>QKMYATIX$_{56}$ELKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{56}$ = Q, A, N, D, C, E, G, I, L, M, F, P, S, T, W, Y, V |
| SEQ ID NO: 125 | NGAL Mutant | QDSTSDLIPAPPLSKVPLQQNFQDNQFQGKWYVVGLAGNAILREDKDP<br>QKMYATIYX$_{57}$LKEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{57}$ = Q, A, N, D, C, E, G, I, L, M, F, P, S, T, W, Y, V |
| SEQ ID NO: 126 | NGAL Mutant | QDSTSDLIPAPPLSKVPLQQNFQDNQFQGKWYVVGLAGNAILREDKDP<br>QKMYATIYEX$_{58}$KEDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{58}$ = Q, A, N, D, C, E, G, I, L, M, F, P, S, T, W, Y, V |
| SEQ ID NO: 127 | NGAL Mutant | QDSTSDLIPAPPLSKVPLQQNFQDNQFQGKWYVVGLAGNAILREDKDP<br>QKMYATIYELX$_{59}$EDKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{59}$ = Q, A, N, D, C, E, G, I, L, M, F, P, S, T, W, Y, V, K |
| SEQ ID NO: 128 | NGAL Mutant | QDSTSDLIPAPPLSKVPLQQNFQDNQFQGKWYVVGLAGNAILREDKDP<br>QKMYATIYELKX$_{60}$DKSYNVTSVLFRKKKCDYWIRTFVPGCQPGEFTLG<br>NIKSYPGLTSYLVRVVSTNYNQHAMVFFKKVSQNREYFKITLYGRTKE<br>LTSELKENFIRFSKSLGLPENHIVFPVPIDQCIDG<br>$X_{60}$ = Q, A, N, D, C, E, G, I, L, M, F, P, S, T, W, Y, V |

-continued

| SEQ ID NO | Name | Sequence |
|---|---|---|
| SEQ ID NO: 129 | NGAL Mutant | QDSTSDLIPAPPLSKVPLQQNFQDNQFQGKWYVVGLAGNAILREDKDP QKMYATIYELKEX$_{61}$KSYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{61}$ = Q, A, N, D, C, E, G, I, L, M, F, P, S, T, W, Y, V |
| SEQ ID NO: 130 | NGAL Mutant | QDSTSDLIPAPPLSKVPLQQNFQDNQFQGKWYVVGLAGNAILREDKDP QKMYATIYELKEDX$_{62}$SYNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{62}$ = Q, A, N, D, C, E, G, I, L, M, F, P, S, T, W, Y, V, K |
| SEQ ID NO: 131 | NGAL Mutant | QDSTSDLIPAPPLSKVPLQQNFQDNQFQGKWYVVGLAGNAILREDKDP QKMYATIYELKEDKX$_{63}$YNVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{63}$ = Q, A, N, D, C, E, G, I, L, M, F, P, S, T, W, Y, V |
| SEQ ID NO: 132 | NGAL Mutant | QDSTSDLIPAPPLSKVPLQQNFQDNQFQGKWYVVGLAGNAILREDKDP QKMYATIYELKEDKSX$_{64}$NVTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{64}$ = Q, A, N, D, C, E, G, I, L, M, F, P, S, T, W, Y, V |
| SEQ ID NO: 133 | NGAL Mutant | QDSTSDLIPAPPLSKVPLQQNFQDNQFQGKWYVVGLAGNAILREDKDP QKMYATIYELKEDKSYX$_{65}$VTSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{65}$ = Q, A, N, D, C, E, G, I, L, M, F, P, S, T, W, Y, V |
| SEQ ID NO: 134 | NGAL Mutant | QDSTSDLIPAPPLSKVPLQQNFQDNQFQGKWYVVGLAGNAILREDKDP QKMYATIYELKEDKSYNX$_{66}$TSVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{66}$ = Q, A, N, D, C, E, G, I, L, M, F, P, S, T, W, Y, V |
| SEQ ID NO: 135 | NGAL Mutant | QDSTSDLIPAPPLSKVPLQQNFQDNQFQGKWYVVGLAGNAILREDKDP QKMYATIYELKEDKSYNVX$_{67}$SVLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{67}$ = Q, A, N, D, C, E, G, I, L, M, F, P, S, T, W, Y, V |
| SEQ ID NO: 136 | NGAL Mutant | QDSTSDLIPAPPLSKVPLQQNFQDNQFQGKWYVVGLAGNAILREDKDP QKMYATIYELKEDKSYNVTX$_{68}$VLFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{68}$ = Q, A, N, D, C, E, G, I, L, M, F, P, S, T, W, Y, V |
| SEQ ID NO: 137 | NGAL Mutant | QDSTSDLIPAPPLSKVPLQQNFQDNQFQGKWYVVGLAGNAILREDKDP QKMYATIYELKEDKSYNVTSX$_{69}$LFRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{69}$ = Q, A, N, D, C, E, G, I, L, M, F, P, S, T, W, Y, V |
| SEQ ID NO: 138 | NGAL Mutant | QDSTSDLIPAPPLSKVPLQQNFQDNQFQGKWYVVGLAGNAILREDKDP QKMYATIYELKEDKSYNVTSVX$_{70}$FRKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{70}$ = Q, A, N, D, C, E, G, I, L, M, F, P, S, T, W, Y, V |

-continued

| SEQ ID NO | Name | Sequence |
|---|---|---|
| SEQ ID NO: 139 | NGAL Mutant | QDSTSDLIPAPPLSKVPLQQNFQDNQFQGKWYVVGLAGNAILREDKDP QKMYATIYELKEDKSYNVTSVLX$_{71}$RKKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{71}$ = Q, A, N, D, C, E, G, I, L, M, F, P, S, T, W, Y, V |
| SEQ ID NO: 140 | NGAL Mutant | QDSTSDLIPAPPLSKVPLQQNFQDNQFQGKWYVVGLAGNAILREDKDP QKMYATIYELKEDKSYNVTSVLFX$_{72}$KKKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{72}$ = Q, A, N, D, C, E, G, I, L, M, F, P, S, T, W, Y, V, R |
| SEQ ID NO: 141 | NGAL Mutant | QDSTSDLIPAPPLSKVPLQQNFQDNQFQGKWYVVGLAGNAILREDKDP QKMYATIYELKEDKSYNVTSVLFRX$_{73}$KKCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{73}$ = Q, A, N, D, C, E, G, I, L, M, F, P, S, T, W, Y, V, K |
| SEQ ID NO: 142 | NGAL Mutant | QDSTSDLIPAPPLSKVPLQQNFQDNQFQGKWYVVGLAGNAILREDKDP QKMYATIYELKEDKSYNVTSVLFRKX$_{74}$KCDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{74}$ = Q, A, N, D, C, E, G, I, L, M, F, P, S, T, W, Y, V, K |
| SEQ ID NO: 143 | NGAL Mutant | QDSTSDLIPAPPLSKVPLQQNFQDNQFQGKWYVVGLAGNAILREDKDP QKMYATIYELKEDKSYNVTSVLFRKKX$_{75}$CDYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{75}$ = Q, A, N, D, C, E, G, I, L, M, F, P, S, T, W, Y, V, K |
| SEQ ID NO: 144 | NGAL Mutant | QDSTSDLIPAPPLSKVPLQQNFQDNQFQGKWYVVGLAGNAILREDKDP QKMYATIYELKEDKSYNVTSVLFRKKKX$_{76}$DYWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{76}$ = Q, A, N, D, C, E, G, I, L, M, F, P, S, T, W, Y, V |
| SEQ ID NO: 145 | NGAL Mutant | QDSTSDLIPAPPLSKVPLQQNFQDNQFQGKWYVVGLAGNAILREDKDP QKMYATIYELKEDKSYNVTSVLFRKKKCX$_{77}$YWIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{77}$ = Q, A, N, D, C, E, G, I, L, M, F, P, S, T, W, Y, V |
| SEQ ID NO: 146 | NGAL Mutant | QDSTSDLIPAPPLSKVPLQQNFQDNQFQGKWYVVGLAGNAILREDKDP QKMYATIYELKEDKSYNVTSVLFRKKKCDX$_{78}$WIRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{78}$ = Q, A, N, D, C, E, G, I, L, M, F, P, S, T, W, Y, V |
| SEQ ID NO: 147 | NGAL Mutant | QDSTSDLIPAPPLSKVPLQQNFQDNQFQGKWYVVGLAGNAILREDKDP QKMYATIYELKEDKSYNVTSVLFRKKKCDYX$_{79}$IRTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{79}$ = Q, A, N, D, C, E, G, I, L, M, F, P, S, T, W, Y, V |
| SEQ ID NO: 148 | NGAL Mutant | QDSTSDLIPAPPLSKVPLQQNFQDNQFQGKWYVVGLAGNAILREDKDP QKMYATIYELKEDKSYNVTSVLFRKKKCDYWX$_{80}$RTFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>X$_{80}$ = Q, A, N, D, C, E, G, I, L, M, F, P, S, T, W, Y, V |

| SEQ ID NO | Name | Sequence |
|---|---|---|
| SEQ ID NO: 149 | NGAL Mutant | QDSTSDLIPAPPLSKVPLQQNFQDNQFQGKWYVVGLAGNAILREDKDP QKMYATIYELKEDKSYNVTSVLFRKKKCDYWI$X_{81}$TFVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{81}$ = Q, A, N, D, C, E, G, I, L, M, F, P, S, T, W, Y, V, R |
| SEQ ID NO: 150 | NGAL Mutant | QDSTSDLIPAPPLSKVPLQQNFQDNQFQGKWYVVGLAGNAILREDKDP QKMYATIYELKEDKSYNVTSVLFRKKKCDYWIR$X_{82}$FVPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{82}$ = Q, A, N, D, C, E, G, I, L, M, F, P, S, T, W, Y, V |
| SEQ ID NO: 151 | NGAL Mutant | QDSTSDLIPAPPLSKVPLQQNFQDNQFQGKWYVVGLAGNAILREDKDP QKMYATIYELKEDKSYNVTSVLFRKKKCDYWIRT$X_{83}$VPGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{83}$ = Q, A, N, D, C, E, G, I, L, M, F, P, S, T, W, Y, V |
| SEQ ID NO: 152 | NGAL Mutant | QDSTSDLIPAPPLSKVPLQQNFQDNQFQGKWYVVGLAGNAILREDKDP QKMYATIYELKEDKSYNVTSVLFRKKKCDYWIRTF$X_{84}$PGCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{84}$ = Q, A, N, D, C, E, G, I, L, M, F, P, S, T, W, Y, V |
| SEQ ID NO: 153 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFV$X_{85}$GCQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{85}$ = Q, A, N, D, C, E, G, I, L, M, F, P, S, T, W, Y, V |
| SEQ ID NO: 154 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVP$X_{86}$CQPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{86}$ = Q, A, N, D, C, E, G, I, L, M, F, P, S, T, W, Y, V |
| SEQ ID NO: 155 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPG$X_{87}$QPGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{87}$ = Q, A, N, D, C, E, G, I, L, M, F, P, S, T, W, Y, V |
| SEQ ID NO: 156 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGC$X_{88}$PGEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{88}$ = Q, A, N, D, C, E, G, I, L, M, F, P, S, T, W, Y, V |
| SEQ ID NO: 157 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQ$X_{89}$GEFTLG NIKSYPGLTSYLVRVVSTNYNQHAMVFFKKVSQNREYFKITLYGRTKE LTSELKENFIRFSKSLGLPENHIVFPVPIDQCIDG<br>$X_{89}$ = Q, A, N, D, C, E, G, I, L, M, F, P, S, T, W, Y, V |
| SEQ ID NO: 158 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQP$X_{90}$EFTLG NIKSYPGLTSYLVRVVSTNYNQHAMVFFKKVSQNREYFKITLYGRTKE LTSELKENFIRFSKSLGLPENHIVFPVPIDQCIDG<br>$X_{90}$ = Q, A, N, D, C, E, G, I, L, M, F, P, S, T, W, Y, V |

| SEQ ID NO | Name | Sequence |
|---|---|---|
| SEQ ID NO: 159 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGX$_{91}$FTLG NIKSYPGLTSYLVRVVSTNYNQHAMVFFKKVSQNREYFKITLYGRTKE LTSELKENFIRFSKSLGLPENHIVFPVPIDQCIDG<br>X$_{91}$ = Q, A, N, D, C, E, G, I, L, M, F, P, S, T, W, Y, V |
| SEQ ID NO: 160 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEX$_{92}$TLG NIKSYPGLTSYLVRVVSTNYNQHAMVFFKKVSQNREYFKITLYGRTKE LTSELKENFIRFSKSLGLPENHIVFPVPIDQCIDG<br>X$_{92}$ = Q, A, N, D, C, E, G, I, L, M, F, P, S, T, W, Y, V |
| SEQ ID NO: 161 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFX$_{93}$LG NIKSYPGLTSYLVRVVSTNYNQHAMVFFKKVSQNREYFKITLYGRTKE LTSELKENFIRFSKSLGLPENHIVFPVPIDQCIDG<br>X$_{93}$ = Q, A, N, D, C, E, G, I, L, M, F, P, S, T, W, Y, V |
| SEQ ID NO: 162 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTX$_{94}$G NIKSYPGLTSYLVRVVSTNYNQHAMVFFKKVSQNREYFKITLYGRTKE LTSELKENFIRFSKSLGLPENHIVFPVPIDQCIDG<br>X$_{94}$ = Q, A, N, D, C, E, G, I, L, M, F, P, S, T, W, Y, V |
| SEQ ID NO: 163 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLX$_{95}$ NIKSYPGLTSYLVRVVSTNYNQHAMVFFKKVSQNREYFKITLYGRTKE LTSELKENFIRFSKSLGLPENHIVFPVPIDQCIDG<br>X$_{95}$ = Q, A, N, D, C, E, G, I, L, M, F, P, S, T, W, Y, V |
| SEQ ID NO: 164 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLG X$_{96}$IKSYPGLTSYLVRVVSTNYNQHAMVFFKKVSQNREYFKITLYGRTKE LTSELKENFIRFSKSLGLPENHIVFPVPIDQCIDG<br>X$_{96}$ = Q, A, N, D, C, E, G, I, L, M, F, P, S, T, W, Y, V |
| SEQ ID NO: 165 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN X$_{97}$KSYPGLTSYLVRVVSTNYNQHAMVFFKKVSQNREYFKITLYGRTKE LTSELKENFIRFSKSLGLPENHIVFPVPIDQCIDG<br>X$_{97}$ = Q, A, N, D, C, E, G, I, L, M, F, P, S, T, W, Y, V |
| SEQ ID NO: 166 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IX$_{98}$SYPGLTSYLVRVVSTNYNQHAMVFFKKVSQNREYFKITLYGRTKE LTSELKENFIRFSKSLGLPENHIVFPVPIDQCIDG<br>X$_{98}$ = Q, A, N, D, C, E, G, I, L, M, F, P, S, T, W, Y, V, K |
| SEQ ID NO: 167 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKX$_{99}$YPGLTSYLVRVVSTNYNQHAMVFFKKVSQNREYFKITLYGRTKE LTSELKENFIRFSKSLGLPENHIVFPVPIDQCIDG<br>X$_{99}$ = Q, A, N, D, C, E, G, I, L, M, F, P, S, T, W, Y, V |
| SEQ ID NO: 168 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSX$_{100}$PGLTSYLVRVVSTNYNQHAMVFFKKVSQNREYFKITLYGRTK ELTSELKENFIRFSKSLGLPENHIVFPVPIDQCIDG<br>X$_{100}$ = Q, A, N, D, C, E, G, I, L, M, F, P, S, T, W, Y, V |
| SEQ ID NO: 169 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYX$_{101}$GLTSYLVRVVSTNYNQHAMVFFKKVSQNREYFKITLYGRTK ELTSELKENFIRFSKSLGLPENHIVFPVPIDQCIDG<br>X$_{101}$ = Q, A, N, D, C, E, G, I, L, M, F, P, S, T, W, Y, V |

| SEQ ID NO | Name | Sequence |
|---|---|---|
| SEQ ID NO: 170 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPX$_{102}$LTSYLVRVVSTNYNQHAMVFFKKVSQNREYFKITLYGRTK ELTSELKENFIRFSKSLGLPENHIVFPVPIDQCIDG<br>X$_{102}$ = Q, A, N, D, C, E, G, I, L, M, F, P, S, T, W, Y, V |
| SEQ ID NO: 171 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGX$_{103}$TSYLVRVVSTNYNQHAMVFFKKVSQNREYFKITLYGRTK ELTSELKENFIRFSKSLGLPENHIVFPVPIDQCIDG<br>X$_{103}$ = Q, A, N, D, C, E, G, I, L, M, F, P, S, T, W, Y, V |
| SEQ ID NO: 172 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLX$_{104}$SYLVRVVSTNYNQHAMVFFKKVSQNREYFKITLYGRTK ELTSELKENFIRFSKSLGLPENHIVFPVPIDQCIDG<br>X$_{104}$ = Q, A, N, D, C, E, G, I, L, M, F, P, S, T, W, Y, V |
| SEQ ID NO: 173 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTX$_{105}$YLVRVVSTNYNQHAMVFFKKVSQNREYFKITLYGRTK ELTSELKENFIRFSKSLGLPENHIVFPVPIDQCIDG<br>X$_{105}$ = Q, A, N, D, C, E, G, I, L, M, F, P, S, T, W, Y, V |
| SEQ ID NO: 174 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSX$_{106}$LVRVVSTNYNQHAMVFFKKVSQNREYFKITLYGRTK ELTSELKENFIRFSKSLGLPENHIVFPVPIDQCIDG<br>X$_{106}$ = Q, A, N, D, C, E, G, I, L, M, F, P, S, T, W, Y, V |
| SEQ ID NO: 175 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYX$_{107}$VRVVSTNYNQHAMVFFKKVSQNREYFKITLYGRTK ELTSELKENFIRFSKSLGLPENHIVFPVPIDQCIDG<br>X$_{107}$ = Q, A, N, D, C, E, G, I, L, M, F, P, S, T, W, Y, V |
| SEQ ID NO: 176 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLX$_{108}$RVVSTNYNQHAMVFFKKVSQNREYFKITLYGRTK ELTSELKENFIRFSKSLGLPENHIVFPVPIDQCIDG<br>X$_{108}$ = Q, A, N, D, C, E, G, I, L, M, F, P, S, T, W, Y, V |
| SEQ ID NO: 177 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVX$_{109}$VVSTNYNQHAMVFFKKVSQNREYFKITLYGRTK ELTSELKENFIRFSKSLGLPENHIVFPVPIDQCIDG<br>X$_{109}$ = Q, A, N, D, C, E, G, I, L, M, F, P, S, T, W, Y, V, R |
| SEQ ID NO: 178 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRX$_{110}$VSTNYNQHAMVFFKKVSQNREYFKITLYGRTK ELTSELKENFIRFSKSLGLPENHIVFPVPIDQCIDG<br>X$_{110}$ = Q, A, N, D, C, E, G, I, L, M, F, P, S, T, W, Y, V |
| SEQ ID NO: 179 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVX$_{111}$STNYNQHAMVFFKKVSQNREYFKITLYGRTK ELTSELKENFIRFSKSLGLPENHIVFPVPIDQCIDG<br>X$_{111}$ = Q, A, N, D, C, E, G, I, L, M, F, P, S, T, W, Y, V |
| SEQ ID NO: 180 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVX$_{112}$TNYNQHAMVFFKKVSQNREYFKITLYGRTK ELTSELKENFIRFSKSLGLPENHIVFPVPIDQCIDG |

| SEQ ID NO | Name | Sequence |
|---|---|---|
| | | $X_{112}$ = Q, A, N, D, C, E, G, I, L, M, F, P, S, T, W, Y, V |
| SEQ ID NO: 181 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSX$_{113}$NYNQHAMVFFKKVSQNREYFKITLYGRTK ELTSELKENFIRFSKSLGLPENHIVFPVPIDQCIDG<br>$X_{113}$ = Q, A, N, D, C, E, G, I, L, M, F, P, S, T, W, Y, V |
| SEQ ID NO: 182 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTX$_{114}$YNQHAMVFFKKVSQNREYFKITLYGRTK ELTSELKENFIRFSKSLGLPENHIVFPVPIDQCIDG<br>$X_{114}$ = Q, A, N, D, C, E, G, I, L, M, F, P, S, T, W, Y, V |
| SEQ ID NO: 183 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNX$_{115}$NQHAMVFFKKVSQNREYFKITLYGRTK ELTSELKENFIRFSKSLGLPENHIVFPVPIDQCIDG<br>$X_{115}$ = Q, A, N, D, C, E, G, I, L, M, F, P, S, T, W, Y, V |
| SEQ ID NO: 184 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYX$_{116}$QHAMVFFKKVSQNREYFKITLYGRTK ELTSELKENFIRFSKSLGLPENHIVFPVPIDQCIDG<br>$X_{116}$ = Q, A, N, D, C, E, G, I, L, M, F, P, S, T, W, Y, V |
| SEQ ID NO: 185 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNX$_{117}$HAMVFFKKVSQNREYFKITLYGRTK ELTSELKENFIRFSKSLGLPENHIVFPVPIDQCIDG<br>$X_{117}$ = Q, A, N, D, C, E, G, I, L, M, F, P, S, T, W, Y, V |
| SEQ ID NO: 186 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQX$_{118}$AMVFFKKVSQNREYFKITLYGRTK ELTSELKENFIRFSKSLGLPENHIVFPVPIDQCIDG<br>$X_{118}$ = Q, A, N, D, C, E, G, I, L, M, F, P, S, T, W, Y, V |
| SEQ ID NO: 187 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHX$_{119}$MVFFKKVSQNREYFKITLYGRTK ELTSELKENFIRFSKSLGLPENHIVFPVPIDQCIDG<br>$X_{119}$ = Q, A, N, D, C, E, G, I, L, M, F, P, S, T, W, Y, V |
| SEQ ID NO: 188 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAX$_{120}$VFFKKVSQNREYFKITLYGRTK ELTSELKENFIRFSKSLGLPENHIVFPVPIDQCIDG<br>$X_{120}$ = Q, A, N, D, C, E, G, I, L, M, F, P, S, T, W, Y, V |
| SEQ ID NO: 189 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMX$_{121}$FFKKVSQNREYFKITLYGRTK ELTSELKENFIRFSKSLGLPENHIVFPVPIDQCIDG<br>$X_{121}$ = Q, A, N, D, C, E, G, I, L, M, F, P, S, T, W, Y, V |
| SEQ ID NO: 190 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVX$_{122}$FKKVSQNREYFKITLYGRTK ELTSELKENFIRFSKSLGLPENHIVFPVPIDQCIDG<br>$X_{122}$ = Q, A, N, D, C, E, G, I, L, M, F, P, S, T, W, Y, V |

-continued

| SEQ ID NO | Name | Sequence |
|---|---|---|
| SEQ ID NO: 191 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFX$_{123}$KKVSQNREYFKITLYGRTK ELTSELKENFIRFSKSLGLPENHIVFPVPIDQCIDG<br>X$_{123}$ = Q, A, N, D, C, E, G, I, L, M, F, P, S, T, W, Y, V |
| SEQ ID NO: 192 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFX$_{124}$KVSQNREYFKITLYGRTK ELTSELKENFIRFSKSLGLPENHIVFPVPIDQCIDG<br>X$_{124}$ = Q, A, N, D, C, E, G, I, L, M, F, P, S, T, W, Y, V |
| SEQ ID NO: 193 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKX$_{125}$VSQNREYFKITLYGRTK ELTSELKENFIRFSKSLGLPENHIVFPVPIDQCIDG<br>X$_{125}$ = Q, A, N, D, C, E, G, I, L, M, F, P, S, T, W, Y, V |
| SEQ ID NO: 194 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKX$_{126}$SQNREYFKITLYGRTK ELTSELKENFIRFSKSLGLPENHIVFPVPIDQCIDG<br>X$_{126}$ = Q, A, N, D, C, E, G, I, L, M, F, P, S, T, W, Y, V |
| SEQ ID NO: 195 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVX$_{127}$QNREYFKITLYGRTK ELTSELKENFIRFSKSLGLPENHIVFPVPIDQCIDG<br>X$_{127}$ = Q, A, N, D, C, E, G, I, L, M, F, P, S, T, W, Y, V |
| SEQ ID NO: 196 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSX$_{128}$NREYFKITLYGRTK ELTSELKENFIRFSKSLGLPENHIVFPVPIDQCIDG<br>X$_{128}$ = Q, A, N, D, C, E, G, I, L, M, F, P, S, T, W, Y, V |
| SEQ ID NO: 197 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQX$_{129}$REYFKITLYGRTK ELTSELKENFIRFSKSLGLPENHIVFPVPIDQCIDG<br>X$_{129}$ = Q, A, N, D, C, E, G, I, L, M, F, P, S, T, W, Y, V |
| SEQ ID NO: 198 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNX$_{130}$EYFKITLYGRTK ELTSELKENFIRFSKSLGLPENHIVFPVPIDQCIDG<br>X$_{130}$ = Q, A, N, D, C, E, G, I, L, M, F, P, S, T, W, Y, V, R |
| SEQ ID NO: 199 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNRX$_{131}$YFKITLYGRTK ELTSELKENFIRFSKSLGLPENHIVFPVPIDQCIDG<br>X$_{131}$ = Q, A, N, D, C, E, G, I, L, M, F, P, S, T, W, Y, V |
| SEQ ID NO: 200 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREX$_{132}$FKITLYGRTK ELTSELKENFIRFSKSLGLPENHIVFPVPIDQCIDG<br>X$_{132}$ = Q, A, N, D, C, E, G, I, L, M, F, P, S, T, W, Y, V |

-continued

| SEQ ID NO | Name | Sequence |
|---|---|---|
| SEQ ID NO: 201 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYX$_{133}$KITLYGRTK ELTSELKENFIRFSKSLGLPENHIVFPVPIDQCIDG<br>X$_{133}$ = Q, A, N, D, C, E, G, I, L, M, F, P, S, T, W, Y, V |
| SEQ ID NO: 202 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFX$_{134}$ITLYGRTK ELTSELKENFIRFSKSLGLPENHIVFPVPIDQCIDG<br>X$_{134}$ = Q, A, N, D, C, E, G, I, L, M, F, P, S, T, W, Y, V, K |
| SEQ ID NO: 203 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKX$_{135}$TLYGRTK ELTSELKENFIRFSKSLGLPENHIVFPVPIDQCIDG<br>X$_{135}$ = Q, A, N, D, C, E, G, I, L, M, F, P, S, T, W, Y, V |
| SEQ ID NO: 204 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKIX$_{136}$LYGRTK ELTSELKENFIRFSKSLGLPENHIVFPVPIDQCIDG<br>X$_{136}$ = Q, A, N, D, C, E, G, I, L, M, F, P, S, T, W, Y, V |
| SEQ ID NO: 205 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITX$_{137}$YGRTK ELTSELKENFIRFSKSLGLPENHIVFPVPIDQCIDG<br>X$_{137}$ = Q, A, N, D, C, E, G, I, L, M, F, P, S, T, W, Y, V, R |
| SEQ ID NO: 206 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLX$_{138}$GRTK ELTSELKENFIRFSKSLGLPENHIVFPVPIDQCIDG<br>X$_{138}$ = Q, A, N, D, C, E, G, I, L, M, F, P, S, T, W, Y, V |
| SEQ ID NO: 207 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYX$_{139}$RTK ELTSELKENFIRFSKSLGLPENHIVFPVPIDQCIDG<br>X$_{139}$ = Q, A, N, D, C, E, G, I, L, M, F, P, S, T, W, Y, V |
| SEQ ID NO: 208 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGX$_{140}$TK ELTSELKENFIRFSKSLGLPENHIVFPVPIDQCIDG<br>X$_{140}$ = Q, A, N, D, C, E, G, I, L, M, F, P, S, T, W, Y, V |
| SEQ ID NO: 209 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRX$_{141}$K ELTSELKENFIRFSKSLGLPENHIVFPVPIDQCIDG<br>X$_{141}$ = Q, A, N, D, C, E, G, I, L, M, F, P, S, T, W, Y, V |
| SEQ ID NO: 210 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTX$_{142}$ ELTSELKENFIRFSKSLGLPENHIVFPVPIDQCIDG<br>X$_{142}$ = Q, A, N, D, C, E, G, I, L, M, F, P, S, T, W, Y, V, K |

-continued

| SEQ ID NO | Name | Sequence |
|---|---|---|
| SEQ ID NO: 211 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTK<br>$X_{143}$LTSELKENFIRFSKSLGLPENHIVFPVPIDQCIDG<br>$X_{143}$ = Q, A, N, D, C, E, G, I, L, M, F, P, S, T, W, Y, V |
| SEQ ID NO: 212 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKE<br>$X_{144}$TSELKENFIRFSKSLGLPENHIVFPVPIDQCIDG<br>$X_{144}$ = Q, A, N, D, C, E, G, I, L, M, F, P, S, T, W, Y, V |
| SEQ ID NO: 213 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>$X_{145}$SELKENFIRFSKSLGLPENHIVFPVPIDQCIDG<br>$X_{145}$ = Q, A, N, D, C, E, G, I, L, M, F, P, S, T, W, Y, V |
| SEQ ID NO: 214 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>T$X_{146}$ELKENFIRFSKSLGLPENHIVFPVPIDQCIDG<br>$X_{146}$ = Q, A, N, D, C, E, G, I, L, M, F, P, S, T, W, Y, V |
| SEQ ID NO: 215 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TS$X_{147}$LKENFIRFSKSLGLPENHIVFPVPIDQCIDG<br>$X_{147}$ = Q, A, N, D, C, E, G, I, L, M, F, P, S, T, W, Y, V |
| SEQ ID NO: 216 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSE$X_{148}$KENFIRFSKSLGLPENHIVFPVPIDQCIDG<br>$X_{148}$ = Q, A, N, D, C, E, G, I, L, M, F, P, S, T, W, Y, V |
| SEQ ID NO: 217 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSEL$X_{149}$ENFIRFSKSLGLPENHIVFPVPIDQCIDG<br>$X_{149}$ = Q, A, N, D, C, E, G, I, L, M, F, P, S, T, W, Y, V, K |
| SEQ ID NO: 218 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELK$X_{150}$NFIRFSKSLGLPENHIVFPVPIDQCIDG<br>$X_{150}$ = Q, A, N, D, C, E, G, I, L, M, F, P, S, T, W, Y, V |
| SEQ ID NO: 219 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKE$X_{151}$FIRFSKSLGLPENHIVFPVPIDQCIDG<br>$X_{151}$ = Q, A, N, D, C, E, G, I, L, M, F, P, S, T, W, Y, V |
| SEQ ID NO: 220 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKEN$X_{152}$IRFSKSLGLPENHIVFPVPIDQCIDG<br>$X_{152}$ = Q, A, N, D, C, E, G, I, L, M, F, P, S, T, W, Y, V |

| SEQ ID NO | Name | Sequence |
|---|---|---|
| SEQ ID NO: 221 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFX$_{153}$RFSKSLGLPENHIVFPVPIDQCIDG<br>X$_{153}$ = Q, A, N, D, C, E, G, I, L, M, F, P, S, T, W, Y, V |
| SEQ ID NO: 222 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIX$_{154}$FSKSLGLPENHIVFPVPIDQCIDG<br>X$_{154}$ = Q, A, N, D, C, E, G, I, L, M, F, P, S, T, W, Y, V, R |
| SEQ ID NO: 223 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRX$_{155}$SKSLGLPENHIVFPVPIDQCIDG<br>X$_{155}$ = Q, A, N, D, C, E, G, I, L, M, F, P, S, T, W, Y, V |
| SEQ ID NO: 224 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFX$_{156}$KSLGLPENHIVFPVPIDQCIDG<br>X$_{156}$ = Q, A, N, D, C, E, G, I, L, M, F, P, S, T, W, Y, V |
| SEQ ID NO: 225 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSX$_{157}$SLGLPENHIVFPVPIDQCIDG<br>X$_{157}$ = Q, A, N, D, C, E, G, I, L, M, F, P, S, T, W, Y, V, K |
| SEQ ID NO: 226 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKX$_{158}$LGLPENHIVFPVPIDQCIDG<br>X$_{158}$ = Q, A, N, D, C, E, G, I, L, M, F, P, S, T, W, Y, V |
| SEQ ID NO: 227 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSX$_{159}$GLPENHIVFPVPIDQCIDG<br>X$_{159}$ = Q, A, N, D, C, E, G, I, L, M, F, P, S, T, W, Y, V |
| SEQ ID NO: 228 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLX$_{160}$LPENHIVFPVPIDQCIDG<br>X$_{160}$ = Q, A, N, D, C, E, G, I, L, M, F, P, S, T, W, Y, V |
| SEQ ID NO: 229 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGX$_{161}$PENHIVFPVPIDQCIDG<br>X$_{161}$ = Q, A, N, D, C, E, G, I, L, M, F, P, S, T, W, Y, V |
| SEQ ID NO: 230 | NGAL Mutant | QDSTSDLIPAPPLSKVPLQQNFQDNQFQGKWYVVGLAGNAILREDKDP<br>QKMYATIYELKEDKSYNVTSVLFRKKKCDYWIRTFVPGCQPGEFTLGN<br>IKSYPGLTSYLVRVVSTNYNQHAMVFFKKVSQNREYFKITLYGRTKEL<br>TSELKENFIRFSKSLGLX$_{162}$ENHIVFPVPIDQCIDG<br>X$_{162}$ = Q, A, N, D, C, E, G, I, L, M, F, P, S, T, W, Y, V |

| SEQ ID NO | Name | Sequence |
|---|---|---|
| SEQ ID NO: 231 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPX$_{163}$NHIVFPVPIDQCIDG<br>X$_{163}$ = Q, A, N, D, C, E, G, I, L, M, F, P, S, T, W, Y, V |
| SEQ ID NO: 232 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPEX$_{164}$HIVFPVPIDQCIDG<br>X$_{164}$ = Q, A, N, D, C, E, G, I, L, M, F, P, S, T, W, Y, V |
| SEQ ID NO: 233 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENX$_{165}$IVFPVPIDQCIDG<br>X$_{165}$ = Q, A, N, D, C, E, G, I, L, M, F, P, S, T, W, Y, V, H |
| SEQ ID NO: 234 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHX$_{166}$VFPVPIDQCIDG<br>X$_{166}$ = Q, A, N, D, C, E, G, I, L, M, F, P, S, T, W, Y, V |
| SEQ ID NO: 235 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIX$_{167}$FPVPIDQCIDG<br>X$_{167}$ = Q, A, N, D, C, E, G, I, L, M, F, P, S, T, W, Y, V |
| SEQ ID NO: 236 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVX$_{168}$PVPIDQCIDG<br>X$_{168}$ = Q, A, N, D, C, E, G, I, L, M, F, P, S, T, W, Y, V |
| SEQ ID NO: 237 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFX$_{169}$VPIDQCIDG<br>X$_{169}$ = Q, A, N, D, C, E, G, I, L, M, F, P, S, T, W, Y, V |
| SEQ ID NO: 238 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPX$_{170}$PIDQCIDG<br>X$_{170}$ = Q, A, N, D, C, E, G, I, L, M, F, P, S, T, W, Y, V |
| SEQ ID NO: 239 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVX$_{171}$IDQCIDG<br>X$_{171}$ = Q, A, N, D, C, E, G, I, L, M, F, P, S, T, W, Y, V |
| SEQ ID NO: 240 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPX$_{172}$DQCIDG<br>X$_{172}$ = Q, A, N, D, C, E, G, I, L, M, F, P, S, T, W, Y, V |
| SEQ ID NO: 241 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIX$_{173}$QCIDG<br>X$_{173}$ = Q, A, N, D, C, E, G, I, L, M, F, P, S, T, W, Y, V |

| SEQ ID NO | Name | Sequence |
|---|---|---|
| SEQ ID NO: 242 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPID$X_{174}$CIDG<br>$X_{174}$ = Q, A, N, D, C, E, G, I, L, M, F, P, S, T, W, Y, V |
| SEQ ID NO: 243 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQ$X_{175}$IDG<br>$X_{175}$ = Q, A, N, D, C, E, G, I, L, M, F, P, S, T, W, Y, V |
| SEQ ID NO: 244 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQC$X_{176}$DG<br>$X_{176}$ = Q, A, N, D, C, E, G, I, L, M, F, P, S, T, W, Y, V |
| SEQ ID NO: 245 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCI$X_{177}$G<br>$X_{177}$ = Q, A, N, D, C, E, G, I, L, M, F, P, S, T, W, Y, V |
| SEQ ID NO: 246 | NGAL Mutant | QDSTSDLIPAPPLSKVPLQQNFQDNQFQGKWYVVGLAGNAILREDKDP QKMYATIYELKEDKSYNVTSVLFRKKKCDYWIRTFVPGCQPGEFTLGN IKSYPGLTSYLVRVVSTNYNQHAMVFFKKVSQNREYFKITLYGRTKEL TSELKENFIRFSKSLGLPENHIVFPVPIDQCID$X_{178}$<br>$X_{178}$ = Q, A, N, D, C, E, G, I, L, M, F, P, S, T, W, Y, V |
| SEQ ID NO: 247 | D1-4-2-1-4-2 | QDSTSDLIPAPPLSKVPLQQNFQDNQFQGKWYVVGLAGNAILREDEDP QTMYATIYELAEDGSYNVTSVLFADDGCDYWIRTFVPGCQPGEFTLGN IASYPGLTSYLVRVVSTDYNQHAMVFFKKVSESAEYFKITLYGRTKEL TSELKENFIRFSKSLGLPENHIVFPVPIDQCIDG |
| SEQ ID NO: 248 | D1-4-2-1-4-3 | QDSTSDLIPAPPLSSVPLQQNFQDNQFQGKWYVVGLAGNAILREDEDP QTMYATIYELAEDGSYNVTSVLFRDDGCDYWIRTFVPGCQPGEFTLGN IASYPGLTSYLVRVVSTDYDEFAMVFFKKVSESAEYFKITLYGRTKEL TSELKENFIRFSKSLGLPENHIVFPVPIDQCIDG |
| SEQ ID NO: 249 | K3-4-2 | QDSTSDLIPAPPLSSVPLQQNFQDNQFQGKWYVVGLAGNAILREDEDP QTMYATIYELKEDGSYNVTSVLFADDGCDYWIRTFVPGCQPGEFTLGN IQSYPGLTSYLVRVVSTNYNQFAMVFFKKVSQNQEYFKITLYGRTKEL TSELQENFIRFSKSLGLPENNIVFPVPIDQCIDG |
| SEQ ID NO: 250 | K3-3Con | QDSTSDLIPAPPLSSVPLQQNFQDNQFQGKWYVVGLAGNAILAEDEDP QKMYATIYELKEDKSYNVTSVLFRDDGCDYWIRTFVPGCQPGEFTLGN IQSYPGLTSYLVRVVSTNYNQFAMVFFKKVSQNQEYFKITLYGATAEL TSELQENFIRFSASLGLPENNIVFPVPIDQCIDG |
| SEQ ID NO: 251 | K3-4Con | QDSTSDLIPAPPLSSVPLQQNFQDNQFQGKWYVVGLAGNAILAEDEDP QKMYATIYELKEDKSYNVTSVLFRDDGCDYWIRTFVPGCQPGEFTLGN IQSYPGLTSYLVRVVSTNYNQFAMVFFKKVSQNQEYFKITLYGRTKEL TSELQENFIRFSASLGLPENNIVFPVPIDQCIDG |
| SEQ ID NO: 252 | K3Cys | QDSTSDLIPAPPLSSVPLQQNFQDNQFQGKWYVVGLAGNAILREDEDP QKMYATIYELKEDKSYNVTSVLFRDDGCDYWIRTFVPGSQPGEFTLGN IQSYPGLTSYLVRVVSTNYNQFAMVFFKKVSQNQEYFKITLYGRTKEL TSELQENFIRFSKSLGLPENNIVFPVPIDQCIDG |

Example 3

The superscripted numbers in this Example refer to the numbered references in the list of references that follows this Example. Ngal mutant Mut1 or mutant 1 refers to the K3 NGAL protein of SEQ ID NO:2. Ngal mutant Mut2 or mutant 2 refers to the K3Cys protein protein of SEQ ID NO:252.

Iron is specifically bound by transferrin in circulation, which preserves its bioavailability and prevents its redox toxicity. However, non-transferrin-bound iron (NTBI) appears in patients with a variety of diseases[1-3]. NTBI damages liver[4-7], heart[8-12], endocrine glands[13-18] and kidney[19-21] and severe overload can be fatal[22,23]. To date, two small molecules, deferoxamine (DFO) and deferiprone are available for the chelation of NTBI and the treatment of iron overload. However, these molecules demonstrate significant toxicity. We have discovered an endogenous mechanism of iron transport (Barasch: Molecular Cell, 2002; Nature N&V, 2005; Nature Chemical Biology, 2010), which we realized could be manipulated to safely export iron from the body.

Figure 6A:
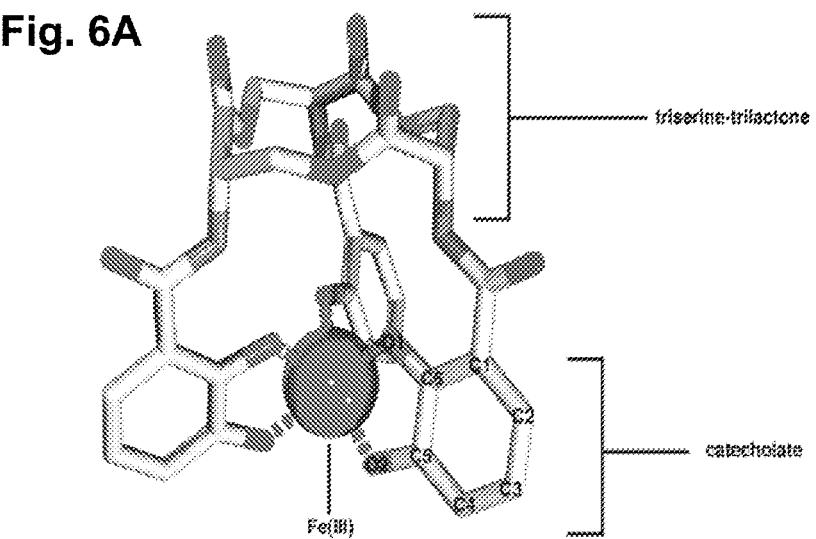
FIGS. 6A-6B.
Figure 6B:
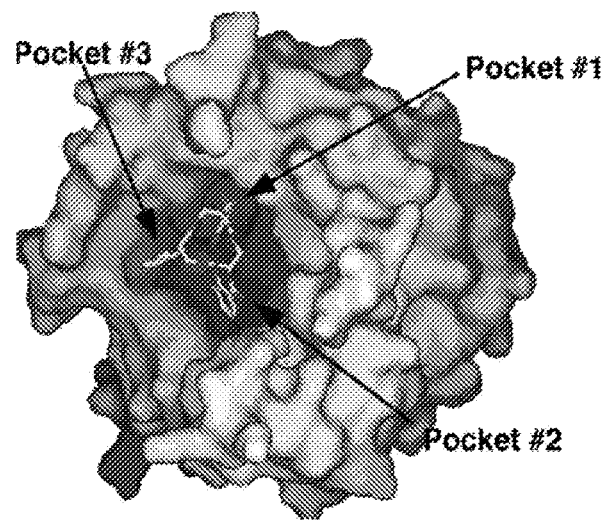

The Ngal protein is expressed by damaged epithelia (AKI: JASN, 2003; JCI, 2005; Lancet, 2005; Ann Int Med, 2008) and then it is rapidly secreted. Ngal captures catecholate-type bacterial siderophores (Enterochelin, Ent)[3] and endogenous catechols[6] (FIGS. 6A-6B). Ngal:catechol:Fe complexes are stable for transport. They are filtered from the blood by the glomerulus and captured by proximal tubule megalin where Ngal is degraded and its iron recycled[38]. Here we evaluated Ngal mutants that we believe bypass megalin, yet still bind Ent:iron, hence providing an unexpected, novel, therapeutic that can safely excrete NTBI in the urine.

Figure 22A:
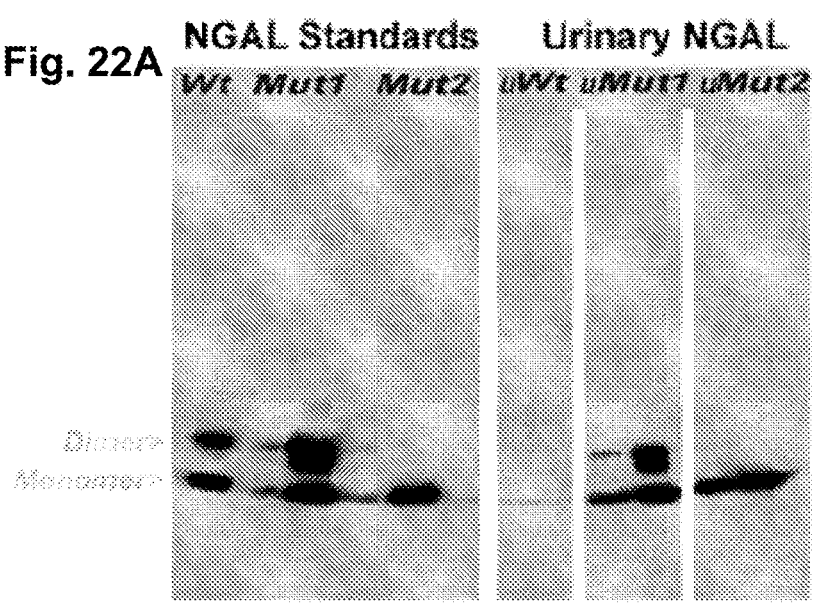
FIGS. 22A-22B.
Figure 22B:
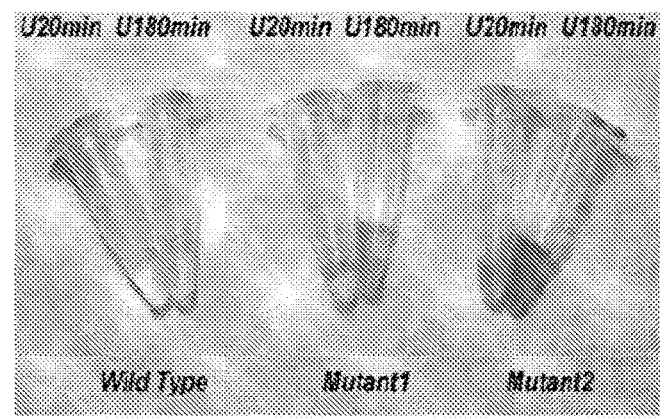
Figure 25:
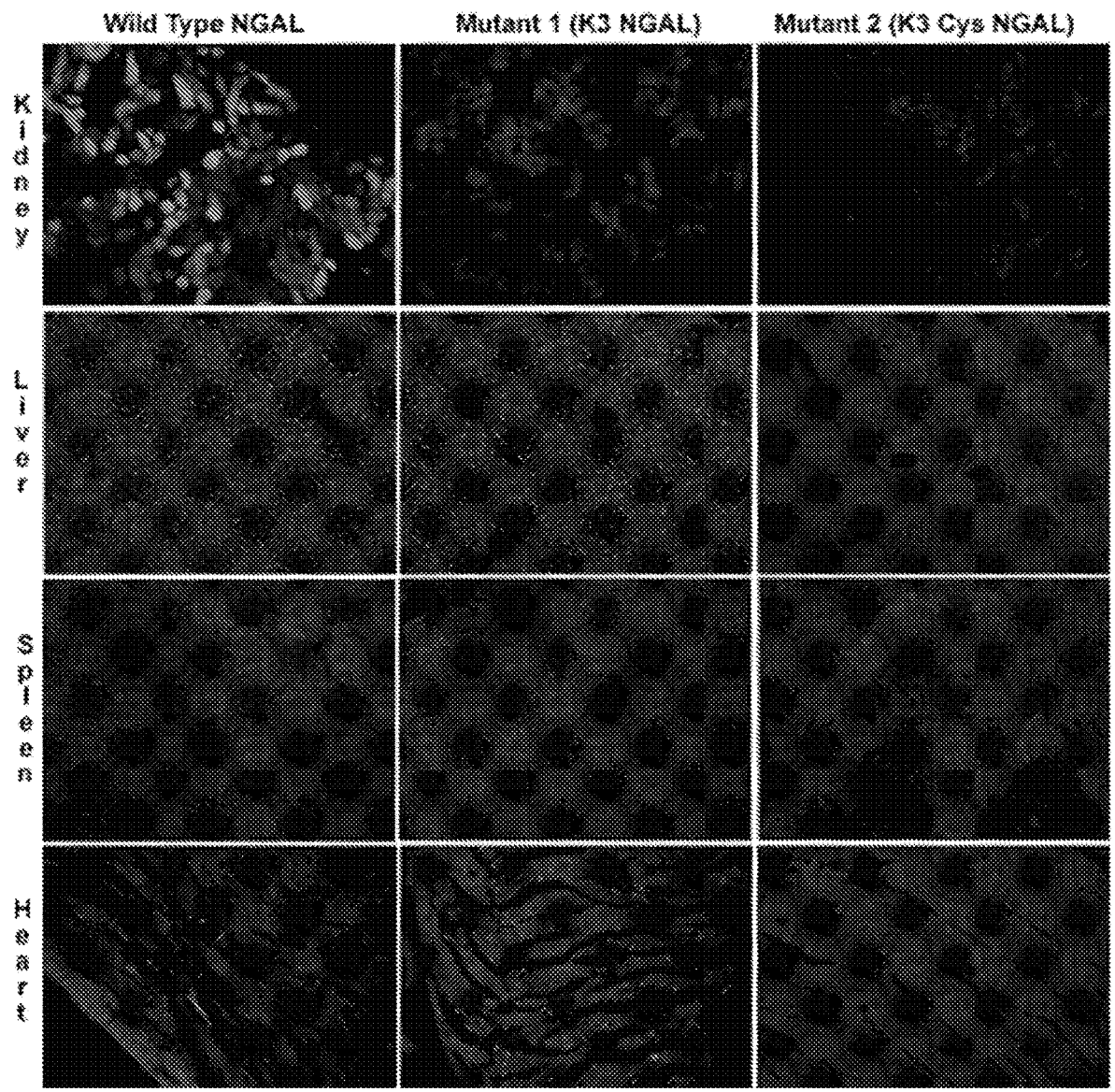
FIG. 25. Distribution of NGAL (Wt, K3 or K3Cys) labeled with the dye Alexa Fluor™ 568 (Molecular Probes—Invitrogen) in the mouse. Note that Wt NGAL is taken up by the kidney's proximal tubule, but limited uptake by K3 and K3Cys. Even more striking is the fact that K3Cys is essentially not found in the body (it is all excreted into the urine) whereas K3 is found in the liver's Kupffer cells (bright red staining).
Figure 26:
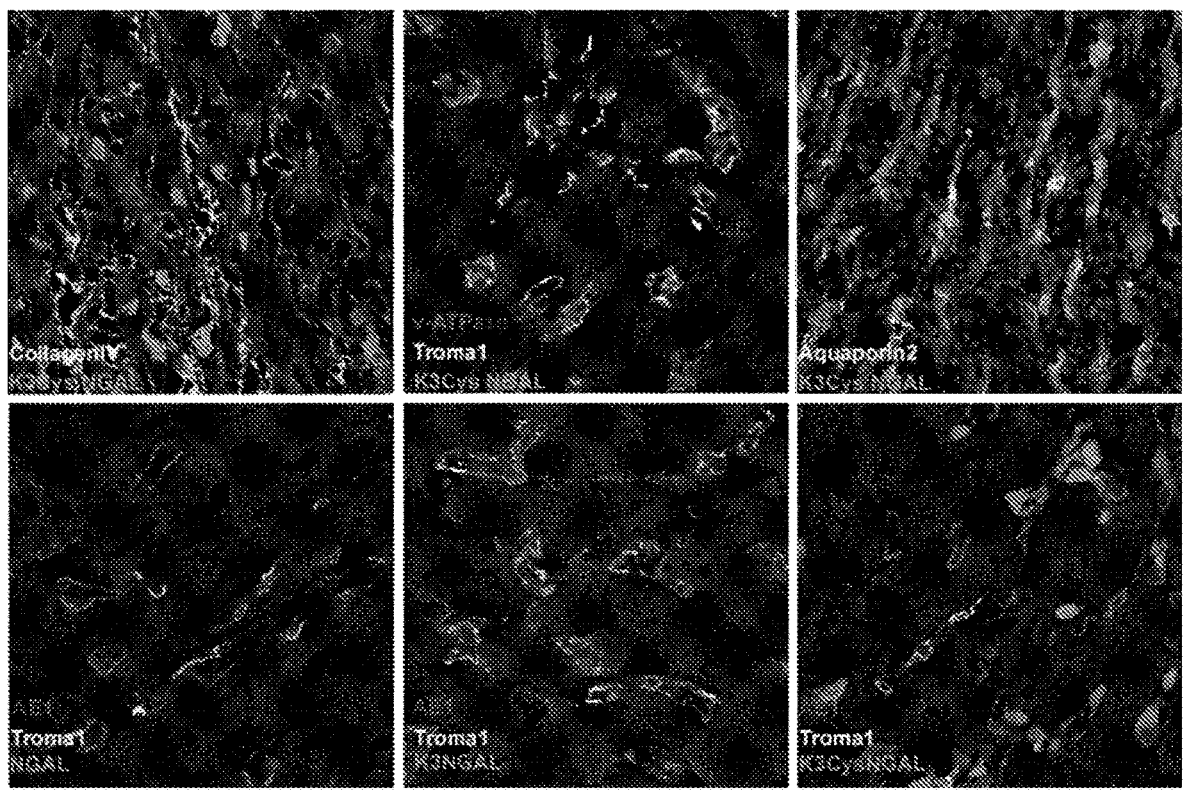
FIG. 26. Top row Alexa Fluor™ 568-mutant NGAL is captured in scattered cells in the collecting ducts outlined by collagen, including ATPase+ intercalated cells and Aquaporin2+ collecting ducts. Bottom row: Comparison wt, mut1, mut2 uptake in AE1+ cells.
Figure 27:
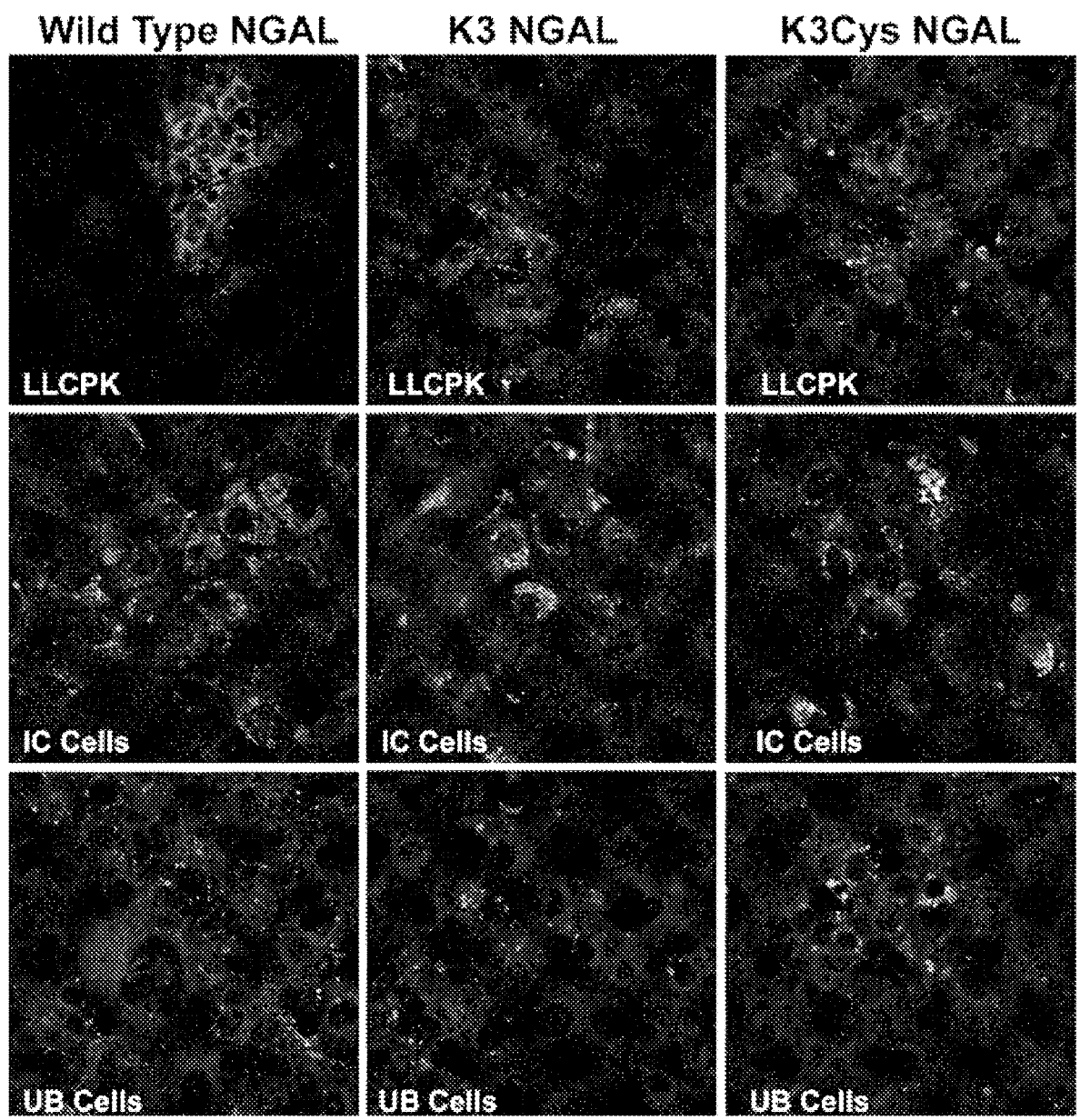
FIG. 27. Three cell lines. LLCPK distinguishes wt and mutant Ngal and takes up only wt Ngal (red uptake), Intercalated cells take up both wild type and mutant Ngal, whereas UB cells take up neither wt nor mutant Ngal Green=fluorescent dextran which demonstrates that all of the cell lines have active endocytosis and highlights the fact that each have distinct NGAL uptake profiles.

Evaluation of the Ngal-Megalin Interaction by the Generation of Ngal Mutants:

We produced a series of defined mutations in the positive surface residues of Ngal and identified clones that traffic into the urine (i.e. bypassing megalin). The appearance in the urine was detected by immunoblot. In order to increase the export of the mutant Ngal, we introduced a new mutation in the so called unpaired cysteine to block the homodimerization of Ngal. This resulted in nearly complete loss of Ngal from the mouse by filtration and urinary excretion—most likely a result of the lower molecular weight of the monomeric—non dimerizable species. This new species of Ngal (called mut2) appeared earlier in the urine than mutants (e.g. mut1) that were still capable of dimerization (FIGS. 22A-22B). We next examined a wide range of organs and found that while wt Ngal was most prominently captured by proximal tubule (and also in Kupfer cells), our mutants were not recognized by the proximal tubule and in fact mutant 2 was depleted from all sites of cellular capture (because it was rapidly excreted, FIG. 25). Further examination revealed that the mutants did in fact have one site of capture in the kidney and that was in cells of the collecting duct. This could be seen when the microscopic image was amplified by increasing exposure time. By staining with antibodies for the two cell types found in the collecting ducts (FIG. 26), both principal and intercalated cells take up the mutant Ngal (in marked contrast to proximal tubules). Numerical counts of the cells that captured Ngal showed that 64.7% were AQ2+ principal cells (n=769/1188) and 27.3% were ATPase+ (n=158/579) and 23.5% (n=190/807) were AE1+ indicating that approximately ⅓ of the cells that captured NGAL expressed marker genes typical of alpha intercalated cells. In order to model these findings and to determine whether the uptake represented a cell autonomous process, we utilized a variety of cell lines. While all cell lines took up fluorescent dextran, LLCPK took up wild type Ngal, not the mutant species, intercalated cells took up both wild type and mutant Ngal and UB cells took up neither wild type nor mutant Ngal (FIG. 27). Taken together, the data indicate that megalin (expressed in the proximal tubule and in the LLCPK cell line) captures Ngal, but the mutant form of Ngal can bypass these cells. Additionally, collecting duct cells may express non-megalin Ngal receptors. This extensive characterization indicated that by manipulating the surface residues and the dimerization site for Ngal, we have created a protein which can traffic from the periphery into the urine.

Ngal:Ent:$Fe^{III}$ Interaction in Ngal Mutants

Figure 28:
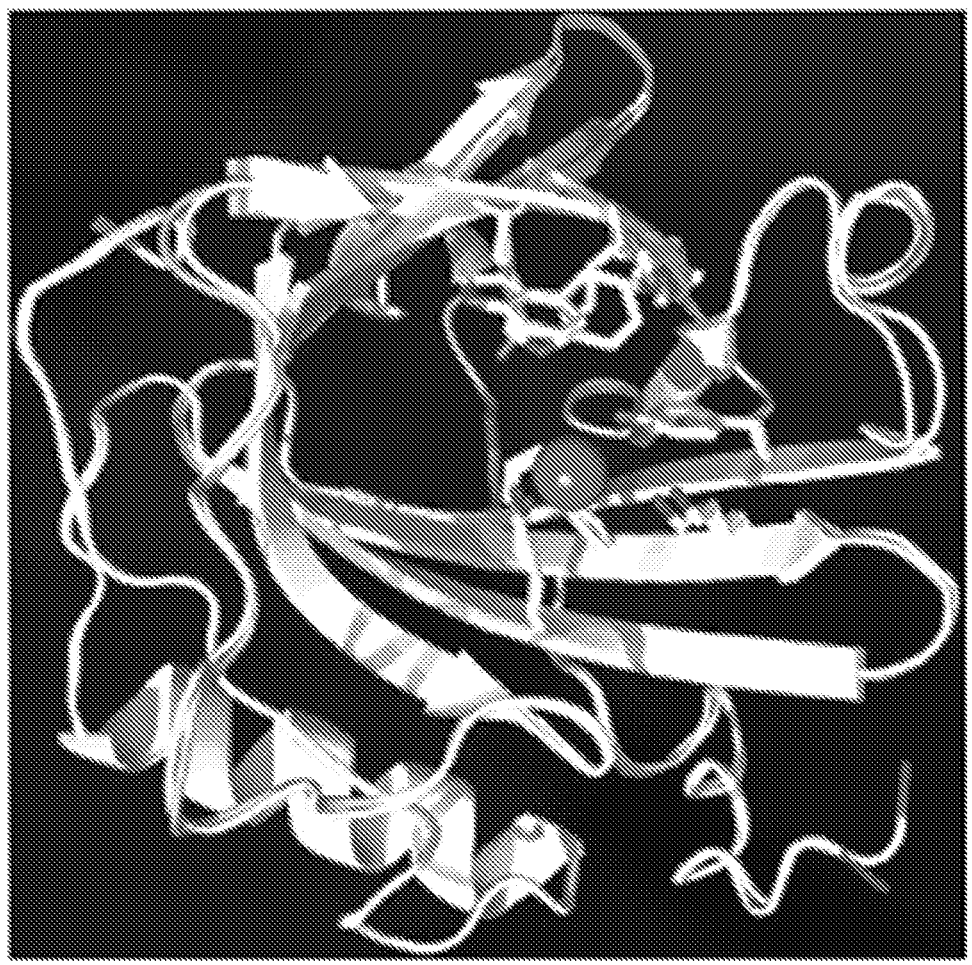
FIG. 28. Superimposed structures of wild type and mutant 1 of Ngal demonstrating nearly identical structures with the potential to bind siderophores and iron (red sphere). Mutant amino acids are indicated in yellow.
Figure 29A:
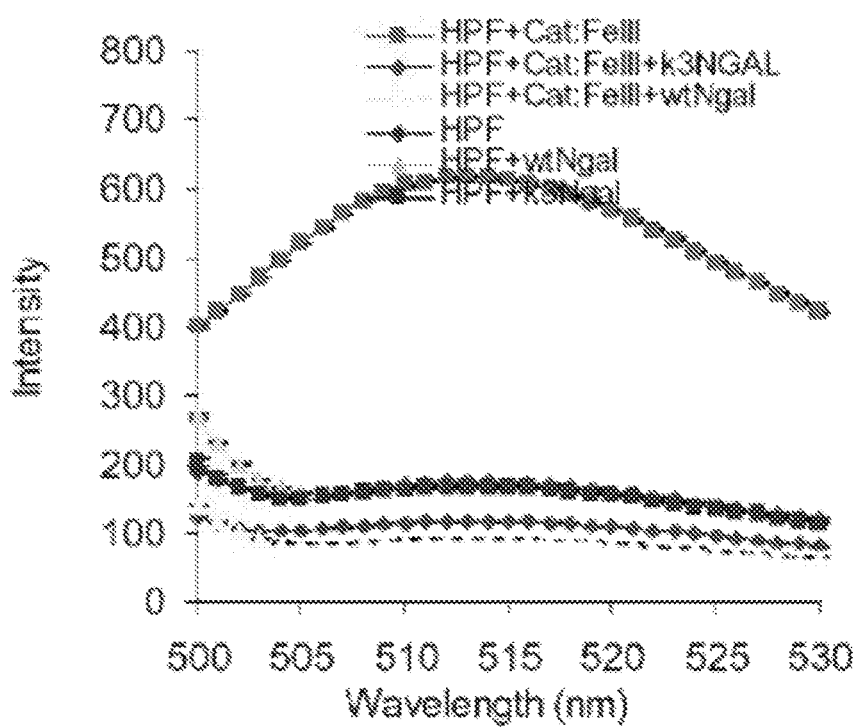
FIGS. 29A-29C. Redox measurements of mutant Ngal.
Figure 29B:
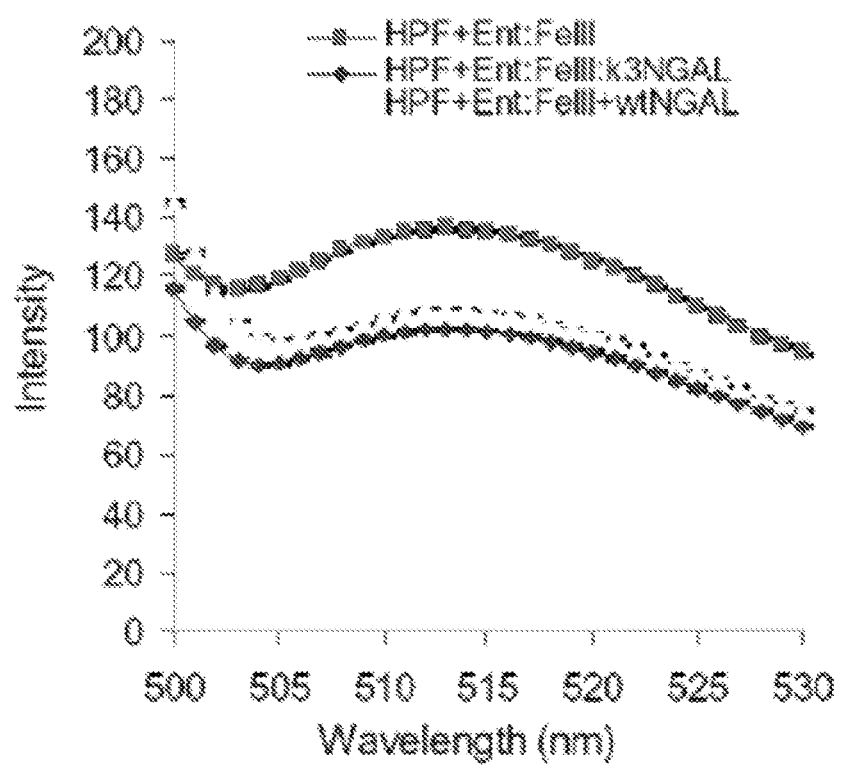
Figure 29C:
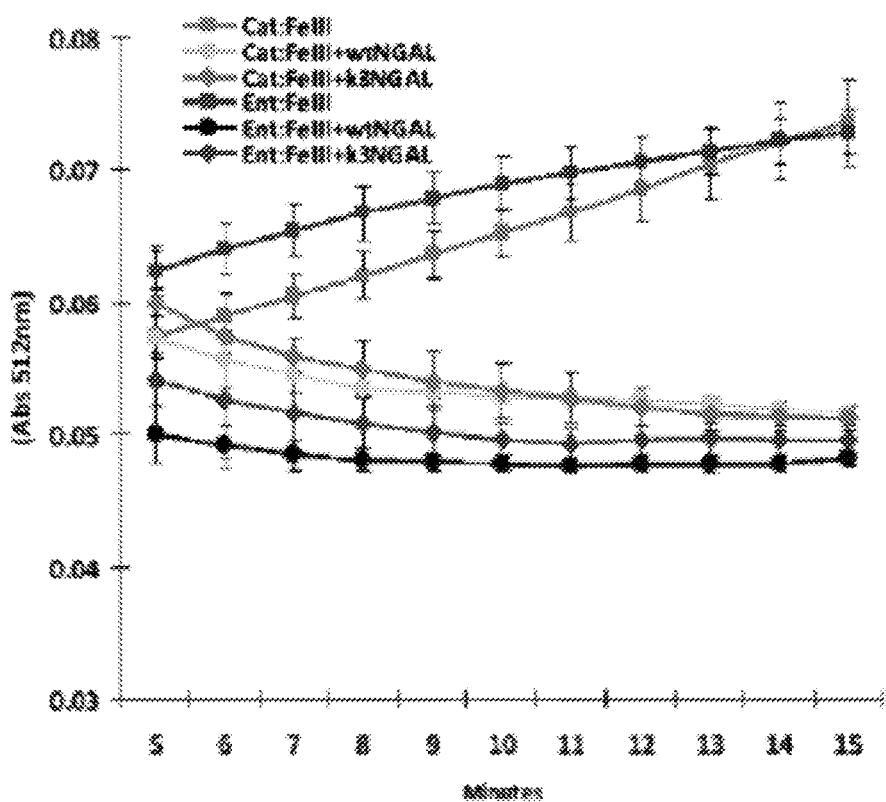

In order to utilize Ngal as a therapeutic agent to remove iron from overloaded mice, we examined the Ngal:iron complex. We decided to use the siderophore Ent as the iron binding co-factor, not only because it has a high affinity for the Ngal calyx (0.4 nM and 3.57 nM, respectively) but also because it fails to release bound iron even at low pH. First, x-ray crystallographic studies of mutant1 were performed. Since our mutants affect crystal contacts in all the known Ngal crystal forms, he approached this as a de novo structural determination. He found that the mutant could be superimposed on wild type Ngal, implying that our extensive mutagenesis did not dramatically alter the overall structure of the protein (FIG. 28). Second, we examined whether ligation by iron siderophores created a stabilized structure that quenched the endogenous chemical reactivity of iron. Using both fluorescein activation assays and ferric reduction assays, we found that the mutants of NGAL bound siderophores and iron without triggering redox activity (FIGS. 29A-29C).

Safe Excretion of Iron by the Delivery of Mutant NGAL: Ent:$Fe^{III}$

Figure 23:
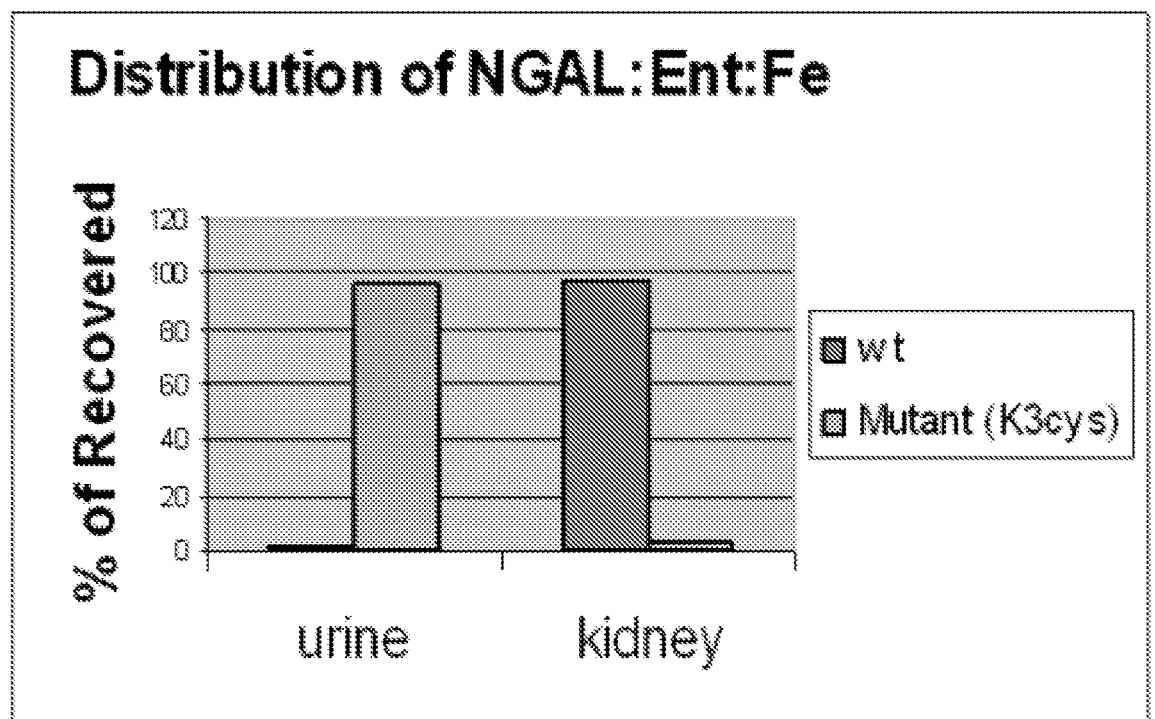
FIG. 23 and FIG. 24. Distribution of NGAL:Ent:Fe in kidney and urine 180 minutes after their introduction in mice. Either wild-type NGAL protein (Wt) or K3Cys protein (Mutant (K3cys)) was introduced in mice and the percentage of iron recovered in either the urine or the kidney of the injected mouse was determined. The Y-axis represents the percentage of recovered iron.
Figure 24:
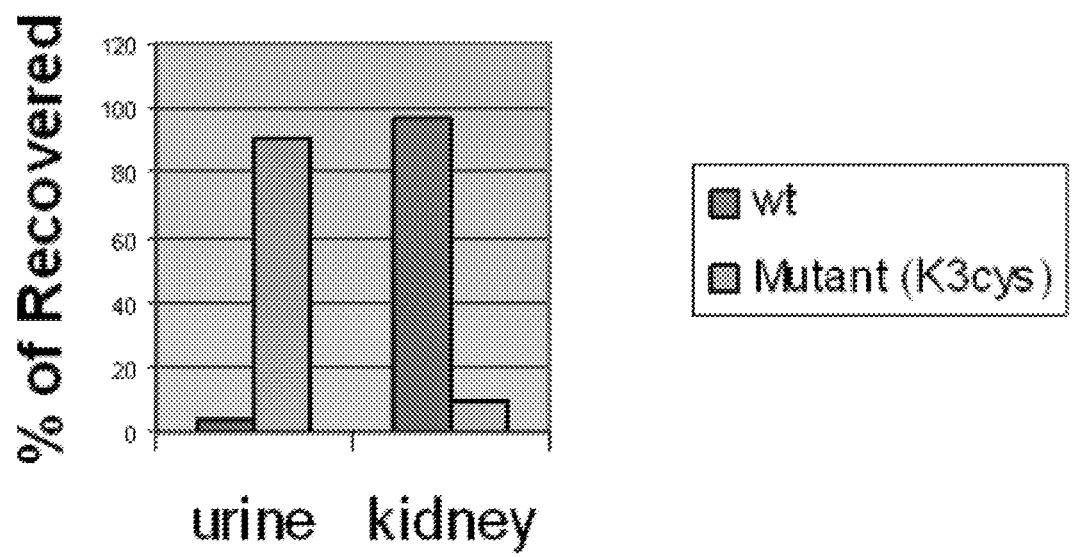

To test whether mutant Ngal can efficiently chelate and deliver NTBI to the urine through the kidney, we introduced the bacterially expressed Ngal ligated to Ent:$^{59}Fe^{III}$ into mice, and collected the urine for 3 hrs. We found that mutant 1 delivered 23% of the injected mutant 1 Ngal-$^{59}Fe^{III}$ complex to the urine, paralleling the percentage of the protein found in the urine, while less than 0.1% of the wild type injectate was excreted. When we injected mutant2 (cysteine mutation), nearly 100% of the iron was found in the urine. In FIG. 23, we can see that only trace amounts of wild type $^{59}Fe^{III}$ (in the Ngal:Ent complex) was found in the urine—almost all of it accumulated in the kidney, but mutant 2 was not retained in the kidney, but rather it was all found in the urine.

Figure 30:
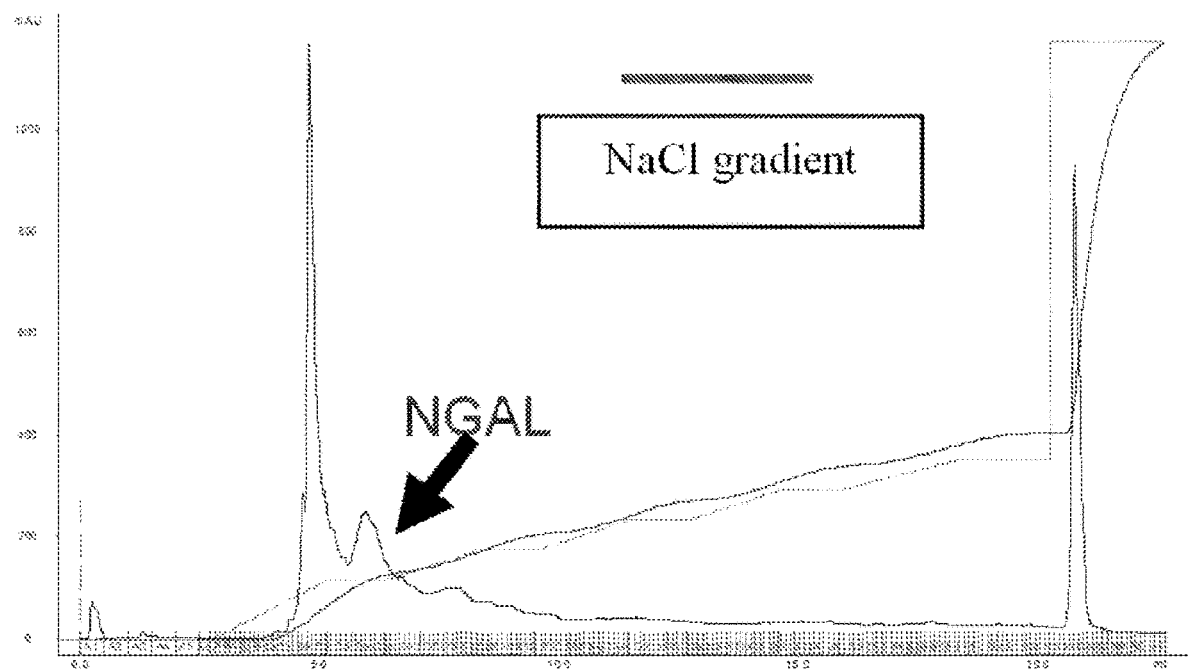
FIG. 30. Purification of NGAL protein. NaCL gradient showing that the small peak contains the majority of the NGAL protein.

Based on these results, we are planning to test whether mutant 2 can capture, chelate, traffic and remove endogenous NTBI. To do this however requires mammalian expressed Ngal rather than the bacterial species to avoid the effects on iron metabolism of endotoxins. We are now quite advanced in purification of Ngal from 293 cells grown in spinner suspension. The purification utilizes Blue and Heparin Sepharose™, gel filtration and anion exchange. The last step of the process is seen in FIG. 30. Note that the small peak contains the majority of Ngal protein. We think this protocol will produce enough Ngal for depletion experiments.

REFERENCES

1. Hershko, C., and Peto, T. E. Non-transferrin plasma iron. Br. J. Haematol. 66: 149-151, 1987.
2. Breuer, W., Ronson, A., Slotki, I. N., Abramov, A., Hershko, C., and Cabantchik, Z. I. The assessment of serum nontransferrin-bound iron in chelation therapy and iron supplementation. Blood. 95: 2975-2982, 2000.
3. Andrews, N. C. Iron metabolism: Iron Deficiency and Iron Overload. Annu. Rev. Genomics Hum. Genet. 1:75-98, 2000.
4. Thakemgpol, K., Fucharoen, S., Boonyaphipat, P., Srisook, K., Sahaphong, S., Vathanophas, V., and Stitnimankarn, T. Liver injury due to iron overload in thalassemia: histopathologic and ultrastructural studies. Biometals. 9: 177-183, 1996.
5. Conte, D., Piperno, A., Mandelli, C., et al. Clinical, biochemical and histological features of primary haemochromatosis: a report of 67 cases. Liver. 6: 310-315, 1986.
6. Tsukamoto, H., Home, W., Kamimura, S., Niemela, O., Parkkila, S., Yla-Herttuala, S., and Brittenham, G. M.

Experimental liver cirrhosis induced by alcohol and iron. J. Clin. Invest. 96: 620-630, 1995.
7. Berdoukas, V., Bohane, T., Tobias, V., et al. Liver iron concentration and fibrosis in a cohort of transfusion-dependent patients on long-term desferrioxamine therapy. Hematol. J. 5: 572-578, 2004.
8. Liu, P., and *Olivieri*, N. Iron overload cardiomyopathies: new insights into an old disease. Cardiovasc. Drugs. Ther. 8:101-110, 1994.
9. Buja, L. M., and Roberts, W. C. Iron in the heart. Etiology and clinical significance. Am. J. Med. 51: 209-221, 1971.
10. Schwartz, K. A., Li, Z., Schwartz, D. E., et al. Earliest cardiac toxicity induced by iron overload selectively inhibits electrical conduction. J. Appl. Physiol. 93: 746-751, 2002.
11. Oudit, G. Y., Trivieri, M. G., Khaper, N., Liu, P. P., and Backx, P. H. Role of L-type Ca2+ channels in iron transport and iron-overload cardiomyopathy. J. Mol. Med. 84: 349-364, 2006.
12. Oudit, G. Y., Sun, H., Trivieri, M. G., Koch, S. E., Dawood, F., Ackerley, C., Yazdanpanah, M., Wilson, G. J., Schwartz, A., Liu, P. P., and Backx, P. H. L-type $Ca^{2+}$ channels provide a major pathway for iron entry into cardiomyocytes in iron-overload cardiomyopathy, Nat. Med. 9: 1187-1194, 2003.
13. Andrews, N.C. Disorders of iron metabolism. N. Engl. J. Med. 341: 1986-1995, 1999.
14. Argyropoulou, M. I., and Astrakas, L. MRI evaluation of tissue iron burden in patients with beta-thalassaemia major. Pediatr. Radiol. 37: 1191-1200, 2007.
15. Argyropoulou, M. I., Kiortsis, D. N., Astrakas, L., Metafratzi, Z., Chalissos, N., Efremidis, S. C. Liver, bone marrow, pancreas and pituitary gland iron overload in young and adult thalassemic patients: a T2 relaxometry study. Eur. Radiol. 17: 3025-3030, 2007.
16. Cunningham, M. J., Macklin, E. A., Neufeld, E. J., and Cohen, A. R. Complications of beta-thalassemia major in North America. Blood. 104: 34-39, 2004.
17. Fung, E., Harmatz, P. R., Lee, P. D., Milet, M., Bellevue, R., Jeng, M. R., Kalinyak, K. A., Hudes, M., Bhatia, S., and Vichinsky, E. P. Increased prevalence of iron-overload associated endocrinopathy in thalassaemia versus sickle-cell disease. Br. J. Haematol. 135: 574-582, 2006.
18. Kattamis, C., and Kattamis, A. C. Management of thalassemias: growth and development, hormone substitution, vitamin supplementation, and vaccination. Semin. Hematol. 32: 269-279, 1995.
19. Eschbach, J. W., and Adamson, J. W. Iron overload in renal failure patients: Changes since the introduction of erythropoietin therapy. Kidney Int. 55: S35-S43, 1999.
20. Lorenz, M., Kletzmayr, J., Huber, A., Hod, A. H., Sunder-Plassmann, G., and Födinger, M. Iron overload in kidney transplants: Prospective analysis of biochemical and genetic markers. Kidney Int. 67, 691-697, 2005.
21. Mandalunis, P. M., and Ubios, A. M. Experimental Renal Failure and Iron Overload: A Histomorphometric Study in Rat Tibia. Toxicol. Pathol. 33; 398-403, 2005.
22. Karnon, J., Zeuner, D., Brown, J., Ades, A. E., Wonke, B., and Modell, B. Lifetime treatment costs of beta-thalassaemia major. Clin. Lab. Haematol. 21: 377-385, 1999.
23. Darbari, D. S., Kple-Faget, P., Kwagyan, J., Rana, S., Gordeuk, V. R., and Castro, O. Circumstances of death in adult sickle cell disease patients. Am. J. Hematol. 81: 858-863, 2006.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

---

What is claimed is:

1. A polypeptide that comprises an amino acid sequence that is at least 99% identical to a sequence selected from the group consisting of SEQ ID NO:3, SEQ ID NO:4 or SEQ ID NO:5.

2. A nucleic acid encoding a polypeptide of claim 1.

3. A pharmaceutical composition comprising the polypeptide of claim 1.

4. A method for treating iron overload in a subject in need thereof, the method comprising administering to the subject an effective amount of a pharmaceutical composition comprising a polypeptide that comprises an amino acid sequence that is at least 99% identical to a sequence selected from the group consisting of SEQ ID NO:3, SEQ ID NO:4 or SEQ ID NO:5, wherein the pharmaceutical composition further comprises a siderophore.

5. The method of claim 4, wherein the siderophore is selected from the group consisting of enterochelin, pyrogallol, carboxymycobactin, bacillibactin, and catechol.

6. The method of claim 4, wherein the siderophore is pH insensitive.

7. The method of claim 4, wherein the siderophore binds to the polypeptide and iron in urine.

8. The method of claim 4, wherein the siderophore binds to the polypeptide and iron at blood pH.

9. The method of claim 4, wherein the siderophore binds to the polypeptide and iron in the blood.

10. The method of claim 4, wherein the polypeptide and the siderophore are present in a 1:1 molar ratio.

11. The method of claim 4, wherein the siderophore binds to the polypeptide and iron at pH 4.0 to 7.5.

* * * * *

SEQUENCE LISTING

```
<160> NUMBER OF SEQ ID NOS: 252

<210> SEQ ID NO 1
<211> LENGTH: 178
<212> TYPE: PRT
<213> ORGANISM: Homo sapiens

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
```

```
                115                 120                 125
Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45
```

Gln Lys Met Tyr Ala Thr Ile Tyr Glu Leu Lys Glu Asp Lys Ser Tyr
            50                  55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Lys Lys Val Ser Gln
            115                 120                 125

Asn Gln Glu Tyr Phe Lys Ile Thr Leu Tyr Gly Arg Thr Lys Glu Leu
            130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Gly Ser Tyr
            50                  55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Gln Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

```
Leu Pro Glu Asn Asn Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Gln Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 8
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
```

```
                85                  90                  95
Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Asp Ser Thr Ser Asp Leu Ile Pro Ala Pro Pro Leu Ser Ser Val
1               5                   10                  15
```

```
Pro Leu Gln Gln Asn Phe Gln Asp Asn Gln Phe Gln Gly Lys Trp Tyr
             20                  25                  30

Val Val Gly Leu Ala Gly Asn Ala Ile Leu Arg Glu Asp Glu Asp Pro
         35                  40                  45

Gln Lys Met Tyr Ala Thr Ile Tyr Glu Leu Lys Glu Asp Lys Ser Tyr
     50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
             100                 105                 110

Thr Asn Tyr Asn Gln Phe Ala Met Val Phe Lys Lys Val Ser Gln
         115                 120                 125

Asn Arg Glu Tyr Phe Lys Ile Thr Leu Tyr Gly Arg Thr Lys Glu Leu
         130                 135                 140

Thr Ser Glu Leu Lys Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                 165                 170                 175

Asp Gly

<210> SEQ ID NO 11
<211> LENGTH: 179
<212> TYPE: PRT
<213> ORGANISM: Equus caballus

<400> SEQUENCE: 11

Arg Asp Pro Ala Pro Lys Leu Ile Pro Ala Pro Pro Leu Asp Arg Val
 1               5                  10                  15

Pro Leu Gln Pro Asp Phe Lys Asp Asp Gln Phe Gln Gly Lys Trp Tyr
             20                  25                  30

Val Val Gly Val Ala Gly Asn Ala Phe Lys Lys Glu Glu Gln Gly Gln
         35                  40                  45

Phe Thr Met Tyr Thr Thr Thr Tyr Glu Leu Lys Glu Asp His Ser Tyr
     50                  55                  60

Asn Val Thr Ser Ile Leu Leu Arg Asp Gln Asn Cys Asp His Trp Ile
 65                  70                  75                  80

Arg Thr Phe Ile Pro Ser Ser Gln Pro Gly Gln Phe Asn Leu Gly Asp
                 85                  90                  95

Ile Lys Arg Tyr Phe Gly Val Gln Ser Tyr Ile Val Arg Val Ala Asp
             100                 105                 110

Thr Asp Tyr Asn Gln Phe Ala Ile Val Phe Phe Arg Lys Val Tyr Lys
         115                 120                 125

Asn Gln Glu Tyr Phe Lys Thr Thr Leu Tyr Arg Arg Thr Lys Glu Leu
         130                 135                 140

Thr Pro Glu Leu Arg Glu Lys Phe Ile Ser Phe Ala Lys Ser Leu Gly
145                 150                 155                 160

Leu Thr Asp Asp His Ile Ile Phe Pro Val Pro Ile Asp Gln Cys Ile
                 165                 170                 175

Asp Glu Glu

<210> SEQ ID NO 12
<211> LENGTH: 178
<212> TYPE: PRT
```

<213> ORGANISM: Canis familiaris

<400> SEQUENCE: 12

Gln Asp Ser Thr Pro Ser Leu Ile Pro Ala Pro Pro Leu Lys Val
1               5                   10                  15

Pro Leu Gln Pro Asp Phe Gln His Asp Gln Phe Gln Gly Lys Trp Tyr
                20                  25                  30

Val Ile Gly Ile Ala Gly Asn Ile Leu Lys Lys Glu Gly His Gly Gln
            35                  40                  45

Leu Lys Met Tyr Thr Thr Thr Tyr Glu Leu Lys Asp Asp Gln Ser Tyr
        50                  55                  60

Asn Val Thr Ser Thr Leu Leu Arg Asn Glu Arg Cys Asp Tyr Trp Asn
65                  70                  75                  80

Arg Asp Phe Val Pro Ser Phe Gln Pro Gly Gln Phe Ser Leu Gly Asp
                85                  90                  95

Ile Gln Leu Tyr Pro Gly Val Gln Ser Tyr Leu Val Gln Val Val Ala
            100                 105                 110

Thr Asn Tyr Asn Gln Tyr Ala Leu Val Tyr Phe Arg Lys Val Tyr Lys
        115                 120                 125

Ser Gln Glu Tyr Phe Lys Ile Thr Leu Tyr Gly Arg Thr Lys Glu Leu
    130                 135                 140

Pro Leu Glu Leu Lys Lys Glu Phe Ile Arg Phe Ala Lys Ser Ile Gly
145                 150                 155                 160

Leu Thr Glu Asp His Ile Ile Phe Pro Val Pro Ile Asp Gln Cys Ile
                165                 170                 175

Asp Glu

<210> SEQ ID NO 13
<211> LENGTH: 179
<212> TYPE: PRT
<213> ORGANISM: Sus scrofa

<400> SEQUENCE: 13

Gln Gly Thr Ile Pro Asn Trp Ile Pro Ala Pro Pro Leu Ser Lys Val
1               5                   10                  15

Pro Leu Gln Pro Asn Phe Gln Ala Asp Gln Phe Gln Gly Lys Trp Tyr
                20                  25                  30

Val Val Gly Leu Ala Gly Asn Ala Val Lys Lys Glu Glu Gln Gly Arg
            35                  40                  45

Phe Lys Met Tyr Thr Thr Thr Tyr Glu Leu Lys Glu Asp Gly Ser Tyr
        50                  55                  60

Asn Val Ile Ser Thr Leu Leu Arg Gly Gln Leu Cys Asp Asn Trp Ile
65                  70                  75                  80

Arg Thr Phe Val Pro Ser Leu Gln Pro Gly Gln Phe Lys Leu Gly Asp
                85                  90                  95

Ile Lys Lys Tyr Ser Gly Leu Gln Ser Tyr Val Val Arg Val Val Ser
            100                 105                 110

Thr Asn Tyr Ser Gln Phe Ala Ile Val Phe Phe Lys Lys Val Ser Asn
        115                 120                 125

Asn Gln Glu Tyr Phe Lys Thr Thr Leu Tyr Gly Arg Thr Lys Val Leu
    130                 135                 140

Ser Pro Glu Leu Lys Glu Asn Phe Val Arg Phe Ala Lys Ser Leu Gly
145                 150                 155                 160

Leu Ser Asp Asp Asn Ile Ile Phe Pro Val Ala Ile Asp Gln Cys Ile
                165                 170                 175

Asp Gly Gln

<210> SEQ ID NO 14
<211> LENGTH: 178
<212> TYPE: PRT
<213> ORGANISM: Pan troglodytes

<400> SEQUENCE: 14

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Arg Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 15
<211> LENGTH: 178
<212> TYPE: PRT
<213> ORGANISM: Macaca mulatta

<400> SEQUENCE: 15

```
Gln Asp Ser Ser Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ser Gly Asn Ala Val Gly Arg Lys Asp Glu Ala Pro
        35                  40                  45

Leu Lys Met Tyr Ala Thr Ile Tyr Glu Leu Lys Glu Asp Lys Ser Tyr
    50                  55                  60

Asn Val Thr Ser Ile Leu Phe Arg Lys Glu Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Gln Asn His Pro Gly Leu Thr Ser Tyr Val Val Arg Val Val Ser
            100                 105                 110

Thr Asn Tyr Lys Gln Tyr Ala Met Val Phe Phe Lys Lys Val Ser Gln
        115                 120                 125

Asn Lys Glu Tyr Phe Lys Ile Thr Leu Tyr Gly Arg Thr Lys Glu Leu
```

```
                130                 135                 140
Thr Ser Glu Leu Lys Glu Asn Phe Ile Arg Phe Ser Lys Ser Leu Gly
145                 150                 155                 160

Leu Pro Glu Asn His Ile Val Phe Ser Val Pro Ile Asp Gln Cys Ile
                165                 170                 175

Asn Gly

<210> SEQ ID NO 16
<211> LENGTH: 179
<212> TYPE: PRT
<213> ORGANISM: Bos taurus

<400> SEQUENCE: 16

Arg Ser Ser Ser Arg Leu Leu Arg Ala Pro Pro Leu Ser Arg Ile
1               5                   10                  15

Pro Leu Gln Pro Asn Phe Gln Ala Asp Gln Phe Gln Gly Lys Trp Tyr
                20                  25                  30

Thr Val Gly Val Ala Gly Asn Ala Ile Lys Lys Glu Glu Gln Asp Pro
            35                  40                  45

Leu Lys Met Tyr Ser Ser Asn Tyr Glu Leu Lys Glu Asp Gly Ser Tyr
50                  55                  60

Asn Val Thr Ser Ile Leu Leu Lys Asp Asp Leu Cys Asp Tyr Trp Ile
65                  70                  75                  80

Arg Thr Phe Val Pro Ser Ser Gln Pro Gly Gln Phe Thr Leu Gly Asn
                85                  90                  95

Ile Lys Ser Tyr Arg Gly Ile Arg Ser Tyr Thr Val Arg Val Val Asn
            100                 105                 110

Thr Asp Tyr Asn Gln Phe Ala Ile Val Tyr Phe Lys Lys Val Gln Arg
        115                 120                 125

Lys Lys Thr Tyr Phe Lys Ile Thr Leu Tyr Gly Arg Thr Lys Glu Leu
130                 135                 140

Thr Pro Glu Val Arg Glu Asn Phe Ile Asn Phe Ala Lys Ser Leu Gly
145                 150                 155                 160

Leu Thr Asp Asp His Ile Val Phe Thr Val Pro Ile Asp Arg Cys Ile
                165                 170                 175

Asp Asp Gln

<210> SEQ ID NO 17
<211> LENGTH: 180
<212> TYPE: PRT
<213> ORGANISM: Mus musculus

<400> SEQUENCE: 17

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
                20                  25                  30

Val Val Gly Leu Ala Gly Asn Ala Val Gln Lys Lys Thr Glu Gly Ser
            35                  40                  45

Phe Thr Met Tyr Ser Thr Ile Tyr Glu Leu Gln Glu Asn Asn Ser Tyr
50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95
```

```
Gly Asn Met His Arg Tyr Pro Gln Val Gln Ser Tyr Asn Val Gln Val
                100                 105                 110

Ala Thr Thr Asp Tyr Asn Gln Phe Ala Met Val Phe Arg Lys Thr
        115                 120                 125

Ser Glu Asn Lys Gln Tyr Phe Lys Ile Thr Leu Tyr Gly Arg Thr Lys
145             130                 135                 140

Glu Leu Ser Pro Glu Leu Lys Glu Arg Phe Thr Arg Phe Ala Lys Ser
145                 150                 155                 160

Leu Gly Leu Lys Asp Asp Asn Ile Ile Phe Ser Val Pro Thr Asp Gln
                165                 170                 175

Cys Ile Asp Asn
            180

<210> SEQ ID NO 18
<211> LENGTH: 178
<212> TYPE: PRT
<213> ORGANISM: Rattus norvegicus

<400> SEQUENCE: 18

Gln Asp Ser Thr Gln Asn Leu Ile Pro Ala Pro Pro Leu Ile Ser Val
1               5                   10                  15

Pro Leu Gln Pro Gly Phe Trp Thr Glu Arg Phe Gln Gly Arg Trp Phe
                20                  25                  30

Val Val Gly Leu Ala Gly Asn Ala Val Gln Lys Glu Arg Gln Ser Arg
            35                  40                  45

Phe Thr Met Tyr Ser Thr Ile Tyr Glu Leu Gln Glu Asp Asn Ser Tyr
        50                  55                  60

Asn Val Thr Ser Ile Leu Val Arg Gly Gln Gly Cys Arg Tyr Trp Ile
65                  70                  75                  80

Arg Thr Phe Val Pro Ser Ser Arg Pro Gly Gln Phe Thr Leu Gly Asn
                85                  90                  95

Ile His Ser Tyr Pro Gln Ile Gln Ser Tyr Asp Val Gln Val Ala Asp
            100                 105                 110

Thr Asp Tyr Asp Gln Phe Ala Met Val Phe Phe Gln Lys Thr Ser Glu
        115                 120                 125

Asn Lys Gln Tyr Phe Lys Val Thr Leu Tyr Gly Arg Thr Lys Gly Leu
    130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 19
<211> LENGTH: 4655
<212> TYPE: PRT
<213> ORGANISM: Homo sapiens

<400> SEQUENCE: 19

Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
                20                  25                  30

Phe Arg Cys Gly Ser Gly His Cys Ile Pro Ala Asp Trp Arg Cys Asp
            35                  40                  45

Gly Thr Lys Asp Cys Ser Asp Asp Ala Asp Glu Ile Gly Cys Ala Val
```

```
            50                  55                  60
Val Thr Cys Gln Gln Gly Tyr Phe Lys Cys Gln Ser Glu Gly Gln Cys
 65                  70                  75                  80

Ile Pro Asn Ser Trp Val Cys Asp Gln Asp Gln Cys Asp Asp Gly
                 85                  90                  95

Ser Asp Glu Arg Gln Asp Cys Ser Gln Ser Thr Cys Ser Ser His Gln
                100                 105                 110

Ile Thr Cys Ser Asn Gly Gln Cys Ile Pro Ser Glu Tyr Arg Cys Asp
                115                 120                 125

His Val Arg Asp Cys Pro Asp Gly Ala Asp Glu Asn Asp Cys Gln Tyr
                130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
                180                 185                 190

Gly Glu Cys Ile Pro Arg Ala Tyr Val Cys Asp His Asp Asn Asp Cys
                195                 200                 205

Gln Asp Gly Ser Asp Glu His Ala Cys Asn Tyr Pro Thr Cys Gly Gly
210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val His Lys Cys Ser Pro Arg Glu Trp Ser
                260                 265                 270

Cys Pro Glu Ser Gly Arg Cys Ile Ser Ile Tyr Lys Val Cys Asp Gly
                275                 280                 285

Ile Leu Asp Cys Pro Gly Arg Glu Asp Glu Asn Asn Thr Ser Thr Gly
                290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
                325                 330                 335

Ile Ile Asn His Asn Asp Ser Arg Thr Cys Val Glu Phe Asp Asp Cys
                340                 345                 350

Gln Ile Trp Gly Ile Cys Asp Gln Lys Cys Glu Ser Arg Pro Gly Arg
                355                 360                 365

His Leu Cys His Cys Glu Glu Gly Tyr Ile Leu Glu Arg Gly Gln Tyr
                370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
                420                 425                 430

Tyr His Leu Gln Arg Val Phe Trp Thr Asp Thr Val Gln Asn Lys Val
                435                 440                 445

Phe Ser Val Asp Ile Asn Gly Leu Asn Ile Gln Glu Val Leu Asn Val
                450                 455                 460

Ser Val Glu Thr Pro Glu Asn Leu Ala Val Asp Trp Val Asn Asn Lys
465                 470                 475                 480
```

```
Ile Tyr Leu Val Glu Thr Lys Val Asn Arg Ile Asp Met Val Asn Leu
                485             490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
            515                 520                 525

Trp Glu Ser Leu Ser Gly Glu Pro Lys Leu Glu Arg Ala Phe Met Asp
            530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val His Gly Gly Ser Leu Ile Pro His Pro Phe Gly Val Ser
            595                 600                 605

Leu Phe Glu Gly Gln Val Phe Phe Thr Asp Trp Thr Lys Met Ala Val
            610                 615                 620

Leu Lys Ala Asn Lys Phe Thr Glu Thr Asn Pro Gln Val Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
            690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Val Gly Ile Asp Phe Asp Ala Gln Asp
            740                 745                 750

Ser Thr Ile Phe Phe Ser Asp Met Ser Lys His Met Ile Phe Lys Gln
    755                 760                 765

Lys Ile Asp Gly Thr Gly Arg Glu Ile Leu Ala Ala Asn Arg Val Glu
    770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
            835                 840                 845

Ala Lys Ile Met Arg Ala Trp Ser Asp Gly Ser His Leu Leu Pro Val
850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895
```

-continued

Ser Thr Phe Asp Gly Leu Asp Arg Arg Leu Gly His Ile Glu Gln
          900                 905                 910

Met Thr His Pro Phe Gly Leu Ala Ile Phe Gly Glu His Leu Phe Phe
          915                 920                 925

Thr Asp Trp Arg Leu Gly Ala Ile Ile Arg Val Arg Lys Ala Asp Gly
          930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
          965                 970                 975

Pro Thr His Pro Asn Gly Asp Cys Ser His Phe Cys Phe Pro Val Pro
          980                 985                 990

Asn Phe Gln Arg Val Cys Gly Cys Pro Tyr Gly Met Arg Leu Ala Ser
          995                 1000                1005

Asn His Leu Thr Cys Glu Gly Asp Pro Thr Asn Glu Pro Pro Thr
          1010                1015                1020

Glu Gln Cys Gly Leu Phe Ser Phe Pro Cys Lys Asn Gly Arg Cys
          1025                1030                1035

Val Pro Asn Tyr Tyr Leu Cys Asp Gly Val Asp Asp Cys His Asp
          1040                1045                1050

Asn Ser Asp Glu Gln Leu Cys Gly Thr Leu Asn Asn Thr Cys Ser
          1055                1060                1065

Ser Ser Ala Phe Thr Cys Gly His Gly Glu Cys Ile Pro Ala His
          1070                1075                1080

Trp Arg Cys Asp Lys Arg Asn Asp Cys Val Asp Gly Ser Asp Glu
          1085                1090                1095

His Asn Cys Pro Thr His Ala Pro Ala Ser Cys Leu Asp Thr Gln
          1100                1105                1110

Tyr Thr Cys Asp Asn His Gln Cys Ile Ser Lys Asn Trp Val Cys
          1115                1120                1125

Asp Thr Asp Asn Asp Cys Gly Asp Gly Ser Asp Glu Lys Asn Cys
          1130                1135                1140

Asn Ser Thr Glu Thr Cys Gln Pro Ser Gln Phe Asn Cys Pro Asn
          1145                1150                1155

His Arg Cys Ile Asp Leu Ser Phe Val Cys Asp Gly Asp Lys Asp
          1160                1165                1170

Cys Val Asp Gly Ser Asp Glu Val Gly Cys Val Leu Asn Cys Thr
          1175                1180                1185

Ala Ser Gln Phe Lys Cys Ala Ser Gly Asp Lys Cys Ile Gly Val
          1190                1195                1200

Thr Asn Arg Cys Asp Gly Val Phe Asp Cys Ser Asp Asn Ser Asp
          1205                1210                1215

Glu Ala Gly Cys Pro Thr Arg Pro Pro Gly Met Cys His Ser Asp
          1220                1225                1230

Glu Phe Gln Cys Gln Glu Asp Gly Ile Cys Ile Pro Asn Phe Trp
          1235                1240                1245

Glu Cys Asp Gly His Pro Asp Cys Leu Tyr Gly Ser Asp Glu His
          1250                1255                1260

Asn Ala Cys Val Pro Lys Thr Cys Pro Ser Ser Tyr Phe His Cys
          1265                1270                1275

Asp Asn Gly Asn Cys Ile His Arg Ala Trp Leu Cys Asp Arg Asp
          1280                1285                1290

Asn Asp Cys Gly Asp Met Ser Asp Glu Lys Asp Cys Pro Thr Gln

-continued

```
            1295                1300                1305
Pro Phe Arg Cys Pro Ser Trp Gln Trp Gln Cys Leu Gly His Asn
    1310                1315                1320
Ile Cys Val Asn Leu Ser Val Val Cys Asp Gly Ile Phe Asp Cys
    1325                1330                1335
Pro Asn Gly Thr Asp Glu Ser Pro Leu Cys Asn Gly Asn Ser Cys
    1340                1345                1350
Ser Asp Phe Asn Gly Gly Cys Thr His Glu Cys Val Gln Glu Pro
    1355                1360                1365
Phe Gly Ala Lys Cys Leu Cys Pro Leu Gly Phe Leu Leu Ala Asn
    1370                1375                1380
Asp Ser Lys Thr Cys Glu Asp Ile Asp Glu Cys Asp Ile Leu Gly
    1385                1390                1395
Ser Cys Ser Gln His Cys Tyr Asn Met Arg Gly Ser Phe Arg Cys
    1400                1405                1410
Ser Cys Asp Thr Gly Tyr Met Leu Glu Ser Asp Gly Arg Thr Cys
    1415                1420                1425
Lys Val Thr Ala Ser Glu Ser Leu Leu Leu Leu Val Ala Ser Gln
    1430                1435                1440
Asn Lys Ile Ile Ala Asp Ser Val Thr Ser Gln Val His Asn Ile
    1445                1450                1455
Tyr Ser Leu Val Glu Asn Gly Ser Tyr Ile Val Ala Val Asp Phe
    1460                1465                1470
Asp Ser Ile Ser Gly Arg Ile Phe Trp Ser Asp Ala Thr Gln Gly
    1475                1480                1485
Lys Thr Trp Ser Ala Phe Gln Asn Gly Thr Asp Arg Arg Val Val
    1490                1495                1500
Phe Asp Ser Ser Ile Ile Leu Thr Glu Thr Ile Ala Ile Asp Trp
    1505                1510                1515
Val Gly Arg Asn Leu Tyr Trp Thr Asp Tyr Ala Leu Glu Thr Ile
    1520                1525                1530
Glu Val Ser Lys Ile Asp Gly Ser His Arg Thr Val Leu Ile Ser
    1535                1540                1545
Lys Asn Leu Thr Asn Pro Arg Gly Leu Ala Leu Asp Pro Arg Met
    1550                1555                1560
Asn Glu His Leu Leu Phe Trp Ser Asp Trp Gly His His Pro Arg
    1565                1570                1575
Ile Glu Arg Ala Ser Met Asp Gly Ser Met Arg Thr Val Ile Val
    1580                1585                1590
Gln Asp Lys Ile Phe Trp Pro Cys Gly Leu Thr Ile Asp Tyr Pro
    1595                1600                1605
Asn Arg Leu Leu Tyr Phe Met Asp Ser Tyr Leu Asp Tyr Met Asp
    1610                1615                1620
Phe Cys Asp Tyr Asn Gly His His Arg Arg Gln Val Ile Ala Ser
    1625                1630                1635
Asp Leu Ile Ile Arg His Pro Tyr Ala Leu Thr Leu Phe Glu Asp
    1640                1645                1650
Ser Val Tyr Trp Thr Asp Arg Ala Thr Arg Arg Val Met Arg Ala
    1655                1660                1665
Asn Lys Trp His Gly Gly Asn Gln Ser Val Val Met Tyr Asn Ile
    1670                1675                1680
Gln Trp Pro Leu Gly Ile Val Ala Val His Pro Ser Lys Gln Pro
    1685                1690                1695
```

```
Asn Ser Val Asn Pro Cys Ala Phe Ser Arg Cys Ser His Leu Cys
        1700            1705            1710

Leu Leu Ser Ser Gln Gly Pro His Phe Tyr Ser Cys Val Cys Pro
        1715            1720            1725

Ser Gly Trp Ser Leu Ser Pro Asp Leu Leu Asn Cys Leu Arg Asp
        1730            1735            1740

Asp Gln Pro Phe Leu Ile Thr Val Arg Gln His Ile Ile Phe Gly
        1745            1750            1755

Ile Ser Leu Asn Pro Glu Val Lys Ser Asn Asp Ala Met Val Pro
        1760            1765            1770

Ile Ala Gly Ile Gln Asn Gly Leu Asp Val Glu Phe Asp Asp Ala
        1775            1780            1785

Glu Gln Tyr Ile Tyr Trp Val Glu Asn Pro Gly Glu Ile His Arg
        1790            1795            1800

Val Lys Thr Asp Gly Thr Asn Arg Thr Val Phe Ala Ser Ile Ser
        1805            1810            1815

Met Val Gly Pro Ser Met Asn Leu Ala Leu Asp Trp Ile Ser Arg
        1820            1825            1830

Asn Leu Tyr Ser Thr Asn Pro Arg Thr Gln Ser Ile Glu Val Leu
        1835            1840            1845

Thr Leu His Gly Asp Ile Arg Tyr Arg Lys Thr Leu Ile Ala Asn
        1850            1855            1860

Asp Gly Thr Ala Leu Gly Val Gly Phe Pro Ile Gly Ile Thr Val
        1865            1870            1875

Asp Pro Ala Arg Gly Lys Leu Tyr Trp Ser Asp Gln Gly Thr Asp
        1880            1885            1890

Ser Gly Val Pro Ala Lys Ile Ala Ser Ala Asn Met Asp Gly Thr
        1895            1900            1905

Ser Val Lys Thr Leu Phe Thr Gly Asn Leu Glu His Leu Glu Cys
        1910            1915            1920

Val Thr Leu Asp Ile Glu Glu Gln Lys Leu Tyr Trp Ala Val Thr
        1925            1930            1935

Gly Arg Gly Val Ile Glu Arg Gly Asn Val Asp Gly Thr Asp Arg
        1940            1945            1950

Met Ile Leu Val His Gln Leu Ser His Pro Trp Gly Ile Ala Val
        1955            1960            1965

His Asp Ser Phe Leu Tyr Tyr Thr Asp Glu Gln Tyr Glu Val Ile
        1970            1975            1980

Glu Arg Val Asp Lys Ala Thr Gly Ala Asn Lys Ile Val Leu Arg
        1985            1990            1995

Asp Asn Val Pro Asn Leu Arg Gly Leu Gln Val Tyr His Arg Arg
        2000            2005            2010

Asn Ala Ala Glu Ser Ser Asn Gly Cys Ser Asn Asn Met Asn Ala
        2015            2020            2025

Cys Gln Gln Ile Cys Leu Pro Val Pro Gly Gly Leu Phe Ser Cys
        2030            2035            2040

Ala Cys Ala Thr Gly Phe Lys Leu Asn Pro Asp Asn Arg Ser Cys
        2045            2050            2055

Ser Pro Tyr Asn Ser Phe Ile Val Val Ser Met Leu Ser Ala Ile
        2060            2065            2070

Arg Gly Phe Ser Leu Glu Leu Ser Asp His Ser Glu Thr Met Val
        2075            2080            2085
```

```
Pro Val Ala Gly Gln Gly Arg Asn Ala Leu His Val Asp Val Asp
    2090                2095                2100

Val Ser Ser Gly Phe Ile Tyr Trp Cys Asp Phe Ser Ser Ser Val
    2105                2110                2115

Ala Ser Asp Asn Ala Ile Arg Arg Ile Lys Pro Asp Gly Ser Ser
    2120                2125                2130

Leu Met Asn Ile Val Thr His Gly Ile Gly Glu Asn Gly Val Arg
    2135                2140                2145

Gly Ile Ala Val Asp Trp Val Ala Gly Asn Leu Tyr Phe Thr Asn
    2150                2155                2160

Ala Phe Val Ser Glu Thr Leu Ile Glu Val Leu Arg Ile Asn Thr
    2165                2170                2175

Thr Tyr Arg Arg Val Leu Leu Lys Val Thr Val Asp Met Pro Arg
    2180                2185                2190

His Ile Val Val Asp Pro Lys Asn Arg Tyr Leu Phe Trp Ala Asp
    2195                2200                2205

Tyr Gly Gln Arg Pro Lys Ile Glu Arg Ser Phe Leu Asp Cys Thr
    2210                2215                2220

Asn Arg Thr Val Leu Val Ser Glu Gly Ile Val Thr Pro Arg Gly
    2225                2230                2235

Leu Ala Val Asp Arg Ser Asp Gly Tyr Val Tyr Trp Val Asp Asp
    2240                2245                2250

Ser Leu Asp Ile Ile Ala Arg Ile Arg Ile Asn Gly Glu Asn Ser
    2255                2260                2265

Glu Val Ile Arg Tyr Gly Ser Arg Tyr Pro Thr Pro Tyr Gly Ile
    2270                2275                2280

Thr Val Phe Glu Asn Ser Ile Ile Trp Val Asp Arg Asn Leu Lys
    2285                2290                2295

Lys Ile Phe Gln Ala Ser Lys Glu Pro Glu Asn Thr Glu Pro Pro
    2300                2305                2310

Thr Val Ile Arg Asp Asn Ile Asn Trp Leu Arg Asp Val Thr Ile
    2315                2320                2325

Phe Asp Lys Gln Val Gln Pro Arg Ser Pro Ala Glu Val Asn Asn
    2330                2335                2340

Asn Pro Cys Leu Glu Asn Asn Gly Gly Cys Ser His Leu Cys Phe
    2345                2350                2355

Ala Leu Pro Gly Leu His Thr Pro Lys Cys Asp Cys Ala Phe Gly
    2360                2365                2370

Thr Leu Gln Ser Asp Gly Lys Asn Cys Ala Ile Ser Thr Glu Asn
    2375                2380                2385

Phe Leu Ile Phe Ala Leu Ser Asn Ser Leu Arg Ser Leu His Leu
    2390                2395                2400

Asp Pro Glu Asn His Ser Pro Pro Phe Gln Thr Ile Asn Val Glu
    2405                2410                2415

Arg Thr Val Met Ser Leu Asp Tyr Asp Ser Val Ser Asp Arg Ile
    2420                2425                2430

Tyr Phe Thr Gln Asn Leu Ala Ser Gly Val Gly Gln Ile Ser Tyr
    2435                2440                2445

Ala Thr Leu Ser Ser Gly Ile His Thr Pro Thr Val Ile Ala Ser
    2450                2455                2460

Gly Ile Gly Thr Ala Asp Gly Ile Ala Phe Asp Trp Ile Thr Arg
    2465                2470                2475

Arg Ile Tyr Tyr Ser Asp Tyr Leu Asn Gln Met Ile Asn Ser Met
```

```
              2480                2485                2490

Ala Glu Asp Gly Ser Asn Arg Thr Val Ile Ala Arg Val Pro Lys
        2495                2500                2505

Pro Arg Ala Ile Val Leu Asp Pro Cys Gln Gly Tyr Leu Tyr Trp
        2510                2515                2520

Ala Asp Trp Asp Thr His Ala Lys Ile Glu Arg Ala Thr Leu Gly
        2525                2530                2535

Gly Asn Phe Arg Val Pro Ile Val Asn Ser Ser Leu Val Met Pro
        2540                2545                2550

Ser Gly Leu Thr Leu Asp Tyr Glu Glu Asp Leu Leu Tyr Trp Val
        2555                2560                2565

Asp Ala Ser Leu Gln Arg Ile Glu Arg Ser Thr Leu Thr Gly Val
        2570                2575                2580

Asp Arg Glu Val Ile Val Asn Ala Ala Val His Ala Phe Gly Leu
        2585                2590                2595

Thr Leu Tyr Gly Gln Tyr Ile Tyr Trp Thr Asp Leu Tyr Thr Gln
        2600                2605                2610

Arg Ile Tyr Arg Ala Asn Lys Tyr Asp Gly Ser Gly Gln Ile Ala
        2615                2620                2625

Met Thr Thr Asn Leu Leu Ser Gln Pro Arg Gly Ile Asn Thr Val
        2630                2635                2640

Val Lys Asn Gln Lys Gln Gln Cys Asn Asn Pro Cys Glu Gln Phe
        2645                2650                2655

Asn Gly Gly Cys Ser His Ile Cys Ala Pro Gly Pro Asn Gly Ala
        2660                2665                2670

Glu Cys Gln Cys Pro His Glu Gly Asn Trp Tyr Leu Ala Asn Asn
        2675                2680                2685

Arg Lys His Cys Ile Val Asp Asn Gly Glu Arg Cys Gly Ala Ser
        2690                2695                2700

Ser Phe Thr Cys Ser Asn Gly Arg Cys Ile Ser Glu Glu Trp Lys
        2705                2710                2715

Cys Asp Asn Asp Asn Asp Cys Gly Asp Gly Ser Asp Glu Met Glu
        2720                2725                2730

Ser Val Cys Ala Leu His Thr Cys Ser Pro Thr Ala Phe Thr Cys
        2735                2740                2745

Ala Asn Gly Arg Cys Val Gln Tyr Ser Tyr Arg Cys Asp Tyr Tyr
        2750                2755                2760

Asn Asp Cys Gly Asp Gly Ser Asp Glu Ala Gly Cys Leu Phe Arg
        2765                2770                2775

Asp Cys Asn Ala Thr Thr Glu Phe Met Cys Asn Asn Arg Arg Cys
        2780                2785                2790

Ile Pro Arg Glu Phe Ile Cys Asn Gly Val Asp Asn Cys His Asp
        2795                2800                2805

Asn Asn Thr Ser Asp Glu Lys Asn Cys Pro Asp Arg Thr Cys Gln
        2810                2815                2820

Ser Gly Tyr Thr Lys Cys His Asn Ser Asn Ile Cys Ile Pro Arg
        2825                2830                2835

Val Tyr Leu Cys Asp Gly Asp Asn Asp Cys Gly Asp Asn Ser Asp
        2840                2845                2850

Glu Asn Pro Thr Tyr Cys Thr His Thr Cys Ser Ser Ser Glu
        2855                2860                2865

Phe Gln Cys Ala Ser Gly Arg Cys Ile Pro Gln His Trp Tyr Cys
        2870                2875                2880
```

-continued

```
Asp Gln Glu Thr Asp Cys Phe Asp Ala Ser Asp Glu Pro Ala Ser
    2885                2890                2895

Cys Gly His Ser Glu Arg Thr Cys Leu Ala Asp Glu Phe Lys Cys
    2900                2905                2910

Asp Gly Gly Arg Cys Ile Pro Ser Glu Trp Ile Cys Asp Gly Asp
    2915                2920                2925

Asn Asp Cys Gly Asp Met Ser Asp Glu Asp Lys Arg His Gln Cys
    2930                2935                2940

Gln Asn Gln Asn Cys Ser Asp Ser Glu Phe Leu Cys Val Asn Asp
    2945                2950                2955

Arg Pro Pro Asp Arg Arg Cys Ile Pro Gln Ser Trp Val Cys Asp
    2960                2965                2970

Gly Asp Val Asp Cys Thr Asp Gly Tyr Asp Glu Asn Gln Asn Cys
    2975                2980                2985

Thr Arg Arg Thr Cys Ser Glu Asn Glu Phe Thr Cys Gly Tyr Gly
    2990                2995                3000

Leu Cys Ile Pro Lys Ile Phe Arg Cys Asp Arg His Asn Asp Cys
    3005                3010                3015

Gly Asp Tyr Ser Asp Glu Arg Gly Cys Leu Tyr Gln Thr Cys Gln
    3020                3025                3030

Gln Asn Gln Phe Thr Cys Gln Asn Gly Arg Cys Ile Ser Lys Thr
    3035                3040                3045

Phe Val Cys Asp Glu Asp Asn Asp Cys Gly Asp Gly Ser Asp Glu
    3050                3055                3060

Leu Met His Leu Cys His Thr Pro Glu Pro Thr Cys Pro Pro His
    3065                3070                3075

Glu Phe Lys Cys Asp Asn Gly Arg Cys Ile Glu Met Met Lys Leu
    3080                3085                3090

Cys Asn His Leu Asp Asp Cys Leu Asp Asn Ser Asp Glu Lys Gly
    3095                3100                3105

Cys Gly Ile Asn Glu Cys His Asp Pro Ser Ile Ser Gly Cys Asp
    3110                3115                3120

His Asn Cys Thr Asp Thr Leu Thr Ser Phe Tyr Cys Ser Cys Arg
    3125                3130                3135

Pro Gly Tyr Lys Leu Met Ser Asp Lys Arg Thr Cys Val Asp Ile
    3140                3145                3150

Asp Glu Cys Thr Glu Met Pro Phe Val Cys Ser Gln Lys Cys Glu
    3155                3160                3165

Asn Val Ile Gly Ser Tyr Ile Cys Lys Cys Ala Pro Gly Tyr Leu
    3170                3175                3180

Arg Glu Pro Asp Gly Lys Thr Cys Arg Gln Asn Ser Asn Ile Glu
    3185                3190                3195

Pro Tyr Leu Ile Phe Ser Asn Arg Tyr Tyr Leu Arg Asn Leu Thr
    3200                3205                3210

Ile Asp Gly Tyr Phe Tyr Ser Leu Ile Leu Glu Gly Leu Asp Asn
    3215                3220                3225

Val Val Ala Leu Asp Phe Asp Arg Val Glu Lys Arg Leu Tyr Trp
    3230                3235                3240

Ile Asp Thr Gln Arg Gln Val Ile Glu Arg Met Phe Leu Asn Lys
    3245                3250                3255

Thr Asn Lys Glu Thr Ile Ile Asn His Arg Leu Pro Ala Ala Glu
    3260                3265                3270
```

```
Ser Leu Ala Val Asp Trp Val Ser Arg Lys Leu Tyr Trp Leu Asp
    3275                3280                3285

Ala Arg Leu Asp Gly Leu Phe Val Ser Asp Leu Asn Gly Gly His
    3290                3295                3300

Arg Arg Met Leu Ala Gln His Cys Val Asp Ala Asn Asn Thr Phe
    3305                3310                3315

Cys Phe Asp Asn Pro Arg Gly Leu Ala Leu His Pro Gln Tyr Gly
    3320                3325                3330

Tyr Leu Tyr Trp Ala Asp Trp Gly His Arg Ala Tyr Ile Gly Arg
    3335                3340                3345

Val Gly Met Asp Gly Thr Asn Lys Ser Val Ile Ile Ser Thr Lys
    3350                3355                3360

Leu Glu Trp Pro Asn Gly Ile Thr Ile Asp Tyr Thr Asn Asp Leu
    3365                3370                3375

Leu Tyr Trp Ala Asp Ala His Leu Gly Tyr Ile Glu Tyr Ser Asp
    3380                3385                3390

Leu Glu Gly His His Arg His Thr Val Tyr Asp Gly Ala Leu Pro
    3395                3400                3405

His Pro Phe Ala Ile Thr Ile Phe Glu Asp Thr Ile Tyr Trp Thr
    3410                3415                3420

Asp Trp Asn Thr Arg Thr Val Glu Lys Gly Asn Lys Tyr Asp Gly
    3425                3430                3435

Ser Asn Arg Gln Thr Leu Val Asn Thr Thr His Arg Pro Phe Asp
    3440                3445                3450

Ile His Val Tyr His Pro Tyr Arg Gln Pro Ile Val Ser Asn Pro
    3455                3460                3465

Cys Gly Thr Asn Asn Gly Gly Cys Ser His Leu Cys Leu Ile Lys
    3470                3475                3480

Pro Gly Gly Lys Gly Phe Thr Cys Glu Cys Pro Asp Asp Phe Arg
    3485                3490                3495

Thr Leu Gln Leu Ser Gly Ser Thr Tyr Cys Met Pro Met Cys Ser
    3500                3505                3510

Ser Thr Gln Phe Leu Cys Ala Asn Asn Glu Lys Cys Ile Pro Ile
    3515                3520                3525

Trp Trp Lys Cys Asp Gly Gln Lys Asp Cys Ser Asp Gly Ser Asp
    3530                3535                3540

Glu Leu Ala Leu Cys Pro Gln Arg Phe Cys Arg Leu Gly Gln Phe
    3545                3550                3555

Gln Cys Ser Asp Gly Asn Cys Thr Ser Pro Gln Thr Leu Cys Asn
    3560                3565                3570

Ala His Gln Asn Cys Pro Asp Gly Ser Asp Glu Asp Arg Leu Leu
    3575                3580                3585

Cys Glu Asn His His Cys Asp Ser Asn Glu Trp Gln Cys Ala Asn
    3590                3595                3600

Lys Arg Cys Ile Pro Glu Ser Trp Gln Cys Asp Thr Phe Asn Asp
    3605                3610                3615

Cys Glu Asp Asn Ser Asp Glu Asp Ser Ser His Cys Ala Ser Arg
    3620                3625                3630

Thr Cys Arg Pro Gly Gln Phe Arg Cys Ala Asn Gly Arg Cys Ile
    3635                3640                3645

Pro Gln Ala Trp Lys Cys Asp Val Asp Asn Asp Cys Gly Asp His
    3650                3655                3660

Ser Asp Glu Pro Ile Glu Glu Cys Met Ser Ser Ala His Leu Cys
```

```
              3665                3670                3675

Asp Asn Phe Thr Glu Phe Ser Cys Lys Thr Asn Tyr Arg Cys Ile
         3680                3685                3690

Pro Lys Trp Ala Val Cys Asn Gly Val Asp Asp Cys Arg Asp Asn
         3695                3700                3705

Ser Asp Glu Gln Gly Cys Glu Arg Thr Cys His Pro Val Gly
         3710                3715                3720

Asp Phe Arg Cys Lys Asn His His Cys Ile Pro Leu Arg Trp Gln
         3725                3730                3735

Cys Asp Gly Gln Asn Asp Cys Gly Asp Asn Ser Asp Glu Glu Asn
         3740                3745                3750

Cys Ala Pro Arg Glu Cys Thr Glu Ser Glu Phe Arg Cys Val Asn
         3755                3760                3765

Gln Gln Cys Ile Pro Ser Arg Trp Ile Cys Asp His Tyr Asn Asp
         3770                3775                3780

Cys Gly Asp Asn Ser Asp Glu Arg Asp Cys Glu Met Arg Thr Cys
         3785                3790                3795

His Pro Glu Tyr Phe Gln Cys Thr Ser Gly His Cys Val His Ser
         3800                3805                3810

Glu Leu Lys Cys Asp Gly Ser Ala Asp Cys Leu Asp Ala Ser Asp
         3815                3820                3825

Glu Ala Asp Cys Pro Thr Arg Phe Pro Asp Gly Ala Tyr Cys Gln
         3830                3835                3840

Ala Thr Met Phe Glu Cys Lys Asn His Val Cys Ile Pro Pro Tyr
         3845                3850                3855

Trp Lys Cys Asp Gly Asp Asp Cys Gly Asp Gly Ser Asp Glu
         3860                3865                3870

Glu Leu His Leu Cys Leu Asp Val Pro Cys Asn Ser Pro Asn Arg
         3875                3880                3885

Phe Arg Cys Asp Asn Asn Arg Cys Ile Tyr Ser His Glu Val Cys
         3890                3895                3900

Asn Gly Val Asp Asp Cys Gly Asp Gly Thr Asp Glu Thr Glu Glu
         3905                3910                3915

His Cys Arg Lys Pro Thr Pro Lys Pro Cys Thr Glu Tyr Glu Tyr
         3920                3925                3930

Lys Cys Gly Asn Gly His Cys Ile Pro His Asp Asn Val Cys Asp
         3935                3940                3945

Asp Ala Asp Asp Cys Gly Asp Trp Ser Asp Glu Leu Gly Cys Asn
         3950                3955                3960

Lys Gly Lys Glu Arg Thr Cys Ala Glu Asn Ile Cys Glu Gln Asn
         3965                3970                3975

Cys Thr Gln Leu Asn Glu Gly Gly Phe Ile Cys Ser Cys Thr Ala
         3980                3985                3990

Gly Phe Glu Thr Asn Val Phe Asp Arg Thr Ser Cys Leu Asp Ile
         3995                4000                4005

Asn Glu Cys Glu Gln Phe Gly Thr Cys Pro Gln His Cys Arg Asn
         4010                4015                4020

Thr Lys Gly Ser Tyr Glu Cys Val Cys Ala Asp Gly Phe Thr Ser
         4025                4030                4035

Met Ser Asp Arg Pro Gly Lys Arg Cys Ala Ala Glu Gly Ser Ser
         4040                4045                4050

Pro Leu Leu Leu Leu Pro Asp Asn Val Arg Ile Arg Lys Tyr Asn
         4055                4060                4065
```

```
Leu Ser Ser Glu Arg Phe Ser Glu Tyr Leu Gln Asp Glu Glu Tyr
    4070            4075            4080

Ile Gln Ala Val Asp Tyr Asp Trp Asp Pro Lys Asp Ile Gly Leu
    4085            4090            4095

Ser Val Val Tyr Tyr Thr Val Arg Gly Glu Gly Ser Arg Phe Gly
    4100            4105            4110

Ala Ile Lys Arg Ala Tyr Ile Pro Asn Phe Glu Ser Gly Arg Asn
    4115            4120            4125

Asn Leu Val Gln Glu Val Asp Leu Lys Leu Lys Tyr Val Met Gln
    4130            4135            4140

Pro Asp Gly Ile Ala Val Asp Trp Val Gly Arg His Ile Tyr Trp
    4145            4150            4155

Ser Asp Val Lys Asn Lys Arg Ile Glu Val Ala Lys Leu Asp Gly
    4160            4165            4170

Arg Tyr Arg Lys Trp Leu Ile Ser Thr Asp Leu Asp Gln Pro Ala
    4175            4180            4185

Ala Ile Ala Val Asn Pro Lys Leu Gly Leu Met Phe Trp Thr Asp
    4190            4195            4200

Trp Gly Lys Glu Pro Lys Ile Glu Ser Ala Trp Met Asn Gly Glu
    4205            4210            4215

Asp Arg Asn Ile Leu Val Phe Glu Asp Leu Gly Trp Pro Thr Gly
    4220            4225            4230

Leu Ser Ile Asp Tyr Leu Asn Asn Asp Arg Ile Tyr Trp Ser Asp
    4235            4240            4245

Phe Lys Glu Asp Val Ile Glu Thr Ile Lys Tyr Asp Gly Thr Asp
    4250            4255            4260

Arg Arg Val Ile Ala Lys Glu Ala Met Asn Pro Tyr Ser Leu Asp
    4265            4270            4275

Ile Phe Glu Asp Gln Leu Tyr Trp Ile Ser Lys Glu Lys Gly Glu
    4280            4285            4290

Val Trp Lys Gln Asn Lys Phe Gly Gln Gly Lys Lys Glu Lys Thr
    4295            4300            4305

Leu Val Val Asn Pro Trp Leu Thr Gln Val Arg Ile Phe His Gln
    4310            4315            4320

Leu Arg Tyr Asn Lys Ser Val Pro Asn Leu Cys Lys Gln Ile Cys
    4325            4330            4335

Ser His Leu Cys Leu Leu Arg Pro Gly Gly Tyr Ser Cys Ala Cys
    4340            4345            4350

Pro Gln Gly Ser Ser Phe Ile Glu Gly Ser Thr Thr Glu Cys Asp
    4355            4360            4365

Ala Ala Ile Glu Leu Pro Ile Asn Leu Pro Pro Pro Cys Arg Cys
    4370            4375            4380

Met His Gly Gly Asn Cys Tyr Phe Asp Glu Thr Asp Leu Pro Lys
    4385            4390            4395

Cys Lys Cys Pro Ser Gly Tyr Thr Gly Lys Tyr Cys Glu Met Ala
    4400            4405            4410

Phe Ser Lys Gly Ile Ser Pro Gly Thr Thr Ala Val Ala Val Leu
    4415            4420            4425

Leu Thr Ile Leu Leu Ile Val Val Ile Gly Ala Leu Ala Ile Ala
    4430            4435            4440

Gly Phe Phe His Tyr Arg Arg Thr Gly Ser Leu Leu Pro Ala Leu
    4445            4450            4455
```

-continued

```
Pro Lys Leu Pro Ser Leu Ser Ser Leu Val Lys Pro Ser Glu Asn
    4460                4465                4470

Gly Asn Gly Val Thr Phe Arg Ser Gly Ala Asp Leu Asn Met Asp
    4475                4480                4485

Ile Gly Val Ser Gly Phe Gly Pro Glu Thr Ala Ile Asp Arg Ser
    4490                4495                4500

Met Ala Met Ser Glu Asp Phe Val Met Glu Met Gly Lys Gln Pro
    4505                4510                4515

Ile Ile Phe Glu Asn Pro Met Tyr Ser Ala Arg Asp Ser Ala Val
    4520                4525                4530

Lys Val Val Gln Pro Ile Gln Val Thr Val Ser Glu Asn Val Asp
    4535                4540                4545

Asn Lys Asn Tyr Gly Ser Pro Ile Asn Pro Ser Glu Ile Val Pro
    4550                4555                4560

Glu Thr Asn Pro Thr Ser Pro Ala Ala Asp Gly Thr Gln Val Thr
    4565                4570                4575

Lys Trp Asn Leu Phe Lys Arg Lys Ser Lys Gln Thr Thr Asn Phe
    4580                4585                4590

Glu Asn Pro Ile Tyr Ala Gln Met Glu Asn Glu Gln Lys Glu Ser
    4595                4600                4605

Val Ala Ala Thr Pro Pro Pro Ser Pro Ser Leu Pro Ala Lys Pro
    4610                4615                4620

Lys Pro Pro Ser Arg Arg Asp Pro Thr Pro Thr Tyr Ser Ala Thr
    4625                4630                4635

Glu Asp Thr Phe Lys Asp Thr Ala Asn Leu Val Lys Glu Asp Ser
    4640                4645                4650

Glu Val
    4655

<210> SEQ ID NO 20
<211> LENGTH: 4660
<212> TYPE: PRT
<213> ORGANISM: Mus musculus

<400> SEQUENCE: 20

Met Glu Arg Gly Ala Ala Ala Ala Trp Met Leu Leu Leu Ala Ile
1               5                   10                  15

Ala Ala Cys Leu Ala Pro Val Ser Gly Gln Glu Cys Gly Ser Asn
                20                  25                  30

Phe Arg Cys Asp Asn Gly Tyr Cys Ile Pro Ala Ser Trp Arg Cys Asp
            35                  40                  45

Gly Thr Arg Asp Cys Leu Asp Asp Thr Asp Glu Ile Gly Cys Pro Pro
    50                  55                  60

Arg Ser Cys Gly Ser Gly Phe Phe Leu Cys Pro Ala Glu Gly Thr Cys
65                  70                  75                  80

Ile Pro Ser Ser Trp Val Cys Asp Gln Asp Lys Asp Cys Ser Asp Gly
                85                  90                  95

Ala Asp Glu Gln Gln Asn Cys Pro Gly Thr Thr Cys Ser Ser Gln Gln
                100                 105                 110

Leu Thr Cys Ser Asn Gly Gln Cys Val Pro Ile Glu Tyr Arg Cys Asp
            115                 120                 125

His Val Ser Asp Cys Pro Asp Gly Ser Asp Glu Arg Asn Cys Tyr Tyr
    130                 135                 140

Pro Thr Cys Asp Gln Leu Thr Cys Ala Asn Gly Ala Cys Tyr Asn Thr
145                 150                 155                 160
```

-continued

```
Ser Gln Lys Cys Asp His Lys Val Asp Cys Arg Asp Ser Ser Asp Glu
            165                 170                 175
Ala Asn Cys Thr Thr Leu Cys Ser Gln Lys Glu Phe Gln Cys Gly Ser
            180                 185                 190
Gly Glu Cys Ile Leu Arg Ala Tyr Val Cys Asp His Asp Asn Asp Cys
            195                 200                 205
Glu Asp Asn Ser Asp Glu His Asn Cys Asn Tyr Asp Thr Cys Gly Gly
            210                 215                 220
His Gln Phe Thr Cys Ser Asn Gly Gln Cys Ile Asn Gln Asn Trp Val
225                 230                 235                 240
Cys Asp Gly Asp Asp Cys Gln Asp Ser Gly Asp Glu Asp Gly Cys
            245                 250                 255
Glu Ser Asn Gln Arg His His Thr Cys Tyr Pro Arg Glu Trp Ala Cys
            260                 265                 270
Pro Gly Ser Gly Arg Cys Ile Ser Met Asp Lys Val Cys Asp Gly Val
            275                 280                 285
Pro Asp Cys Pro Glu Gly Glu Asp Glu Asn Asn Ala Thr Ser Gly Arg
            290                 295                 300
Tyr Cys Gly Thr Gly Leu Cys Ser Ile Leu Asn Cys Glu Tyr Gln Cys
305                 310                 315                 320
His Gln Thr Pro Tyr Gly Gly Glu Cys Phe Cys Pro Pro Gly His Ile
            325                 330                 335
Ile Asn Ser Asn Asp Ser Arg Thr Cys Ile Asp Phe Asp Asp Cys Gln
            340                 345                 350
Ile Trp Gly Ile Cys Asp Gln Lys Cys Glu Ser Arg Gln Gly Arg His
            355                 360                 365
Gln Cys Leu Cys Glu Glu Gly Tyr Ile Leu Glu Arg Gly Gln His Cys
            370                 375                 380
Lys Ser Asn Asp Ser Phe Ser Ala Ala Ser Ile Ile Phe Ser Asn Gly
385                 390                 395                 400
Arg Asp Leu Leu Val Gly Asp Leu His Gly Arg Asn Phe Arg Ile Leu
            405                 410                 415
Ala Glu Ser Lys Asn Arg Gly Ile Val Met Gly Val Asp Phe His Tyr
            420                 425                 430
Gln Lys His Arg Val Phe Trp Thr Asp Pro Met Gln Ala Lys Val Phe
            435                 440                 445
Ser Thr Asp Ile Asn Gly Leu Asn Thr Gln Glu Ile Leu Asn Val Ser
450                 455                 460
Ile Asp Ala Pro Glu Asn Leu Ala Val Asp Trp Ile Asn Asn Lys Leu
465                 470                 475                 480
Tyr Leu Val Glu Thr Arg Val Asn Arg Ile Asp Val Val Asn Leu Glu
            485                 490                 495
Gly Asn Gln Arg Val Thr Leu Ile Thr Glu Asn Leu Gly His Pro Arg
            500                 505                 510
Gly Ile Ala Leu Asp Pro Thr Val Gly Tyr Leu Phe Phe Ser Asp Trp
            515                 520                 525
Gly Ser Leu Ser Gly Gln Pro Lys Val Glu Arg Ala Phe Met Asp Gly
            530                 535                 540
Ser Asn Arg Lys Asp Leu Val Thr Thr Lys Leu Gly Trp Pro Ala Gly
545                 550                 555                 560
Ile Thr Leu Asp Leu Val Ser Lys Arg Val Tyr Trp Val Asp Ser Arg
            565                 570                 575
```

-continued

Tyr Asp Tyr Ile Glu Thr Val Thr Tyr Asp Gly Ile Gln Arg Lys Thr
            580                 585                 590

Val Ala Arg Gly Gly Ser Leu Val Pro His Pro Phe Gly Ile Ser Leu
        595                 600                 605

Phe Glu Glu His Val Phe Phe Thr Asp Trp Thr Lys Met Ala Val Met
    610                 615                 620

Lys Ala Asn Lys Phe Thr Asp Thr Asn Pro Gln Val Tyr His Gln Ser
625                 630                 635                 640

Ser Leu Thr Pro Phe Gly Val Thr Val Tyr His Ala Leu Arg Gln Pro
                645                 650                 655

Asn Ala Thr Asn Pro Cys Gly Asn Asn Gly Gly Cys Ala Gln Ile
            660                 665                 670

Cys Val Leu Ser His Arg Thr Asp Asn Gly Gly Leu Gly Tyr Arg Cys
        675                 680                 685

Lys Cys Glu Phe Gly Phe Glu Leu Asp Ala Asp Glu His His Cys Val
    690                 695                 700

Ala Val Lys Asn Phe Leu Leu Phe Ser Ser Gln Thr Ala Val Arg Gly
705                 710                 715                 720

Ile Pro Phe Thr Leu Ser Thr Gln Glu Asp Val Met Val Pro Val Thr
                725                 730                 735

Gly Ser Pro Ser Phe Phe Val Gly Ile Asp Phe Asp Ala Gln His Ser
            740                 745                 750

Thr Ile Phe Tyr Ser Asp Leu Ser Lys Asn Ile Ile Tyr Gln Gln Lys
        755                 760                 765

Ile Asp Gly Thr Gly Lys Glu Val Ile Thr Ala Asn Arg Leu Gln Asn
    770                 775                 780

Val Glu Cys Leu Ser Phe Asp Trp Ile Ser Arg Asn Leu Tyr Trp Thr
785                 790                 795                 800

Asp Gly Gly Ser Lys Ser Val Thr Val Met Lys Leu Ala Asp Lys Ser
                805                 810                 815

Arg Arg Gln Ile Ile Ser Asn Leu Asn Asn Pro Arg Ser Ile Val Val
            820                 825                 830

His Pro Ala Ala Gly Tyr Met Phe Leu Ser Asp Trp Phe Arg Pro Ala
        835                 840                 845

Lys Ile Met Arg Ala Trp Ser Asp Gly Ser His Leu Met Pro Ile Val
    850                 855                 860

Asn Thr Ser Leu Gly Trp Pro Asn Gly Leu Ala Ile Asp Trp Ser Thr
865                 870                 875                 880

Ser Arg Leu Tyr Trp Val Asp Ala Phe Phe Asp Lys Ile Glu His Ser
                885                 890                 895

Asn Leu Asp Gly Leu Asp Arg Lys Arg Leu Gly His Val Asp Gln Met
            900                 905                 910

Thr His Pro Phe Gly Leu Thr Val Phe Lys Asp Asn Val Phe Leu Thr
        915                 920                 925

Asp Trp Arg Leu Gly Ala Ile Ile Arg Val Arg Lys Ser Asp Gly Gly
    930                 935                 940

Asp Met Thr Val Val Arg Arg Gly Ile Ser Ser Ile Met His Val Lys
945                 950                 955                 960

Ala Tyr Asp Ala Asp Leu Gln Thr Gly Thr Asn Tyr Cys Ser Gln Thr
                965                 970                 975

Thr His Pro Asn Gly Asp Cys Ser His Phe Cys Phe Pro Val Pro Asn
            980                 985                 990

Phe Gln Arg Val Cys Gly Cys Pro  Tyr Gly Met Lys Leu  Gln Arg Asp

-continued

```
               995                 1000                1005
Gln Met Thr Cys Glu Gly Asp Pro Ala Arg Glu Pro Pro Thr Gln
   1010                1015                1020

Gln Cys Gly Ser Ser Ser Phe Pro Cys Asn Asn Gly Lys Cys Val
   1025                1030                1035

Pro Ser Ile Phe Arg Cys Asp Gly Val Asp Asp Cys His Asp Asn
   1040                1045                1050

Ser Asp Glu His Gln Cys Gly Ala Leu Asn Asn Thr Cys Ser Ser
   1055                1060                1065

Ser Ala Phe Thr Cys Val His Gly Gly Gln Cys Ile Pro Gly Gln
   1070                1075                1080

Trp Arg Cys Asp Lys Gln Asn Asp Cys Leu Asp Gly Ser Asp Glu
   1085                1090                1095

Gln Asn Cys Pro Thr Arg Ser Pro Ser Ser Thr Cys Pro Pro Thr
   1100                1105                1110

Ser Phe Thr Cys Asp Asn His Met Cys Ile Pro Lys Glu Trp Val
   1115                1120                1125

Cys Asp Thr Asp Asn Asp Cys Ser Asp Gly Ser Asp Glu Lys Asn
   1130                1135                1140

Cys Gln Ala Ser Gly Thr Cys His Pro Thr Gln Phe Arg Cys Pro
   1145                1150                1155

Asp His Arg Cys Ile Ser Pro Leu Tyr Val Cys Asp Gly Asp Lys
   1160                1165                1170

Asp Cys Val Asp Gly Ser Asp Glu Ala Gly Cys Val Leu Asn Cys
   1175                1180                1185

Thr Ser Ser Gln Phe Lys Cys Ala Asp Gly Ser Ser Cys Ile Asn
   1190                1195                1200

Ser Arg Tyr Arg Cys Asp Gly Val Tyr Asp Cys Lys Asp Asn Ser
   1205                1210                1215

Asp Glu Ala Gly Cys Pro Thr Arg Pro Pro Gly Met Cys His Pro
   1220                1225                1230

Asp Glu Phe Gln Cys Gln Gly Asp Gly Thr Cys Ile Pro Asn Thr
   1235                1240                1245

Trp Glu Cys Asp Gly His Pro Asp Cys Ile Gln Gly Ser Asp Glu
   1250                1255                1260

His Asn Gly Cys Val Pro Lys Thr Cys Ser Pro Ser His Phe Leu
   1265                1270                1275

Cys Asp Asn Gly Asn Cys Ile Tyr Asn Ser Trp Val Cys Asp Gly
   1280                1285                1290

Asp Asn Asp Cys Arg Asp Met Ser Asp Glu Lys Asp Cys Pro Thr
   1295                1300                1305

Gln Pro Phe His Cys Pro Ser Ser Gln Trp Gln Cys Pro Gly Tyr
   1310                1315                1320

Ser Ile Cys Val Asn Leu Ser Ala Leu Cys Asp Gly Val Phe Asp
   1325                1330                1335

Cys Pro Asn Gly Thr Asp Glu Ser Pro Leu Cys Asn Gln Asp Ser
   1340                1345                1350

Cys Leu His Phe Asn Gly Gly Cys Thr His Arg Cys Ile Gln Gly
   1355                1360                1365

Pro Phe Gly Ala Thr Cys Val Cys Pro Ile Gly Tyr Gln Leu Ala
   1370                1375                1380

Asn Asp Thr Lys Thr Cys Glu Asp Val Asn Glu Cys Asp Ile Pro
   1385                1390                1395
```

-continued

```
Gly Phe Cys Ser Gln His Cys Val Asn Met Arg Gly Ser Phe Arg
    1400                1405                1410

Cys Ala Cys Asp Pro Glu Tyr Thr Leu Glu Ser Asp Gly Arg Thr
    1415                1420                1425

Cys Lys Val Thr Ala Ser Glu Asn Leu Leu Leu Val Val Ala Ser
    1430                1435                1440

Arg Asp Lys Ile Ile Met Asp Asn Ile Thr Ala His Thr His Asn
    1445                1450                1455

Ile Tyr Ser Leu Val Gln Asp Val Ser Phe Val Val Ala Leu Asp
    1460                1465                1470

Phe Asp Ser Val Thr Gly Arg Val Phe Trp Ser Asp Leu Leu Glu
    1475                1480                1485

Gly Lys Thr Trp Ser Ala Phe Gln Asn Gly Thr Asp Lys Arg Val
    1490                1495                1500

Val His Asp Ser Gly Leu Ser Leu Thr Glu Met Ile Ala Val Asp
    1505                1510                1515

Trp Ile Gly Arg Asn Ile Tyr Trp Thr Asp Tyr Thr Leu Glu Thr
    1520                1525                1530

Ile Glu Val Ser Lys Ile Asp Gly Ser His Arg Thr Val Leu Ile
    1535                1540                1545

Ser Lys Asn Val Thr Lys Pro Arg Gly Leu Ala Leu Asp Pro Arg
    1550                1555                1560

Met Gly Asp Asn Val Met Phe Trp Ser Asp Trp Gly His His Pro
    1565                1570                1575

Arg Ile Glu Arg Ala Ser Met Asp Gly Thr Met Arg Thr Val Ile
    1580                1585                1590

Val Gln Glu Lys Ile Tyr Trp Pro Cys Gly Leu Ser Ile Asp Tyr
    1595                1600                1605

Pro Asn Arg Leu Ile Tyr Phe Met Asp Ala Tyr Leu Asp Tyr Ile
    1610                1615                1620

Glu Phe Cys Asp Tyr Asp Gly Gln Asn Arg Arg Gln Val Ile Ala
    1625                1630                1635

Ser Asp Leu Val Leu His His Pro His Ala Leu Thr Leu Phe Glu
    1640                1645                1650

Asp Ser Val Phe Trp Thr Asp Arg Gly Thr His Gln Val Met Gln
    1655                1660                1665

Ala Asn Lys Trp His Gly Arg Asn Gln Ser Val Val Met Tyr Ser
    1670                1675                1680

Val Pro Gln Pro Leu Gly Ile Ile Ala Ile His Pro Ser Arg Gln
    1685                1690                1695

Pro Ser Ser Pro Asn Pro Cys Ala Ser Ala Thr Cys Ser His Leu
    1700                1705                1710

Cys Leu Leu Ser Ala Gln Glu Pro Arg His Tyr Ser Cys Ala Cys
    1715                1720                1725

Pro Ser Gly Trp Asn Leu Ser Asp Asp Ser Val Asn Cys Val Arg
    1730                1735                1740

Gly Asp Gln Pro Phe Leu Ile Ser Val Arg Glu Asn Val Ile Phe
    1745                1750                1755

Gly Ile Ser Leu Asp Pro Glu Val Lys Ser Asn Asp Ala Met Val
    1760                1765                1770

Pro Ile Ser Gly Ile Gln His Gly Tyr Asp Val Glu Phe Asp Asp
    1775                1780                1785
```

```
Ser Glu Gln Phe Ile Tyr Trp Val Glu Asn Pro Gly Glu Ile His
1790                1795                1800

Arg Val Lys Thr Asp Gly Ser Asn Arg Thr Ala Phe Ala Pro Leu
1805                1810                1815

Ser Leu Leu Gly Ser Ser Leu Gly Leu Ala Leu Asp Trp Val Ser
1820                1825                1830

Arg Asn Ile Tyr Tyr Thr Thr Pro Ala Ser Arg Ser Ile Glu Val
1835                1840                1845

Leu Thr Leu Arg Gly Asp Thr Arg Tyr Gly Lys Thr Leu Ile Thr
1850                1855                1860

Asn Asp Gly Thr Pro Leu Gly Val Gly Phe Pro Val Gly Ile Ala
1865                1870                1875

Val Asp Pro Ala Arg Gly Lys Leu Tyr Trp Ser Asp His Gly Thr
1880                1885                1890

Asp Ser Gly Val Pro Ala Lys Ile Ala Ser Ala Asn Met Asp Gly
1895                1900                1905

Thr Ser Leu Lys Ile Leu Phe Thr Gly Asn Met Glu His Leu Glu
1910                1915                1920

Val Val Thr Leu Asp Ile Gln Glu Gln Lys Leu Tyr Trp Ala Val
1925                1930                1935

Thr Ser Arg Gly Val Ile Glu Arg Gly Asn Val Asp Gly Thr Glu
1940                1945                1950

Arg Met Ile Leu Val His His Leu Ala His Pro Trp Gly Leu Val
1955                1960                1965

Val His Gly Ser Phe Leu Tyr Tyr Ser Asp Glu Gln Tyr Glu Val
1970                1975                1980

Ile Glu Arg Val Asp Lys Ser Ser Gly Ser Asn Lys Val Val Phe
1985                1990                1995

Arg Asp Asn Ile Pro Tyr Leu Arg Gly Leu Arg Val Tyr His His
2000                2005                2010

Arg Asn Ala Ala Asp Ser Ser Asn Gly Cys Ser Asn Asn Pro Asn
2015                2020                2025

Ala Cys Gln Gln Ile Cys Leu Pro Val Pro Gly Gly Met Phe Ser
2030                2035                2040

Cys Ala Cys Ala Ser Gly Phe Lys Leu Ser Pro Asp Gly Arg Ser
2045                2050                2055

Cys Ser Pro Tyr Asn Ser Phe Ile Val Val Ser Met Leu Pro Ala
2060                2065                2070

Val Arg Gly Phe Ser Leu Glu Leu Ser Asp His Ser Glu Ala Met
2075                2080                2085

Val Pro Val Ala Gly Gln Gly Arg Asn Val Leu His Ala Asp Val
2090                2095                2100

Asp Val Ala Asn Gly Phe Ile Tyr Trp Cys Asp Phe Ser Ser Ser
2105                2110                2115

Val Arg Ser Ser Asn Gly Ile Arg Arg Ile Lys Pro Asn Gly Ser
2120                2125                2130

Asn Phe Thr Asn Ile Val Thr Tyr Gly Ile Gly Ala Asn Gly Ile
2135                2140                2145

Arg Gly Val Ala Val Asp Trp Val Ala Gly Asn Leu Tyr Phe Thr
2150                2155                2160

Asn Ala Phe Val Tyr Glu Thr Leu Ile Glu Val Ile Arg Ile Asn
2165                2170                2175

Thr Thr Tyr Arg Arg Val Leu Leu Lys Val Ser Val Asp Met Pro
```

-continued

```
                2180                2185                2190
Arg His Ile Val Val Asp Pro Lys His Arg Tyr Leu Phe Trp Ala
    2195                2200                2205
Asp Tyr Gly Gln Lys Pro Lys Ile Glu Arg Ser Phe Leu Asp Cys
    2210                2215                2220
Thr Asn Arg Thr Val Leu Val Ser Glu Gly Ile Val Thr Pro Arg
    2225                2230                2235
Gly Leu Ala Val Asp His Asp Thr Gly Tyr Ile Tyr Trp Val Asp
    2240                2245                2250
Asp Ser Leu Asp Ile Ile Ala Arg Ile His Arg Asp Gly Gly Glu
    2255                2260                2265
Ser Gln Val Val Arg Tyr Gly Ser Arg Tyr Pro Thr Pro Tyr Gly
    2270                2275                2280
Ile Thr Val Phe Gly Glu Ser Ile Ile Trp Val Asp Arg Asn Leu
    2285                2290                2295
Arg Lys Val Phe Gln Ala Ser Lys Gln Pro Gly Asn Thr Asp Pro
    2300                2305                2310
Pro Thr Val Ile Arg Asp Ser Ile Asn Leu Leu Arg Asp Val Thr
    2315                2320                2325
Ile Phe Asp Glu His Val Gln Pro Leu Ser Pro Ala Glu Leu Asn
    2330                2335                2340
Asn Asn Pro Cys Leu Gln Ser Asn Gly Gly Cys Ser His Phe Cys
    2345                2350                2355
Phe Ala Leu Pro Glu Leu Pro Thr Pro Lys Cys Gly Cys Ala Phe
    2360                2365                2370
Gly Thr Leu Glu Asp Asp Gly Lys Asn Cys Ala Thr Ser Arg Glu
    2375                2380                2385
Asp Phe Leu Ile Tyr Ser Leu Asn Asn Ser Leu Arg Ser Leu His
    2390                2395                2400
Phe Asp Pro Gln Asp His Asn Leu Pro Phe Gln Ala Ile Ser Val
    2405                2410                2415
Glu Gly Met Ala Ile Ala Leu Asp Tyr Asp Arg Arg Asn Asn Arg
    2420                2425                2430
Ile Phe Phe Thr Gln Lys Leu Asn Pro Ile Arg Gly Gln Ile Ser
    2435                2440                2445
Tyr Val Asn Leu Tyr Ser Gly Ala Ser Ser Pro Thr Ile Leu Leu
    2450                2455                2460
Ser Asn Ile Gly Val Thr Asp Gly Ile Ala Phe Asp Trp Ile Asn
    2465                2470                2475
Arg Arg Ile Tyr Tyr Ser Asp Phe Ser Asn Gln Thr Ile Asn Ser
    2480                2485                2490
Met Ala Glu Asp Gly Ser Asn Arg Ala Val Ile Ala Arg Val Ser
    2495                2500                2505
Lys Pro Arg Ala Ile Val Leu Asp Pro Cys Arg Gly Tyr Met Tyr
    2510                2515                2520
Trp Thr Asp Trp Gly Thr Asn Ala Lys Ile Glu Arg Ala Thr Leu
    2525                2530                2535
Gly Gly Asn Phe Arg Val Pro Ile Val Asn Thr Ser Leu Val Trp
    2540                2545                2550
Pro Asn Gly Leu Thr Leu Asp Leu Glu Thr Asp Leu Leu Tyr Trp
    2555                2560                2565
Ala Asp Ala Ser Leu Gln Lys Ile Glu Arg Ser Thr Leu Thr Gly
    2570                2575                2580
```

-continued

Ser Asn Arg Glu Val Val Ile Ser Thr Ala Phe His Ser Phe Gly
2585                2590                2595

Leu Thr Val Tyr Gly Gln Tyr Ile Tyr Trp Thr Asp Phe Tyr Thr
2600                2605                2610

Lys Lys Ile Tyr Arg Ala Asn Lys Tyr Asp Gly Ser Asp Leu Ile
2615                2620                2625

Ala Met Thr Thr Arg Leu Pro Thr Gln Pro Ser Gly Ile Ser Thr
2630                2635                2640

Val Val Lys Thr Gln Gln Gln Cys Ser Asn Pro Cys Asp Gln
2645                2650                2655

Phe Asn Gly Gly Cys Ser His Ile Cys Ala Pro Gly Pro Asn Gly
2660                2665                2670

Ala Glu Cys Gln Cys Pro His Glu Gly Ser Trp Tyr Leu Ala Asn
2675                2680                2685

Asp Asn Lys Tyr Cys Val Val Asp Thr Gly Ala Arg Cys Asn Gln
2690                2695                2700

Phe Gln Phe Thr Cys Leu Asn Gly Arg Cys Ile Ser Gln Asp Trp
2705                2710                2715

Lys Cys Asp Asn Asp Asn Asp Cys Gly Asp Gly Ser Asp Glu Leu
2720                2725                2730

Pro Thr Val Cys Ala Phe His Thr Cys Arg Ser Thr Ala Phe Thr
2735                2740                2745

Cys Ala Asn Gly Arg Cys Val Pro Tyr His Tyr Arg Cys Asp Phe
2750                2755                2760

Tyr Asn Asp Cys Gly Asp Asn Ser Asp Glu Ala Gly Cys Leu Phe
2765                2770                2775

Arg Ser Cys Asn Ser Thr Thr Glu Phe Thr Cys Ser Asn Gly Arg
2780                2785                2790

Cys Ile Pro Leu Ser Tyr Val Cys Asn Gly Ile Asn Asn Cys His
2795                2800                2805

Asp Asn Asp Thr Ser Asp Glu Lys Asn Cys Pro Pro Ile Thr Cys
2810                2815                2820

Gln Pro Asp Phe Ala Lys Cys Gln Thr Thr Asn Ile Cys Val Pro
2825                2830                2835

Arg Ala Phe Leu Cys Asp Gly Asp Asn Asp Cys Gly Asp Gly Ser
2840                2845                2850

Asp Glu Asn Pro Ile Tyr Cys Ala Ser His Thr Cys Arg Ser Asn
2855                2860                2865

Glu Phe Gln Cys Val Ser Pro His Arg Cys Ile Pro Ser Tyr Trp
2870                2875                2880

Phe Cys Asp Gly Glu Ala Asp Cys Val Asp Ser Ser Asp Glu Pro
2885                2890                2895

Asp Thr Cys Gly His Ser Leu Asn Ser Cys Ser Ala Asn Gln Phe
2900                2905                2910

His Cys Asp Asn Gly Arg Cys Ile Ser Ser Ser Trp Val Cys Asp
2915                2920                2925

Gly Asp Asn Asp Cys Gly Asp Met Ser Asp Glu Asp Gln Arg His
2930                2935                2940

His Cys Glu Leu Gln Asn Cys Ser Ser Thr Glu Phe Thr Cys Ile
2945                2950                2955

Asn Ser Arg Pro Pro Asn Arg Arg Cys Ile Pro Gln His Trp Val
2960                2965                2970

| | | | | | | | | | | |
|---|---|---|---|---|---|---|---|---|---|---|
|Cys|Asp|Gly|Asp|Ala|Asp|Cys|Ala|Asp|Ala|Leu|Asp|Glu|Leu|Gln|
|2975| | | | |2980| | | | |2985| | | | |

Cys Asp Gly Asp Ala Asp Cys Ala Asp Ala Leu Asp Glu Leu Gln
2975                2980                2985

Asn Cys Thr Met Arg Ala Cys Ser Thr Gly Glu Phe Ser Cys Ala
2990                2995                3000

Asn Gly Arg Cys Ile Arg Gln Ser Phe Arg Cys Asp Arg Arg Asn
3005                3010                3015

Asp Cys Gly Asp Tyr Ser Asp Glu Arg Gly Cys Ser Tyr Pro Pro
3020                3025                3030

Cys Arg Asp Asp Gln Phe Thr Cys Gln Asn Gly Gln Cys Ile Thr
3035                3040                3045

Lys Leu Tyr Val Cys Asp Glu Asp Asn Asp Cys Gly Asp Gly Ser
3050                3055                3060

Asp Glu Gln Glu His Leu Cys His Thr Pro Glu Pro Thr Cys Pro
3065                3070                3075

Pro His Gln Phe Arg Cys Asp Asn Gly His Cys Ile Glu Met Gly
3080                3085                3090

Thr Val Cys Asn His Val Asp Asp Cys Ser Asp Asn Ser Asp Glu
3095                3100                3105

Lys Gly Cys Gly Ile Asn Glu Cys Gln Asp Ser Ser Ile Ser His
3110                3115                3120

Cys Asp His Asn Cys Thr Asp Thr Ile Thr Ser Phe Tyr Cys Ser
3125                3130                3135

Cys Leu Pro Gly Tyr Lys Leu Met Ser Asp Lys Arg Thr Cys Val
3140                3145                3150

Asp Ile Asp Glu Cys Lys Glu Thr Pro Gln Leu Cys Ser Gln Lys
3155                3160                3165

Cys Glu Asn Val Ile Gly Ser Tyr Ile Cys Lys Cys Ala Pro Gly
3170                3175                3180

Tyr Ile Arg Glu Pro Asp Gly Lys Ser Cys Arg Gln Asn Ser Asn
3185                3190                3195

Ile Glu Pro Tyr Leu Val Phe Ser Asn Arg Tyr Tyr Ile Arg Asn
3200                3205                3210

Leu Thr Ile Asp Gly Thr Ser Tyr Ser Leu Ile Leu Gln Gly Leu
3215                3220                3225

Gly Asn Val Val Ala Leu Asp Phe Asp Arg Val Glu Glu Arg Leu
3230                3235                3240

Tyr Trp Ile Asp Ala Glu Lys Gln Ile Ile Glu Arg Met Phe Leu
3245                3250                3255

Asn Lys Thr Asn Gln Glu Thr Ile Ile Ser His Arg Leu Arg Arg
3260                3265                3270

Ala Glu Ser Leu Ala Val Asp Trp Val Ser Arg Lys Leu Tyr Trp
3275                3280                3285

Leu Asp Ala Ile Leu Asp Cys Leu Phe Val Ser Asp Leu Glu Gly
3290                3295                3300

Arg Gln Arg Lys Met Leu Ala Gln His Cys Val Asp Ala Asn Asn
3305                3310                3315

Thr Phe Cys Phe Glu Asn Pro Arg Gly Ile Val Leu His Pro Gln
3320                3325                3330

Arg Gly Tyr Val Tyr Trp Ala Asp Trp Gly Asp His Ala Tyr Ile
3335                3340                3345

Ala Arg Ile Gly Met Asp Gly Thr Asn Lys Thr Val Ile Ile Ser
3350                3355                3360

Thr Lys Ile Glu Trp Pro Asn Ala Ile Thr Ile Asp Tyr Thr Asn

-continued

```
            3365                3370                3375

Asp Leu Leu Tyr Trp Ala Asp Ala His Leu Gly Tyr Ile Glu Phe
        3380                3385                3390

Ser Asp Leu Glu Gly His His Arg His Thr Val Tyr Asp Gly Thr
        3395                3400                3405

Leu Pro His Pro Phe Ala Leu Thr Ile Phe Glu Asp Thr Val Phe
        3410                3415                3420

Trp Thr Asp Trp Asn Thr Arg Thr Val Glu Lys Gly Asn Lys Tyr
        3425                3430                3435

Asp Gly Ser Gly Arg Val Val Leu Val Asn Thr Thr His Lys Pro
        3440                3445                3450

Phe Asp Ile His Val Leu His Pro Tyr Arg Gln Pro Ile Met Ser
        3455                3460                3465

Asn Pro Cys Ala Thr Asn Asn Gly Gly Cys Ser His Leu Cys Leu
        3470                3475                3480

Ile Lys Ala Gly Gly Arg Gly Phe Thr Cys Glu Cys Pro Asp Asp
        3485                3490                3495

Phe Gln Thr Val Gln Leu Arg Asp Arg Thr Leu Cys Met Pro Met
        3500                3505                3510

Cys Ser Ser Thr Gln Phe Leu Cys Gly Asn Asn Glu Lys Cys Ile
        3515                3520                3525

Pro Ile Trp Trp Lys Cys Asp Gly Gln Lys Asp Cys Ser Asp Gly
        3530                3535                3540

Ser Asp Glu Ser Asp Leu Cys Pro His Arg Phe Cys Arg Leu Gly
        3545                3550                3555

Gln Phe Gln Cys Arg Asp Gly Asn Cys Thr Ser Pro Gln Ala Leu
        3560                3565                3570

Cys Asn Ala Arg Gln Asp Cys Ala Asp Gly Ser Asp Glu Asp Arg
        3575                3580                3585

Val Leu Cys Glu His His Arg Cys Glu Ala Asn Glu Trp Gln Cys
        3590                3595                3600

Ala Asn Lys Arg Cys Ile Pro Glu Tyr Trp Gln Cys Asp Ser Val
        3605                3610                3615

Asp Asp Cys Leu Asp Asn Ser Asp Glu Asp Pro Ser His Cys Ala
        3620                3625                3630

Ser Arg Thr Cys Arg Pro Gly Gln Phe Lys Cys Asn Asn Gly Arg
        3635                3640                3645

Cys Ile Pro Gln Ser Trp Lys Cys Asp Val Asp Asn Asp Cys Gly
        3650                3655                3660

Asp Tyr Ser Asp Glu Pro Ile His Glu Cys Met Thr Ala Ala Tyr
        3665                3670                3675

Asn Cys Asp Asn His Thr Glu Phe Ser Cys Lys Thr Asn Tyr Arg
        3680                3685                3690

Cys Ile Pro Gln Trp Ala Val Cys Asn Gly Phe Asp Asp Cys Arg
        3695                3700                3705

Asp Asn Ser Asp Glu Gln Gly Cys Glu Ser Val Pro Cys His Pro
        3710                3715                3720

Ser Gly Asp Phe Arg Cys Gly Asn His His Cys Ile Pro Leu Arg
        3725                3730                3735

Trp Lys Cys Asp Gly Ile Asp Asp Cys Gly Asp Asn Ser Asp Glu
        3740                3745                3750

Glu Ser Cys Val Pro Arg Glu Cys Thr Glu Ser Glu Phe Arg Cys
        3755                3760                3765
```

```
Ala Asp Gln Gln Cys Ile Pro Ser Arg Trp Val Cys Asp Gln Glu
3770                 3775                 3780

Asn Asp Cys Gly Asp Asn Ser Asp Glu Arg Asp Cys Glu Met Lys
3785                 3790                 3795

Thr Cys His Pro Glu His Phe Gln Cys Thr Ser Gly His Cys Val
3800                 3805                 3810

Pro Lys Ala Leu Ala Cys Asp Gly Arg Ala Asp Cys Leu Asp Ala
3815                 3820                 3825

Ser Asp Glu Ser Ala Cys Pro Thr Arg Phe Pro Asn Gly Thr Tyr
3830                 3835                 3840

Cys Pro Ala Ala Met Phe Glu Cys Lys Asn His Val Cys Ile Gln
3845                 3850                 3855

Ser Phe Trp Ile Cys Asp Gly Glu Asn Asp Cys Val Asp Gly Ser
3860                 3865                 3870

Asp Glu Glu Ile His Leu Cys Phe Asn Val Pro Cys Glu Ser Pro
3875                 3880                 3885

Gln Arg Phe Arg Cys Asp Asn Ser Arg Cys Ile Tyr Gly His Gln
3890                 3895                 3900

Leu Cys Asn Gly Val Asp Asp Cys Gly Asp Gly Ser Asp Glu Lys
3905                 3910                 3915

Glu Glu His Cys Arg Lys Pro Thr His Lys Pro Cys Thr Asp Thr
3920                 3925                 3930

Glu Tyr Lys Cys Ser Asn Gly Asn Cys Val Ser Gln His Tyr Val
3935                 3940                 3945

Cys Asp Asn Val Asp Asp Cys Gly Asp Leu Ser Asp Glu Thr Gly
3950                 3955                 3960

Cys Asn Leu Gly Glu Asn Arg Thr Cys Ala Glu Lys Ile Cys Glu
3965                 3970                 3975

Gln Asn Cys Thr Gln Leu Ser Asn Gly Gly Phe Ile Cys Ser Cys
3980                 3985                 3990

Arg Pro Gly Phe Lys Pro Ser Thr Leu Asp Lys Asn Ser Cys Gln
3995                 4000                 4005

Asp Ile Asn Glu Cys Glu Glu Phe Gly Ile Cys Pro Gln Ser Cys
4010                 4015                 4020

Arg Asn Ser Lys Gly Ser Tyr Glu Cys Phe Cys Val Asp Gly Phe
4025                 4030                 4035

Lys Ser Met Ser Thr His Tyr Gly Glu Arg Cys Ala Ala Asp Gly
4040                 4045                 4050

Ser Pro Pro Leu Leu Leu Pro Glu Asn Val Arg Ile Arg Lys
4055                 4060                 4065

Tyr Asn Ile Ser Ser Glu Lys Phe Ser Glu Tyr Leu Glu Glu Glu
4070                 4075                 4080

Glu His Ile Gln Ala Ile Asp Tyr Asp Trp Asp Pro Glu Gly Ile
4085                 4090                 4095

Gly Leu Ser Val Val Tyr Tyr Thr Val Leu Ser Gln Gly Ser Gln
4100                 4105                 4110

Phe Gly Ala Ile Lys Arg Ala Tyr Leu Pro Asp Phe Glu Ser Gly
4115                 4120                 4125

Ser Asn Asn Pro Val Arg Glu Val Asp Leu Gly Leu Lys Tyr Leu
4130                 4135                 4140

Met Gln Pro Asp Gly Leu Ala Val Asp Trp Val Gly Arg His Ile
4145                 4150                 4155
```

-continued

Tyr Trp Ser Asp Ala Lys Ser Gln Arg Ile Glu Val Ala Thr Leu
4160                4165              4170

Asp Gly Arg Tyr Arg Lys Trp Leu Ile Thr Thr Gln Leu Asp Gln
4175                4180              4185

Pro Ala Ala Ile Ala Val Asn Pro Lys Leu Gly Leu Met Phe Trp
4190                4195              4200

Thr Asp Gln Gly Lys Gln Pro Lys Ile Glu Ser Ala Trp Met Asn
4205                4210              4215

Gly Glu His Arg Ser Val Leu Ala Ser Ala Asn Leu Gly Trp Pro
4220                4225              4230

Asn Gly Leu Ser Ile Asp Tyr Leu Asn Gly Asp Arg Ile Tyr Trp
4235                4240              4245

Ser Asp Ser Lys Glu Asp Val Ile Glu Ser Ile Lys Tyr Asp Gly
4250                4255              4260

Thr Asp Arg Arg Leu Ile Ile Asn Asp Ala Met Lys Pro Phe Ser
4265                4270              4275

Leu Asp Ile Phe Glu Asp Gln Leu Tyr Trp Val Ala Lys Glu Lys
4280                4285              4290

Gly Glu Val Trp Arg Gln Asn Lys Phe Gly Lys Gly Asn Lys Glu
4295                4300              4305

Lys Leu Leu Val Val Asn Pro Trp Leu Thr Gln Val Arg Ile Phe
4310                4315              4320

His Gln Leu Arg Tyr Asn Gln Ser Val Ser Asn Pro Cys Lys Gln
4325                4330              4335

Val Cys Ser His Leu Cys Leu Leu Arg Pro Gly Gly Tyr Ser Cys
4340                4345              4350

Ala Cys Pro Gln Gly Ser Asp Phe Val Thr Gly Ser Thr Val Glu
4355                4360              4365

Cys Asp Ala Ala Ser Glu Leu Pro Ile Thr Met Pro Ser Pro Cys
4370                4375              4380

Arg Cys Met His Gly Gly Ser Cys Tyr Phe Asp Glu Asn Asp Leu
4385                4390              4395

Pro Lys Cys Lys Cys Ser Ser Gly Tyr Ser Gly Glu Tyr Cys Glu
4400                4405              4410

Ile Gly Leu Ser Arg Gly Ile Pro Pro Gly Thr Thr Met Ala Leu
4415                4420              4425

Leu Leu Thr Phe Ala Met Val Ile Ile Val Gly Ala Leu Val Leu
4430                4435              4440

Val Gly Phe Phe His Tyr Arg Lys Thr Gly Ser Leu Leu Pro Ser
4445                4450              4455

Leu Pro Lys Leu Pro Ser Leu Ser Ser Leu Ala Lys Pro Ser Glu
4460                4465              4470

Asn Gly Asn Gly Val Thr Phe Arg Ser Gly Ala Asp Val Asn Met
4475                4480              4485

Asp Ile Gly Val Ser Pro Phe Gly Pro Glu Thr Ile Ile Asp Arg
4490                4495              4500

Ser Met Ala Met Asn Glu Gln Phe Val Met Glu Val Gly Lys Gln
4505                4510              4515

Pro Val Ile Phe Glu Asn Pro Met Tyr Ala Ala Lys Asp Ser Thr
4520                4525              4530

Ser Lys Val Gly Leu Ala Val Gln Gly Pro Ser Val Ser Ser Gln
4535                4540              4545

Val Thr Val Pro Glu Asn Val Glu Asn Gln Asn Tyr Gly Arg Ser

```
                    4550                 4555                 4560
Ile Asp Pro Ser Glu Ile Val Pro Glu Pro Lys Pro Ala Ser Pro
            4565                 4570                 4575

Gly Ala Asp Glu Thr Gln Gly Thr Lys Trp Asn Ile Phe Lys Arg
            4580                 4585                 4590

Lys Pro Lys Gln Thr Thr Asn Phe Glu Asn Pro Ile Tyr Ala Glu
            4595                 4600                 4605

Met Asp Thr Glu Gln Lys Glu Ala Val Ala Val Ala Pro Pro Pro
            4610                 4615                 4620

Ser Pro Ser Leu Pro Ala Lys Ala Ser Lys Arg Ser Ser Thr Pro
            4625                 4630                 4635

Gly Tyr Thr Ala Thr Glu Asp Thr Phe Lys Asp Thr Ala Asn Leu
            4640                 4645                 4650

Val Lys Glu Asp Ser Asp Val
            4655                 4660
```

<210> SEQ ID NO 21
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 22
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

-continued

```
Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Gln Thr Gln Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 23
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Gln Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

```
<210> SEQ ID NO 24
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

```
<210> SEQ ID NO 25
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser

```
                      100                 105                 110
Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 26
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 27
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30
```

```
Val Val Gly Leu Ala Gly Asn Ala Ile Leu Arg Glu Asp Glu Asp Pro
         35                  40                  45

Gln Lys Met Tyr Ala Thr Ile Tyr Glu Leu Lys Glu Asp Gly Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Lys Lys Val Ser Gln
                115                 120                 125

Asn Arg Glu Tyr Phe Lys Ile Thr Leu Tyr Gly Arg Thr Lys Glu Leu
130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 28
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
         35                  40                  45

Gln Thr Met Tyr Ala Thr Ile Tyr Glu Leu Lys Glu Asp Lys Ser Tyr
 50                  55                  60

Asn Val Thr Ser Val Leu Phe Gln Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Gln Glu Tyr Phe Lys Ile Thr Leu Tyr Gly Arg Thr Lys Glu Leu
130                 135                 140

Thr Ser Glu Leu Gln Glu Asn Phe Ile Arg Phe Ser Gln Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 29
<211> LENGTH: 178
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 29

```
Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Thr Met Tyr Ala Thr Ile Tyr Glu Leu Lys Glu Asp Lys Ser Tyr
50                  55                  60

Asn Val Thr Ser Val Leu Phe Gln Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Gln Glu Asn Phe Ile Arg Phe Ser Gln Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 30
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Gln Glu Tyr Phe Lys Ile Thr Leu Tyr Gly Arg Thr Lys Glu Leu
130                 135                 140
```

```
Thr Ser Glu Leu Lys Glu Asn Phe Ile Arg Phe Ser Gln Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 31
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Gln Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Gln Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 32
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Asp Asp Gly Cys Asp Tyr Trp Ile
```

65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Lys Lys Val Ser Gln
                    115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 33
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                    20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Gly Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Lys Lys Val Ser Gln
                    115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 34
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Gln Thr Gln Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 35
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Gln Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 36
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Lys Met Tyr Ala Thr Ile Tyr Glu Leu Gln Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 37
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Gln Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 38
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Gln Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Gln Thr Gln Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 39
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro

```
                35                  40                  45
Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Gln Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 41
<211> LENGTH: 178
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 41

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Phe Lys Lys Val Ser Gln
                115                 120                 125

Asn Gln Glu Tyr Phe Lys Ile Thr Leu Tyr Gly Arg Thr Lys Glu Leu
            130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 42
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln Phe Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140
```

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 43
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Asp Asp Gly Cys Asp Tyr Trp Ile
65                  70                  75                  80

```
Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 45
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Asp Ser Thr Ser Asp Leu Ile Pro Ala Pro Pro Leu Ser Lys Val
```

```
               1               5                  10                 15
    Pro Leu Gln Gln Asn Phe Gln Asp Asn Gln Phe Gln Gly Lys Trp Tyr
                    20                  25                  30

Val Val Gly Leu Ala Gly Asn Ala Ile Leu Gln Glu Asp Lys Asp Pro
                    35                  40                  45

Gln Lys Met Tyr Ala Thr Ile Tyr Glu Leu Lys Glu Asp Lys Ser Tyr
                50                  55                  60

Asn Val Thr Ser Val Leu Phe Arg Lys Lys Cys Asp Tyr Trp Ile
     65                  70                  75                  80

Arg Thr Phe Val Pro Gly Cys Gln Pro Gly Glu Phe Thr Leu Gly Asn
                        85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Phe Lys Lys Val Ser Gln
                    115                 120                 125

Asn Arg Glu Tyr Phe Lys Ile Thr Leu Tyr Gly Gln Thr Gln Glu Leu
                130                 135                 140

Thr Ser Glu Leu Lys Glu Asn Phe Ile Arg Phe Ser Gln Ser Leu Gly
    145                 150                 155                 160

Leu Pro Glu Asn His Ile Val Phe Pro Val Pro Ile Asp Gln Cys Ile
                        165                 170                 175

Asp Gly

<210> SEQ ID NO 47
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Asp Ser Thr Ser Asp Leu Ile Pro Ala Pro Pro Leu Ser Ser Val
    1               5                   10                  15

Pro Leu Gln Gln Asn Phe Gln Asp Asn Gln Phe Gln Gly Lys Trp Tyr
                    20                  25                  30

Val Val Gly Leu Ala Gly Asn Ala Ile Leu Gln Glu Asp Lys Asp Pro
                    35                  40                  45

Gln Lys Met Tyr Ala Thr Ile Tyr Glu Leu Lys Glu Asp Lys Ser Tyr
                50                  55                  60

Asn Val Thr Ser Val Leu Phe Arg Lys Lys Cys Asp Tyr Trp Ile
     65                  70                  75                  80

Arg Thr Phe Val Pro Gly Cys Gln Pro Gly Glu Phe Thr Leu Gly Asn
                        85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Phe Lys Lys Val Ser Gln
                    115                 120                 125

Asn Arg Glu Tyr Phe Lys Ile Thr Leu Tyr Gly Gln Thr Gln Glu Leu
                130                 135                 140

Thr Ser Glu Leu Lys Glu Asn Phe Ile Arg Phe Ser Gln Ser Leu Gly
    145                 150                 155                 160

Leu Pro Glu Asn His Ile Val Phe Pro Val Pro Ile Asp Gln Cys Ile
                        165                 170                 175

Asp Gly
```

<210> SEQ ID NO 48
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Asp Ser Thr Ser Asp Leu Ile Pro Ala Pro Pro Leu Ser Lys Val
1               5                   10                  15

Pro Leu Ala Pro Asp Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Gly Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 49
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Asp Ser Thr Ser Asp Leu Ile Pro Ala Pro Pro Leu Ser Lys Val
1               5                   10                  15

Pro Leu Ala Pro Asp Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Ala Glu Asp Gly Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

```
Thr Asn Tyr Asn Gln Phe Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 50
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Gly Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asp Tyr Asn Gln Phe Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 51
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45
```

```
Gln Lys Met Tyr Ala Thr Ile Tyr Glu Leu Lys Glu Asp Lys Ser Tyr
            50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Ala Thr Ala Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 52
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Ala Glu Asp Lys Asp Pro
             35                  40                  45

Gln Lys Met Tyr Ala Thr Ile Tyr Glu Leu Lys Glu Asp Lys Ser Tyr
            50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Ala Thr Ala Glu Leu
            130                 135                 140

Thr Ser Glu Leu Lys Glu Asn Phe Ile Arg Phe Ser Ala Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 53
<211> LENGTH: 178
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 53

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Ala Thr Ala Glu Leu
    130                 135                 140

Thr Ser Glu Leu Lys Glu Asn Phe Ile Arg Phe Ser Ala Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 54
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Ala Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Ala Thr Ala Glu Leu
    130                 135                 140

Thr Ser Glu Leu Lys Glu Asn Phe Ile Arg Phe Ser Ala Ser Leu Gly

```
                145                 150                 155                 160

Leu Pro Glu Asn His Ile Val Phe Pro Val Pro Ile Asp Gln Cys Ile
                165                 170                 175

Asp Gly

<210> SEQ ID NO 55
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Ala Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Ala Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Ala Thr Ala Glu Leu
            130                 135                 140

Thr Ser Glu Leu Lys Glu Asn Phe Ile Arg Phe Ser Ala Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 56
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Asp Ser Thr Ser Asp Leu Ile Pro Ala Pro Pro Leu Ser Lys Val
1               5                   10                  15

Pro Leu Ala Pro Asp Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Asp Asp Gly Cys Asp Tyr Trp Ile
65                  70                  75                  80
```

```
Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 57
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 58
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Ala Glu Asp Gly Ser Tyr
 50                      55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asp Ala Ile Val Phe Pro Val Pro Ile Asp Gln Cys Ile
                165                 170                 175

Asp Gly

<210> SEQ ID NO 59
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Ala Glu Asp Gly Ser Tyr
 50                      55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 60
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Lys Met Tyr Ala Thr Ile Tyr Glu Leu Ala Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Glu
            115                 120                 125

Ser Ala Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 61
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Thr Met Tyr Ala Thr Ile Tyr Glu Leu Ala Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Glu
```

```
                115                 120                 125
Ser Ala Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 62
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Ala Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
            100                 105                 110

Thr Asp Tyr Asn Gln His Ala Met Val Phe Phe Lys Lys Val Ser Glu
        115                 120                 125

Ser Ala Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 63
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45
```

```
Gln Thr Met Tyr Ala Thr Ile Tyr Glu Leu Ala Glu Asp Gly Ser Tyr
        50                  55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Ala Ser Tyr Pro Gly Leu Thr Ser Tyr Leu Val Arg Val Val Ser
                100                 105                 110

Thr Asp Tyr Asn Gln His Ala Met Val Phe Lys Lys Val Ser Glu
        115                 120                 125

Ser Ala Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 64
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Asp Ser Thr Ser Asp Leu Ile Pro Ala Pro Pro Leu Ser Ser Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Thr Met Tyr Ala Thr Ile Tyr Glu Leu Ala Glu Asp Gly Ser Tyr
        50                  55                  60

Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Ala Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Glu
        115                 120                 125

Ser Ala Glu Tyr Phe Lys Ile Thr Leu Tyr Gly Arg Thr Lys Glu Leu
        130                 135                 140

Thr Ser Glu Leu Ala Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 65
<211> LENGTH: 178
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 65

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Thr Met Tyr Ala Thr Ile Tyr Glu Leu Ala Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Glu
        115                 120                 125

Ser Ala Glu Tyr Phe Lys Ile Thr Leu Tyr Gly Arg Thr Lys Glu Leu
    130                 135                 140

Thr Ser Glu Leu Ala Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 66
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Thr Met Tyr Ala Thr Ile Tyr Glu Leu Ala Glu Asp Gly Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Glu
        115                 120                 125

Ser Ala Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

```
Leu Pro Glu Asn His Ile Val Phe Pro Val Pro Ile Asp Gln Cys Ile
            165                 170                 175

Asp Gly

<210> SEQ ID NO 67
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Thr Met Tyr Ala Thr Ile Tyr Glu Leu Lys Glu Asp Lys Ser Tyr
    50                  55                  60

Asn Val Thr Ser Val Leu Phe Ala Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Gln Ser Tyr Pro Gly Leu Thr Ser Tyr Leu Val Arg Val Val Ser
            100                 105                 110

Thr Asn Tyr Asn Gln Phe Ala Met Val Phe Phe Lys Lys Val Ser Gln
        115                 120                 125

Asn Gln Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 68
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Glu Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Ala Asp Asp Gly Cys Asp Tyr Trp Ile
65                  70                  75                  80

Arg Thr Phe Val Pro Gly Cys Gln Pro Gly Glu Phe Thr Leu Gly Asn
```

```
                    85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Phe Lys Lys Val Ser Gln
            115                 120                 125

Asn Gln Glu Tyr Phe Lys Ile Thr Leu Tyr Gly Arg Thr Lys Glu Leu
        130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 69
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 69

Xaa Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 70
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MOD_RES
<222> LOCATION: (2)..(2)
<223> OTHER INFORMATION: Gln, Ala, Asn, Asp, Cys, Glu, Gly, Ile, Leu,
     Met, Phe, Pro, Ser, Thr, Trp, Tyr, or Val

<400> SEQUENCE: 70

```
Gln Xaa Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 71
<211> LENGTH: 178
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (3)..(3)
<223> OTHER INFORMATION: Gln, Ala, Asn, Asp, Cys, Glu, Gly, Ile, Leu,
     Met, Phe, Pro, Ser, Thr, Trp, Tyr, or Val

<400> SEQUENCE: 71

```
Gln Asp Xaa Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110
```

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 72
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 72

Gln Asp Ser Xaa Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 73
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 73

```
Gln Asp Ser Thr Xaa Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
Asn Arg Glu Tyr Phe Lys Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 74
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (6)..(6)
<223> OTHER INFORMATION: Gln, Ala, Asn, Asp, Cys, Glu, Gly, Ile, Leu, Met, Phe, Pro, Ser, Thr, Trp, Tyr, or Val

<400> SEQUENCE: 74

```
Gln Asp Ser Thr Ser Xaa Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
Asn Arg Glu Tyr Phe Lys Ile Thr Leu Tyr Gly Arg Thr Lys Glu Leu
130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 75
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 75

Gln Asp Ser Thr Ser Asp Xaa Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 76
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 76

Gln Asp Ser Thr Ser Asp Leu Xaa Pro Ala Pro Pro Leu Ser Lys Val
1               5                   10                  15
```

```
Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 77
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 77

Gln Asp Ser Thr Ser Asp Leu Ile Xaa Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

Asp Gly

<210> SEQ ID NO 78
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 78

Gln Asp Ser Thr Ser Asp Leu Ile Pro Xaa Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 79
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 79

Gln Asp Ser Thr Ser Asp Leu Ile Pro Ala Xaa Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

```
Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 80
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 80

Gln Asp Ser Thr Ser Asp Leu Ile Pro Ala Pro Xaa Leu Ser Lys Val
  1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 81
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 81

Gln Asp Ser Thr Ser Asp Leu Ile Pro Ala Pro Xaa Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 82
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 82

Gln Asp Ser Thr Ser Asp Leu Ile Pro Ala Pro Leu Xaa Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
```

```
              65                  70                  75                  80
    Arg Thr Phe Val Pro Gly Cys Gln Pro Gly Glu Phe Thr Leu Gly Asn
                        85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
    145                 150                 155                 160

Leu Pro Glu Asn His Ile Val Phe Pro Val Pro Ile Asp Gln Cys Ile
                    165                 170                 175

Asp Gly

<210> SEQ ID NO 83
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 83

Gln Asp Ser Thr Ser Asp Leu Ile Pro Ala Pro Pro Leu Ser Xaa Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 84
<211> LENGTH: 178
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 84

Gln Asp Ser Thr Ser Asp Leu Ile Pro Ala Pro Pro Leu Ser Lys Xaa
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 85
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 85

Gln Asp Ser Thr Ser Asp Leu Ile Pro Ala Pro Pro Leu Ser Lys Val
1               5                   10                  15

Xaa Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95
```

```
Ile Lys Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 86
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 86

Gln Asp Ser Thr Ser Asp Leu Ile Pro Ala Pro Pro Leu Ser Lys Val
1               5                   10                  15

Pro Xaa Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 87
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
```

```
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 87

Gln Asp Ser Thr Ser Asp Leu Ile Pro Ala Pro Pro Leu Ser Lys Val
1               5                   10                  15

Pro Leu Xaa Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 88
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 88

Gln Asp Ser Thr Ser Asp Leu Ile Pro Ala Pro Pro Leu Ser Lys Val
1               5                   10                  15

Pro Leu Gln Xaa Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125
```

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 89
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 89

Gln Asp Ser Thr Ser Asp Leu Ile Pro Ala Pro Pro Leu Ser Lys Val
1               5                   10                  15

Pro Leu Gln Gln Xaa Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 90
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 90

Gln Asp Ser Thr Ser Asp Leu Ile Pro Ala Pro Pro Leu Ser Lys Val
1               5                   10                  15

Pro Leu Gln Gln Asn Xaa Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
            85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 91
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 91

Gln Asp Ser Thr Ser Asp Leu Ile Pro Ala Pro Pro Leu Ser Lys Val
1               5                   10                  15

Pro Leu Gln Gln Asn Phe Xaa Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
            85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly

Leu Pro Glu Asn His Ile Val Phe Pro Val Pro Ile Asp Gln Cys Ile
            165                 170                 175

Asp Gly

<210> SEQ ID NO 92
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 92

Gln Asp Ser Thr Ser Asp Leu Ile Pro Ala Pro Pro Leu Ser Lys Val
1               5                   10                  15

Pro Leu Gln Gln Asn Phe Gln Xaa Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 93
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 93

Gln Asp Ser Thr Ser Asp Leu Ile Pro Ala Pro Pro Leu Ser Lys Val
1               5                   10                  15

Pro Leu Gln Gln Asn Phe Gln Asp Xaa Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 94
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 94

Gln Asp Ser Thr Ser Asp Leu Ile Pro Ala Pro Pro Leu Ser Lys Val
1               5                   10                  15

Pro Leu Gln Gln Asn Phe Gln Asp Asn Xaa Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 95
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 95

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Xaa Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 96
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 96

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Xaa Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr

```
            50                  55                  60
Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 97
<211> LENGTH: 178
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (29)..(29)
<223> OTHER INFORMATION: Gln, Ala, Asn, Asp, Cys, Glu, Gly, Ile, Leu, Met, Phe, Pro, Ser, Thr, Trp, Tyr, or Val

<400> SEQUENCE: 97

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Xaa Lys Trp Tyr
                 20                  25                  30

Val Val Gly Leu Ala Gly Asn Ala Ile Leu Arg Glu Asp Lys Asp Pro
                 35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 98
<211> LENGTH: 178

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 98

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Xaa Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 99
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 99

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Xaa Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80
```

-continued

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 100
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 100

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Xaa
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 101
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (33)..(33)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 101
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Xaa Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 102
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 102
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Xaa Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

```
Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 103
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 103

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Xaa Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 104
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (36)..(36)
<223> OTHER INFORMATION: Gln, Ala, Asn, Asp, Cys, Glu, Gly, Ile, Leu,
      Met, Phe, Pro, Ser, Thr, Trp, Tyr, or Val
```

<400> SEQUENCE: 104

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Xaa Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 105
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 105

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Xaa Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu

```
                130                 135                 140
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 106
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (38)..(38)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 106

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Xaa Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65              70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 107
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (39)..(39)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 107

Gln Asp Ser Thr Ser Asp Leu Ile Pro Ala Pro Pro Leu Ser Lys Val
1               5                   10                  15
```

Pro Leu Gln Gln Asn Phe Gln Asp Asn Gln Phe Gln Gly Lys Trp Tyr
            20                  25                  30

Val Val Gly Leu Ala Gly Xaa Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 108
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 108

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Xaa Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 109
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 109

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Xaa Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 110
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 110

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Xaa Arg Glu Asp Lys Asp Pro

```
                35                  40                  45
Gln Lys Met Tyr Ala Thr Ile Tyr Glu Leu Lys Glu Asp Lys Ser Tyr
 50                  55                  60
Asn Val Thr Ser Val Leu Phe Arg Lys Lys Lys Cys Asp Tyr Trp Ile
 65                  70                  75                  80
Arg Thr Phe Val Pro Gly Cys Gln Pro Gly Glu Phe Thr Leu Gly Asn
                 85                  90                  95
Ile Lys Ser Tyr Pro Gly Leu Thr Ser Tyr Leu Val Arg Val Val Ser
                100                 105                 110
Thr Asn Tyr Asn Gln His Ala Met Val Phe Phe Lys Lys Val Ser Gln
                115                 120                 125
Asn Arg Glu Tyr Phe Lys Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 111
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 111

Gln Asp Ser Thr Ser Asp Leu Ile Pro Ala Pro Pro Leu Ser Lys Val
  1               5                  10                  15
Pro Leu Gln Gln Asn Phe Gln Asp Asn Gln Phe Gln Gly Lys Trp Tyr
                 20                  25                  30
Val Val Gly Leu Ala Gly Asn Ala Ile Leu Xaa Glu Asp Lys Asp Pro
                 35                  40                  45
Gln Lys Met Tyr Ala Thr Ile Tyr Glu Leu Lys Glu Asp Lys Ser Tyr
 50                  55                  60
Asn Val Thr Ser Val Leu Phe Arg Lys Lys Lys Cys Asp Tyr Trp Ile
 65                  70                  75                  80
Arg Thr Phe Val Pro Gly Cys Gln Pro Gly Glu Phe Thr Leu Gly Asn
                 85                  90                  95
Ile Lys Ser Tyr Pro Gly Leu Thr Ser Tyr Leu Val Arg Val Val Ser
                100                 105                 110
Thr Asn Tyr Asn Gln His Ala Met Val Phe Phe Lys Lys Val Ser Gln
                115                 120                 125
Asn Arg Glu Tyr Phe Lys Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 112
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (44)..(44)
<223> OTHER INFORMATION: Gln, Ala, Asn, Asp, Cys, Glu, Gly, Ile, Leu,
    Met, Phe, Pro, Ser, Thr, Trp, Tyr, or Val

<400> SEQUENCE: 112

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Xaa Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 113
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (45)..(45)
<223> OTHER INFORMATION: Gln, Ala, Asn, Asp, Cys, Glu, Gly, Ile, Leu,
    Met, Phe, Pro, Ser, Thr, Trp, Tyr, or Val

<400> SEQUENCE: 113

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Xaa Lys Asp Pro
            35                  40                  45

Gln Lys Met Tyr Ala Thr Ile Tyr Glu Leu Lys Glu Asp Lys Ser Tyr
    50                  55                  60

```
Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 114
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (46)..(46)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 114

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Xaa Asp Pro
                 35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 115
<211> LENGTH: 178
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (47)..(47)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 115
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Xaa Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 116
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (48)..(48)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 116
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Xaa
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 117
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 117

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Xaa Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 118
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (50)..(50)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 118

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Xaa Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 119
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (51)..(51)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 119

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Xaa Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 120
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (52)..(52)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 120

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Xaa Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 121
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (53)..(53)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 121

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Xaa Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 122
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (54)..(54)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 122

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Xaa Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140
```

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 123
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 123

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Xaa Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 124
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (56)..(56)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 124

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr

```
            20                  25                  30
Val Val Gly Leu Ala Gly Asn Ala Ile Leu Arg Glu Asp Lys Asp Pro
            35                  40                  45

Gln Lys Met Tyr Ala Thr Ile Xaa Glu Leu Lys Glu Asp Lys Ser Tyr
    50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 125
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (57)..(57)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 125

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Xaa Leu Lys Glu Asp Lys Ser Tyr
    50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

<210> SEQ ID NO 126
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (58)..(58)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 126

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Xaa Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 127
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 127

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

```
Gln Lys Met Tyr Ala Thr Ile Tyr Glu Leu Xaa Glu Asp Lys Ser Tyr
        50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 128
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (60)..(60)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 128

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Xaa Asp Lys Ser Tyr
        50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 129
```

<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 129

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Xaa Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 130
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 130

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Xaa Ser Tyr
        50                  55                  60

Asn Val Thr Ser Val Leu Phe Arg Lys Lys Lys Cys Asp Tyr Trp Ile
65                  70                  75                  80

```
Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 131
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 131

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Xaa Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 132
<211> LENGTH: 178
<212> TYPE: PRT
<213> ORGANISM: Artificial Sequence
<220> FEATURE:
<223> OTHER INFORMATION: Description of Artificial Sequence: Synthetic
```

```
                polypeptide
<220> FEATURE:
<221> NAME/KEY: MOD_RES
<222> LOCATION: (64)..(64)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 132

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Xaa
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 133
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 133

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Xaa Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
```

```
                    100                 105                 110
Thr Asn Tyr Asn Gln His Ala Met Val Phe Lys Lys Val Ser Gln
            115                 120                 125
Asn Arg Glu Tyr Phe Lys Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 134
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (66)..(66)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 134

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Xaa Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Lys Lys Val Ser Gln
            115                 120                 125
Asn Arg Glu Tyr Phe Lys Ile Thr Leu Tyr Gly Arg Thr Lys Glu Leu
            130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 135
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (67)..(67)
<223> OTHER INFORMATION: Gln, Ala, Asn, Asp, Cys, Glu, Gly, Ile, Leu,
```

Met, Phe, Pro, Ser, Thr, Trp, Tyr, or Val

<400> SEQUENCE: 135

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Xaa Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 136
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (68)..(68)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 136

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Xaa Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

```
Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 137
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (69)..(69)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 137

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Xaa Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 138
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (70)..(70)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 138

Gln Asp Ser Thr Ser Asp Leu Ile Pro Ala Pro Pro Leu Ser Lys Val
```

```
                1               5                      10                        15
        Pro Leu Gln Gln Asn Phe Gln Asp Asn Gln Phe Gln Gly Lys Trp Tyr
                        20                      25                      30

Val Val Gly Leu Ala Gly Asn Ala Ile Leu Arg Glu Asp Lys Asp Pro
                        35                      40                      45

Gln Lys Met Tyr Ala Thr Ile Tyr Glu Leu Lys Glu Asp Lys Ser Tyr
                50                      55                      60

Asn Val Thr Ser Val Xaa Phe Arg Lys Lys Cys Asp Tyr Trp Ile
         65                      70                      75                      80

Arg Thr Phe Val Pro Gly Cys Gln Pro Gly Glu Phe Thr Leu Gly Asn
                                85                      90                      95

Ile Lys Ser Tyr Pro Gly Leu Thr Ser Tyr Leu Val Arg Val Val Ser
                        100                     105                     110

Thr Asn Tyr Asn Gln His Ala Met Val Phe Phe Lys Lys Val Ser Gln
                        115                     120                     125

Asn Arg Glu Tyr Phe Lys Ile Thr Leu Tyr Gly Arg Thr Lys Glu Leu
                        130                     135                     140

Thr Ser Glu Leu Lys Glu Asn Phe Ile Arg Phe Ser Lys Ser Leu Gly
        145                     150                     155                     160

Leu Pro Glu Asn His Ile Val Phe Pro Val Pro Ile Asp Gln Cys Ile
                        165                     170                     175

Asp Gly
```

<210> SEQ ID NO 139
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 139

```
        Gln Asp Ser Thr Ser Asp Leu Ile Pro Ala Pro Pro Leu Ser Lys Val
         1               5                      10                      15

Pro Leu Gln Gln Asn Phe Gln Asp Asn Gln Phe Gln Gly Lys Trp Tyr
                        20                      25                      30

Val Val Gly Leu Ala Gly Asn Ala Ile Leu Arg Glu Asp Lys Asp Pro
                        35                      40                      45

Gln Lys Met Tyr Ala Thr Ile Tyr Glu Leu Lys Glu Asp Lys Ser Tyr
                50                      55                      60

Asn Val Thr Ser Val Leu Xaa Arg Lys Lys Cys Asp Tyr Trp Ile
         65                      70                      75                      80

Arg Thr Phe Val Pro Gly Cys Gln Pro Gly Glu Phe Thr Leu Gly Asn
                                85                      90                      95

Ile Lys Ser Tyr Pro Gly Leu Thr Ser Tyr Leu Val Arg Val Val Ser
                        100                     105                     110

Thr Asn Tyr Asn Gln His Ala Met Val Phe Phe Lys Lys Val Ser Gln
                        115                     120                     125

Asn Arg Glu Tyr Phe Lys Ile Thr Leu Tyr Gly Arg Thr Lys Glu Leu
                        130                     135                     140

Thr Ser Glu Leu Lys Glu Asn Phe Ile Arg Phe Ser Lys Ser Leu Gly
        145                     150                     155                     160
```

Leu Pro Glu Asn His Ile Val Phe Pro Val Pro Ile Asp Gln Cys Ile
                165                 170                 175

Asp Gly

<210> SEQ ID NO 140
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (72)..(72)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 140

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Xaa Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 141
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (73)..(73)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 141

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

```
Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Xaa Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 142
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (74)..(74)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 142

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Xaa Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 143
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(75)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 143

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Xaa Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 144
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (76)..(76)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 144

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60
```

```
Asn Val Thr Ser Val Leu Phe Arg Lys Lys Lys Xaa Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 145
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (77)..(77)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 145

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Xaa Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 146
<211> LENGTH: 178
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (78)..(78)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 146

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Xaa Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 147
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (79)..(79)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 147

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Xaa Ile
65                  70                  75                  80

Arg Thr Phe Val Pro Gly Cys Gln Pro Gly Glu Phe Thr Leu Gly Asn
```

```
                    85                  90                  95
Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 148
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (80)..(80)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 148

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Xaa
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 149
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MOD_RES
<222> LOCATION: (81)..(81)
<223> OTHER INFORMATION: Gln, Ala, Asn, Asp, Cys, Glu, Gly, Ile, Leu,
    Met, Phe, Pro, Ser, Thr, Trp, Tyr, Val, or Arg

<400> SEQUENCE: 149

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Xaa Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 150
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (82)..(82)
<223> OTHER INFORMATION: Gln, Ala, Asn, Asp, Cys, Glu, Gly, Ile, Leu,
    Met, Phe, Pro, Ser, Thr, Trp, Tyr, or Val

<400> SEQUENCE: 150

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Xaa Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 151
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (83)..(83)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 151

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Xaa Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 152
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (84)..(84)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 152

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Xaa Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 153
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (85)..(85)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 153

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Xaa Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 154
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (86)..(86)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 154

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Xaa Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 155
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (87)..(87)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 155

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Xaa Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 156
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (88)..(88)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 156

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Xaa Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

-continued

```
                165                 170                 175
Asp Gly

<210> SEQ ID NO 157
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (89)..(89)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 157

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Xaa Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 158
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (90)..(90)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 158

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45
```

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Xaa Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 159
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (91)..(91)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 159

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Xaa Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 160
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (92)..(92)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 160

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Xaa Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 161
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (93)..(93)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 161

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
```

```
                65                  70                  75                  80
Arg Thr Phe Val Pro Gly Cys Gln Pro Gly Glu Phe Xaa Leu Gly Asn
                    85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Phe Lys Lys Val Ser Gln
                    115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 162
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (94)..(94)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 162

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Xaa Gly Asn
                    85                  90                  95

Ile Lys Ser Tyr Pro Gly Leu Thr Ser Tyr Leu Val Arg Val Val Ser
                    100                 105                 110

Thr Asn Tyr Asn Gln His Ala Met Val Phe Phe Lys Lys Val Ser Gln
                    115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 163
<211> LENGTH: 178
<212> TYPE: PRT
<213> ORGANISM: Artificial Sequence
<220> FEATURE:
```

-continued

```
<223> OTHER INFORMATION: Description of Artificial Sequence: Synthetic
      polypeptide
<220> FEATURE:
<221> NAME/KEY: MOD_RES
<222> LOCATION: (95)..(95)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 163

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Xaa Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 164
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (96)..(96)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 164

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Xaa
                85                  90                  95
```

```
Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 165
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 165

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Xaa Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 166
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (98)..(98)
```

<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 166

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Xaa Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 167
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (99)..(99)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 167

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Xaa Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

```
Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 168
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 168

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Xaa Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 169
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (101)..(101)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 169
```

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Xaa Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 170
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 170

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Xaa Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
```

```
                    145                 150                 155                 160

Leu Pro Glu Asn His Ile Val Phe Pro Val Pro Ile Asp Gln Cys Ile
                165                 170                 175

Asp Gly

<210> SEQ ID NO 171
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (103)..(103)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 171

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Xaa Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 172
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (104)..(104)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 172

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30
```

```
Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
     50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Xaa Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 173
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (105)..(105)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 173

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
             20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
     50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Xaa Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

```
<210> SEQ ID NO 174
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (106)..(106)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 174
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Xaa Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 175
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (107)..(107)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 175
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr

```
                50            55              60
Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Xaa Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 176
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (108)..(108)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 176

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Xaa Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 177
<211> LENGTH: 178
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (109)..(109)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 177

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Xaa Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 178
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (110)..(110)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 178

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80
```

-continued

```
Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Xaa Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 179
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (111)..(111)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 179

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Xaa Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 180
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (112)..(112)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 180
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Xaa
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 181
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (113)..(113)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 181
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

```
Xaa Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 182
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (114)..(114)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 182

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Xaa Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 183
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (115)..(115)
<223> OTHER INFORMATION: Gln, Ala, Asn, Asp, Cys, Glu, Gly, Ile, Leu,
      Met, Phe, Pro, Ser, Thr, Trp, Tyr, or Val
```

<400> SEQUENCE: 183

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Xaa Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 184
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (116)..(116)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 184

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Xaa Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu

```
                130                 135                 140
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 185
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (117)..(117)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 185

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Xaa His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 186
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (118)..(118)
<223> OTHER INFORMATION: Gln, Ala, Asn, Asp, Cys, Glu, Gly, Ile, Leu,
      Met, Phe, Pro, Ser, Thr, Trp, Tyr, Val, or His

<400> SEQUENCE: 186

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln Xaa Ala Met Val Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 187
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (119)..(119)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 187

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Xaa Met Val Phe Lys Lys Val Ser Gln
                115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
                165                 170                 175

Asp Gly

<210> SEQ ID NO 188
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (120)..(120)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 188

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Xaa Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 189
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (121)..(121)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 189

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro

```
                35                  40                  45
Gln Lys Met Tyr Ala Thr Ile Tyr Glu Leu Lys Glu Asp Lys Ser Tyr
         50                  55                  60
Asn Val Thr Ser Val Leu Phe Arg Lys Lys Lys Cys Asp Tyr Trp Ile
 65                  70                  75                  80
Arg Thr Phe Val Pro Gly Cys Gln Pro Gly Glu Phe Thr Leu Gly Asn
                 85                  90                  95
Ile Lys Ser Tyr Pro Gly Leu Thr Ser Tyr Leu Val Arg Val Val Ser
                100                 105                 110
Thr Asn Tyr Asn Gln His Ala Met Xaa Phe Phe Lys Lys Val Ser Gln
            115                 120                 125
Asn Arg Glu Tyr Phe Lys Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 190
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (122)..(122)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 190

Gln Asp Ser Thr Ser Asp Leu Ile Pro Ala Pro Pro Leu Ser Lys Val
  1               5                  10                  15
Pro Leu Gln Gln Asn Phe Gln Asp Asn Gln Phe Gln Gly Lys Trp Tyr
                 20                  25                  30
Val Val Gly Leu Ala Gly Asn Ala Ile Leu Arg Glu Asp Lys Asp Pro
             35                  40                  45
Gln Lys Met Tyr Ala Thr Ile Tyr Glu Leu Lys Glu Asp Lys Ser Tyr
         50                  55                  60
Asn Val Thr Ser Val Leu Phe Arg Lys Lys Lys Cys Asp Tyr Trp Ile
 65                  70                  75                  80
Arg Thr Phe Val Pro Gly Cys Gln Pro Gly Glu Phe Thr Leu Gly Asn
                 85                  90                  95
Ile Lys Ser Tyr Pro Gly Leu Thr Ser Tyr Leu Val Arg Val Val Ser
                100                 105                 110
Thr Asn Tyr Asn Gln His Ala Met Val Xaa Phe Lys Lys Val Ser Gln
            115                 120                 125
Asn Arg Glu Tyr Phe Lys Ile Thr Leu Tyr Gly Arg Thr Lys Glu Leu
        130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 191
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (123)..(123)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 191

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Xaa Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 192
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (124)..(124)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 192

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Xaa Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 193
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (125)..(125)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 193

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Xaa Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 194
<211> LENGTH: 178
<212> TYPE: PRT
<213> ORGANISM: Artificial Sequence -continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (126)..(126)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 194
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Xaa Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 195
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (127)..(127)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 195
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

```
Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Xaa Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 196
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (128)..(128)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 196

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Xaa
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 197
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

-continued

```
<222> LOCATION: (129)..(129)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 197

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Xaa Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 198
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (130)..(130)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 198

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
```

115             120             125

Asn Xaa Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 199
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (131)..(131)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 199

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Xaa Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 200
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (132)..(132)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 200

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Xaa Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 201
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (133)..(133)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 201

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Xaa Lys Ile Thr Leu Tyr Gly Arg Thr Lys Glu Leu
130                 135                 140
```

-continued

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 202
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (134)..(134)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 202

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Xaa Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 203
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (135)..(135)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 203

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
```

-continued

```
                20                  25                  30
Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Xaa Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 204
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (136)..(136)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 204

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Xaa Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

-continued

Asp Gly

<210> SEQ ID NO 205
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (137)..(137)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 205

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Xaa Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 206
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (138)..(138)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 206

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

```
Gln Lys Met Tyr Ala Thr Ile Tyr Glu Leu Lys Glu Asp Lys Ser Tyr
             50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Xaa Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 207
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (139)..(139)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 207

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
             50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Xaa Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 208
```

```
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (140)..(140)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 208

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Xaa Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 209
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (141)..(141)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 209

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80
```

```
Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Xaa Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 210
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (142)..(142)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 210

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Xaa Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 211
<211> LENGTH: 178
<212> TYPE: PRT
<213> ORGANISM: Artificial Sequence
<220> FEATURE:
<223> OTHER INFORMATION: Description of Artificial Sequence: Synthetic -continued

```
    polypeptide
<220> FEATURE:
<221> NAME/KEY: MOD_RES
<222> LOCATION: (143)..(143)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 211

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Xaa Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 212
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (144)..(144)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 212

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
```

-continued

```
                100             105             110
Thr Asn Tyr Asn Gln His Ala Met Val Phe Lys Lys Val Ser Gln
            115                 120             125

Asn Arg Glu Tyr Phe Lys Ile Thr Leu Tyr Gly Arg Thr Lys Glu Xaa
            130                 135             140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 213
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (145)..(145)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 213

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
            130                 135                 140

Xaa Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 214
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (146)..(146)
<223> OTHER INFORMATION: Gln, Ala, Asn, Asp, Cys, Glu, Gly, Ile, Leu,
```

Met, Phe, Pro, Ser, Thr, Trp, Tyr, or Val

<400> SEQUENCE: 214

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Xaa Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 215
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (147)..(147)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 215

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125
```

-continued

```
Asn Arg Glu Tyr Phe Lys Ile Thr Leu Tyr Gly Arg Thr Lys Glu Leu
            130                 135                 140

Thr Ser Xaa Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 216
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (148)..(148)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 216

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Xaa Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 217
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (149)..(149)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 217

Gln Asp Ser Thr Ser Asp Leu Ile Pro Ala Pro Pro Leu Ser Lys Val
```

```
1               5                   10                  15
Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Xaa Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 218
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (150)..(150)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 218

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Xaa Asn Phe Ile Arg Phe Ser Lys Ser Leu Gly
145                 150                 155                 160
```

Leu Pro Glu Asn His Ile Val Phe Pro Val Pro Ile Asp Gln Cys Ile
            165                 170                 175

Asp Gly

<210> SEQ ID NO 219
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (151)..(151)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 219

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Xaa Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 220
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (152)..(152)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 220

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

```
Val Val Gly Leu Ala Gly Asn Ala Ile Leu Arg Glu Asp Lys Asp Pro
         35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
130                 135                 140

Thr Ser Glu Leu Lys Glu Asn Xaa Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 221
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (153)..(153)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 221

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
         35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Xaa Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 222
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (154)..(154)
<223> OTHER INFORMATION: Gln, Ala, Asn, Asp, Cys, Glu, Gly, Ile, Leu,
      Met, Phe, Pro, Ser, Thr, Trp, Tyr, Val, or Arg

<400> SEQUENCE: 222

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Xaa Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 223
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (155)..(155)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 223

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

```
Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Xaa Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 224
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (156)..(156)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 224

```
Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Xaa Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 225
<211> LENGTH: 178
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (157)..(157)
<223> OTHER INFORMATION: Gln, Ala, Asn, Asp, Cys, Glu, Gly, Ile, Leu,
      Met, Phe, Pro, Ser, Thr, Trp, Tyr, Val, or Lys

<400> SEQUENCE: 225

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Xaa Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 226
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (158)..(158)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 226

Gln Asp Ser Thr Ser Asp Leu Ile Pro Ala Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn

```
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Xaa Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 227
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (159)..(159)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 227

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Xaa Gly
145                 150                 155                 160

Leu Pro Glu Asn His Ile Val Phe Pro Val Pro Ile Asp Gln Cys Ile
                165                 170                 175

Asp Gly

<210> SEQ ID NO 228
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<221> NAME/KEY: MOD_RES
<222> LOCATION: (160)..(160)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 228

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
Asn Arg Glu Tyr Phe Lys Ile Thr Leu Tyr Gly Arg Thr Lys Glu Leu
    130                 135                 140
Thr Ser Glu Leu Lys Glu Asn Phe Ile Arg Phe Ser Lys Ser Leu Xaa
145                 150                 155                 160
Leu Pro Glu Asn His Ile Val Phe Pro Val Pro Ile Asp Gln Cys Ile
                165                 170                 175
Asp Gly
```

<210> SEQ ID NO 229
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (161)..(161)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 229

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
```

```
Thr Asn Tyr Asn Gln His Ala Met Val Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Xaa Pro Glu Asn His Ile Val Phe Pro Val Pro Ile Asp Gln Cys Ile
                165                 170                 175

Asp Gly

<210> SEQ ID NO 230
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (162)..(162)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 230

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
    115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Xaa Glu Asn His Ile Val Phe Pro Val Pro Ile Asp Gln Cys Ile
                165                 170                 175

Asp Gly

<210> SEQ ID NO 231
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (163)..(163)
<223> OTHER INFORMATION: Gln, Ala, Asn, Asp, Cys, Glu, Gly, Ile, Leu,
      Met, Phe, Pro, Ser, Thr, Trp, Tyr, or Val
```

<400> SEQUENCE: 231

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Xaa Asn His Ile Val Phe Pro Val Pro Ile Asp Gln Cys Ile
                165                 170                 175

Asp Gly

<210> SEQ ID NO 232
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (164)..(164)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 232

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
130                 135                 140

```
Thr Ser Glu Leu Lys Glu Asn Phe Ile Arg Phe Ser Lys Ser Leu Gly
145                 150                 155                 160

Leu Pro Glu Xaa His Ile Val Phe Pro Val Pro Ile Asp Gln Cys Ile
                165                 170                 175

Asp Gly

<210> SEQ ID NO 233
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (165)..(165)
<223> OTHER INFORMATION: Gln, Ala, Asn, Asp, Cys, Glu, Gly, Ile, Leu,
      Met, Phe, Pro, Ser, Thr, Trp, Tyr, Val, or His

<400> SEQUENCE: 233

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn Xaa Ile Val Phe Pro Val Pro Ile Asp Gln Cys Ile
                165                 170                 175

Asp Gly

<210> SEQ ID NO 234
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (166)..(166)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 234

Gln Asp Ser Thr Ser Asp Leu Ile Pro Ala Pro Pro Leu Ser Lys Val
1               5                   10                  15
```

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Xaa Val Phe Pro Val Pro Ile Asp Gln Cys Ile
                165                 170                 175

Asp Gly

<210> SEQ ID NO 235
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (167)..(167)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 235

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Xaa Phe Pro Val Pro Ile Asp Gln Cys Ile

Asp Gly

<210> SEQ ID NO 236
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (168)..(168)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 236

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Xaa Pro Val Pro Ile Asp Gln Cys Ile
                165                 170                 175

Asp Gly

<210> SEQ ID NO 237
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (169)..(169)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 237

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
         50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                     85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Xaa Val Pro Ile Asp Gln Cys Ile
                165                 170                 175

Asp Gly

<210> SEQ ID NO 238
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (170)..(170)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 238

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Lys Asp Pro
             35                  40                  45

Gln Lys Met Tyr Ala Thr Ile Tyr Glu Leu Lys Glu Asp Lys Ser Tyr
         50                  55                  60

Asn Val Thr Ser Val Leu Phe Arg Lys Lys Cys Asp Tyr Trp Ile
 65                  70                  75                  80

Arg Thr Phe Val Pro Gly Cys Gln Pro Gly Glu Phe Thr Leu Gly Asn
                     85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Xaa Pro Ile Asp Gln Cys Ile
                165                 170                 175

Asp Gly

-continued

```
<210> SEQ ID NO 239
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (171)..(171)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 239

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Xaa Ile Asp Gln Cys Ile
                165                 170                 175

Asp Gly

<210> SEQ ID NO 240
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (172)..(172)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 240

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
```

```
                65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Xaa Asp Gln Cys Ile
                165                 170                 175

Asp Gly

<210> SEQ ID NO 241
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (173)..(173)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 241

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                    85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
                115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Xaa Gln Cys Ile
                165                 170                 175

Asp Gly

<210> SEQ ID NO 242
<211> LENGTH: 178
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (174)..(174)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 242

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Xaa Cys Ile
                165                 170                 175

Asp Gly

<210> SEQ ID NO 243
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (175)..(175)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 243

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95
```

```
Ile Lys Ser Tyr Pro Gly Leu Thr Ser Tyr Leu Val Arg Val Val Ser
            100                 105                 110

Thr Asn Tyr Asn Gln His Ala Met Val Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Xaa Ile
                165                 170                 175

Asp Gly

<210> SEQ ID NO 244
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (176)..(176)
<223> OTHER INFORMATION: Gln, Ala, Asn, Asp, Cys, Glu, Gly, Ile, Leu,
      Met, Phe, Pro, Ser, Thr, Trp, Tyr, or Val

<400> SEQUENCE: 244

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Xaa
                165                 170                 175

Asp Gly

<210> SEQ ID NO 245
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (177)..(177)
```

<223> OTHER INFORMATION: Gln, Ala, Asn, Asp, Cys, Glu, Gly, Ile, Leu,
    Met, Phe, Pro, Ser, Thr, Trp, Tyr, or Val

<400> SEQUENCE: 245

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
Asn Arg Glu Tyr Phe Lys Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Xaa Gly
```

<210> SEQ ID NO 246
<211> LENGTH: 178
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (178)..(178)
<223> OTHER INFORMATION: Gln, Ala, Asn, Asp, Cys, Glu, Gly, Ile, Leu,
    Met, Phe, Pro, Ser, Thr, Trp, Tyr, or Val

<400> SEQUENCE: 246

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe Gln Gly Lys Trp Tyr
            20                  25                  30
Val Val Gly Leu Ala Gly Asn Ala Ile Leu Arg Glu Asp Lys Asp Pro
        35                  40                  45
Gln Lys Met Tyr Ala Thr Ile Tyr Glu Leu Lys Glu Asp Lys Ser Tyr
    50                  55                  60
Asn Val Thr Ser Val Leu Phe Arg Lys Lys Lys Cys Asp Tyr Trp Ile
65                  70                  75                  80
Arg Thr Phe Val Pro Gly Cys Gln Pro Gly Glu Phe Thr Leu Gly Asn
                85                  90                  95
Ile Lys Ser Tyr Pro Gly Leu Thr Ser Tyr Leu Val Arg Val Val Ser
            100                 105                 110
Thr Asn Tyr Asn Gln His Ala Met Val Phe Phe Lys Lys Val Ser Gln
        115                 120                 125
```

```
Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Xaa

<210> SEQ ID NO 247
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Thr Met Tyr Ala Thr Ile Tyr Glu Leu Ala Glu Asp Gly Ser Tyr
    50                  55                  60

Asn Val Thr Ser Val Leu Phe Ala Asp Asp Gly Cys Asp Tyr Trp Ile
65                  70                  75                  80

Arg Thr Phe Val Pro Gly Cys Gln Pro Gly Glu Phe Thr Leu Gly Asn
                85                  90                  95

Ile Ala Ser Tyr Pro Gly Leu Thr Ser Tyr Leu Val Arg Val Val Ser
                100                 105                 110

Thr Asp Tyr Asn Gln His Ala Met Val Phe Phe Lys Lys Val Ser Glu
            115                 120                 125

Ser Ala Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 248
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Thr Met Tyr Ala Thr Ile Tyr Glu Leu Ala Glu Asp Gly Ser Tyr
    50                  55                  60
```

```
                                50                  55                  60
Asn Val Thr Ser Val Leu Phe Arg Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Ala Ser Tyr Pro Gly Leu Thr Ser Tyr Leu Val Arg Val Val Ser
                100                 105                 110

Thr Asp Tyr Asp Glu Phe Ala Met Val Phe Lys Lys Val Ser Glu
            115                 120                 125

Ser Ala Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 249
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Gln Asp Ser Thr Ser Asp Leu Ile Pro Ala Pro Pro Leu Ser Ser Val
 1               5                  10                  15

Pro Leu Gln Gln Asn Phe Gln Asp Asn Gln Phe Gln Gly Lys Trp Tyr
                 20                  25                  30

Val Val Gly Leu Ala Gly Asn Ala Ile Leu Arg Glu Asp Glu Asp Pro
             35                  40                  45

Gln Thr Met Tyr Ala Thr Ile Tyr Glu Leu Lys Glu Asp Gly Ser Tyr
         50                  55                  60

Asn Val Thr Ser Val Leu Phe Ala Asp Asp Gly Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Lys Lys Val Ser Gln
            115                 120                 125

Asn Gln Glu Tyr Phe Lys Ile Thr Leu Tyr Gly Arg Thr Lys Glu Leu
            130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly
```

<210> SEQ ID NO 250
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Ala Glu Asp Glu Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
            85                  90                  95

Ile Gln Ser Tyr Pro Gly Leu Thr Ser Tyr Leu Val Arg Val Val Ser
        100                 105                 110

Thr Asn Tyr Asn Gln Phe Ala Met Val Phe Phe Lys Lys Val Ser Gln
    115                 120                 125

Asn Gln Glu Tyr Phe Lys Ile Thr Leu Tyr Gly Ala Thr Ala Glu Leu
130                 135                 140

Thr Ser Glu Leu Gln Glu Asn Phe Ile Arg Phe Ser Ala Ser Leu Gly
145                 150                 155                 160

Leu Pro Glu Asn Asn Ile Val Phe Pro Val Pro Ile Asp Gln Cys Ile
                165                 170                 175

Asp Gly

<210> SEQ ID NO 251
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Asp Ser Thr Ser Asp Leu Ile Pro Ala Pro Pro Leu Ser Ser Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Ala Glu Asp Glu Asp Pro
        35                  40                  45

Gln Lys Met Tyr Ala Thr Ile Tyr Glu Leu Lys Glu Asp Lys Ser Tyr
50                  55                  60

Asn Val Thr Ser Val Leu Phe Arg Asp Asp Gly Cys Asp Tyr Trp Ile
65                  70                  75                  80

Arg Thr Phe Val Pro Gly Cys Gln Pro Gly Glu Phe Thr Leu Gly Asn
            85                  90                  95

Ile Gln Ser Tyr Pro Gly Leu Thr Ser Tyr Leu Val Arg Val Val Ser
        100                 105                 110

Thr Asn Tyr Asn Gln Phe Ala Met Val Phe Phe Lys Lys Val Ser Gln
    115                 120                 125

Asn Gln Glu Tyr Phe Lys Ile Thr Leu Tyr Gly Arg Thr Lys Glu Leu
130                 135                 140

Thr Ser Glu Leu Gln Glu Asn Phe Ile Arg Phe Ser Ala Ser Leu Gly
145                 150                 155                 160

```
Leu Pro Glu Asn Asn Ile Val Phe Pro Val Pro Ile Asp Gln Cys Ile
                165                 170                 175

Asp Gly

<210> SEQ ID NO 252
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gln Asp Ser Thr Ser Asp Leu Ile Pro Ala Pro Pro Leu Ser Ser Val
1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Glu Asp Pro
            35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Asp Asp Gly Cys Asp Tyr Trp Ile
65                  70                  75                  80

Arg Thr Phe Val Pro Gly Ser Gln Pro Gly Glu Phe Thr Leu Gly Asn
                85                  90                  95

Ile Gln Ser Tyr Pro Gly Leu Thr Ser Tyr Leu Val Arg Val Val Ser
                100                 105                 110

Thr Asn Tyr Asn Gln Phe Ala Met Val Phe Phe Lys Lys Val Ser Gln
            115                 120                 125

Asn Gln Glu Tyr Phe Lys Ile Thr Leu Tyr Gly Arg Thr Lys Glu Leu
    130                 135                 140

Thr Ser Glu Leu Gln Glu Asn Phe Ile Arg Phe Ser Lys Ser Leu Gly
145                 150                 155                 160

Leu Pro Glu Asn Asn Ile Val Phe Pro Val Pro Ile Asp Gln Cys Ile
                165                 170                 175

Asp Gly
```